United States Patent
Crow et al.

(10) Patent No.: US 12,065,653 B2
(45) Date of Patent: Aug. 20, 2024

(54) PLANT REGULATORY ELEMENTS AND METHODS OF USE THEREOF

(71) Applicant: PIONEER HI-BRED INTERNATIONAL, INC., Johnston, IA (US)

(72) Inventors: Andrew Crow, Grimes, IA (US); Scott Diehn, West Des Moines, IA (US); Lynne Sims, Polk City, IA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 16/311,893

(22) PCT Filed: Jun. 8, 2017

(86) PCT No.: PCT/US2017/036503
§ 371 (c)(1),
(2) Date: Dec. 20, 2018

(87) PCT Pub. No.: WO2017/222821
PCT Pub. Date: Dec. 28, 2017

(65) Prior Publication Data
US 2019/0194676 A1    Jun. 27, 2019

Related U.S. Application Data

(60) Provisional application No. 62/354,374, filed on Jun. 24, 2016.

(51) Int. Cl.
*C12N 15/82* (2006.01)
*C12N 5/04* (2006.01)
*C12N 15/62* (2006.01)

(52) U.S. Cl.
CPC .......... *C12N 15/8227* (2013.01); *C12N 5/04* (2013.01); *C12N 15/62* (2013.01); *C12N 15/8216* (2013.01)

(58) Field of Classification Search
None
See application file for complete search history.

(56) References Cited

U.S. PATENT DOCUMENTS

| | | | |
|---|---|---|---|
| 6,388,066 B1 | 5/2002 | Bruce et al. | |
| 8,058,420 B2 | 11/2011 | Milligan et al. | |
| 9,322,028 B1 | 4/2016 | Maiti et al. | |
| 9,453,234 B2 * | 9/2016 | Conner et al. | ....... C12N 15/823 |
| 9,909,133 B2 | 3/2018 | Owens et al. | |
| 2013/0031672 A1 | 1/2013 | Flasinski et al. | |
| 2014/0208455 A1 * | 7/2014 | Kirsch | ............... C12N 15/8279 800/278 |
| 2014/0283205 A1 | 9/2014 | Crow et al. | |
| 2014/0283206 A1 | 9/2014 | Crow et al. | |
| 2015/0247155 A1 | 9/2015 | Owens et al. | |

FOREIGN PATENT DOCUMENTS

| | | |
|---|---|---|
| FR | 2 791 699 A1 | 10/2000 |
| WO | 1999/014316 A2 | 3/1999 |
| WO | 2009/139649 A1 | 11/2009 |
| WO | 2010019872 A1 | 2/2010 |
| WO | 2010/033922 A2 | 3/2010 |
| WO | 2012112411 A1 | 8/2012 |

OTHER PUBLICATIONS

Benfey et al, Science 250: 959-966, 1990 (Year: 1990).*
Benfey et al, The Embo J 9(6): 1685-1696, 1990 (Year: 1990).*
Potenza et al. (2004) In Vitro Cell Dev Biol Plant 40:1-22.*
Priest et al. (989) Curr Opin Plant Biol 12:643-49.*
Saha et al. (2007) In Silico Biol 7(1):7-19.*
Omirulleh, S., et al.: "Activity of a chimeric promoter with the doubled CaMV 35S enhancer element in protoplast-derived cells and transgenic plants in maize", Plant Molecular Biology, Jan. 1, 1993 (Jan. 1, 1993), vol. 21, No. 3, pp. 415-428.
International Search Report and Written Opinion, International Application No. PCT/US2017/036503 dated Jan. 10, 2018.
Dey, Nrisingha; et al.: "Synthetic promoters in planta," Planta, Aug. 7, 2015 (Aug. 7, 2015), vol. 242, pp. 1077-1094.
Extended European Search Report for European Application No. 22168029.1, mailed Sep. 30, 2022, 09 Pages.
International Preliminary Report on Patentability for International Application No. PCT/US2017/036503, mailed Jan. 3, 2019, 8 Pages.
Wang R., et al., "Novel Green Tissue-Specific Synthetic Promoters and Cis-Regulatory Elements in Rice," Scientific Reports, Dec. 2015.

* cited by examiner

Primary Examiner — Russell T Boggs

(57) ABSTRACT

The present disclosure relates to the field of plant molecular biology, more particularly to regulation of gene expression in plants.

8 Claims, 3 Drawing Sheets
Specification includes a Sequence Listing.

FIG. 2

| Root Hybrid SEQ ID NO: | Segments assembled (5' – 3') | Segment A SEQ ID NO: | Segment B SEQ ID NO: | Segment C SEQ ID NO: |
|---|---|---|---|---|
| 13 | ZM-CYCLO:SB-RCC3:ZM-PCOa | 71 | 70 | 69 |
| 35 | ZM-PCOa:ZM-CYCLO:SB-RCC3 | 69 | 71 | 70 |
| 36 | SB-RCC3:ZM-PCOa:ZM-CYCLO | 70 | 69 | 71 |
| 37 | ZM-PCOa:SB-RCC3:ZM-CYCLO | 69 | 70 | 71 |
| 17 | SI-TIP2-3B:SB-PLTP:BD-RCC3B | 73 | 72 | 74 |
| 38 | BD-RCC3B:SI-TIP2-3B:SB-PLTP | 74 | 73 | 72 |
| 39 | SB-PLTP:BD-RCC3B:SI-TIP2-3B | 72 | 74 | 73 |
| 40 | BD-RCC3B:SB-PLTP:SI-TIP2-3B | 74 | 72 | 73 |
| 13 | ZM-CYCLO:SB-RCC3:ZM-PCOa | 71 | 70 | 69 |
| 41 | SB-RCC3:ZM-PCOa | n/a | 70 | 69 |
| 42 | ZM-CYCLO:SB-RCC3 | n/a | 71 | 70 |
| 43 | SB-RCC3:ZM-CYCLO | n/a | 70 | 71 |
| 44 | ZM-CYCLO:PCOa | n/a | 71 | 69 |
| 45 | ZM-PCOa:ZM-CYCLO | n/a | 69 | 71 |
| 46 | ZM-PCOa:SB-RCC3 | n/a | 69 | 70 |

FIG. 3

| Aerial Hybrid SEQ ID NO: | Segments assembled (5' – 3') | Segment 5 SEQ ID NO: | Segment 4 SEQ ID NO: | Segment 3 SEQ ID NO: | Segment 2 SEQ ID NO: | Segment 1 SEQ ID NO: |
|---|---|---|---|---|---|---|
| 47 | silk-green | | | | 61 | 48 |
| 50 | (3x)silk-green-core | 62 | 62 | 62 | 64 | 67 |
| 51 | (3x)silk-green-core | 62 | 62 | 62 | 64 | 66 |
| 52 | (3x)silk-green-core | 62 | 62 | 62 | 64 | 65 |
| 53 | silk-silk-green-green | | 62 | 62 | 64 | 49 |
| 54 | green-silk-silk-green | | 63 | 62 | 61 | 48 |
| 55 | silk-silk-green-green | | 61 | 62 | 63 | 48 |
| 56 | silk-silk-green | | | 62 | 61 | 48 |
| 57 | green-silk-green | | | 64 | 61 | 48 |
| 58 | (3x)silk-green | | 62 | 62 | 64 | 49 |
| 59 | green-green-silk-silk | | 64 | 64 | 62 | 60 |

SEQUENCE LISTING

```
<160> NUMBER OF SEQ ID NOS: 74

<210> SEQ ID NO 1
<211> LENGTH: 962
<212> TYPE: DNA
<213> ORGANISM: Brachypodium distachyon
<220> FEATURE:
<221> NAME/KEY: misc_feature
<223> OTHER INFORMATION: BD-RCI2 PRO (MOD 1)

<400> SEQUENCE: 1
tttgacttgg accgactagc actccccgc taggcacgta gtacgtggta tgtgtggaaa      60
cgattggttc gttgtaggga gtcagtcaga tcagatatga tgcttctcgt gtgttgattt    120
tcttcctctg aactgaaagg aagcatgcaa gttttacaag ctaaactcag cagcggaagc    180
tatgcatacg ttccactggc tgcagaacag ggcaggccgg cggctagctc ctgtgagctg    240
tgttggagga gaataaatatc ttgtcgtttg gctttgctcg ggtggatact tttttttctt    300
ttgacagctg ctcgggtgga tactgataca ctatgaagac cgaaaaaaag aagcgaagca   360
```

-continued

| | |
|---|---|
| tataaacaga cggatcattg ggggccaagc cagcaggtag tgcggtggaa cattatgtag | 420 |
| aatgaatcgg ttcttgctgt gcagacagct cagctcagca cactcctggc ccaaaacaaa | 480 |
| gtgcatgtgg tgtattttcg tatactagct aacaaatgct taagcccctg tttgaaatat | 540 |
| tgtattttcg gcggacgggc actggcttac tgaaatcttg ccaggaggca cggacaggtg | 600 |
| cttagcagcc aagtaatgta cagtaaatcc ggcaaattgc caggggagtg gttcgattca | 660 |
| atcaacgaat gcgattcccg atataaatta tccccagttt attttgatt ttatacaacg | 720 |
| cgtcgccgac gcggtcccca ccccgtgcgc gtcgcaaggt ccacacgtgt cctctctccg | 780 |
| acgcttccta gctcacgccg tccttgattg acctgcctcg ccatctataa atggcaaacc | 840 |
| aggctaaggc tcatttctat actccctctt cctgctctgc tctctgctct agtttactcc | 900 |
| actgacccaa agagagaaaa gaaagcactc agaacttgag atcagcatcc aggagatcgg | 960 |
| cc | 962 |

<210> SEQ ID NO 2
<211> LENGTH: 1792
<212> TYPE: DNA
<213> ORGANISM: Brachypodium distachyon
<220> FEATURE:
<221> NAME/KEY: misc_feature
<223> OTHER INFORMATION: BD-GRP3 PRO (MOD 1)

<400> SEQUENCE: 2

| | |
|---|---|
| tctggcgtag tgtggatagt ttacgtcaaa ttctattgcg tcggtagtag atttttgcaa | 60 |
| aacatcagct taacatttca caagtttaag tgtttaacca ctgagtgact ttttaatcgt | 120 |
| ttagttctaa cttaagaaca tgatgttttg tagatggaga acatgtgcat tccagaagtc | 180 |
| agaactagaa gcgatcgaaa tgaactgatc tgaagagatc gagctgtgtt agtactatat | 240 |
| tattgttgat tctagaccat taaagatcgg atcgcgtcaa ctaatatggc aactagctag | 300 |
| gatctgttac cttaattctc gtttctatcg atctatttgg ggctcttcta cacatgagct | 360 |
| agctggagaa tcgaatacca agtcctaacc tgcaacttgg acactgcaat tttcatcgat | 420 |
| cgacatctct cgttgtgtgc gttgccataa ctattcgaag atagactaat aactgataca | 480 |
| gtgcgttcct gtctgtacgg tcaaacttct ggacccctgg caatgcgtaa acccctaggt | 540 |
| caccacacgg tacggtgtga cacagctaag cgcaattaat acccaagtca acactctgcg | 600 |
| tcgtcgttta ccaacagatt aattagctca actcgctcaa ctcgccgagt agctagcagt | 660 |
| gaaaagggaa acgcgcggca ctacattact gcggcgcttg ctcaaacttc atgcaccaat | 720 |
| aattgaaaca cggtcaattg tatgcattac tagtgtaatt aagtgcatgt aacgaatgaa | 780 |
| ctaccttagg attttaggag aatcgaagaa tatctccatc catttaccaa atcaaactta | 840 |
| ttaagaagaa aatattatgt acttcctacg tccaaaaaag atgtctcaag tttgtcaaat | 900 |
| tttggatgta tctagacatg acttaatgta tagatgcatt caaattttga caaacttaag | 960 |
| acatcctttt ttggacggag ggagtacaag atttgttaat aagttacatt aaaaaactac | 1020 |
| acagtactgt ctactcgttt tttttctaa agaaaatcac ggatctatta ataatcacca | 1080 |
| acatgagcct tacttaatta agtacttaga gacgacgtcg agcgtttgga gagtctttgt | 1140 |
| acaatgtcaa aggtacctat aatccggccg gcgggtgat ttgaatcgcg cgcctagcta | 1200 |
| gatcgatcca tgcatgcgat ccacagctag cttgatgctt gcgccagtgt gtgatcgatc | 1260 |
| atgagctcat gacccatga catcgagcga gttagctaga gaagccatgc acgcacgttc | 1320 |
| tttcacgtgg aagagttata aaaagctagc gtaatacgtt tatatatgtc aggagatggg | 1380 |

| | |
|---|---|
| aatctctagc taattaggct tcgagagaaa ccaagcaaca gctagtaatt aacttcagat | 1440 |
| ccttccgcac tcgataatca agtcttgatc tgcatagccc agtgaagtgc caataaatct | 1500 |
| aagatgtgaa gagatgtgca acagtgcaag agaaaattta atgctgtcta gttgcttgat | 1560 |
| cgatgcagtc aatactagta ctgtcaccct gattagaaaa attatcactc atcgaatcac | 1620 |
| ccacttgata attcacagcc cgaagtcgtc ccgaagcgcg cggtcgcctc cttgagatat | 1680 |
| ccaaccccat gcatctcatc taccactata aatactcagg ccaccctctc tgctaagcac | 1740 |
| cccaccacct catctcacac gtactctagc tacaaattaa gctacgtcgg ca | 1792 |

<210> SEQ ID NO 3
<211> LENGTH: 2001
<212> TYPE: DNA
<213> ORGANISM: Brachypodium distachyon
<220> FEATURE:
<221> NAME/KEY: misc_feature
<223> OTHER INFORMATION: BD-RCC3B PRO (MOD 1)

<400> SEQUENCE: 3

| | |
|---|---|
| aaaactaggt tcaagacaca tttcaactcc tcccttcatc ccatttttaag tgctgaaata | 60 |
| ttacatgtat ctaaacgtct tttaggtata catacattca gatgttcatt aaatgacagg | 120 |
| gtgctgacgt ggcatacacg ctatgtgtat cagatgaaaa acatagctag caaacacatc | 180 |
| tggctttcat acgtacatca gcagatgcaa ggtcgacgaa tacatgcatt cgtcaacctc | 240 |
| tagcggctgg tagcaacatc ctcacaacga aaacgctagc cggaagccaa cgtaccatag | 300 |
| gcgcacacaa atccacgacc acgactatga accggatacc tgaagtcaag catctctcgg | 360 |
| taccggccgc cgaaagcaac aacaacacca gaaacaacct gacaaaataa tgaagatttc | 420 |
| gtgtctaacg ttaaaaagaa attatgaaag agtcgtagag gccaattgat gatgtgccta | 480 |
| atagatacat atggtaagga taataatcat ttcttactac attattcata caaaaaataa | 540 |
| ttaagaatca aaaattatga gaaacaccct ttggtgtggt gtagttgtgg gtgcatcact | 600 |
| ccacccatta gggtccaaat cttggtgctc acattatgcc ggggtctccc ttacattctt | 660 |
| cctatcaatt ttttttgtaa atctacagta gatgtctata atgaaaattt tcaaatatct | 720 |
| aaaatagcaa cgaaaatctc atatgttacc tgtagaagct caaacttttt gtattgcaca | 780 |
| caatgttaat aaaataaaac tcttgctaaa acttgtaatg actacctaat aacaacatat | 840 |
| tgtgttgtat atgaatttaa gcccatctaa atattcggaa tattcgctta tcattcaaaa | 900 |
| gatttagatc aacaaaaaga agtgaagaac tttatatttt ggtaggtaaa atgtataaca | 960 |
| aaacaaatct ttcagaaaat cacttgatat ttccaaacac aatacatcta aattgcaata | 1020 |
| aaaaagaatt ttagaaaaca aaaacataaa aatatgggtg ttgctgtttg aatttcaata | 1080 |
| ctacaaaagg acatatatgt gacgtcatat tagtgtcggg cccagcagga ccgccaatga | 1140 |
| tgtatagcat cagtgttggt cggtgcaaaa cccgccactg atatacagct gcgcgttttcc | 1200 |
| cactttcgac ctgatgaaca tcagtggcgg gcgttcacc cgcccgccac taattttttaa | 1260 |
| gtagaggacc ttaaatctaa gttgacgtat gagaaccatt ggattaagat ataatggcac | 1320 |
| tctcttctct tctacttgct atcgttggat taatatccga cggtcaagca catcggctca | 1380 |
| tgtctaacaa aaaaaaggca acttcttaat agcaaaaccg taaaaatata tattttatta | 1440 |
| tacaagtcta gcccgcgagc tgcttggttc accctgctag ttaagatagt aacttgtagc | 1500 |
| tcttcttgtt gcgtataagt tgttaaacat tgtaaaagcc tcctcaagta tcatgtatac | 1560 |
| ctgtgatacc tcacgacgat ttaaacgcac aattgctgta taatggatat agattggttc | 1620 |

| taggctccag cgatcgatta tccatgtaac tacgtacaaa cgagtaaacc tccaaaatca | 1680 |
| caccgctgtc acacatcgtc tgcacgcagt tgcctgaaac caatccactg cacctagccc | 1740 |
| acgggttgaa taaaaccgcc cgcgccggcc tcttcaacgt gcatccacgc agtgtgtcat | 1800 |
| tcccgtcacg gactctcgtc tcatccggcc ccttctctcg agcaacaccc accaatctcc | 1860 |
| tcgtgggtcg tggcggcctc tatataacgc aagacatcg atcagacatc catccatcca | 1920 |
| tccacactca cacagtcgct gtagtagcta gcaagcccct aggtgcttgc ttgacctact | 1980 |
| gctctgcccg tgaccagtcg t | 2001 |

<210> SEQ ID NO 4
<211> LENGTH: 1843
<212> TYPE: DNA
<213> ORGANISM: Zea mays
<220> FEATURE:
<221> NAME/KEY: misc_feature
<223> OTHER INFORMATION: ZM-PCO118362A PRO (FL)
<220> FEATURE:
<221> NAME/KEY: misc_feature
<223> OTHER INFORMATION: ZM-PCO118362A PRO (TR 1)

<400> SEQUENCE: 4

| agcaagatcg gtgaacaaca ctgagcatgg gcttttgagg cttttgactg atgacagcac | 60 |
| agataaaatt gaggatagta catcagtttt agttgcagca ctaaaacaat gctagtctac | 120 |
| taatggcttt cagccaagag aactgctggt gctcagttta gttctgcaa ggctatcctt | 180 |
| tccaacatca gcaagctttt ccctacttaa tgcagagggc atgctttgta tatcttcact | 240 |
| aattttgttt tattaggatg ccgcaaaggc caaaggttg atctttcatc cctccattta | 300 |
| ttttgcccac ttgcatttga aaaaagaaa agggtgtcga tgtttagaac ggaggtagta | 360 |
| ataactagct gcttaatcta gttgtcacca tggatggaga atcagataa acctgcatta | 420 |
| gcactaagca caaatgtgta tgtatggtta tgtaatggta gcatggagca tgattttcat | 480 |
| ttttcatatg aacatagagc atatataata atatgtgtaa gcaccaaggg gtaagatgtg | 540 |
| ttctaacctt actcaaatac taggcttaaa tctagagcaa gcactatata agtagaagtc | 600 |
| tatctaacct aggcacttta taaacacct acgctaatta ggagtgattc ttttgaacaa | 660 |
| ttgggtatct ggagctacta gagataagcg ttaactttct taatatttc cttaattacc | 720 |
| tcccatacat cttaaatgtc tagtggtagc atatatacct ccaaagtcca aagctagttg | 780 |
| taagtgacac aaaaaattat gcgtactcat tgaacatatc tgttacactc actaactaga | 840 |
| catgtttagt gcatctacgt tagctagttg cagaccccaa tcctatattg ttcataaatt | 900 |
| tttatcataa ggttccctgc tgcaatttag atatccagca tgctcttcaa ttttggtgct | 960 |
| caccctacg ggtatgccct cactgccttt tataattgta tagggaaat attattcaat | 1020 |
| ataatgtcct aaaaattggc aatatcaatc taaaaatcgt tatgaatagg atgtaaacaa | 1080 |
| agctactatc tgtccatata taacgtcaca ggaaggacaa aaaattcagt cagcgatcga | 1140 |
| gaacggcaaa gaaaaaccat attattgttg cttgccgaca taaatttaag tataggacaa | 1200 |
| aaaaaaagc cacatcatat tacatactat gggcttacca gacaaaatga ataaacgtg | 1260 |
| tgcatgcatg catgcatggt acgaacgtct ggatagagtc tccgagctga gtgtggtccg | 1320 |
| acgtggaagt gtacgtctca acacacgacg catgtgaccg acaagggcaa gttgaagtct | 1380 |
| atgcatggat gggcctgagc gccgcgctga atgaatctgg acgggtggta gggcatctcg | 1440 |
| gtgggcaaaa caaataactc cgtgtgctgc atggctgcct ttggaatctt tgcatgcagc | 1500 |
| tgtgtgctga actgaaaccc ttcgctctat ctatataaac agatgcccttt cgctctcgtc | 1560 |

-continued

| | | | | |
|---|---|---|---|---|
| tcagcaggca | gcatcgtctc | aagttttgtt | ctcctctcct | agctagccag cacctgcaga | 1620 |
| tctgctcgtt | gccttggtaa | ttcatcatgt | agtacgtagc | atcagctagt atttatctca | 1680 |
| agtatatata | tacgcatatg | tgtcgtcgca | gtactttccc | ttatctctct atacacacta | 1740 |
| cacgcataca | taccaatacc | atccgtctta | actcttaatc | tttgcctgca tacgtacact | 1800 |
| gcacgtacgt | actgcagggc | tactgatttt | gtggaacgaa | gcg | 1843 |

<210> SEQ ID NO 5
<211> LENGTH: 1397
<212> TYPE: DNA
<213> ORGANISM: Sorghum bicolor
<220> FEATURE:
<221> NAME/KEY: misc_feature
<223> OTHER INFORMATION: SB-PLTP PRO

<400> SEQUENCE: 5

| | | | | |
|---|---|---|---|---|
| caaactcagt | ttatcaccaa | agaccaaaca | tgtggaaatc | agtctctatt ttgtccaaga | 60 |
| gcatgtggcc | cttggagctt | tgcggcttct | tcatgttgct | acatctcttc aatatgccga | 120 |
| tatatttact | aagggttgtc | aattgttatc | ttcatcaact | tctgatctaa tctcaatgtt | 180 |
| tgctcctctt | ccggttgaga | ctactggggg | atattagaat | atgaatagcc aaaaagtctt | 240 |
| gtatagtcta | aaataaagag | tctcaaatag | ttcacttgag | cttaggaacc gaatttgtcg | 300 |
| tcagcagtgt | tttttgctca | tagtaaatta | gccaacaata | cttctatca cccttaaca | 360 |
| gagtactttc | tttctgccat | ggcttatcaa | ccaacagtat | ttttgtcaa agcagtgat | 420 |
| tatctgtcaa | tcactagcgc | ccctctgcc | ggtatatcta | gcgctcccat cggatctgac | 480 |
| tagagcagat | cttgagcgtg | ggttggtggc | tcagggcttg | caggaggcgt tggccgtcgc | 540 |
| cggcgtagag | cagtagtcgt | aggcggatct | gcatcttcaa | gctctcctcc ggtcgattcg | 600 |
| tgtgagtctt | cgacctctgc | tcaggtcgat | tcatgccggc | gaggggctca gtgctcggct | 660 |
| cacgacgcga | aattacgagc | ggcagcagca | aaccgggctt | tcaagcccgg ctctcctcgt | 720 |
| gagctgcctt | agggctcgtt | cgtttaacta | ttgttcccga | tggattcatt cctgatgata | 780 |
| aaaatagtat | aaatttacac | aatgttcctg | gctggaatca | tttcagacct gcattccatg | 840 |
| agaaacgaac | ggggctttag | cgggccacgt | gacagtgacg | aagggtcgca gtcgctgctg | 900 |
| gacggactac | agacagagag | gcgaagcatg | caattgaatt | ttcgctagcg gaaagttatc | 960 |
| atctaatctc | caaccctcct | tcctacggct | ggatctgaaa | attgacgacc tgaacccctg | 1020 |
| aacggtgccg | gtagcaattg | caggtctcac | tcacatgcta | aatccagcaa ccaaacacga | 1080 |
| aggaatatat | gtgatctgga | cagaacatgc | aagcgaataa | tacatagagt cgtaccaacc | 1140 |
| ctacacagtt | caacgaatta | atcactgggt | tcacgggcat | gctcacgtcc aaaatcccag | 1200 |
| cgacattta | taagcgctaa | gcggaatgat | ccagacgggg | ccagctcgag cacccatgg | 1260 |
| cgtcgctcca | tctcgcatct | ataaatacca | ttggccatgc | acaccgcac tcccacacag | 1320 |
| caatacagca | cactagcagc | agcagcagca | gctcgagcta | gcttagctac tacgtgtgtg | 1380 |
| caatcagctc | gatcgcc | | | | 1397 |

<210> SEQ ID NO 6
<211> LENGTH: 1710
<212> TYPE: DNA
<213> ORGANISM: Sorghum bicolor
<220> FEATURE:
<221> NAME/KEY: misc_feature
<223> OTHER INFORMATION: SB-RCC3 PRO (MOD 1) [RCST fix]

<400> SEQUENCE: 6

```
ttttaagtat gaccaatttt taagtataaa cccctcacga ttggttatttt ttttaagtat    60
aaccaatttt taagtataaa cccctcacca atttttaagt ataaacctag cgactaataa   120
acacaacttc ttgccaaagt gtgagcatca ccattggatc tgcgcccctc acgaacagtc   180
ttcgccgggg taaaattctc caaattaaag tcatcttgat gtccttgatc acctgtccat   240
aaggcccaat cccagctcca cgtatacttc tgataagatt gacatagtca cttgcatgcc   300
agtgtggaac tctggatgcc taggtcagag gctagtgact ggccttcccg gcatgctagc   360
atgtagcatg ccaaggatct ggctgctcca ggtttgttat gcctgacatc accatagggga  420
tgagagcaag tataataata ggctgtaagc tttaaatgct caggtggaga aaaaaaggag   480
aggagaggag agagaaaagt gggctataag cttatagctg tgttagacat aagaatcaga   540
aacttcgtat gagagacagg tgagctatat attaataaca aagagctaac tattatatga   600
gtgaaccgag agaaggctgt aaaaaaactt acacaatcaa cgatcgacat tattattaac   660
cttgctctgt cttgcgagac ctcttttgaca aagctacatc aatgccggcc aagtgccttg   720
ggatttggga atggcttctt tcctcccttc ctcggttgtc ccccaaggcc taggcttgcc   780
acgctgtatt cagtcgcagc cgcctttact tttgcccttt gtggaagttt tgtaataaat   840
ggtctgattc tatcttcgga tagatgaagc cggatgtttc atccattatc taaaaaaaag   900
ttggttgctt tgctgagcta agaaagtgta atccagagtg ctcgtaacgt attaatgtac   960
ataactatta tctaatataa atcttctttt gtcgcaaaaa aaggtcggcc catcagaaca  1020
aatgatcaat gtaaggccca aaatttgtgt ctcaaatgtc atttacgttt ccaagctaaa  1080
caaaaacaca ggattcatat aattttgctg gtggcttagg cttcgtccaa tagtgcttag  1140
tttaatttgt atatacctgc accatggtat tcgtctggcc ttggatcttg cgcatcaatt  1200
gcctatggac gatgatcgca gccacgccac attcattttt aatcgccatt tgcttgacac  1260
ccaatgcctc tgcaccactt gcgcacgcta cgcaccgtct gatacgccaa gatcccgagc  1320
taaaataaca cccaatcatc agatgaaaac aagcgcgagt gcgagccagc ccatggcagc  1380
gatcttggcc atttgcggag ccaactgaaa gccgtgcaca aaatattcga caccgtataa  1440
gggaaaacac tagttatacg aggtgggcaa taatccagat ctcggactct tcctaacccg  1500
gttcacatgc atagcatata tgatggccgg ccggggttca catgaacgcc atcccgtgcc  1560
ctagtgcact gatttcttaa tcccgggtct caactataaa taccccttg gtgacaccgc   1620
gatcaaagca tcgcaaacaa gcctagctaa gagctctcta actacattag atagagtgat  1680
ctcgagaggt aactggcttg tgatcgagca                                    1710
```

<210> SEQ ID NO 7
<211> LENGTH: 1745
<212> TYPE: DNA
<213> ORGANISM: Sorghum bicolor
<220> FEATURE:
<221> NAME/KEY: misc_feature
<223> OTHER INFORMATION: SB-TIP2-3 PRO (FL)

<400> SEQUENCE: 7

```
gcgcagttaa gcgcacttgt ggattggact gttgccaata tcattgtgat aataatcaga    60
accagttgca tgactcctct ccatactgca aaattacatt ctactaatgt atcatcatcc   120
ttttcagttt atttgtcact accaaaactac tatggcagtt ttttttttaat aaacgtaaaa  180
atgtggcaaa ttttaccgct cgttttcctc aggctatgca tttggttttta accaacaatt  240
```

-continued

```
cggttcgatt tatacgcttc atagaaattt cggttcccag aaactaaaaa ccgatcagtt        300
attcatgaaa ttaaaagtgc catgttttcc ccctaaagtt tatatatacc tgaaagtgta        360
caatgctaag tatgtttcac tataaatcaa ttcatgagga attttcaagc atttataatc        420
tttcccaaaa aaaggtgcg caatcaaaat ttcttacaaa acattccagt gacagatcat         480
cagacaatag tgtttctgat aaaccccca cgtaggatca gagaaagttt agagaatatt         540
cccacagtgg cccaaaacat tttgtctgac acgcagggag cgcataagtt ttttttattt        600
tattattgaa aagtgagttc taggaaactc tatacacaca taggctgaac aaccgtaagg        660
atagcataaa gaaataaggc ctttttggtg tcatcatctt cgtttgtgca ataatactgc        720
aactcaatga agtcactgcg actcataaga gccctgtcat caccttgcaa ctggcagttt        780
tcaattggtg taccagcgca agatccatag attaatcttg tttgcctcac ctaccccaaa        840
tggaggatgt tcactgcatt gatgtcacaa tccgaccttc ttaaccgctc tatgtcacaa        900
ctttaacatg aatgatatat cgtttcctca aaaacatgaa tgatatatca ctacagaact        960
cagtatgcag tagattcctg aacgcaagag ctgttgcaat gttaatctac taggtgatat       1020
cttactcggt aagatactca ggccgaggtc cgaggaatta cccttttgtt gcaggagaac       1080
caagtcatat gaatgaagca gcagctcagt aatgatccac cgactacgct acttctagca       1140
tagaattagt aatcttttct aatactgttg taaatttgta acaacaaaac aagaaccacg       1200
ccacggaaga acggtgagaa aaagaaacct ttgctaacgt actattcatg aatttgaaga       1260
ttttgtatgg atgcatcagt agacgatgca gggtagaaat aaaggatcga ttcagataat       1320
caatccgcac cgccattgat ttgtttaggg atgagatgag aattgagaat tgggataaca       1380
tatatctgct ccaaggtctt gttctcctcg ctgtcttatg gtgtatccta acgtggctcg       1440
gcctaaacaa ccacaattcc acagcagttt agcgagttag ggcggttggt cggccaatat       1500
cagccacaaa acacgaagca aaatttaaat tatcaatcat gtggtgatca ttgcacaccg       1560
cccatagtat tgtattgcac atctgaggca gggctccagc ctccaggtcc attagcgcct       1620
tatgatgtgt atttaaggag actgagctga aggaactctc gcatcagcct gataagctat       1680
agccagccat cttctctgaa ttccaactca gtccaagggc tggaagctag aagtaccgtc       1740
agaga                                                                   1745
```

<210> SEQ ID NO 8
<211> LENGTH: 1139
<212> TYPE: DNA
<213> ORGANISM: Zea mays
<220> FEATURE:
<221> NAME/KEY: misc_feature
<223> OTHER INFORMATION: ZM-CYCLO1 PRO

<400> SEQUENCE: 8

```
ctcctcgcct tgtggctcct cctgaaccac ctgctcttct cctgtggggg ggtgtgagac         60
agcaagggtg agctcacaca tgatcatagc tcaacaagtt gtgggaacc agtggacatg         120 aactcacaaa ggtgggagtt catgtgatgg ttcctctaga tgctcaactt gttgcattat        180
attacgcaat tgctccgacg cttcatcaat taatcctcct tagtgatatt aaataacgga        240
ataatattag agaaataaac aataatctaa gacattagcg cataaagatg tgacaaaatg        300
attgagtctg gtcatattac cctccttcat cctttattgc ataaaagatt gtagtttaca        360
ccttcggctt tacaaaggag agctcgaagg taatatttaca gcttcgaagg cggagtgatt       420
tgattctccc ttgttcaaaa agcgagatct cttcatatca ttgtgcctct atttatagta       480
```

| | |
|---|---|
| accaagtaca atttcatatg aaattacaaa catgctcatg gacatgataa ttccagtgca | 540 |
| catccaaccc tgcttgatac aaaacatgct cataatcatg atgattcaag tgcacatcca | 600 |
| ccctgctcga tacaacagtt ggcgacctgg tgtgagagtc agaccagacg ggctttcaca | 660 |
| atcgccatgc atgtcattct ctcgtggtcc acgtgtttat taatattgcc attaattgga | 720 |
| gggaaataaa atcaacaaga atagcttatt gatgagtcat atattatgaa tacatcttat | 780 |
| catcttacca aacaaaaaca tatgaccgtc gatgacctga aactagacta ttcgggatct | 840 |
| gcaatgatct gcttgtaaat attaatttgc acatcacgcc attgcatgca catcggcgtg | 900 |
| ggcattatta atttggattg gacgaaaaat caaccagagg gcgtcaccct tttgctagtt | 960 |
| ggccttgtaa tacttataat aattatccgt atagtctagt acgtacggga catcacgcca | 1020 |
| ttgcctgttg tgtataaaaa gcgagcatga gctaggttgg gagcagagca aagcgtagtc | 1080 |
| atcacctgtg tctaggttgg gagcaaagca aagagagaga ggaaagctag ctagctagc | 1139 |

<210> SEQ ID NO 9
<211> LENGTH: 1343
<212> TYPE: DNA
<213> ORGANISM: Zea mays
<220> FEATURE:
<221> NAME/KEY: misc_feature
<223> OTHER INFORMATION: ZM-ROOTMET2 PRO

<400> SEQUENCE: 9

| | |
|---|---|
| tttttactaa attcatgtaa taattaatgt atgcgttata tatatatgtc taggtttata | 60 |
| attattcata tgaatatgaa cataaaaatc tagggctaaa acgactacta ttttgaaaac | 120 |
| ggaaggagta gtaagttatt taagcggagg ggaaccatga tgggctagtg atttaattta | 180 |
| catatatata ttggtgttct gggctcttac atgagaagat ctagttaact gttgttactg | 240 |
| aacagcgaag acaaatatat aatttaagct ccccaactgc tagtgattct gttaagaggt | 300 |
| aatgtttaaa gtaaatttac aagagcccgt ctagctcagt cggtagagcg caaggctctt | 360 |
| aaccttgtgg tcgtgggttc gagccccacg gtgggcgcac aatttttgt tttttgacat | 420 |
| tttttgtttg yttagttgca gacggttttt cccctgctag gagatttccg agagaaaaaa | 480 |
| aaggcactac aggttaacca aaaccaccaa cctttggagc gtcgaggtcg acgggcattt | 540 |
| gcgtagttga agcttacaaa gttgcatatg agatgagtgc cggacatgaa gcggataacg | 600 |
| ttttaaactg gcaacaatat ctagctgttt caaattcagg cgtgggaagc tacgcctacg | 660 |
| cgccctggac ggcgtgtaaa gagccagcat cggcatcatt gtcaaacgat cgacaaggcc | 720 |
| aagaaattcc aaatatatta ttaataaaaa agaaggcaca aattagtttg gttttttagt | 780 |
| atgtgtggcg gaggaaattt tgagaacgaa cgtatcaaag aaggcacaag acgatataga | 840 |
| ttgacgcggc tagaagttgc agcaagacag tgggtacggt cttatatatc ctaataaata | 900 |
| aaaaataaaa ctatagtgtg tcaaatgtca acaagaggag gaggcagcca aattagcaga | 960 |
| gggagacaag tagagcacgc cttattagct tgcttattta tcgtggtggt gtacttgtta | 1020 |
| attactggca cgcattatca acaacgcagt tctggatgtg aatctagaca aacatttgtc | 1080 |
| taggttccgc acgtatagtt ttttcctct ttttttgg gggggggtgg gggggggaac | 1140 |
| ggaagctgta ataaacggta ctaggaacga aagcaaccgc cgcgcgcatg tttttgcaat | 1200 |
| agattacggt gaccttgatg caccaccgcg tgctataaaa accagtgtcc ccgagtctac | 1260 |
| tcatcaacca atccataact cgaaaccttt tcttgtgctc tgttctgtct gtgtgtttcc | 1320 |
| aaagcaagcg aaagaggtcg agg | 1343 |

<210> SEQ ID NO 10
<211> LENGTH: 2078
<212> TYPE: DNA
<213> ORGANISM: Setaria italica
<220> FEATURE:
<221> NAME/KEY: misc_feature
<223> OTHER INFORMATION: SI-TIP2-3B (MOD 1)

<400> SEQUENCE: 10

| | | | | | |
|---|---|---|---|---|---|
| aaagctccta | ccattttatt | tgcaatagta | gatgcatata | attgatggac | acagagttct | 60 |
| gaaccgtgag | attctcttta | acttcagagt | tctgtcacta | ttttaacgtg | gatctggagt | 120 |
| tttgcaggaa | ctgtgaagaa | ggaaccgtac | ctaaaactaa | aagtctcacg | aagaccaaat | 180 |
| gggcaagcca | gacagtcaga | gagacagggc | ttcttcggcc | aactggacaa | gggatgtgcc | 240 |
| tacatgtgct | gagagattac | caaatccgca | atttgcagac | gtgccttctc | aatcagtttg | 300 |
| cacaaagcga | taaggtaaac | aaccattgga | gcattgttaa | cagcagccta | gcatggcagg | 360 |
| atgcgtcatc | tgaataatgc | ggagggcagg | acagtaggac | aggacaccta | atccctgcaa | 420 |
| attctagtgg | ctctgggaca | ctgatcaagg | cccaaaagtg | ctaaccactg | cattactaaa | 480 |
| acgtgtgggt | gttgcgagtt | ccaagttggc | tgttgtcatg | gaatggtatg | aaaatgcaaa | 540 |
| agattctcgc | tgttttgttg | agagttagta | aattgggatg | acttcggcat | gacaacagca | 600 |
| caaaccttac | atatttggta | agacttgcaa | caaaaatcaa | aagaatgcta | gtagatacca | 660 |
| acaaaaagga | aaaacagagc | tagcatgaac | acttctttga | tcacagttga | tcaaaggtgt | 720 |
| atggccctca | gacaaagctg | ttgatgatgg | tcaaacactt | ttgctaccga | atatcgcagt | 780 |
| tgtcctttgg | tacattcaca | agtttgatct | tatcatcacc | atcagaagtt | cagaaagtct | 840 |
| cgtagaaaac | aaatggaaat | gaatactgct | tacttagctc | aaattcatat | tccgttgtta | 900 |
| caggatactt | aaaaaaggta | ccaaaggctg | ttcctaatca | tacgctgaag | tcgttgccac | 960 |
| caatggcagc | tgtactgtca | tattgtcgtg | gtttttcaat | tgctgtacct | gatgcaaacg | 1020 |
| taatgggttt | actaatcttg | cacccgccga | cttcaaaatg | aagagtgcta | atttggttca | 1080 |
| cgtcaccatc | accggttcga | actgtctaga | atggcaggca | agatgattg | gacaggcatg | 1140 |
| cagggaaaaa | gagcaccgat | gacgatctat | gcgagttccc | accattgcga | gcaatgatta | 1200 |
| tcagccacac | gacttactct | tcagagctaa | ccactgccat | gcagagaaaa | agtgaagcat | 1260 |
| attgtcagga | tctacaacga | agtgaaacaa | tcaggcatgc | taaagtgctg | aaactttact | 1320 |
| gatctctcat | gttggacaac | aaagaatacg | ggaatacatc | agcaacgcaa | ctcttgagct | 1380 |
| ttgcttgctg | aatgaccagc | tagaatttcc | aagcatttac | aggaacatga | ctttaagttt | 1440 |
| cagaaaaaca | aatacaaggc | cactaagggc | atgttcactt | cagcttataa | gccggctgaa | 1500 |
| aagctgaaac | ggctgatttg | ttgtgagagg | aaaacactgt | ttggtggctg | ataagccggc | 1560 |
| tgaataagct | gaagcgaaca | ggctgtaaat | aagcgtgggg | ataacatatc | ctccagatga | 1620 |
| caggcaatct | gcaacttgca | gcgattcaaa | tgtacgatta | acaaaatatt | taagcgctac | 1680 |
| atgagataat | atatcctcca | attagggcct | ttagtattgt | cattagctca | taagcatggt | 1740 |
| gcatcctcac | atggacgctg | cataagaagt | tcataatagc | aacagacata | tgaacaaagc | 1800 |
| atggtgcgcc | tgcccggccg | gactagctag | tactaccaat | catggaataa | gctagtaccc | 1860 |
| taaatgaaat | taaatggtt | tttagcgatt | atccacgccg | tccagaatac | tctaatccac | 1920 |
| aagttgaggc | cgcccatgaa | gccgcgagag | ggcgacgcca | tgtgtataaa | aggggcctaa | 1980 |
| gctgagtgga | cttgctgcat | cagattagta | agcaatctca | agcgcagaga | gccaaagctt | 2040 |

```
tcggtgtagc tcgaagagca aagcgaaggc aaggtcgt                              2078
```

<210> SEQ ID NO 11
<211> LENGTH: 4112
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: 3X CYCLO-PCOa

<400> SEQUENCE: 11

```
ctcctcgcct tgtggctcct cctgaaccac ctgctcttct cctgtggggg ggtgtgagac        60
agcaagggtg agctcacaca tgatcatagc tcaacaagtt gtggggaacc agtggacatg       120
aactcacaaa ggtgggagtt catgtgatgg ttcctctaga tgctcaactt gttgcattat       180
attacgcaat tgctccgacg cttcatcaat taatcctcct tagtgatatt aaataacgga       240
ataatattag agaaataaac aataatctaa gacattagcg cataaagatg tgacaaaatg       300
attgagtctg gtcatattac cctccttcat cctttattgc ataaagattg tagtttaca        360
ccttcggctt tacaaaggag agctcgaagg taatattaca gcttcgaagg cggagtgatt       420
tgattctccc ttgttcaaaa agcgagatct cttcatatca ttgtgcctct atttatagta       480
accaagtaca atttcatatg aaattacaaa catgctcatg gacatgataa ttccagtgca       540
catccaaccc tgcttgatac aaaacatgct cataatcatg atgattcaag tgcacatcca       600
ccctgctcga tacaacagtt ggcgacctgg tgtgagagtc agaccagacg ggctttcaca       660
atcgccatgc atgtcattct ctcgtggtcc acgtgtttat taatattgcc attaattgga       720
gggaaataaa tcaacaaga atagcttatt gatgagtcat atattatgaa tacatcttat        780
catcttacca acaaaaaca tatgaccgtc gatgacctga aactagacta ttcgggatct        840
gcaatgatct gcttgtaaat attaatttgc acatcacgcc attgcatgca catcggcgtg       900
ggcattatta atttggattg gacgaaaaat caaccagagg gcgtcaccct tttgctagtt       960
ggccttgtaa tacctcgacc tcctcgcctt gtggctcctc ctgaaccacc tgctcttctc      1020
ctgtgggggg gtgtgagaca gcaagggtga gctcacacat gatcatagct caacaagttg      1080
tggggaacca gtggacatga actcacaaag gtgggagttc atgtgatggt tcctctagat      1140
gctcaacttg ttgcattata ttacgcaatt gctccgacgc ttcatcaatt aatcctcctt      1200
agtgatatta ataacggaa taatattaga gaaataaaca ataatctaag acattagcgc      1260
ataaagatgt gacaaaatga ttgagtctgg tcatattacc ctccttcatc ctttattgca      1320
taaagattg tagtttacac cttcggcttt acaaggaga gctcgaaggt aatattacag       1380
cttcgaaggc ggagtgattt gattctccct tgttcaaaaa gcgagatctc ttcatatcat      1440
tgtgcctcta tttatagtaa ccaagtacaa tttcatatga aattacaaac atgctcatgg      1500
acatgataat tccagtgcac atccaaccct gcttgataca aaacatgctc ataatcatga      1560
tgattcaagt gcacatccac cctgctcgat acaacagttg gcgacctggt gtgagagtca      1620
gaccagacgg gctttcacaa tcgccatgca tgtcattctc tcgtggtcca cgtgtttatt      1680
aatattgcca ttaattggag ggaaataaaa tcaacaagaa tagcttattg atgagtcata      1740
tattatgaat acatcttatc atcttaccaa acaaaaacat atgaccgtcg atgacctgaa      1800
actagactat tcgggatctg caatgatctg cttgtaaata ttaatttgca catcacgcca      1860
ttgcatgcac atcggcgtgg gcattattaa tttggattgg acgaaaaatc aaccagaggg      1920
```

```
cgtcacccTT TTgcTAgTTg gccTTgTAAT AccTcgAccT ccTcgccTTg TggcTccTcc    1980

TgAAccAccT gcTcTTcTcc TgTgggggg TgTgAgAcAg cAAgggTgAg cTcAcAcATg     2040

ATcATAgcTc AAcAAgTTgT ggggAAccAg TggAcATgAA cTcAcAAAgg TgggAgTTcA    2100

TgTgATggTT ccTcTAgATg cTcAAcTTgT TgcATTATAT TAcgcAATTg cTccgAcgcT    2160

TcATcAATTA ATccTccTTA gTgATATTAA ATAAcggAAT AATATTAgAg AAATAAAcAA    2220

TAATcTAAgA cATTAgcgcA TAAAgATgTg AcAAAATgAT TgAgTcTggT cATATTAccc    2280

TccTTcATcc TTTATTgcAT AAAAgATTgT AgTTTAcAcc TTcggcTTTA cAAggAgAg     2340 cTcgAAggTA ATATTAcAgc TTcgAAggcg gAgTgATTTg ATTcTcccTT gTTcAAAAAg    2400
cgAgATcTcT TcATATcATT gTgccTcTAT TTATAgTAAc cAAgTAcAAT TcATATgAA     2460

ATTAcAAAcA TgcTcATggA cATgATAATT ccAgTgcAcA TccAAcccTg cTTgATAcAA    2520

AAcATgcTcA TAATcATgAT gATTcAAgTg cAcATccAcc cTgcTcgATA cAAcAgTTgg    2580
cgAccTggTg TgAgAgTcAg AccAgAcggg cTTTcAcAAT cgccATgcAT gTcATTcTcT    2640
cgTggTccAc gTgTTTATTA ATATTgccAT TAATTggAgg gAAATAAAAT cAAcAAgAAT    2700

AgcTTATTgA TgAgTcATAT ATTATgAATA cATcTTATcA TcTTAccAAA cAAAAAcATA    2760

TgAccgTcgA TgAccTgAAA cTAgAcTATT cgggATcTgc AATgATcTgc TTgTAAATAT    2820

TAATTTgcAc ATcAcgccAT TgcATgcAcA TcggcgTggg cATTATTAAT TTggATTggA    2880
cgAAAAATcA AccAgAgggc gTcAcccTTT TgcTAgTTgg ccTTgTAATA cTTATAATAA    2940

TTATccgTAT AgTcTAgTAc AAcTTTcTTA ATATTTTccT TAATTAccTc cATAcATcT     3000

TAAATgTcTA gTggTAgcAT ATATAcccTc AAAgTccAAA gcTAgTTgTA AgTgAcAcAA    3060

AAAATTATgc gTAcTcATTg AAcATATcTg TTAcAcTcAc TAAcTAgAcA TgTTTAgTgc    3120

ATcTAcgTTA gcTAgTTgcA gAccccAATc cTATATTgTT cATAAATTTT TATcATAAgg    3180

TTcccTgcTg cAATTTAgAT ATccAgcATg cTcTTcAATT TTggTgcTcA cccTTAcggg    3240

TATgcccTcA cTgccTTTTA TAATTgTATA AgggAAATAT TATTcAATAT AATgTccTAA    3300

AAATTggcAA TATcAATcTA AAAATcgTTA TgAATAggAT gTAAAcAAAg cTAcTATcTg    3360

TccATATATA AcgTcAcAgg AAggAcAAAA AATTcAgTcA gcgATcgAgA AcggcAAAgA    3420

AAAAccATAT TATTgTTgcT TgccgAcATA AATTTAAgTA TAggAcAAAA AAAAAAgccA    3480
cATcATATTA cATAcTATgg gcTTAccAgA cAAAATgAAA TAAAcgTgTg cATgcATgcA    3540

TgcATggTAc gAAcgTcTgg ATAgAgTcTc cgAgcTgAgT gTggTccgAc gTggAAgTgT    3600

AcgTcTcAAc AcAcgAcgcA TgTgAccgAc AAgggcAAgT TgAAgTcTAT gcATggATgg    3660
gccTgAgcgc cgcgcTgAAT gAATcTggAc gggTggTAgg gcATcTcggT gggcAAAAcA    3720

AATAAcTccg TgTgcTgcAT ggcTgccTTT ggAATcTTTg cATgcAgcTg TgTgcTgAAc    3780

TgAAAcccTT cgcTcTATcT ATATAAAcAg ATgcccTTcg cTcTcgTcTc AgcAggcAgc    3840

ATcgTcTcAA gTTTTgTTcT ccTcTccTAg cTAgccAgcA ccTgcAgATc TgcTcgTTgc    3900
cTTggTAATT cATcATgTAg TAcgTAgcAT cAgcTAgTAT TTATcTcAAg TATATATATA    3960
cgcATATgTg TcgTcgcAgT AcTTTcccTT ATcTcTcTAT AcAcAcTAcA cgcATAcATA    4020
ccAATAccAT ccgTcTTAAc TcTTAATcTT TgccTgcATA cgTAcAcTgc AcgTAcgTAc    4080

TgcAgggcTA cTgATTTTgT ggAAcgAAgc gg                                  4112
```

<210> SEQ ID NO 12
<211> LENGTH: 5676
<212> TYPE: DNA
<213> ORGANISM: Artificial Sequence

```
<220> FEATURE:
<223> OTHER INFORMATION: synthetic
<220> FEATURE:
<221> NAME/KEY: misc_feature
<223> OTHER INFORMATION: 3X RCC3-PCOa(TR2)

<400> SEQUENCE: 12
ttttaagtat gaccaattt  taagtataaa ccccctcacga ttggttattt ttttaagtat      60
aaccaatttt taagtataaa ccccctcacca atttttaagt ataaacctag cgactaataa     120
acacaacttc ttgccaaagt gtgagcatca ccattggatc tgcgcccctc acgaacagtc     180
ttcgccgggg taaaattctc caaattaaag tcatcttgat gtccttgatc acctgtccat     240
aaggcccaat cccagctcca cgtatacttc tgataagatt gacatagtca cttgcatgcc     300
agtgtggaac tctggatgcc taggtcagag gctagtgact ggccttcccg gcatgctagc     360
atgtagcatg ccaaggatct ggctgctcca ggtttgttat gcctgacatc accataggga     420
tgagagcaag tataataata ggctgtaagc tttaaatgct caggtggaga aaaaaggag      480
aggagaggag agagaaaagt gggctataag cttatagctg tgttagacat aagaatcaga     540
aacttcgtat gagagacagg tgagctatat attaataaca aagagctaac tattatatga     600
gtgaaccgag agaaggctgt aaaaaaactt acacaatcaa cgatcgacat tattattaac     660
cttgctctgt cttgcgagac ctctttgaca aagctacatc aatgccggcc aagtgccttg     720
ggatttggga atggcttctt tcctcccttc ctcggttgtc ccccaaggcc taggcttgcc     780
acgctgtatt cagtcgcagc cgcctttact tttgcccttt gtggaagttt tgtaataaat     840
ggtctgattc tatcttcgga tagatgaagc cggatgtttc atccattatc taaaaaaag    900
ttggttgctt tgctgagcta agaaagtgta atccagagtg cccgtaacgt attcatgtac     960
ataactatta tctaatataa atcttctttt gtcgcaaaaa aaggtcggcc catcagaaca    1020
aatgatcaat gtaaggccca aaatttgtgt ctcaaatgtc atttacgttt ccaagctaaa    1080
caaaaacaca ggattcatat aatttgctg gtggcttagg cttcgtccaa tagtgcttag    1140
tttaatttgt atatacctgc accatggtat tcgtctggcc ttggatcttg cgcatcaatt    1200
gcctatggac gatgatcgca gccacgccac attcattttt aatcgccatt tgcttgacac    1260
ccaatgcctc tgcaccactt gcgcacgcta cgcaccgtct gatacgccaa gatcccgagc    1320
taaaataaca cccaatcatc agatgaaaac aagcgcgagt gcgagccagc ccatggcagc    1380
gatcttggcc atttgcggag ccaactgaaa gccgtgcaca aaatattcga caccgtataa    1440
gggaaaacac tagttatacg aggtgggcaa taatccagat ctcggactct tcctaacccg    1500
gttcacatgc atagcatata tgatggccgg ccggggttca catgaacgcc atcccgtgcc    1560
ctagtgcact gatttcttaa tttcgaattt taagtatgac caatttttaa gtataaaccc    1620
ctcacgattg gttattttt  taagtataac caatttttaa gtataaaccc ctcaccaatt    1680
tttaagtata aacctagcga ctaataaaca caacttcttg ccaaagtgtg agcatcacca    1740
ttggatctgc gcccctcacg aacagtcttc gccggggtaa aattctccaa attaaagtca    1800
tcttgatgtc cttgatcacc tgtccataag gcccaatccc agctccacgt atacttctga    1860
taagattgac atagtcactt gcatgccagt gtggaactct ggatgcctag gtcagaggct    1920
agtgactggc cttcccggca tgctagcatg tagcatgcca aggatctggc tgctccaggt    1980
ttgttatgcc tgacatcacc atagggatga gagcaagtat aataataggc tgtaagcttt    2040
aaatgctcag gtggagaaaa aaggagagg agaggagaga gaaagtggg ctataagctt    2100
atagctgtgt tagacataag aatcagaaac ttcgtatgag agacaggtga gctatatatt    2160
```

```
aataacaaag agctaactat tatatgagtg aaccgagaga aggctgtaaa aaaacttaca    2220
caatcaacga tcgacattat tattaacctt gctctgtctt gcgagacctc tttgacaaag    2280
ctacatcaat gccggccaag tgccttggga tttgggaatg gcttcttttcc tcccttcctc    2340 ggttgtcccc caaggcctag gcttgccacg ctgtattcag tcgcagccgc ctttactttt    2400 gcccttttgtg gaagttttgt aataaatggt ctgattctat cttcggatag atgaagccgg    2460
atgtttcatc cattatctaa aaaaaagttg gttgctttgc tgagctaaga aagtgtaatc    2520
cagagtgccc gtaacgtatt catgtacata actattatct aatataaatc ttcttttgtc    2580
gcaaaaaaag gtcggcccat cagaacaaat gatcaatgta aggcccaaaa tttgtgtctc    2640
aaatgtcatt tacgtttcca agctaaacaa aaacacagga ttcatataat tttgctggtg    2700
gcttaggctt cgtccaatag tgcttagttt aatttgtata tacctgcacc atggtattcg    2760
tctggccttg gatcttgcgc atcaattgcc tatggacgat gatcgcagcc acgccacatt    2820
catttttaat cgccatttgc ttgacaccca atgcctctgc accacttgcg cacgctacgc    2880
accgtctgat acgccaagat cccgagctaa aataacaccc aatcatcaga tgaaaacaag    2940
cgcgagtgcg agccagccca tggcagcgat cttggccatt tgcggagcca actgaaagcc    3000
gtgcacaaaa tattcgacac cgtataaggg aaaacactag ttatacgagg tgggcaataa    3060
tccagatctc ggactcttcc taacccggtt cacatgcata gcatatatga tggccggccg    3120
gggttcacat gaacgccatc ccgtgcccta gtgcactgat ttcttaatgt cgacgggccg    3180
cttttaagta tgaccaattt ttaagtataa accccctcacg attggttatt tttttaagta    3240
taaccaattt ttaagtataa acccctcacc aatttttaag tataaaccta gcgactaata    3300
aacacaactt cttgccaaag tgtgagcatc accattggag ctgcgcccct cacgaacagt    3360
cttcgccggg gtaaaattct ccaaattaaa gtcatcttga tgtccttgat cacctgtcca    3420
taaggcccaa tcccagctcc acgtatactt ctgataagat tgacatagtc acttgcatgc    3480
cagtgtggaa ctctggatgc ctaggtcaga ggctagtgac tggccttccc ggcatgctag    3540
catgtagcat gccaaggatc tggctgctcc aggtttgtta tgcctgacat caccataggg    3600
atgagagcaa gtataataat aggctgtaag ctttaaatgc tcaggtggag aaaaaaagga    3660
gaggagagga gagagaaaag tgggctataa gcttatagct gtgttagaca taagaatcag    3720
aaacttcgta tgagagacag gtgagctata tattaataac aaagagctaa ctattatatg    3780
agtgaaccga gagaaggctg taaaaaaact tacacaatca acgatcgaca ttattattaa    3840
ccttgctctg tcttgcgaga cctctttgac aaagctacat caatgccggc caagtgcctt    3900
gggatttggg aatggcttct ttcctcccctt cctcggttgt ccccaaggc ctaggcttgc    3960 cacgctgtat tcagtcgcag ccgcctttac ttttgccctt tgtggaagtt ttgtaataaa    4020
tggtctgatt ctatcttcgg atagatgaag ccggatgttt catccattat ctaaaaaaaa    4080
gttggttgct tgctgagct aagaaagtgt aatccagagt gttcgtaacg tattcatgta    4140
cataactatt atctaatata aatcttcttt tgtcgcaaaa aaggtcggc ccatcagaac    4200 aaatgatcaa tgtaaggccc aaaatttgtg tctcaaatgt catttacgtt tccaagctaa    4260
acaaaaacac aggattcata attttgct ggtggcttag gcttcgtcca atagtgctta    4320
gtttaatttg tatatacctg caccatggta ttcgtctggc cttggatctt gcgcatcaat    4380
tgcctatgga cgatgatcgc agccacgcca cattcatttt taatcgccat ttgcttgaca    4440
cccaatgcct ctgcaccact tgcgcacgct acgcaccgtc tgatacgcca agatcccgag    4500
```

```
ctaaaataac acccaatcat cagatgaaaa caagcgcgag tgcgagccag cccatggcag    4560
cgatcttggc catttgcgga gccaactgaa agccgtgcac aaaatattcg acaccgtata    4620
agggaaaaca ctagttatac gaggtgggca ataatccaga tctcggactc ttcctaaccc    4680
ggttcacatg catagcatat atgatggccg gccggggttc acatgaacgc catcccgtgc    4740
cctagtgcac tgatttctta atcccatcca gcatgctctt caattttggt gctcaccctt    4800
acgggtatgc cctcactgcc ttttataatt gtaaaggga aatattattc aatataatgt    4860
cctaaaaatt ggcaatatca atctaaaaat cgttatgaat aggatgtaaa caaagctact    4920
atctgtccat atataacgtc acaggaagga caaaaaattc agtcagcgat cgagaacggc    4980
aaagaaaaac catattattg ttgcttgccg acataaattt aagtatagga caaaaaaaaa    5040
agccacatca tattacatac tatgggctta ccagacaaaa tgaaataaac gtgtgcatgc    5100
atgcatgcat ggtacgaacg tctggataga gtctccgagc tgagtgtggt ccgacgtgga    5160
agtgtacgtc tcaacacacg acgcatgtga ccgacaaggg caagttgaag tctatgcatg    5220
gatgggcctg agcgccgcgc tgaatgaatc tggacgggtg gtagggcatc tcggtgggca    5280
aaacaaataa ctccgtgtgc tgcatggctg cctttggaat ctttgcatgc agctgtgtgc    5340
tgaactgaaa cccttcgctc tatctatata aacagatgcc cttcgctctc gtctcagcag    5400
gcagcatcgt ctcaagtttt gttctcctct cctagctagc cagcacctgc agatctgctc    5460
gttgccttgg taattcatca tgtagtacgt agcatcagct agtatttatc tcaagtatat    5520
atatacgcat atgtgtcgtc gcagtacttt cccttatctc tctatacaca ctacacgcat    5580
acataccaat accatccgtc ttaactctta atctttgcct gcatacgtac actgcacgta    5640
cgtactgcag ggctactgat tttgtggaac gaagcg                             5676
```

<210> SEQ ID NO 13
<211> LENGTH: 2789
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 2

<400> SEQUENCE: 13

```
ctactcgcct tgtggctcct cctgaaccac ctgctcttct cctgtggggg ggtgtgagac      60
agcaagggtg agctcacaca tgatcatagc tcaacaagtt gtggggaacc agtggacatg     120
aactcacaaa ggtgggagtt catgtgatgg ttcctctaga tgctcaactt gttgcattat     180
attacgcaat tgctccgacg cttcatcaat taatcctcct tagtgatatt aaataacgga     240
ataatattag agaaataaac aataatctaa gacattagcg cataaagatg tgacaaaatg     300
attgagtctg gtcatattac cctccttcat cctttattgc ataaaagatt gtagtttaca     360
ccttcggctt tacaaggag agctcgaagg taatattaca gcttcgaagg cggagtgatt     420
tgattctccc ttgttcaaaa agcgagatct cttcatatca ttgtgcctct atttatagta     480
accaagtaca atttcatatg aaattacaaa catgctcatg gacatgataa ttccagtgca     540
catccaaccc tgcttgatac aaaacatgct cataatcatg atgattcaag tgcacatcca     600
ccctgctcga tacaacagtt ggcgacctgg tgtgagagtc agaccagacg ggctttcaca     660
atcgccatgc atgtcattct ctcgtggtcc acgtgtttat taatattgcc attaattgga     720
gggaaataaa atcaacaaga atagcttatt gatgagtcat atattatgaa tacatcttat     780
```

```
catcttacca aacaaaaaca tatgaccgtc gatgacctga aactagacta ttcgggatct    840
gcaatgatct gcttgtaaat attaatttgc acatcacgcc attgcatgca catcggcgtg    900
ggcattatta atttggattg acgaaaaat caaccagagg gcgtcaccct tttgctagtt    960
ggccttgtaa tacctagcat gtagcatgcc aaggatctgg ctgctccagg tttgttatgc   1020
ctgacatcac catagggatg agagcaagta taataatagg ctgtaagctt taaatgctca   1080
ggtggagaaa aaaggagag gagaggagag agaaagtgg gctataagct tatagctgtg    1140
ttagacataa gaatcagaaa cttcgtatga gagacaggtg agctatatat taataacaaa   1200
gagctaacta ttatatgagt gaaccgagag aaggctgtaa aaaaacttac acaatcaacg   1260
atcgacatta ttattaacct tgctctgtct tgcgagacct ctttgacaaa gctacatcaa   1320
tgccggccaa gtgccttggg atttgggaat ggcttctttc ctcccttcct cggttgtccc   1380
ccaaggccta ggcttgccac gctgtattca gtcgcagccg cctttacttt tgcccttgt    1440 ggaagttttg taataaatgg tctgattcta tcttcggata gatgaagccg gatgtttcat   1500
ccattatcta aaaaaaagtt ggttgctttg ctgagctaag aaagtgtaat ccagagtgct   1560
cgtaacgtat taatgtacat aactattatc taatataaat cttctttgt cgcaaaaaaa   1620 ggtcggccca tcagaacaaa tgatcaatgt aaggcccaaa atttgtgtct caaatgtcat   1680 ttacgttcc aagctaaaca aaaacacagg attcatataa ttttgctggt ggcttaggct   1740
tcgtccaata gtgcttagtt taatttgtat ataccgtcac catggtatc gtctggcctt   1800 ggatcttgcg catcaattgc ctatggacga tgatcgcagc cacgccacat tcatttttaa   1860
tcgccatttg cttgacaccc aatgcctctg caccacttgc gcacgctacg caccgtctga   1920
tacgccaaga tcccgagcta aaataacacc caatcatcag atgaaaacaa gcgcgagtgc   1980
gagccagccc atggcagcga tcttggccat ttgcggagcc aactgaaagc cgtgcacaaa   2040
atattcgaca ccgtataagg gaaaacacta gttatacgag gtgggcaata atccagatct   2100
cggactcttc ctaacccggt tcacatgcat agcatatatg atggccggcc ggggttcaca   2160
tgaacgccat cccgtgccct agtgcactga tttcttaatc cccgtgtgca tgcatgcatg   2220
catggtacga acgtctggat agagtctccg agctgagtgt ggtccgacgt ggaagtgtac   2280
gtctcaacac acgacgcatg tgaccgacaa gggcaagttg aagtctatgc atggatgggc   2340
ctgagcgccg cgctgaatga atctggacgg gtggtagggc atctcggtgg gcaaaacaaa   2400
taactccgtg tgctgcatgg ctgcctttgg aatctttgca tgcagctgtg tgctgaactg   2460
aaacccttcg ctctatctat ataaacagat gcccttcgct ctcgtctcag caggcagcat   2520
cgtctcaagt tttgttctcc tctcctagct agccagcacc tgcagatctg ctcgttgcct   2580
tggtaattca tcatgtagta cgtagcatca gctagtattt atctcaagta tatatacg   2640 catatgtgtc gtcgcagtac tttcccttat ctctctatac acactacacg catacatacc   2700
aataccatcc gtcttaactc ttaatctttg cctgcatacg tacactgcac gtacgtactg   2760
cagggctact gattttgtgg aacgaagcg                                      2789
```

<210> SEQ ID NO 14
<211> LENGTH: 3137
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 13

```
<400> SEQUENCE: 14
ttttaagtat gaccaatttt taagtataaa cccctcacga ttggttattt ttttaagtat      60
aaccaatttt taagtataaa cccctcacca atttttaagt ataaacctag cgactaataa     120
acacaacttc ttgccaaagt gtgagcatca ccattggatc tgcgcccctc acgaacagtc     180
ttcgccgggg taaaattctc caaattaaag tcatcttgat gtccttgatc acctgtccat     240
aaggcccaat cccagctcca cgtatacttc tgataagatt gacatagtca cttgcatgcc     300
agtgtggaac tctggatgcc taggtcagag gctagtgact ggccttcccg gcatgctagc     360
atgtagcatg ccaaggatct ggctgctcca ggtttgttat gcctgacatc accataggga     420
tgagagcaag tataataata ggctgtaagc tttaaatgct caggtggaga aaaaaggag      480
aggagaggag agagaaaagt gggctataag cttatagctg tgttagacat aagaatcaga     540
aacttcgtat gagagacagg tgagctatat attaataaca aagagctaac tattatatga     600
gtgaaccgag agaaggctgt aaaaaaactt acacaatcaa cgatcgacat tattattaac     660
cttgctctgt cttgcgagac ctctttgaca aagctacatc aatgccggcc aagtgccttg     720
ggatttggga atggcttctt tcctcccttc ctcggttgtc ccccaaggcc taggcttgcc     780
acgctgtatt cagtcgcagc cgcctttact tttgcccttt gtggaagttt tgtaataaat     840
ggtctgattc tatcttcgga tagatgaagc cggatgtttc atccattatc taaaaaaag     900
ttggttgctt tgctgagcta agaaagtgta atccagagtg cccgtaacgt attcatgtac     960
ataactatta tctaatataa atcttctttt gtcgcaaaaa aaggtcggcc catcagaaca    1020
aatgatcaat gtaaggccca aaatttgtgt ctcaaatgtc atttacgttt ccaagctaaa    1080
caaaaacaca ggattcatat aattttgctg gtggcttagg cttcgtccaa tagtgcttag    1140
tttaatttgt atatacctgc accatggtat tcgtctggcc ttggatcttg cgcatcaatt    1200
gcctatggac gatgatcgca gccacgccac attcattttt aatcgccatt gcttgacac     1260
ccaatgcctc tgcaccactt gcgcacgcta cgcaccgtct gatacgccaa gatcccgagc    1320
taaaataaca cccaatcatc agatgaaaac aagcgcgagt gcgagccagc ccatggcagc    1380
gatcttggcc atttgcggag ccaactgaaa gccgtgcaca aaatattcga caccgtataa    1440
gggaaaacac tagttatacg aggtgggcaa taatccagat ctcggactct tcctaacccg    1500
gttcacatgc atagcatata tgatggccgg ccggggttca catgaacgcc atcccgtgcc    1560
ctagtgcact gatttcttaa tatttcagac ctgcattcca tgagaaacga acggggcttt    1620
agcgggccac gtgacagtga cgaagggtcg cagtcgctgc tggacggact acagacagag    1680
aggcgaagca tgcaattgaa ttttcgctag cggaaagtta tcatctaatc tccaacccte    1740
cttcctacgg ctggatctga aaattgacga cctgaacccc tgaacggtgc cggtagcaat    1800
tgcaggtctc actcacatgc taaatccagc aaccaaacac gaaggaatat atgtgatctg    1860
gacagaacat gcaagcgaat aatacataga gtcgtaccaa ccctacacag ttcaacgaat    1920
taatcactgg gttcacgggc atgctcacgt ccaaaatccc agcgacattt tataagcgct    1980
aagcggaatg atccagacgg ggccagctcg agcaccacat gggcactaca ttactgcggc    2040
gcttgctcaa acttcatgca ccaataattg aaacacggtc aattgtatgc attactagtg    2100
taattaagtg catgtaacga atgaactacc ttaggatttt aggagaatcg aagaatatct    2160
ccatccattt accaaatcaa acttattaag aagaaaatat tatgtacttc ctacgtccaa    2220
aaaagatgtc tcaagtttgt caaattttgg atgtatctag acatgactta atgtatagat    2280
gcattcaaat tttgacaaac ttaagacatc ctttttttgga cggagggagt acaagatttg    2340
```

```
ttaataagtt acattaaaaa actacacagt actgtctact cgttttttt tctaaagaaa      2400
atcacggatc tattaataat caccaacatg agccttactt aattaagtac ttagagacga      2460
cgtcgagcgt ttggagagtc tttgtacaat gtcaaaggta cctataatcc ggccggccgg      2520
gtgatttgaa tcgcgcgcct agctagatcg atccatgcat gcgatccaca gctagcttga      2580
tgcttgcgcc agtgtgtgat cgatcatgag ctcatgaccc catgacatcg agcgagttag      2640
ctagagaagc catgcacgca cgttctttca cgtggaagag ttataaaaag ctagcgtaat      2700
acgtttatat atgtcaggag atgggaatct ctagctaatt aggcttcgag agaaaccaag      2760
caacagctag taattaactt cagatccttc cgcactcgat aatcaagtct tgatctgcat      2820
agcccagtga agtgccaata aatctaagat gtgaagagat gtgcaacagt gcaagagaaa      2880
atttaatgct gtctagttgc ttgatcgatg cagtcaatac tagtactgtc acctgatta      2940
gaaaaattat cactcatcga atcacccact tgataattca cagcccgaag tcgtcccgaa      3000
gcgcgcggtc gcctccttga gatatccaac cccatgcatc tcatctacca ctataaatac      3060
tcaggccacc ctctctgcta agcaccccac cacctcatct cacacgtact ctagctacaa      3120
attaagctac gtcggca                                                    3137
```

```
<210> SEQ ID NO 15
<211> LENGTH: 2337
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 17

<400> SEQUENCE: 15
```

```
ttagttgcag acggttttc ccctgctagg agatttccga gagaaaaaaa aggcactaca        60
ggttaaccaa aaccaccaac ctttggagcg tcgaggtcga cgggcatttg cgtagttgaa       120
gcttacaaag ttgcatatga gatgagtgcc ggacatgaag cggataacgt tttaaactgg       180
caacaatatc tagctgtttc aaattcaggc gtgggaagct acgcctacgc gccctggacg       240
gcgtgtaaag agccagcatc ggcatcattg tcaaacgatc gacaaggcca agaaattcca       300
aatatattat taataaaaaa gaaggcacaa attagtttgg ttttttagta tgtgtggcgg       360
aggaaatttt gagaacgaac gtatcaaaga aggcacaaga cgatatagat tgacgcggct       420
agaagttgca gcaagacagt gggtacggtc ttatatatcc taataaataa aaataaaaac       480
tatagtgtgt caaatgtcaa caagaggagg aggcagccaa attagcagag ggagacaagt       540
agagcacgcc ttattagctt gcttatttat cgtggtggtg tacttgttaa ttactggcac       600
gcattatcaa caacgcagtt ctggatgtga atctagacaa acatttgtct aggttccgca       660
cgtatagttt ttttcctctt ttttttgggg ggggggtggg ggggggaacg gaagctgtaa       720
taaacggtac taggaacgaa agcaaccgcc gcgcgcatgt ttttgcaata gattacggtg       780
aatttcagac ctgcattcca tgagaaacga acggggcttt agcgggccac gtgacagtga       840
cgaagggtcg cagtcgctgc tggacggact acagacagag aggcgaagca tgcaattgaa       900
ttttcgctag cggaaagtta tcatctaatc tccaaccctc cttcctacgg ctggatctga       960
aaattgacga cctgaacccc tgaacggtgc cggtagcaat tgcaggtctc actcacatgc      1020
taaatccagc aaccaaacac gaaggaatat atgtgatctg acagaacat gcaagcgaat       1080
aatacataga gtcgtaccaa ccctacacag ttcaacgaat taatcactgg gttcacgggc      1140
```

```
atgctcacgt ccaaaatccc agcgacattt tataagcgct aagcggaatg atccagacgg    1200
ggccagctcg agcaccacat gggcactaca ttactgcggc gcttgctcaa acttcatgca    1260
ccaataattg aaacacggtc aattgtatgc attactagtg taattaagtg catgtaacga    1320
atgaactacc ttaggatttt aggagaatcg aagaatatct ccatccattt accaaatcaa    1380
acttattaag aagaaaatat tatgtacttc ctacgtccaa aaagatgtc tcaagtttgt     1440 caaattttgg atgtatctag acatgactta atgtatagat gcattcaaat tttgacaaac    1500
ttaagacatc cttttttgga cggagggagt acaagatttg ttaataagtt acattaaaaa    1560
actacacagt actgtctact cgtttttttt tctaaagaaa atcacggatc tattaataat    1620
caccaacatg agccttactt aattaagtac ttagagacga cgtcgagcgt ttggagagtc    1680
tttgtacaat gtcaaaggta cctataatcc ggccggccgg gtgatttgaa tcgcgcgcct    1740
agctagatcg atccatgcat gcgatccaca gctagcttga tgcttgcgcc agtgtgtgat    1800
cgatcatgag ctcatgaccc catgacatcg agcgagttag ctagagaagc catgcacgca    1860
cgttctttca cgtggaagag ttataaaaag ctagcgtaat acgtttatat atgtcaggag    1920
atgggaatct ctagctaatt aggcttcgag agaaaccaag caacagctag taattaactt    1980
cagatccttc cgcactcgat aatcaagtct tgatctgcat agcccagtga agtgccaata    2040
aatctaagat gtgaagagat gtgcaacagt gcaagagaaa atttaatgct gtctagttgc    2100
ttgatcgatg cagtcaatac tagtactgtc accctgatta gaaaaattat cactcatcga    2160
atcacccact tgataattca cagcccgaag tcgtcccgaa gcgcgcggtc gcctccttga    2220
gatatccaac cccatgcatc tcatctacca ctataaatac tcaggccacc ctctctgcta    2280
agcaccccac cacctcatct cacacgtact ctagctacaa attaagctac gtcggca      2337
```

<210> SEQ ID NO 16  
<211> LENGTH: 2984  
<212> TYPE: DNA  
<213> ORGANISM: Artificial Sequence  
<220> FEATURE:  
<223> OTHER INFORMATION: Synthetic  
<220> FEATURE:  
<221> NAME/KEY: misc_feature  
<223> OTHER INFORMATION: Root Hybrid 14

<400> SEQUENCE: 16

```
ttttaagtat gaccaatttt taagtataaa cccctcacga ttggttattt ttttaagtat      60
aaccaatttt taagtataaa cccctcacca attttttaagt ataaacctag cgactaataa    120
acacaacttc ttgccaaagt gtgagcatca ccattggatc tgcgcccctc acgaacagtc    180
ttcgccgggg taaattctc caaattaaag tcatcttgat gtccttgatc acctgtccat     240
aaggcccaat cccagctcca cgtatacttc tgataagatt gacatagtca cttgcatgcc    300
agtgtggaac tctggatgcc taggtcagag gctagtgact ggccttcccg gcatgctagc    360
atgtagcatg ccaaggatct ggctgctcca ggtttgttat gcctgacatc accataggga    420
tgagagcaag tataataata ggctgtaagc tttaaatgct caggtggaga aaaaaaggag    480
aggagaggga agagaaaagt gggctataag cttatagctg tgttagacat aagaatcaga    540
aacttcgtat gagagacagg tgagctatat attaataaca aagagctaac tattatatga    600
gtgaaccgag agaaggctgt aaaaaaactt acacaatcaa cgatcgacat tattattaac    660
cttgctctgt cttgcgagac ctctttgaca aagctcatc aatgccggcc aagtgccttg     720
ggatttggga atggcttctt tcctccctttc ctcggttgtc ccccaaggcc taggcttgcc    780
```

```
acgctgtatt cagtcgcagc cgcctttact tttgcccttt gtggaagttt tgtaataaat      840
ggtctgattc tatcttcgga tagatgaagc cggatgtttc atccattatc taaaaaaaag      900
ttggttgctt tgctgagcta agaaagtgta atccagagtg cccgtaacgt attcatgtac      960
ataactatta tctaatataa atcttctttt gtcgcaaaaa aaggtcggcc catcagaaca     1020
aatgatcaat gtaaggccca aaatttgtgt ctcaaatgtc atttacgttt ccaagctaaa     1080 caaaacaca  ggattcatat aatttgctg  gtggcttagg cttcgtccaa tagtgcttag     1140
tttaatttgt atatacctgc accatggtat tcgtctggcc ttggatcttg cgcatcaatt     1200
gcctatggac gatgatcgca gccacgccac attcattttt aatcgccatt tgcttgacac     1260
ccaatgcctc tgcaccactt gcgcacgcta cgcaccgtct gatacgccaa gatcccgagc     1320
taaaataaca cccaatcatc agatgaaaac aagcgcgagt gcgagccagc ccatggcagc     1380
gatcttggcc atttgcggag ccaactgaaa gccgtgcaca aaatattcga caccgtataa     1440
gggaaaacac tagttatacg aggtgggcaa taatccagat ctcggactct tcctaacccg     1500
gttcacatgc atagcatata tgatggccgg ccggggttca catgaacgcc atcccgtgcc     1560
ctagtgcact gatttcttaa tatttcagac ctgcattcca tgagaaacga acggggcttt     1620
agcgggccac gtgacagtga cgaagggtcg cagtcgctgc tggacggact acagacagag     1680
aggcgaagca tgcaattgaa ttttcgctag cggaaagtta tcatctaatc tccacccctc     1740
cttcctacgg ctggatctga aaattgacga cctgaacccc tgaacggtgc cggtagcaat     1800
tgcaggtctc actcacatgc taaatccagc aaccaaacac gaaggaatat atgtgatctg     1860
gacagaacat gcaagcgaat aatacataga gtcgtaccaa ccctacacag ttcaacgaat     1920
taatcactgg gttcacgggc atgctcacgt ccaaaatccc agcgacattt tataagcgct     1980
aagcggaatg atccagacgg ggccagctcg agcaccacat ggtttgactt ggaccgacta     2040
gcactccccc gctaggcacg tagtacgtgg tatgtgtgga aacgattggt tcgttgtagg     2100
gagtcagtca gatcagatat gatgcttctc gtgtgttgat tttcttcctc tgaactgaaa     2160
ggaagcatgc aagttttaca agctaaactc agcagcggaa gctatgcata cgttccactg     2220
gctgcagaac agggcaggcc ggcggctagc tcctgtgagc tgtgttggag gagaataata     2280
tcttgtcgtt tggctttgct cgggtggata cttttttttc ttttgacagc tgctcgggtg     2340
gatactgata cactatgaag accgaaaaaa agaagcgaag catataaaca gacggatcat     2400
tgggggccaa gccagcaggt agtgcggtgg aacattatgt agaatgaatc ggttcttgct     2460
gtgcagacag ctcagctcag cacactcctg gcccaaaaca aagtgcatgt ggtgtatttt     2520
cgtatactag ctaacaaatg cttaagcccc tgtttgaaat attgtatttt cggcggacgg     2580
gcactggctt actgaaatct tgccaggagg cacggacagg tgcttagcag ccaagtaatg     2640
tacagtaaat ccggcaaatt gccaggggag tggttcgatt caatcaacga atgcgattcc     2700
cgatataaat tatccccagt ttattttttga ttttatacaa cgcgtcgccg acgcggtccc     2760
caccccgtgc gcgtcgcaag gtccacacgt gtcctctctc cgacgcttcc tagctcacgc     2820
cgtccttgat tgacctgcct cgccatctat aaatggcaaa ccaggctaag gctcatttct     2880
atactccctc ttcctgctct gctctctgct ctagtttact ccactgaccc aaagagagaa     2940
aagaaagcac tcagaacttg agatcagcat ccaggagatc ggcc                     2984
```

<210> SEQ ID NO 17
<211> LENGTH: 3982
<212> TYPE: DNA

<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 4

<400> SEQUENCE: 17

| | | | | | |
|---|---|---|---|---|---|
| tacgcagttg | tcctttggta | cattcacaag | tttgatctta | tcatcaccat | cagaagttca | 60 |
| gaaagtctcg | tagaaaacaa | atggaaatga | atactgctta | cttagctcaa | attcatattc | 120 |
| cgttgttaca | ggatacttaa | aaaaggtacc | aaaggctgtt | cctaatcata | cgctgaagtc | 180 |
| gttgccacca | atggcagctg | tactgtcata | ttgtcgtggt | ttttcaattg | ctgtacctga | 240 |
| tgcaaacgta | atgggtttac | taatcttgca | cccgccgact | tcaaaatgaa | gagtgctaat | 300 |
| ttggttcacg | tcaccatcac | cggttcgaac | tgtctagaat | ggcaggcaaa | gatgattgga | 360 |
| caggcatgca | gggaaaaaga | gcaccgatga | cgatctatgc | gagttcccac | cattgcgagc | 420 |
| aatgattatc | agccacacga | cttactcttc | agagctaacc | actgccatgc | agagaaaaag | 480 |
| tgaagcatat | tgtcaggatc | tacaacgaag | tgaaacaatc | aggcatgcta | aagtgctgaa | 540 |
| actttactga | tctctcatgt | tggacaacaa | agaatacggg | aatacatcag | caacgcaact | 600 |
| cttgagcttt | gcttgctgaa | tgaccagcta | gaatttccaa | gcatttacag | gaacatgact | 660 |
| ttaagtttca | gaaaaacaaa | tacaaggcca | ctaagggcat | gttcacttca | gcttataagc | 720 |
| cggctgaaaa | gctgaaacgg | ctgatttgtt | gtgagaggaa | aacactgttt | ggtggctgat | 780 |
| aagccggctg | aataagctga | gcgaacagg | ctgtaaataa | gcgtggggat | aacatatcct | 840 |
| ccagatgaca | ggcaatctgc | aacttgcagc | gattcaaatg | tacgattaac | aaaatattta | 900 |
| agcgctacat | gagataatat | atcctccaat | tagggccttt | agtattgtca | ttagctcata | 960 |
| agcatggtgc | atcctcacat | ggacgctgca | taagaagttc | ataatagcaa | cagacatatg | 1020 |
| aacaaagcat | ggtgcgcctg | cccggccgga | ctagctagta | ctaccaatca | tggaataagc | 1080 |
| tagtacccta | aatgaaatta | aaatggtttt | tagcgattat | ccacgccgtc | cagaatactc | 1140 |
| taatccacaa | gttgaggccg | cccatgaagc | cgcaaactca | gtttatcacc | aaagaccaaa | 1200 |
| catgtggaaa | tcagtctcta | ttttgtccaa | gagcatgtgg | cccttggagc | tttgcggctt | 1260 |
| cttcatgttg | ctacatctct | tcaatatgcc | gatatattta | ctaaggggttg | tcaattgtta | 1320 |
| tcttcatcaa | cttctgatct | aatctcaatg | tttgctcctc | ttccggttga | gactactggg | 1380 |
| ggatattaga | atatgaatag | ccaaaaagtc | ttgtatagtc | taaaataaag | agtctcaaat | 1440 |
| agttcacttg | agcttaggaa | ccgaatttgt | cgtcagcagt | gttttttgct | catagtaaat | 1500 |
| tagccaacaa | tactttctat | cacaccttaa | cagagtactt | tctttctgcc | atggcttatc | 1560 |
| aaccaacagt | attttttgtc | aaaagcagtg | attatctgtc | aatcactagc | gcccctctg | 1620 |
| ccggtatatc | tagcgctccc | atcggatctg | actagagcag | atcttgagcg | tgggttggtg | 1680 |
| gctcagggct | tgcaggaggc | gttggccgtc | gccggcgtag | agcagtagtc | gtaggcggat | 1740 |
| ctgcatcttc | aagctctcct | ccggtcgatt | cgtgtgagtc | ttcgacctct | gctcaggtcg | 1800 |
| attcatgccg | gcgaggggct | cagtgctcgg | ctcacgacgc | gaaattacga | gcggcagcag | 1860 |
| caaaccgggc | tttcaagccc | ggctctcctc | gtgagctgcc | ttagggctcg | ttcgtttaac | 1920 |
| tattgttccc | gatggattca | ttcctgatga | taaaaatagt | ataaatttac | acaatgttcc | 1980 |
| tggctggaat | catttcagac | ctgcattcca | tgagaaacga | acggggcttt | agcgggccac | 2040 |
| gtgacagtga | cgaagggtcg | cagtcgctgc | tggacggact | acagacagag | aggcgaagca | 2100 |

| | |
|---|---|
| tgcaattgaa ttttcgctag cggaaagtta tcatctaatc tccaaccctc cttcctacgg | 2160 |
| ctggatctga aaattgacga cctgaacccc tgaacggtgc cggtagcaat tgcaggtctc | 2220 |
| actcacatgc taaatccagc aaccaaacac gaaggaatat atgtgatctg acagaacat | 2280 |
| gcaagcgaat aatacataga gtcgtaccaa ccctacacag ttcaacgaat taatcactgg | 2340 |
| gttcacgggc atgctcacgt ccaaaatccc agcgacattt tataagcgct aagcggaatg | 2400 |
| atccagacgg ggccagctcg agcaccacat gagtcgtaga ggccaattga tgatgtgcct | 2460 |
| aatagataca tatggtaagg ataataatca tttcttacta cattattcat acaaaaaata | 2520 |
| attaagaatc aaaaattatg agaaacacct cttggtgtgg tgtagttgtg ggtgcatcac | 2580 |
| tccacccatt agggtccaaa tcttggtgct cacattatgc cggggtctcc cttacattct | 2640 |
| tcctatcaat ttttttgta aatctacagt agatgtctat aatgaaaatt ttcaaatatc | 2700 |
| taaaatagca acgaaaatct catatgttac ctgtagaagc tcaacacttt tgtattgcac | 2760 |
| acaatgttaa taaataaaa ctcttgctaa aacttgtaat gactacctaa taacaacata | 2820 |
| ttgtgttgta tatgaattta agcccatcta aatattcgga atattcgctt atcattcaaa | 2880 |
| agatttagat caacaaaaag aagtgaagaa ctttatattt tggtaggtaa aatgtataac | 2940 |
| aaaacaaatc tttcagaaaa tcacttgata tttccaaaca caatacatct aaattgcaat | 3000 |
| aaaaagaat tttagaaaac aaaaacataa aaatatgggt gttgctgttt gaatttcaat | 3060 |
| actacaaaag gacatatatg tgacgtcata ttagtgtcgg gcccagcagg accgccaatg | 3120 |
| atgtatagca tcagtgttgg tcggtgcaaa acccgccact gatatacagc tgcgcgtttc | 3180 |
| ccactttcga cctgatgaac atcagtggcg ggcgttgcac ccgcccgcca ctaatttta | 3240 |
| agtagaggac cttaaatcta agttgacgta tgagaaccat tggattaaga tataatggca | 3300 |
| ctctcttctc ttctacttgc tatcgttgga ttaatatccg acggtcaagc acatcggctc | 3360 |
| atgtctaaca aaaaaaaggc aacttcttaa tagcaaaacc gtaaaaatat atattttatt | 3420 |
| atacaagtct agcccgcgag ctgcttggtt caccctgcta gttaagatag taacttgtag | 3480 |
| ctcttcttgt tgcgtataag ttgttaaaca ttgtaaaagc ctcctcaagt atcatgtata | 3540 |
| cctgtgatac ctcacgacga tttaaacgca caattgctgt ataatggata tagattggtt | 3600 |
| ctaggctcca gcgatcgatt atccatgtaa ctacgtacaa acgagtaaac ctccaaaatc | 3660 |
| acaccgctgt cacacatcgt ctgcacgcag ttgcctgaaa ccaatccact gcacctagcc | 3720 |
| cacgggttga ataaaaccgc ccgcgccggc ctcttcaacg tgcatccacg cagtgtgtca | 3780 |
| ttcccgtcac ggactctcgt ctcatccggc cccttctctc gagcaacacc caccaatctc | 3840 |
| ctcgtgggtc gtggcggcct ctatataacg ccaagacatc gatcagacat ccatccatcc | 3900 |
| atccacactc acacagtcgc tgtagtagct agcaagcccc taggtgcttg cttgacctac | 3960 |
| tgctctgccc gtgaccagtc gt | 3982 |

<210> SEQ ID NO 18
<211> LENGTH: 3539
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 5

<400> SEQUENCE: 18

| | |
|---|---|
| tacgcagttg tcctttggta cattcacaag tttgatctta tcatcaccat cagaagttca | 60 |

```
gaaagtctcg tagaaaacaa atggaaatga atactgctta cttagctcaa attcatattc    120
cgttgttaca ggatacttaa aaaaggtacc aaaggctgtt cctaatcata cgctgaagtc    180
gttgccacca atggcagctg tactgtcata ttgtcgtggt ttttcaattg ctgtacctga    240
tgcaaacgta atgggtttac taatcttgca cccgccgact tcaaaatgaa gagtgctaat    300
ttggttcacg tcaccatcac cggttcgaac tgtctagaat ggcaggcaaa gatgattgga    360
caggcatgca gggaaaaaga gcaccgatga cgatctatgc gagttcccac cattgcgagc    420
aatgattatc agccacacga cttactcttc agagctaacc actgccatgc agagaaaaag    480
tgaagcatat tgtcaggatc tacaacgaag tgaaacaatc aggcatgcta aagtgctgaa    540
actttactga tctctcatgt tggacaacaa agaatacggg aatacatcag caacgcaact    600
cttgagcttt gcttgctgaa tgaccagcta gaatttccaa gcatttacag gaacatgact    660
ttaagtttca gaaaaacaaa tacaaggcca ctaagggcat gttcacttca gcttataagc    720
cggctgaaaa gctgaaacgg ctgatttgtt gtgagaggaa acactgtttt ggtggctgat    780
aagccggctg aataagctga agcgaacagg ctgtaaataa gcgtggggat aacatatcct    840
ccagatgaca ggcaatctgc aacttgcagc gattcaaatg tacgattaac aaaatattta    900
agcgctacat gagataatat atcctccaat tagggccttt agtattgtca ttagctcata    960
agcatggtgc atcctcacat ggacgctgca taagaagttc ataatagcaa cagacatatg   1020
aacaaagcat ggtgcgcctg cccggccgga ctagctagta ctaccaatca tggaataagc   1080
tagtacccta aatgaaatta aaatggtttt tagcgattat ccacgccgtc cagaatactc   1140
taatccacaa gttgaggccg cccatgaagc cgccttttg gtgtcatcat cttcgtttgt    1200
gcaataatac tgcaactcaa tgaagtcact gcgactcata agagccctgt catcaccttg   1260
caactggcag ttttcaattg gtgtaccagc gcaagatcca tagattaatc ttgtttgcct   1320
cacctacccc aaatggagga tgttcactgc attgatgtca caatccgacc ttcttaaccg   1380
ctctatgtca caactttaac atgaatgata tatcgtttcc tcaaaaacat gaatgatata   1440
tcactacaga actcagtatg cagtagattc ctgaacgcaa gagctgttgc aatgttaatc   1500
tactaggtga tatcttactc ggtaagatac tcaggccgag gtccgaggaa ttacccttttt   1560 gttgcaggag aaccaagtca tatgaatgaa gcagcagctc agtaatgatc caccgactac   1620
gctacttcta gcatagaatt agtaatcttt tctaatactg ttgtaaattt gtaacaacaa   1680
aacaagaacc acgccacgga agaacggtga gaaaaagaaa cctttgctaa cgtactattc   1740
atgaatttga agattttgta tggatgcatc agtagacgat gcagggtaga aataaaggat   1800
cgattcagat aatcaatccg caccgccatt gatttgttta gggatgagat gagaattgag   1860
aattgggata acatatatct gctccaaggt cttgttctcc tcgctgtctt atggtgtatc   1920
ctaacgtggc tcggcctaaa caaccacaat tccacagcag tttagcgagt tagggcggtt   1980
ggtcggccag tcgtagaggc caattgatga tgtgcctaat agatacatat ggtaaggata   2040
ataatcattt cttactacat tattcataca aaaataatt aagaatcaaa aattatgaga   2100
aacacctctt ggtgtggtgt agttgtgggt gcatcactcc acccattagg gtccaaatct   2160
tggtgctcac attatgccgg ggtctcccctt acattcttcc tatcaattttt ttttgtaaat   2220 ctacagtaga tgtctataat gaaaattttc aaatatctaa aatagcaacg aaaatctcat   2280
atgttacctg tagaagctca acacttttgt attgcacaca atgttaataa aataaaactc   2340
ttgctaaaac ttgtaatgac tacctaataa caacatattg tgttgtatat gaatttaagc   2400
ccatctaaat attcggaata ttcgcttatc attcaaaaga tttagatcaa caaaaagaag   2460
```

```
tgaagaactt tatattttgg taggtaaaat gtataacaaa acaaatctttt cagaaaatca    2520 cttgatattt ccaaacacaa tacatctaaa ttgcaataaa aagaatttt agaaaacaaa     2580 aacataaaaa tatgggtgtt gctgtttgaa tttcaatact acaaaaggac atatatgtga    2640
cgtcatatta gtgtcgggcc cagcaggacc gccaatgatg tatagcatca gtgttggtcg    2700
gtgcaaaacc cgccactgat atacagctgc gcgtttccca ctttcgacct gatgaacatc    2760
agtggcgggc gttgcacccg cccgccacta atttttaagt agaggacctt aaatctaagt    2820
tgacgtatga gaaccattgg attaagatat aatggcactc tcttctcttc tacttgctat    2880
cgttggatta atatccgacg gtcaagcaca tcggctcatg tctaacaaaa aaaaggcaac    2940
ttcttaatag caaaaccgta aaaatatata ttttattata caagtctagc ccgcgagctg    3000
cttggttcac cctgctagtt aagatagtaa cttgtagctc ttcttgttgc gtataagttg    3060
ttaaacattg taaaagcctc ctcaagtatc atgtatacct gtgatacctc acgacgattt    3120
aaacgcacaa ttgctgtata atggatatag attggttcta ggctccagcg atcgattatc    3180
catgtaacta cgtacaaacg agtaaacctc caaaatcaca ccgctgtcac acatcgtctg    3240
cacgcagttg cctgaaacca atccactgca cctagcccac gggttgaata aaaccgcccg    3300
cgccggcctc ttcaacgtgc atccacgcag tgtgtcattc ccgtcacgga ctctcgtctc    3360
atccggcccc ttctctcgag caacacccac caatctcctc gtgggtcgtg gcggcctcta    3420
tataacgcca agacatcgat cagacatcca tccatccatc cacactcaca cagtcgctgt    3480
agtagctagc aagcccctag gtgcttgctt gacctactgc tctgcccgtg accagtcgt    3539
```

<210> SEQ ID NO 19
<211> LENGTH: 3789
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 1 Pro
<400> SEQUENCE: 19

```
ctactcgcct tgtggctcct cctgaaccac ctgctcttct cctgtggggg ggtgtgagac      60
agcaagggtg agctcacaca tgatcatagc tcaacaagtt gtgggaacc agtggacatg     120 aactcacaaa ggtgggagtt catgtgatgg ttcctctaga tgctcaactt gttgcattat     180
attacgcaat tgctccgacg cttcatcaat taatcctcct tagtgatatt aaataacgga     240
ataatattag agaaataaac aataatctaa gacattagcg cataaagatg tgacaaaatg     300
attgagtctg gtcatattac cctccttcat cctttattgc ataaaagatt gtagtttaca     360
ccttcggctt tacaaaggag agctcgaagg taatattaca gcttcgaagg cggagtgatt     420
tgattctccc ttgttcaaaa agcgagatct cttcatatca ttgtgcctct atttatagta     480
accaagtaca atttcatatg aaattacaaa catgctcatg gacatgataa ttccagtgca     540
catccaaccc tgcttgatac aaaacatgct cataatcatg atgattcaag tgcacatcca     600
ccctgctcga tacaacagtt ggcgacctgg tgtgagagtc agaccagacg ggctttcaca     660
atcgccatgc atgtcattct ctcgtggtcc acgtgtttat taatattgcc attaattgga     720
gggaaataaa atcaacaaga atagcttatt gatgagtcat atattatgaa tacatcttat     780
catcttacca aacaaaaaca tatgaccgtc gatgacctga aactagacta ttcgggatct     840
gcaatgatct gcttgtaaat attaatttgc acatcacgcc attgcatgca catcggcgtg     900
```

```
ggcattatta atttggattg gacgaaaaat caaccagagg gcgtcaccct tttgctagtt    960
ggccttgtaa tacctagcat gtagcatgcc aaggatctgg ctgctccagg tttgttatgc   1020
ctgacatcac cataggatg agagcaagta taataatagg ctgtaagctt taaatgctca    1080
ggtggagaaa aaaggagag gagaggagag agaaaagtgg gctataagct tatagctgtg    1140
ttagacataa gaatcagaaa cttcgtatga gagacaggtg agctatatat taataacaaa   1200
gagctaacta ttatatgagt gaaccgagag aaggctgtaa aaaaacttac acaatcaacg   1260
atcgacatta ttattaacct tgctctgtct tgcgagacct ctttgacaaa gctacatcaa   1320
tgccggccaa gtgccttggg atttgggaat ggcttctttc ctcccttcct cggttgtccc   1380
ccaaggccta ggcttgccac gctgtattca gtcgcagccg cctttacttt tgcccttttgt  1440
ggaagttttg taataaatgg tctgattcta tcttcggata gatgaagccg gatgtttcat   1500
ccattatcta aaaaaagtt ggttgctttg ctgagctaag aaagtgtaat ccagagtgct    1560
cgtaacgtat taatgtacat aactattatc taatataaat cttcttttgt cgcaaaaaaa   1620
ggtcggccca tcagaacaaa tgatcaatgt aaggcccaaa atttgtgtct caaatgtcat   1680
ttacgttttcc aagctaaaca aaaacacagg attcatataa ttttgctggt ggcttaggct  1740
tcgtccaata gtgcttagtt taatttgtat ataccttgcac catggtattc gtctggcctt  1800
ggatcttgcg catcaattgc ctatggacga tgatcgcagc cacgccacat tcatttttaa   1860
tcgccatttg cttgacaccc aatgcctctg caccacttgc gcacgctacg caccgtctga   1920
tacgccaaga tcccgagcta aaataacacc caatcatcag atgaaaacaa gcgcgagtgc   1980
gagccagccc atggcagcga tcttggccat ttgcggagcc aactgaaagc cgtgcacaaa   2040
atattcgaca ccgtataagg gaaaacacta gttatacgag gtgggcaata atccagatct   2100
cggactcttc ctaacccggt tcacatgcat agcatatatg atggccggcc ggggttcaca   2160
tgaacgccat cccgtgccct agtgcactga tttcttaatc ccctaggtca actataatac   2220
tgtactccct ccgtcctcga aagcttcaac tcttagaatc cgtgccagtc aaacttttct   2280
aactttgacc aactttataa gagtaagttt aataatacag cccacttgct ggctgtaagg   2340
tttcttacag ccttcttcca gcccacccat acaatagtta gctattcact attaatacat   2400
ggcccacttg tctctctcac aaagttcctt ggttcctgtc cctaagctgg ctgtaagctt   2460
acagcccgct tctcctctct ctcctctctt ctctcctcca cctcagcatt tagccagctt   2520
acagcccact ataatacttg ctctaaaaaa gagtatcaat atctatgaca taaaataagt   2580
atcttacgaa aatatattct ataataaatt taatggtatt aatttggtac tataaatctt   2640
agcattttt tctataaatt tagtcaaagt tgtaaaagtt tgacttaaga caactctaaa   2700
aattgcagcg ggagtatgta tgatcgatgc tgctctagtt tttccagccc acctctcgtt   2760
gtttgcgact tcgagtttac tgcatctata tctctgaaag aaaatgccta cagggcttgg   2820
ccggtgtcag cttcagggct ctctgtaggc gttgaatccg aggccgccgt agggtggtgg   2880
cagcgcgacc atcgagccgt ggagcaagta cgagtcaaac acgctgagcc gcgtaaccgt   2940
tttaataaaa tgaactctac tcgatcgcta ggtcacagca gcacgatcac agtgaagaat   3000
gcgtgagggg ctcgagcgtt ggcgttgttg ctgtgctttg atcaaactgc accggcgaga   3060
aggaagtaat ataagcaact cgatcataat ccaagcagta aacgcctgat caattgtcga   3120
catctggctg gcactagtat tactagattg tagaatacgc cgcgtgatgt gatttgttat   3180
tttaggtcca aattcatgaa gaattgtgga gtagttgagt agatgagtac agtgacttgc   3240
```

-continued

| | |
|---|---|
| agttgcagca aacgattgat gttcacatga cagggttcag gggtcctgta gtcctgttac | 3300 |
| ttgcagtatt gccgtatcgt gaatctgaag tcgaacagag atagatcgat ggcgtaatgt | 3360 |
| cccaaggagg agagaaataa tatgactgta tcactgtagt gtgtagtcga tgggaatcta | 3420 |
| tagctctcgt tattaggctc ttaattttaa cagaaaccaa agcaactaca agctaattaa | 3480 |
| ttccagagac ttctacagtg ccacatcatt caattggcac cagaattaaa atagtttttc | 3540 |
| aagaaatcgc atctcagaaa aagatgctaa tggtttcttt atcgttgtgg tgaacactag | 3600 |
| tgccatccag attacagaat tctctcctga tcggatctca tcgcacatgg acagccctgc | 3660 |
| aaacccaaca cggaaaccct gaaagatcgc gtccatgcac dacccccac agctataaat | 3720 |
| acccatgcaa cgcagcaggt catcatccac ctcgcctcat tctcactgca tcaccgagct | 3780 |
| cactggcta | 3789 |

<210> SEQ ID NO 20
<211> LENGTH: 4280
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 3 PRO

<400> SEQUENCE: 20

| | |
|---|---|
| ctactcgcct tgtggctcct cctgaaccac ctgctcttct cctgtggggg ggtgtgagac | 60 |
| agcaagggtg agctcacaca tgatcatagc tcaacaagtt gtggggaacc agtggacatg | 120 |
| aactcacaaa ggtgggagtt catgtgatgg ttcctctaga tgctcaactt gttgcattat | 180 |
| attacgcaat tgctccgacg cttcatcaat taatcctcct tagtgatatt aaataacgga | 240 |
| ataatattag agaaataaac aataatctaa gacattagcg cataaagatg tgacaaaatg | 300 |
| attgagtctg gtcatattac cctccttcat cctttattgc ataaaagatt gtagtttaca | 360 |
| ccttcggctt tacaaaggag agctcgaagg taatattaca gcttcgaagg cggagtgatt | 420 |
| tgattctccc ttgttcaaaa agcgagatct cttcatatca ttgtgcctct atttatagta | 480 |
| accaagtaca atttcatatg aaattacaaa catgctcatg acatgataa ttccagtgca | 540 |
| catccaaccc tgcttgatac aaaacatgct cataatcatg atgattcaag tgcacatcca | 600 |
| ccctgctcga tacaacagtt ggcgacctgg tgtgagagtc agaccagacg ggctttcaca | 660 |
| atcgccatgc atgtcattct ctcgtggtcc acgtgtttat taatattgcc attaattgga | 720 |
| gggaaataaa atcaacaaga atagcttatt gatgagtcat atattatgaa tacatcttat | 780 |
| catcttacca aacaaaaaca tatgaccgtc gatgacctga aactagacta ttcgggatct | 840 |
| gcaatgatct gcttgtaaat attaatttgc acatcacgcc attgcatgca catcggcgtg | 900 |
| ggcattatta atttggattg gacgaaaaat caaccagagg gcgtcaccct tttgctagtt | 960 |
| ggccttgtaa tacctagcat gtagcatgcc aaggatctgg ctgctccagg tttgttatgc | 1020 |
| ctgacatcac catagggatg agagcaagta taataatagg ctgtaagctt taaatgctca | 1080 |
| ggtggagaaa aaaaggagag gagaggagag agaaagtgg gctataagct tatagctgtg | 1140 |
| ttagacataa gaatcagaaa cttcgtatga gagacaggtg agctatatat taataacaaa | 1200 |
| gagctaacta ttatatgagt gaaccgagag aaggctgtaa aaaaacttac acaatcaacg | 1260 |
| atcgacatta ttattaacct tgctctgtct tgcgagacct ctttgacaaa gctacatcaa | 1320 |
| tgccggccaa gtgccttggg atttgggaat ggcttctttc ctcccttcct cggttgtccc | 1380 |

```
ccaaggccta ggcttgccac gctgtattca gtcgcagccg cctttacttt tgcccttttgt    1440 ggaagttttg taataaatgg tctgattcta tcttcggata gatgaagccg gatgtttcat    1500
ccattatcta aaaaaaagtt ggttgctttg ctgagctaag aaagtgtaat ccagagtgct    1560
cgtaacgtat taatgtacat aactattatc taatataaat cttcttttgt cgcaaaaaaa    1620
ggtcggccca tcagaacaaa tgatcaatgt aaggcccaaa atttgtgtct caaatgtcat    1680 ttacgttttcc aagctaaaca aaaacacagg attcatataa ttttgctggt ggcttaggct    1740
tcgtccaata gtgcttagtt taatttgtat atacctgcac catggtattc gtctggcctt    1800
ggatcttgcg catcaattgc ctatggacga tgatcgcagc cacgcccat tcattttaa    1860 tcgccatttg cttgacaccc aatgcctctg caccacttgc gcacgctacg caccgtctga    1920
tacgccaaga tcccgagcta aaataacacc caatcatcag atgaaaacaa gcgcgagtgc    1980
gagccagccc atggcagcga tcttggccat ttgcggagcc aactgaaagc cgtgcacaaa    2040
atattcgaca ccgtataagg gaaaacacta gttatacgag gtgggcaata atccagatct    2100
cggactcttc ctaacccggt tcacatgcat agcatatatg atggccggcc ggggttcaca    2160
tgaacgccat cccgtgccct agtgcactga tttcttaatc ccctaggtca actataatac    2220
tgtactccct ccgtcctcga aagcttcaac tcttagaatc cgtgccagtc aaacttttct    2280
aactttgacc aactttataa gagtaagttt aataatacag cccacttgct ggctgtaagg    2340
tttcttacag ccttcttcca gcccacccat acaatagtta gctattcact attaatacat    2400
ggcccacttg tctctctcac aaagttcctt ggttcctgtc cctaagctgg ctgtaagctt    2460
acagcccgct tctcctctct ctcctctctt ctctcctcca cctcagcatt tagccagctt    2520
acagcccact ataatacttg ctctaaaaaa gagtatcaat atctatgaca taaaataagt    2580
atcttacgaa aatatattct ataataaatt taatggtatt aatttggtac tataaatctt    2640
agcatttttt tctataaatt tagtcaaagt tgtaaaagtt tgacttaaga caactctaaa    2700
aattgcagcg ggagtatgta tgatcgatgc tgctctagtt ttccagccc acctctcgtt    2760 gtttgcgact tcgagtttac tgcatctata tctctgaaag aaaatgccta cagggcttgg    2820
ccggtgtcag cttcagggct ctctgtaggc gttgaatccg aggccgccgt agggtggtgg    2880
cagcgcgacc atcgagccgt ggagcaagta cgagtcaaac acgctgagcc gcgtaaccgt    2940
tttaataaaa tgaactctac tcgatcgcta ggtcacagca gcacgatcac agtgaagaat    3000
gcgtgagggg ctcgagcgtt ggcgttgttg ctgtgctttg atcaaactgc accggcgaga    3060
aggaagtaat ataagcaact cgatcataat ccaagcagta aacgcctgat caattgtcga    3120
catctggctg gcactagtat tactagattg tagaatacgc cgcgtgatgt gatttgttat    3180
tttaggtcca aattcatgaa gaattgtgga gtagttgagt agatgagtac agtgacttgc    3240
agttgcagca aacgattgat gttcacatga cagggttcag gggtcctgta gtcctgttac    3300
ttgcagtatt gccgtatcgt gaatctgaag tcgaacagag atagatcgat ggcgtaatgt    3360
cccaaggagg agagaaataa tatgactgta tcactgtagt gtgtagtcga tgggaatcta    3420
tagctctcgt tattaggctc ttaattttaa cagaaaccaa agcaactaca agctaattaa    3480
ttccagagac ttctacagtg ccacatcatt caattggcac cagaattaaa atagtttttc    3540
aagaaatcgc atctcagaaa aagatgctaa tggtttcttt atcgttgtgg tcaacactag    3600
tgccatccag attacagaat tctctcctga tcggatctca tcgcacatgg acagccctgc    3660
aaacccaaca cggaaaccct gaaagatcgc gtccgtgtgc atgcatgcat gcatggtacg    3720
aacgtctgga tagagtctcc gagctgagtg tggtccgacg tggaagtgta cgtctcaaca    3780
```

```
cacgacgcat gtgaccgaca agggcaagtt gaagtctatg catggatggg cctgagcgcc    3840
gcgctgaatg aatctggacg ggtggtaggg catctcggtg ggcaaaacaa ataactccgt    3900
gtgctgcatg gctgcctttg gaatctttgc atgcagctgt gtgctgaact gaaacccttc    3960
gctctatcta tataaacaga tgcccttcgc tctcgtctca gcaggcagca tcgtctcaag    4020
ttttgttctc ctctcctagc tagccagcac ctgcagatct gctcgttgcc ttggtaattc    4080
atcatgtagt acgtagcatc agctagtatt tatctcaagt atatatatac gcatatgtgt    4140
cgtcgcagta ctttccctta tctctctata cacactacac gcatacatac caataccatc    4200
cgtcttaact cttaatcttt gcctgcatac gtacactgca cgtacgtact gcagggctac    4260
tgattttgtg gaacgaagcg                                                4280
```

<210> SEQ ID NO 21
<211> LENGTH: 3384
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 6 PRO

<400> SEQUENCE: 21

```
ctactcgcct tgtggctcct cctgaaccac ctgctcttct cctgtggggg ggtgtgagac      60
agcaagggtg agctcacaca tgatcatagc tcaacaagtt gtggggaacc agtggacatg     120
aactcacaaa ggtgggagtt catgtgatgg ttcctctaga tgctcaactt gttgcattat     180
attacgcaat tgctccgacg cttcatcaat taatcctcct tagtgatatt aaataacgga     240
ataatattag agaaataaac aataatctaa gacattagcg cataaagatg tgacaaaatg     300
attgagtctg gtcatattac cctccttcat cctttattgc ataaagatt gtagtttaca      360 ccttcggctt tacaaaggag agctcgaagg taatatttaca gcttcgaagg cggagtgatt    420
tgattctccc ttgttcaaaa agcgagatct cttcatatca ttgtgcctct atttatagta    480
accaagtaca atttcatatg aaattacaaa catgctcatg gacatgataa ttccagtgca    540
catccaaccc tgcttgatac aaaacatgct cataatcatg atgattcaag tgcacatcca    600
ccctgctcga tacaacagtt ggcgacctgg tgtgagagtc agaccagacg ggcttttcaca    660 atcgccatgc atgtcattct ctcgtggtcc acgtgtttat taatattgcc attaattgga    720
gggaaataaa atcaacaaga atagcttatt gatgagtcat atattatgaa tacatcttat    780
catcttacca aacaaaaaca tatgaccgtc gatgacctga aactagacta ttcgggatct    840
gcaatgatct gcttgtaaat attaatttgc acatcacgcc attgcatgca catcggcgtg    900
ggcattatta atttggattg gacgaaaaat caaccagagg gcgtcaccct tttgctagtt    960
ggccttgtaa taccaccact tgtgaactat gaatacatgg aagcttgctt tgccgataag    1020
ctagccacag gaaagttcgc aatgggatct aactagcctt tggggaaacc cattgaagta    1080
gagggtttag aaaagcctat tgatttggag ggtggagaaa ccaatggtga aggttttgtg    1140
caaggtcaag tccccttcga tttaggagtt caaggcctcg gagcaagtac agcttcacct    1200
tctggctcaa caaataataa aaagaggaag cgggttctga gtgatgaaga tgcaattcag    1260
ataaacaaca tgtctcatgc attgcgtgat gtggctggtg ctatcaataa cacttgccat    1320
accgaaacac atcctgattt gtgcaaaacg gttatggacc ttaccaattt cgacatggat    1380
caacgctcgg ctgttttgga ttatttgacg gagcataagg gtaaaggcct taatttcatg    1440
```

```
aaaatggaag ctgatgtttg tgaagcctca ttcaagcgtt gttctgtgtt gatgcaactt     1500
caaaatctat atcttttgta atgcctagta tattatgatg cagacttggt tatttggacg     1560
tatttcgtat gttagctttt atatattttg gtgatgttga catgctgaat tatgtactca     1620
agtaagcctt ggtaatatat cattttgcgg tattttggtg ctgtatattt ttgctgtaaa     1680
ttatgtttcg aatttatgat gtaatggatg aaatttgaat aagtttgtgt ggtcattgca     1740
ccaagtcaga gacgtataat cacatcttac tcgcgtgcac tctaccaaac aaagtctgag     1800
ttcaacatgc ctaaacagac acagcccacc aaacgacatc tcaactcatc atacctcgac     1860
agatacagtc tgccaaacac atgtgaaaat ctcagctcaa cttgactaga gtcagcttgt     1920
tagggatgaa atgggaattc tggattcacc acggacacca acacaccct tagatgctcc      1980 tggatgctcc agtgcacgcg gtcagccagg agaatagcgt caaagcaacg tatatctgat     2040
atcctggatg ctccagtgta atgtgatatt gagtcgattg caatactttg ctcacaggcg     2100
atatttcgag aagagaaaaa gacacaggaa aagattatat atgtccactt caacatcatg     2160
atctgaacac gtacgtatac aaaaatcata ctccgtagca gagactgaga ggcatgaaac     2220
cagcctcatt ggcctggacg cgtgaagttt gcgtgcatgc gcatgcgctt tttcttgttg     2280
ctagatttag atcaacaaaa agaagtgaag aactttatat tttggtaggt aaaatgtata     2340
acaaaacaaa tctttcagaa aatcacttga tatttccaaa cacaatacat ctaaattgca     2400 ataaaaaga attttagaaa acaaaaacat aaaaatatgg gtgttgctgt ttgaatttca     2460
atactacaaa aggacatata tgtgacgtca tattagtgtc gggcccagca ggaccgccaa     2520
tgatgtatag catcagtgtt ggtcggtgca aaacccgcca ctgatataca gctgcgcgtt     2580
tcccactttc gacctgatga acatcagtgg cgggcgttgc acccgcccgc cactaatttt     2640
taagtagagg accttaaatc taagttgacg tatgagaacc attggattaa gatataatgg     2700
cactctcttc tcttctactt gctatcgttg gattaatatc cgacggtcaa gcacatcggc     2760
tcatgtctaa caaaaaaaag gcaacttctt aatagcaaaa ccgtaaaaat atatatttta     2820
ttatacaagt ctagcccgcg agctgcttgg ttcaccctgc tagttaagat agtaacttgt     2880
agctcttctt gttgcgtata agttgttaaa cattgtaaaa gcctcctcaa gtatcatgta     2940
tacctgtgat acctcacgac gatttaaacg cacaattgct gtataatgga tatagattgg     3000
ttctaggctc cagcgatcga ttatccatgt aactacgtac aaacgagtaa acctccaaaa     3060
tcacaccgct gtcacacatc gtctgcacgc agttgcctga aaccaatcca ctgcacctag     3120
cccacgggtt gaataaaacc gcccgcgccg gcctcttcaa cgtgcatcca cgcagtgtgt     3180
cattcccgtc acggactctc gtctcatccg gccccttctc tcgagcaaca cccaccaatc     3240
tcctcgtggg tcgtggcggc ctctatataa cgccaagaca tcgatcagac atccatccat     3300
ccatccacac tcacacagtc gctgtagtag ctagcaagcc cctaggtgct tgcttgacct     3360
actgctctgc ccgtgaccag tcgt                                            3384
```

<210> SEQ ID NO 22
<211> LENGTH: 3453
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 7 PRO

<400> SEQUENCE: 22

```
ctactcgcct tgtggctcct cctgaaccac ctgctcttct cctgtggggg ggtgtgagac    60
agcaagggtg agctcacaca tgatcatagc tcaacaagtt gtggggaacc agtggacatg   120
aactcacaaa ggtgggagtt catgtgatgg ttcctctaga tgctcaactt gttgcattat   180
attacgcaat tgctccgacg cttcatcaat taatcctcct tagtgatatt aaataacgga   240
ataatattag agaaataaac aataatctaa gacattagcg cataaagatg tgacaaaatg   300
attgagtctg gtcatattac cctccttcat cctttattgc ataaaagatt gtagtttaca   360
ccttcggctt tacaaaggag agctcgaagg taatattaca gcttcgaagg cggagtgatt   420
tgattctccc ttgttcaaaa agcgagatct cttcatatca ttgtgcctct atttatagta   480
accaagtaca atttcatatg aaattacaaa catgctcatg gacatgataa ttccagtgca   540
catccaaccc tgcttgatac aaaacatgct cataatcatg atgattcaag tgcacatcca   600
ccctgctcga tacaacagtt ggcgacctgg tgtgagagtc agaccagacg ggctttcaca   660
atcgccatgc atgtcattct ctcgtggtcc acgtgtttat taatattgcc attaattgga   720
gggaaataaa atcaacaaga atagcttatt gatgagtcat atattatgaa tacatcttat   780
catcttacca aacaaaaaca tatgaccgtc gatgacctga aactagacta ttcgggatct   840
gcaatgatct gcttgtaaat attaatttgc acatcacgcc attgcatgca catcggcgtg   900
ggcattatta atttggattg gacgaaaaat caaccagagg gcgtcaccct tttgctagtt   960
ggccttgtaa taccaccact tgtgaactat gaatacatgg aagcttgctt tgccgataag  1020
ctagccacag gaaagttcgc aatgggatct aactagcctt tggggaaacc cattgaagta  1080
gagggtttag aaaagcctat tgatttggag ggtggagaaa ccaatggtga aggttttgtg  1140
caaggtcaag tccccttcga tttaggagtt caaggcctcg gagcaagtac agcttcacct  1200
tctggctcaa caaataataa aaagaggaag cgggttctga gtgatgaaga tgcaattcag  1260
ataaacaaca tgtctcatgc attgcgtgat gtggctggtg ctatcaataa cacttgccat  1320
accgaaacac atcctgattt gtgcaaaacg gttatggacc ttaccaattt cgacatggat  1380
caacgctcgg ctgttttgga ttatttgacg gagcataagg gtaaaggcct taatttcatg  1440
aaaatggaag ctgatgtttg tgaagcctca ttcaagcgtt gttctgtgtt gatgcaactt  1500
caaaatctat atcttttgta atgcctagta tattatgatg cagacttggt tatttggacg  1560
tatttcgtat gttagctttt atatattttg gtgatgttga catgctgaat tatgtactca  1620
agtaagcctt ggtaatatat cattttgcgg tattttggtg ctgtatattt ttgctgtaaa  1680
ttatgtttcg aatttatgat gtaatggatg aaatttgaat aagtttgtgt ggtcattgca  1740
ccaagtcaga gacgtataat cacatcttac tcgcgtgcac tctaccaaac aaagtctgag  1800
ttcaacatgc ctaaacagac acagcccacc aaacgacatc tcaactcatc atacctcgac  1860
agatacagtc tgccaaacac atgtgaaaat ctcagctcaa cttgactaga gtcagcttgt  1920
tagggatgaa atgggaattc tggattcacc acggacacca aacacaccct tagatgctcc  1980
tggatgctcc agtgcacgcg gtcagccagg agaatagcgt caaagcaacg tatatctgat  2040
atcctggatg ctccagtgta atgtgatatt gagtcgattg caatactttg ctcacaggcg  2100
atatttcgag aagagaaaaa gacacaggaa aagattatat atgtccactt caacatcatg  2160
atctgaacac gtacgtatac aaaaatcata ctccgtagca gagactgaga ggcatgaaac  2220
cagcctcatt ggcctggacg cgtgaagttt gcgtgcatgc gcatgcgctt tttcttgttg  2280
ctgactatat attacccttc tcaagtaaat gggtaagttt taatttgcgc cactgattat  2340
```

```
ttgcatggaa aaacataaac cgatattgca ccgacgcgag ccccaatttt taaactagca    2400
aatctctagc ggcgcctaga aatgaatata atcgggatct atctcttgaa acacgcatag    2460
atggcagcac gcggtggaga ccaagaagcc ctggagaagg agccgttgta gctggccggg    2520
gttcaaaact gaactgcagg agcacgtacc atctcatact agtactaaat ctttaatctt    2580
ctcaagtgga gttcctcttg ccacccgaag cggaaggagg tcaaccctac gcaccacgag    2640
gcacaatagc aaaccgtgtc cctctagtta agtaattac cccatgtaaa cgtgttcttc     2700 cttcagact tgcaatgggt aatgttcaca agtactgtag ttgcattact ggtaataacg     2760
cgatggagta tttagcgatg caaaatttcc aaaacaagct tgtctcgtca gtgacacgat    2820
ttggcgacac tcaacacaac agtttctcac ctttacaaat actgcccgtt atagatttgt    2880
taatactctc ttcatctcat attaagtgtc gaaatattac atgtatctag acgctttcta    2940
gacatagata aattcatatt tcgacaactt tgagacagtt aatatgggac agagggagta    3000
cctgagacga gcttagccac tctctctttt ttcagaacgt aaactcatgc gtgtgactga    3060
gtttcttcca agagtttgta aagaaattaa tcgataatgt tcagaactta tcctctctct    3120
ttatatattt tcagacacag tatgatccac ttgggcatcg agatccaccc ttccatatag    3180
tactatattc tactgccacg agcccatatc gagtgtctac caaactagga gctcgatcgt    3240
gatgcacatg accgaatcac actccacatg cacacaacac atgggatgtg tctaccaaac    3300
tggctcccct tgggtaggta gatatgcaac atttggctag ctaaagttct ataaataccc    3360
tcttggcacc ccttgcatat ctcacacaca gcttcttctt ctatctatcc cacacaaagc    3420
cttccagctc cttaagccta caactgacca acc                                 3453

<210> SEQ ID NO 23
<211> LENGTH: 2529
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 8 PRO

<400> SEQUENCE: 23
ctactcgcct tgtggctcct cctgaaccac ctgctcttct cctgtggggg ggtgtgagac      60
agcaagggtg agctcacaca tgatcatagc tcaacaagtt gtggggaacc agtggacatg     120
aactcacaaa ggtgggagtt catgtgatgg ttcctctaga tgctcaactt gttgcattat     180
attacgcaat tgctccgacg cttcatcaat taatcctcct tagtgatatt aaataacgga     240
ataatattag agaaataaac aataatctaa gacattagcg cataaagatg tgacaaaatg     300
attgagtctg tcatattac cctccttcat cctttattgc ataaaagatt gtagtttaca      360
ccttcggctt tacaaaggag agctcgaagg taatattaca gcttcgaagg cggagtgatt     420
tgattctccc ttgttcaaaa agcgagatct cttcatatca ttgtgcctct atttatagta     480
accaagtaca atttcatatg aaattacaaa catgctcatg gacatgataa ttccagtgca     540
catccaaccc tgcttgatac aaaacatgct cataatcatg atgattcaag tgcacatcca     600
ccctgctcga tacaacagtt ggcgacctgg tgtgagagtc agaccagacg ggctttcaca     660
atcgccatgc atgtcattct ctcgtggtcc acgtgtttat taatattgcc attaattgga     720
gggaaataaa atcaacaaga atagcttatt gatgagtcat atattatgaa tacatcttat     780
catcttacca aacaaaaaca tatgaccgtc gatgacctga aactagacta ttcgggatct     840
```

```
gcaatgatct gcttgtaaat attaatttgc acatcacgcc attgcatgca catcggcgtg    900
ggcattatta atttggattg gacgaaaaat caaccagagg gcgtcaccct tttgctagtt    960
ggccttgtaa tacatttcag acctgcattc catgagaaac gaacggggct ttagcgggcc   1020
acgtgacagt gacgaagggt cgcagtcgct gctggacgga ctacagacag agaggcgaag   1080
catgcaattg aattttcgct agcggaaagt tatcatctaa tctccaaccc tccttcctac   1140
ggctggatct gaaaattgac gacctgaacc cctgaacggt gccggtagca attgcaggtc   1200
tcactcacat gctaaatcca gcaaccaaac acgaaggaat atatgtgatc tggacagaac   1260
atgcaagcga ataatacata gagtcgtacc aaccctacac agttcaacga attaatcact   1320
gggttcacgg gcatgctcac gtccaaaatc ccagcgacat tttataagcg ctaagcggaa   1380
tgatccagac ggggccagct cgagcaccac atgggcacta cattactgcg gcgcttgctc   1440
aaacttcatg caccaataat tgaaacacgg tcaattgtat gcattactag tgtaattaag   1500
tgcatgtaac gaatgaacta ccttaggatt ttaggagaat cgaagaatat ctccatccat   1560
ttaccaaatc aaacttatta agaagaaaat attatgtact tcctacgtcc aaaaaagatg   1620
tctcaagttt gtcaaatttt ggatgtatct agacatgact taatgtatag atgcattcaa   1680
attttgacaa acttaagaca tcctttttg gacggaggga gtacaagatt tgttaataag    1740
ttacattaaa aaactacaca gtactgtcta ctcgttttt tttctaaaga aaatcacgga    1800
tctattaata atcaccaaca tgagccttac ttaattaagt acttagagac gacgtcgagc   1860
gtttggagag tctttgtaca atgtcaaagg tacctataat ccggccggcc gggtgatttg   1920
aatcgcgcgc ctagctagat cgatccatgc atgcgatcca cagctagctt gatgcttgcg   1980
ccagtgtgtg atcgatcatg agctcatgac cccatgacat cgagcgagtt agctagagaa   2040
gccatgcacg cacgttcttt cacgtggaag agttataaaa agctagcgta atacgtttat   2100
atatgtcagg agatgggaat ctctagctaa ttaggcttcg agagaaacca agcaacagct   2160
agtaattaac ttcagatcct tccgcactcg ataatcaagt cttgatctgc atagcccagt   2220
gaagtgccaa taaatctaag atgtgaagag atgtgcaaca gtgcaagaga aaatttaatg   2280
ctgtctagtt gcttgatcga tgcagtcaat actagtactg tcaccctgat tagaaaaatt   2340
atcactcatc gaatcaccca cttgataatt cacagcccga agtcgtcccg aagcgcgcgg   2400
tcgcctcctt gagatatcca accccatgca tctcatctac cactataaat actcaggcca   2460
ccctctctgc taagcacccc accacctcat ctcacacgta ctctagctac aaattaagct   2520
acgtcggca                                                           2529

<210> SEQ ID NO 24
<211> LENGTH: 2376
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 9 PRO

<400> SEQUENCE: 24
ctactcgcct tgtggctcct cctgaaccac ctgctcttct cctgtggggg ggtgtgagac     60
agcaagggtg agctcacaca tgatcatagc tcaacaagtt gtgggaacc agtggacatg     120
aactcacaaa ggtgggagtt catgtgatgg ttcctctaga tgctcaactt gttgcattat    180
attacgcaat tgctccgacg cttcatcaat taatcctcct tagtgatatt aaataacgga    240
```

|  |  |  |  |  |  |
|---|---|---|---|---|---|
| ataatattag | agaaataaac | aataatctaa | gacattagcg | cataaagatg | tgacaaaatg | 300 |
| attgagtctg | gtcatattac | cctccttcat | cctttattgc | ataaaagatt | gtagtttaca | 360 |
| ccttcggctt | tacaaaggag | agctcgaagg | taatattaca | gcttcgaagg | cggagtgatt | 420 |
| tgattctccc | ttgttcaaaa | agcgagatct | cttcatatca | ttgtgcctct | atttatagta | 480 |
| accaagtaca | atttcatatg | aaattacaaa | catgctcatg | gacatgataa | ttccagtgca | 540 |
| catccaaccc | tgcttgatac | aaaacatgct | cataatcatg | atgattcaag | tgcacatcca | 600 |
| ccctgctcga | tacaacagtt | ggcgacctgg | tgtgagagtc | agaccagacg | ggctttcaca | 660 |
| atcgccatgc | atgtcattct | ctcgtggtcc | acgtgtttat | taatattgcc | attaattgga | 720 |
| gggaaataaa | atcaacaaga | atagcttatt | gatgagtcat | atattatgaa | tacatcttat | 780 |
| catcttacca | aacaaaaaca | tatgaccgtc | gatgacctga | aactagacta | ttcgggatct | 840 |
| gcaatgatct | gcttgtaaat | attaatttgc | acatcacgcc | attgcatgca | catcggcgtg | 900 |
| ggcattatta | atttggattg | gacgaaaaat | caaccagagg | gcgtcaccct | tttgctagtt | 960 |
| ggccttgtaa | tacatttcag | acctgcattc | catgagaaac | gaacggggct | ttagcgggcc | 1020 |
| acgtgacagt | gacgaagggt | cgcagtcgct | gctggacgga | ctacagacag | agaggcgaag | 1080 |
| catgcaattg | aattttcgct | agcggaaagt | tatcatctaa | tctccaaccc | tccttcctac | 1140 |
| ggctggatct | gaaaattgac | gacctgaacc | cctgaacggt | gccggtagca | attgcaggtc | 1200 |
| tcactcacat | gctaaatcca | gcaaccaaac | acgaaggaat | atatgtgatc | tggacagaac | 1260 |
| atgcaagcga | ataatacata | gagtcgtacc | aaccctacac | agttcaacga | attaatcact | 1320 |
| gggttcacgg | gcatgctcac | gtccaaaatc | ccagcgacat | tttataagcg | ctaagcggaa | 1380 |
| tgatccagac | ggggccagct | cgagcaccac | atggtttgac | ttggaccgac | tagcactccc | 1440 |
| ccgctaggca | cgtagtacgt | ggtatgtgtg | gaaacgattg | gttcgttgta | gggagtcagt | 1500 |
| cagatcagat | atgatgcttc | tcgtgtgttg | attttcttcc | tctgaactga | aaggaagcat | 1560 |
| gcaagtttta | caagctaaac | tcagcagcgg | aagctatgca | tacgttccac | tggctgcaga | 1620 |
| acagggcagg | ccggcggcta | gctcctgtga | gctgtgttgg | aggagaataa | tatcttgtcg | 1680 |
| tttggctttg | ctcgggtgga | tacttttttt | tcttttgaca | gctgctcggg | tggatactga | 1740 |
| tacactatga | agaccgaaaa | aaagaagcga | agcatataaa | cagacggatc | attggggcc | 1800 |
| aagccagcag | gtagtgcggt | ggaacattat | gtagaatgaa | tcggttcttg | ctgtgcagac | 1860 |
| agctcagctc | agcacactcc | tggcccaaaa | caaagtgcat | gtggtgtatt | ttcgtatact | 1920 |
| agctaacaaa | tgcttaagcc | cctgtttgaa | atattgtatt | ttcggcggac | gggcactggc | 1980 |
| ttactgaaat | cttgccagga | ggcacggaca | ggtgcttagc | agccaagtaa | tgtacagtaa | 2040 |
| atccggcaaa | ttgccagggg | agtggttcga | ttcaatcaac | gaatgcgatt | cccgatataa | 2100 |
| attatcccca | gtttattttt | gattttatac | aacgcgtcgc | cgacgcggtc | cccaccccgt | 2160 |
| gcgcgtcgca | aggtccacac | gtgtcctctc | tccgacgctt | cctagctcac | gccgtccttg | 2220 |
| attgacctgc | ctcgccatct | ataaatggca | aaccaggcta | aggctcattt | ctatactccc | 2280 |
| tcttcctgct | ctgctctctg | ctctagttta | ctccactgac | ccaaagagag | aaaagaaagc | 2340 |
| actcagaact | tgagatcagc | atccaggaga | tcggcc |  |  | 2376 |

<210> SEQ ID NO 25
<211> LENGTH: 3280
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<223> OTHER INFORMATION: Root Hybrid 10 PRO

<400> SEQUENCE: 25
caccacttgt gaactatgaa tacatggaag cttgctttgc cgataagcta gccacaggaa        60
agttcgcaat gggatctaac tagcctttgg ggaaacccat tgaagtagag ggtttagaaa       120
agcctattga tttggagggt ggagaaacca atggtgaagg ttttgtgcaa ggtcaagtcc       180
ccttcgattt aggagttcaa ggcctcggag caagtacagc ttcaccttct ggctcaacaa       240
ataataaaaa gaggaagcgg ttctgagtg atgaagatgc aattcagata aacaacatgt        300
ctcatgcatt gcgtgatgtg gctggtgcta tcaataacac ttgccatacc gaaacacatc       360
ctgatttgtg caaaacggtt atggacctta ccaatttcga catggatcaa cgctcggctg       420
ttttggatta tttgacggag cataagggta aaggccttaa tttcatgaaa atggaagctg       480
atgtttgtga agcctcattc aagcgttgtt ctgtgttgat gcaacttcaa aatctatatc       540
ttttgtaatg cctagtatat tatgatgcag acttggttat ttggacgtat ttcgtatgtt       600
agcttttata tattttggtg atgttgacat gctgaattat gtactcaagt aagccttggt       660
aatatatcat tttgcggtat tttggtgctg tatattttg ctgtaaatta tgtttcgaat        720
ttatgatgta atggatgaaa tttgaataag tttgtgtggt cattgcacca agtcagagac       780
gtataatcac atcttactcg cgtgcactct accaaacaaa gtctgagttc aacatgccta       840
aacagacaca gcccaccaaa cgacatctca actcatcata cctcgacaga tacagtctgc       900
caaacacatg tgaaaatctc agctcaactt gactagagtc agcttgttag ggatgaaatg       960
ggaattctgg attcaccacg acaccaaac acacccttag atgctcctgg atgctccagt      1020
gcacgcggtc agccaggaga atagcgtcaa agcaacgtat atctgatatc ctggatgctc      1080
cagtgtaatg tgatattgag tcgattgcaa tactttgctc acaggcgata tttcgagaag      1140
agaaaaagac acaggaaaag attatatatg tccacttcaa catcatgatc tgaacacgta      1200
cgtatacaaa aatcatactc cgtagcagag actgagaggc atgaaaccag cctcattggc      1260
ctggacgcgt gaagtttgcg tgcatgcgca tgcgcttttt cttgttgctg cactacatta      1320
ctgcggcgct tgctcaaact tcatgcacca ataattgaaa cacggtcaat tgtatgcatt      1380
actagtgtaa ttaagtgcat gtaacgaatg aactaccta ggattttagg agaatcgaag       1440
aatatctcca tccatttacc aaatcaaact tattaagaag aaaatattat gtacttccta      1500
cgtccaaaaa agatgtctca gtttgtcaa attttggatg tatctagaca tgacttaatg       1560
tatagatgca ttcaaatttt gacaaactta agacatcctt ttttggacgg agggagtaca      1620
agatttgtta ataagttaca ttaaaaaact acacagtact gtctactcgt ttttttttct      1680
aaagaaaatc acggatctat taataatcac caacatgagc cttacttaat taagtactta      1740
gagacgacgt cgagcgtttg gagagtcttt gtacaatgtc aaaggtacct ataatccggc      1800
cggccgggtg atttgaatcg cgcgcctagc tagatcgatc catgcatgcg atccacagct      1860
agcttgatgc ttgcgccagt gtgtgatcga tcatgagctc atgacccat gacatcgagc       1920
gagttagcta gagaagccat gcacgcacgt tctttcacgt ggaagagtta taaaagcta       1980
gcgtaatacg tttatatatg tcaggagatg ggaatctcta gctaattagg cttcgagaga      2040
aaccaagcaa cagctagtaa ttaacttcag atccttccgc actcgataat caagtcttga      2100
tctgcatagc ccagtgaagt gccaataaat ctaagatgtg aagagatgtg caacagtgca      2160
agagaaaatt taatgctgtc tagttgcttg atcgatgcag tcaatactag tactgtcacc      2220
```

```
ctgattagaa aaattatcac tcatcgaatc acccacttga taattcacag cccgaagtcg    2280
tcccgaagcg cgcggtcgcc tccttgagat atccaacctt tgacttggac cgactagcac    2340
tcccccgcta ggcacgtagt acgtggtatg tgtggaaacg attggttcgt tgtagggagt    2400
cagtcagatc agatatgatg cttctcgtgt gttgattttc ttcctctgaa ctgaaaggaa    2460
gcatgcaagt tttacaagct aaactcagca gcggaagcta tgcatacgtt ccactggctg    2520
cagaacaggg caggccggcg gctagctcct gtgagctgtg ttggaggaga ataatatctt    2580
gtcgtttggc tttgctcggg tggatacttt tttttctttt gacagctgct cgggtggata    2640
ctgatacact atgaagaccg aaaaaaagaa gcgaagcata taaacagacg gatcattggg    2700
ggccaagcca gcaggtagtg cggtggaaca ttatgtagaa tgaatcggtt cttgctgtgc    2760
agacagctca gctcagcaca ctcctggccc aaaacaaagt gcatgtggtg tattttcgta    2820
tactagctaa caaatgctta agccctgtt tgaaatattg tattttcggc ggacgggcac    2880
tggcttactg aaatcttgcc aggaggcacg gacaggtgct tagcagccaa gtaatgtaca    2940
gtaaatccgg caaattgcca ggggagtggt tcgattcaat caacgaatgc gattcccgat    3000
ataaattatc cccagtttat ttttgatttt atacaacgcg tcgccgacgc ggtccccacc    3060
ccgtgcgcgt cgcaaggtcc acacgtgtcc tctctccgac gcttcctagc tcacgccgtc    3120
cttgattgac ctgcctcgcc atctataaat ggcaaaccag gctaaggctc atttctatac    3180
tccctcttcc tgctctgctc tctgctctag tttactccac tgacccaaag agagaaaga    3240 aagcactcag aacttgagat cagcatccag gagatcggcc                           3280
```

<210> SEQ ID NO 26
<211> LENGTH: 3318
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 11 PRO

<400> SEQUENCE: 26

```
caccacttgt gaactatgaa tacatggaag cttgctttgc cgataagcta gccacaggaa      60
agttcgcaat gggatctaac tagcctttgg ggaaacccat tgaagtagag ggtttagaaa     120
agcctattga tttggagggt ggagaaacca atggtgaagg ttttgtgcaa ggtcaagtcc     180
ccttcgattt aggagttcaa ggcctcggag caagtacagc ttcaccttct ggctcaacaa     240
ataataaaaa gaggaagcgg gttctgagtg atgaagatgc aattcagata acaacatgt      300 ctcatgcatt gcgtgatgtg gctggtgcta tcaataacac ttgccatacc gaaacacatc     360
ctgatttgtg caaaacggtt atggacctta ccaatttcga catggatcaa cgctcggctg     420
ttttggatta tttgacggag cataagggta aaggccttaa tttcatgaaa atggaagctg     480
atgtttgtga agcctcattc aagcgttgtt ctgtgttgat gcaacttcaa aatctatatc     540
ttttgtaatg cctagtatat tatgatgcag acttggttat ttggacgtat ttcgtatgtt     600
agcttttata tattttggtg atgttgacat gctgaattat gtactcaagt aagccttggt     660
aatatatcat tttgcggtat tttggtgctg tatattttg ctgtaaatta tgtttcgaat     720
ttatgatgta atggatgaaa tttgaataag tttgtgtggt cattgcacca agtcagagac     780
gtataatcac atcttactcg cgtgcactct accaaacaaa gtctgagttc aacatgccta     840
aacagacaca gcccaccaaa cgacatctca actcatcata cctcgacaga tacagtctgc     900
```

```
caaacacatg tgaaaatctc agctcaactt gactagagtc agcttgttag ggatgaaatg      960
ggaattctgg attcaccacg acaccaaac acacccttag atgctcctgg atgctccagt     1020
gcacgcggtc agccaggaga atagcgtcaa agcaacgtat atctgatatc ctggatgctc     1080
cagtgtaatg tgatattgag tcgattgcaa tactttgctc acaggcgata tttcgagaag     1140
agaaaaagac acaggaaaag attatatatg tccacttcaa catcatgatc tgaacacgta     1200
cgtatacaaa aatcatactc cgtagcgag actgagaggc atgaaaccag cctcattggc      1260
ctggacgcgt gaagtttgcg tgcatgcgca tgcgcttttt cttgttgctg actatatatt     1320
acccttctca agtaaatggg taagttttaa tttgcgccac tgattatttg catggaaaaa     1380
cataaaccga tattgcaccg acgcgagccc caattttaa actagcaaat ctctagcggc      1440
gcctagaaat gaatataatc gggatctatc tcttgaaaca cgcatagatg gcagcacgcg     1500
gtggagacca agaagccctg agaaggagc cgttgtagct ggccggggtt caaaactgaa      1560
ctgcaggagc acgtaccatc tcatactagt actaaatctt taatcttctc aagtggagtt     1620
cctcttgcca cccgaagcgg aaggaggtca accctacgca ccacgaggca caatagcaaa     1680
ccgtgtccct ctagttaagt taattacccc atgtaaacgt gttcttcctt tcagacttgc     1740
aatgggtaat gttcacaagt actgtagttg cattactggt aataacgcga tggagtattt     1800
agcgatgcaa aatttccaaa acaagcttgt ctcgtcagtg acacgatttg gcgacactca     1860
acacaacagt ttctcacctt tacaaatact gcccgttata gatttgttaa tactctcttc     1920
atctcatatt aagtgtcgaa atattacatg tatctagacg cttctagac atagataaat      1980
tcatatttcg acaactttga gacagttaat atgggacaga gggagtacct gagacgagct     2040
tagccactct ctcttttttc agaacgtaaa ctcatgcgtg tgactgagtt tcttccaaga     2100
gtttgtaaag aaattaatcg ataatgttca gaacttatcc tctctcttta tatattttca     2160
gacacagtat gatccacttg ggcatcgaga tccaccctttc catatagtac tatattctac    2220
tgccacgagc ccatatcgag tgtctaccaa actaggagct cgatcgtgat gcacatgacc     2280
gaatcacact ccacatgcac acaacacatg ggatgtgtct accaaactgg ctccccttgg     2340
gtaggtagat atgcaatttg acttggaccg actagcactc ccccgctagg cacgtagtac     2400
gtggtatgtg tggaaacgat tggttcgttg tagggagtca gtcagatcag atatgatgct     2460
tctcgtgtgt tgattttctt cctctgaact gaaaggaagc atgcaagttt tacaagctaa     2520
actcagcagc ggaagctatg catacgttcc actggctgca gaacagggca ggccggcggc     2580
tagctcctgt gagctgtgtt ggaggagaat aatatcttgt cgtttggctt tgctcgggtg     2640
gatactttt tttcttttga cagctgctcg ggtggatact gatacactat gaagaccgaa      2700
aaaagaagc gaagcatata aacagacgga tcattggggg ccaagccagc aggtagtgcg      2760
gtggaacatt atgtagaatg aatcggttct tgctgtgcag acagctcagc tcagcacact     2820
cctggcccaa aacaaagtgc atgtggtgta ttttcgtata ctagctaaca aatgcttaag     2880
cccctgtttg aaatattgta ttttcggcgg acgggcactg gcttactgaa atcttgccag     2940
gaggcacgga caggtgctta gcagccaagt aatgtacagt aaatccggca aattgccagg     3000
ggagtggttc gattcaatca acgaatgcga ttcccgatat aaattatccc cagtttattt     3060
ttgattttat acaacgcgtc gccgacgcgg tccccacccc gtgcgcgtcg caaggtccac     3120
acgtgtcctc tctccgacgc ttcctagctc acgccgtcct tgattgacct gcctcgccat     3180
ctataaatgg caaaccaggc taaggctcat ttctatactc cctcttcctg ctctgctctc     3240
```

```
<210> SEQ ID NO 27
<211> LENGTH: 3652
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 12 PRO

<400> SEQUENCE: 27
```

| | | | | | |
|---|---|---|---|---|---|
| tgctctagtt | tactccactg | acccaaagag | agaaagaaa | gcactcagaa | cttgagatca | 3300 |
| gcatccagga | gatcggcc | | | | 3318 |

| | | | | | |
|---|---|---|---|---|---|
| caccacttgt | gaactatgaa | tacatggaag | cttgctttgc | cgataagcta | gccacaggaa | 60 |
| agttcgcaat | gggatctaac | tagcctttgg | ggaaacccat | tgaagtagag | ggtttagaaa | 120 |
| agcctattga | tttggagggt | ggagaaacca | atggtgaagg | ttttgtgcaa | ggtcaagtcc | 180 |
| ccttcgattt | aggagttcaa | ggcctcggag | caagtacagc | ttcaccttct | ggctcaacaa | 240 |
| ataataaaaa | gaggaagcgg | gttctgagtg | atgaagatgc | aattcagata | acaacatgt | 300 |
| ctcatgcatt | gcgtgatgtg | gctggtgcta | tcaataacac | ttgccatacc | gaaacacatc | 360 |
| ctgatttgtg | caaaacggtt | atggacctta | ccaatttcga | catggatcaa | cgctcggctg | 420 |
| ttttggatta | tttgacggag | cataagggta | aaggccttaa | tttcatgaaa | atggaagctg | 480 |
| atgtttgtga | agcctcattc | aagcgttgtt | ctgtgttgat | gcaacttcaa | aatctatatc | 540 |
| ttttgtaatg | cctagtatat | tatgatgcag | acttggttat | ttggacgtat | ttcgtatgtt | 600 |
| agcttttata | tattttggtg | atgttgacat | gctgaattat | gtactcaagt | aagccttggt | 660 |
| aatatatcat | tttgcggtat | tttggtgctg | tatattttg | ctgtaaatta | tgtttcgaat | 720 |
| ttatgatgta | atggatgaaa | tttgaataag | tttgtgtggt | cattgcacca | agtcagagac | 780 |
| gtataatcac | atcttactcg | cgtgcactct | accaaacaaa | gtctgagttc | aacatgccta | 840 |
| aacagacaca | gcccaccaaa | cgacatctca | actcatcata | cctcgacaga | tacagtctgc | 900 |
| caaacacatg | tgaaaatctc | agctcaactt | gactagagtc | agcttgttag | ggatgaaatg | 960 |
| ggaattctgg | attcaccacg | gacaccaaac | acacccttag | atgctcctgg | atgctccagt | 1020 |
| gcacgcggtc | agccaggaga | atagcgtcaa | agcaacgtat | atctgatatc | ctggatgctc | 1080 |
| cagtgtaatg | tgatattgag | tcgattgcaa | tactttgctc | acaggcgata | tttcgagaag | 1140 |
| agaaaaagac | acaggaaaag | attatatatg | tccacttcaa | catcatgatc | tgaacacgta | 1200 |
| cgtatacaaa | aatcatactc | cgtagcgagg | actgagaggc | atgaaaccag | cctcattggc | 1260 |
| ctggacgcgt | gaagtttgcg | tgcatgcgca | tgcgcttttt | cttgttgctt | acgcagttgt | 1320 |
| cctttggtac | attcacaagt | ttgatcttat | catcaccatc | agaagttcag | aaagtctcgt | 1380 |
| agaaaacaaa | tggaaatgaa | tactgcttac | ttagctcaaa | ttcatattcc | gttgttacag | 1440 |
| gatacttaaa | aaaggtacca | aaggctgttc | ctaatcatac | gctgaagtcg | ttgccaccaa | 1500 |
| tggcagctgt | actgtcatat | tgtcgtggtt | tttcaattgc | tgtacctgat | gcaaacgtaa | 1560 |
| tgggtttact | aatcttgcac | ccgccgactt | caaaatgaag | agtgctaatt | tggttcacgt | 1620 |
| caccatcacc | ggttcgaact | gtctagaatg | gcaggcaaag | atgattggac | aggcatgcag | 1680 |
| ggaaaaagag | caccgatgac | gatctatgcg | agttcccacc | attgcgagca | atgattatca | 1740 |
| gccacacgac | ttactcttca | gagctaacca | ctgccatgca | gagaaaaagt | gaagcatatt | 1800 |
| gtcaggatct | acaacgaagt | gaaacaatca | ggcatgctaa | agtgctgaaa | ctttactgat | 1860 |

-continued

| | |
|---|---|
| ctctcatgtt ggacaacaaa gaatacggga atacatcagc aacgcaactc ttgagctttg | 1920 |
| cttgctgaat gaccagctag aatttccaag catttacagg aacatgactt taagtttcag | 1980 |
| aaaaacaaat acaaggccac taagggcatg ttcacttcag cttataagcc ggctgaaaag | 2040 |
| ctgaaacggc tgatttgttg tgagaggaaa acactgtttg gtggctgata agccggctga | 2100 |
| ataagctgaa gcgaacaggc tgtaaataag cgtggggata acatatcctc cagatgacag | 2160 |
| gcaatctgca acttgcagcg attcaaatgt acgattaaca aaatatttaa gcgctacatg | 2220 |
| agataatata tcctccaatt agggccttta gtattgtcat tagctcataa gcatggtgca | 2280 |
| tcctcacatg gacgctgcat aagaagttca taatagcaac agacatatga acaaagcatg | 2340 |
| gtgcgcctgc ccggccggac tagctagtac taccaatcat ggaataagct agtaccctaa | 2400 |
| atgaaattaa aatggttttt agcgattatc cacgccgtcc agaatactct aatccacaag | 2460 |
| ttgaggccgc ccatgaagcc ggactatata ttacccttct caagtaaatg ggtaagtttt | 2520 |
| aatttgcgcc actgattatt tgcatggaaa acataaacc gatattgcac cgacgcgagc | 2580 |
| cccaattttt aaactagcaa atctctagcg gcgcctagaa atgaatataa tcgggatcta | 2640 |
| tctcttgaaa cacgcataga tggcagcacg cggtggagac caagaagccc tggagaagga | 2700 |
| gccgttgtag ctggccgggg ttcaaaactg aactgcagga gcacgtacca tctcatacta | 2760 |
| gtactaaatc tttaatcttc tcaagtggag ttcctcttgc cacccgaagc ggaaggaggt | 2820 |
| caaccctacg caccacgagg cacaaatgca aaccgtgtcc ctctagttaa gttaattacc | 2880 |
| ccatgtaaac gtgttcttcc tttcagactt gcaatgggta atgttcacaa gtactgtagt | 2940 |
| tgcattactg gtaataacgc gatggagtat ttagcgatgc aaaatttcca aaacaagctt | 3000 |
| gtctcgtcag tgacacgatt tggcgacact caacacaaca gtttctcacc tttacaaata | 3060 |
| ctgcccgtta tagatttgtt aatactctct tcatctcata ttaagtgtcg aaatattaca | 3120 |
| tgtatctaga cgctttctag acatagataa attcatattt cgacaacttt gagacagtta | 3180 |
| atatgggaca gagggagtac ctgagacgag cttagccact ctctcttttt tcagaacgta | 3240 |
| aactcatgcg tgtgactgag tttcttccaa gagtttgtaa agaaattaat cgataatgtt | 3300 |
| cagaacttat cctctctctt tatatatttt cagacacagt atgatccact tgggcatcga | 3360 |
| gatccaccct tccatatagt actatattct actgccacga gcccatatcg agtgtctacc | 3420 |
| aaactaggag ctcgatcgtg atgcacatga ccgaatcaca ctccacatgc acacaacaca | 3480 |
| tgggatgtgt ctaccaaact ggctccctt gggtaggtag atatgcaaca tttggctagc | 3540 |
| taaagttcta taaataccct cttggcaccc cttgcatatc tcacacacag cttcttcttc | 3600 |
| tatctatccc acacaaagcc ttccagctcc ttaagcctac aactgaccaa cc | 3652 |

<210> SEQ ID NO 28
<211> LENGTH: 2662
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 15 PRO

<400> SEQUENCE: 28

| | |
|---|---|
| ttagttgcag acggtttttc ccctgctagg agatttccga gagaaaaaaa aggcactaca | 60 |
| ggttaaccaa aaccaccaac ctttggagcg tcgaggtcga cgggcatttg cgtagttgaa | 120 |
| gcttacaaag ttgcatatga gatgagtgcc ggacatgaag cggataacgt tttaaactgg | 180 |

```
caacaatatc tagctgtttc aaattcaggc gtgggaagct acgcctacgc gccctggacg    240
gcgtgtaaag agccagcatc ggcatcattg tcaaacgatc gacaaggcca agaaattcca    300
aatatattat taataaaaaa gaaggcacaa attagtttgg ttttttagta tgtgtggcgg    360
aggaaatttt gagaacgaac gtatcaaaga aggcacaaga cgatatagat tgacgcggct    420
agaagttgca gcaagacagt gggtacggtc ttatatatcc taataaataa aaataaaaac    480
tatagtgtgt caaatgtcaa caagaggagg aggcagccaa attagcagag ggagacaagt    540
agagcacgcc ttattagctt gcttatttat cgtggtggtg tacttgttaa ttactggcac    600
gcattatcaa caacgcagtt ctggatgtga atctagacaa acatttgtct aggttccgca    660
cgtatagttt ttttcctctt ttttttgggg ggggggtggg gggggaacg gaagctgtaa    720 taaacggtac taggaacgaa agcaaccgcc gcgcgcatgt ttttgcaata gattacggtg    780
aaatctatat cttttgtaat gcctagtata ttatgatgca gacttggtta tttggacgta    840
tttcgtatgt tagcttttat atattttggt gatgttgaca tgctgaatta tgtactcaag    900
taagccttgg taatatatca ttttgcgtta ttttggtgct gtatatttt gctgtaaatt    960 atgtttcgaa tttatgatgt aatggatgaa atttgaataa gtttgtgtgg tcattgcacc   1020
aagtcagaga cgtataatca catcttactc gcgtgcactc taccaaacaa agtctgagtt   1080
caacatgcct aaacagacac agcccaccaa acgacatctc aactcatcat acctcgacag   1140
atacagtctg ccaaacacat gtgaaaatct cagctcaact tgactagagt cagcttgtta   1200
gggatgaaat gggaattctg gattcaccac ggacaccaaa cacaccctta gatgctcctg   1260
gatgctccag tgcacgcggt cagccaggag aatagcgtca aagcaacgta tatctgatat   1320
cctggatgct ccagtgtaat gtgatattga gtcgattgca atactttgct cacaggcgat   1380
atttcgagaa gagaaaaaga cacaggaaaa gattatatat gtccacttca acatcatgat   1440
ctgaacacgt acgtatacaa aaatcatact ccgtagcaga gactgagagg catgaaaacca   1500 gcctcattgg cctggacgcg tgaagtttgc gtgcatgcgc atgcgctttt tcttgttgct   1560
agatttagat caacaaaaag aagtgaagaa ctttatattt tggtaggtaa aatgtataac   1620
aaaacaaatc tttcagaaaa tcacttgata tttccaaaca caatacatct aaattgcaat   1680 aaaaagaat tttagaaaac aaaaacataa aaatatgggt gttgctgttt gaatttcaat   1740
actacaaaag gacatatatg tgacgtcata ttagtgtcgg gcccagcagg accgccaatg   1800
atgtatagca tcagtgttgg tcggtgcaaa acccgccact gatatacagc tgcgcgtttc   1860
ccactttcga cctgatgaac atcagtgcg ggcgttgcac ccgcccgcca ctaattttta   1920
agtagaggac cttaaatcta agttgacgta tgagaaccat tggattaaga tataatggca   1980
ctctcttctc ttctacttgc tatcgttgga ttaatatccg acggtcaagc acatcggctc   2040
atgtctaaca aaaaaaggc aacttcttaa tagcaaaacc gtaaaaatat atattttatt   2100
atacaagtct agcccgcgag ctgcttggtt caccctgcta gttaagatag taacttgtag   2160
ctcttcttgt tgcgtataag ttgttaaaca ttgtaaaagc ctcctcaagt atcatgtata   2220
cctgtgatac ctcacgacga tttaaacgca caattgctgt ataatggata tagattggtt   2280
ctaggctcca gcgatcgatt atccatgtaa ctacgtacaa acgagtaaac ctccaaaatc   2340
acaccgctgt cacacatcgt ctgcacgcag ttgcctgaaa ccaatccact gcacctagcc   2400
cacgggttga ataaaaccgc ccgcgccggc ctcttcaacg tgcatccacg cagtgtgtca   2460
ttcccgtcac ggactctcgt ctcatccggc cccttctctc gagcaacacc caccaatctc   2520
ctcgtgggtc gtggcggcct ctatataacg ccaagacatc gatcagacat ccatccatcc   2580
```

```
atccacactc acacagtcgc tgtagtagct agcaagcccc taggtgcttg cttgacctac      2640
tgctctgccc gtgaccagtc gt                                                2662

<210> SEQ ID NO 29
<211> LENGTH: 2732
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 16 PRO-V1

<400> SEQUENCE: 29
ttagttgcag acggtttttc ccctgctagg agatttccga gagaaaaaaa aggcactaca        60
ggttaaccaa aaccaccaac ctttggagcg tcgaggtcga cgggcatttg cgtagttgaa       120
gcttacaaag ttgcatatga gatgagtgcc ggacatgaag cggataacgt tttaaactgg       180
caacaatatc tagctgtttc aaattcaggc gtgggaagct acgcctacgc gccctggacg       240
gcgtgtaaag agccagcatc ggcatcattg tcaaacgatc gacaaggcca agaaattcca       300
aatatattat taataaaaaa gaaggcacaa attagtttgg tttttttagta tgtgtggcgg      360 aggaaatttt gagaacgaac gtatcaaaga aggcacaaga cgatatagat tgacgcggct       420
agaagttgca gcaagacagt gggtacggtc ttatatatcc taataaataa aaaataaaac       480
tatagtgtgt caaatgtcaa caagaggagg aggcagccaa attagcagag ggagacaagt       540
agagcacgcc ttattagctt gcttatttat cgtggtggtg tacttgttaa ttactggcac       600
gcattatcaa caacgcagtt ctggatgtga atctagacaa acatttgtct aggttccgca       660
cgtatagttt ttttcctctt tttttgggg gggggtggg gggggaacg gaagctgtaa        720 taaacggtac taggaacgaa agcaaccgcc gcgcgcatgt ttttgcaata gattacggtg       780
aaatctatat cttttgtaat gcctagtata ttatgatgca gacttggtta tttggacgta       840
tttcgtatgt tagcttttat atattttggt gatgttgaca tgctgaatta tgtactcaag       900
taagccttgg taatatatca ttttgcggta ttttggtgct gtatatttt gctgtaaatt       960 atgtttcgaa tttatgatgt aatggatgaa atttgaataa gtttgtgtgg tcattgcacc      1020
aagtcagaga cgtataatca catcttactc gcgtgcactc taccaaacaa agtctgagtt      1080
caacatgcct aaacagacac agcccaccaa acgacatctc aactcatcat acctcgacag      1140
atacagtctg ccaaacacat gtgaaaatct cagctcaact tgactagagt cagcttgtta      1200
gggatgaaat gggaattctg gattcaccac ggacaccaaa cacacccta gatgctcctg      1260 gatgctccag tgcacgcggt cagccaggag aatagcgtca aagcaacgta tatctgatat      1320
cctggatgct ccagtgtaat gtgatattga gtcgattgca atactttgct cacaggcgat      1380
atttcgagaa gagaaaaaga cacaggaaaa gattatatat gtccacttca acatcatgat      1440
ctgaacacgt acgtatacaa aaatcatact ccgtagcaga gactgagagg catgaaacca      1500
gcctcattgg cctggacgcg tgaagtttgc gtgcatgcgc atgcgctttt tcttgttgct      1560
cgactatata ttacccttct caagtaaatg ggtaagtttt aatttgcgcc actgattatt      1620
tgcatggaaa aacataaacc gatattgcac cgacgcgagc cccaattttt aaactagcaa      1680
atctctagcg gcgcctagaa atgaataaa tcgggatcta tctcttgaaa cacgcataga      1740
tggcagcacg cggtggagac caagaagccc tggagaagga gccgttgtag ctggccgggg      1800
ttcaaaactg aactgcagga gcacgtacca tctcatacta gtactaaatc tttaatcttc      1860
```

```
tcaagtggag ttcctcttgc cacccgaagc ggaaggaggt caaccctacg caccacgagg    1920
cacaatagca aaccgtgtcc ctctagttaa gttaattacc ccatgtaaac gtgttcttcc    1980
tttcagactt gcaatgggta atgttcacaa gtactgtagt tgcattactg gtaataacgc    2040
gatggagtat ttagcgatgc aaaatttcca aaacaagctt gtctcgtcag tgacacgatt    2100
tggcgacact caacacaaca gtttctcacc tttacaaata ctgcccgtta tagatttgtt    2160
aatactctct tcatctcata ttaagtgtcg aaatattaca tgtatctaga cgctttctag    2220
acatagataa attcatattt cgacaacttt gagacagtta atatgggaca gagggagtac    2280
ctgagacgag cttagccact ctctcttttt tcagaacgta aactcatgcg tgtgactgag    2340
tttcttccaa gagtttgtaa agaaattaat cgataatgtt cagaacttat cctctctctt    2400
tatatatttt cagacacagt atgatccact tgggcatcga gatccaccct tccatatagt    2460
actatattct actgccacga gcccatatcg agtgtctacc aaactaggag ctcgatcgtg    2520
atgcacatga ccgaatcaca ctccacatgc acacaacaca tgggatgtgt ctaccaaact    2580
ggctcccctt gggtaggtag atatgcaaca tttggctagc taaagttcta taaatacccc    2640
cttggcaccc cttgcatatc tcacacacag cttcttcttc tatctatccc acacaaagcc    2700
ttccagctcc ttaagcctac aactgaccaa cc                                 2732
```

<210> SEQ ID NO 30
<211> LENGTH: 2184
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Root Hybrid 18 PRO

<400> SEQUENCE: 30

```
ttagttgcag acggtttttc ccctgctagg agatttccga gagaaaaaaa aggcactaca      60
ggttaaccaa aaccaccaac ctttggagcg tcgaggtcga cgggcatttg cgtagttgaa     120
gcttacaaag ttgcatatga gatgagtgcc ggacatgaag cggataacgt tttaaactgg     180
caacaatatc tagctgtttc aaattcaggc gtgggaagct acgcctacgc gccctggacg     240
gcgtgtaaag agccagcatc ggcatcattg tcaaacgatc gacaaggcca agaaattcca     300
aatatattat taataaaaaa gaaggcacaa attagtttgg ttttttagta tgtgtggcgg     360
aggaaatttt gagaacgaac gtatcaaaga aggcacaaga cgatatagat tgacgcggct     420
agaagttgca gcaagacagt gggtacggtc ttatatatcc taataaataa aaaataaaac     480
tatagtgtgt caaatgtcaa caagaggagg aggcagccaa attagcagag ggagacaagt     540
agagcacgcc ttattagctt gcttatttat cgtggtggtg tacttgttaa ttactggcac     600
gcattatcaa caacgcagtt ctggatgtga atctagacaa acatttgtct aggttccgca     660
cgtatagttt ttttcctctt ttttttgggg gggggtggg gggggaacg gaagctgtaa      720 taaacggtac taggaacgaa agcaaccgcc gcgcgcatgt ttttgcaata gattacggtg     780
aatttcagac ctgcattcca tgagaaacga acggggcttt agcgggccac gtgacagtga     840
cgaagggtcg cagtcgctgc tggacggact acagacagag aggcgaagca tgcaattgaa     900
ttttcgctag cggaaagtta tcatctaatc tccaaccctc cttcctacgg ctggatctga     960
aaattgacga cctgaacccc tgaacggtgc cggtagcaat tgcaggtctc actcacatgc    1020
taaatccagc aaccaaacac gaaggaatat atgtgatctg gacagaacat gcaagcgaat    1080
```

```
aatacataga gtcgtaccaa ccctacacag ttcaacgaat taatcactgg gttcacgggc    1140
atgctcacgt ccaaaatccc agcgacattt tataagcgct aagcggaatg atccagacgg    1200
ggccagctcg agcaccacat ggtttgactt ggaccgacta gcactccccc gctaggcacg    1260
tagtacgtgg tatgtgtgga aacgattggt tcgttgtagg gagtcagtca gatcagatat    1320
gatgcttctc gtgtgttgat tttcttcctc tgaactgaaa ggaagcatgc aagttttaca    1380
agctaaactc agcagcggaa gctatgcata cgttccactg gctgcagaac agggcaggcc    1440
ggcggctagc tcctgtgagc tgtgttggag gagaataata tcttgtcgtt tggctttgct    1500
cgggtggata cttttttttc ttttgacagc tgctcgggtg gatactgata cactatgaag    1560
accgaaaaaa agaagcgaag catataaaca gacggatcat tggggccaa gccagcaggt    1620 agtgcggtgg aacattatgt agaatgaatc ggttcttgct gtgcagacag ctcagctcag    1680
cacactcctg gcccaaaaca aagtgcatgt ggtgtatttt cgtatactag ctaacaaatg    1740
cttaagcccc tgtttgaaat attgtatttt cggcggacgg gcactggctt actgaaatct    1800
tgccaggagg cacggacagg tgcttagcag ccaagtaatg tacagtaaat ccggcaaatt    1860
gccaggggag tggttcgatt caatcaacga atgcgattcc cgatataaat tatccccagt    1920
ttatttttga ttttatacaa cgcgtcgccg acgcggtccc caccccgtgc gcgtcgcaag    1980
gtccacacgt gtcctctctc cgacgcttcc tagctcacgc cgtccttgat tgacctgcct    2040
cgccatctat aaatggcaaa ccaggctaag gctcatttct atactccctc ttcctgctct    2100
gctctctgct ctagtttact ccactgaccc aaagagagaa agaaagcac tcagaacttg    2160 agatcagcat ccaggagatc ggcc                                           2184
```

<210> SEQ ID NO 31
<211> LENGTH: 1151
<212> TYPE: DNA
<213> ORGANISM: Zea mays
<220> FEATURE:
<221> NAME/KEY: misc_feature
<223> OTHER INFORMATION: ZM-PCO118362A PRO (TR 1)

<400> SEQUENCE: 31

```
aactttctta atattttcct taattacctc ccatacatct taaatgtcta gtggtagcat      60
atatacctcc aaagtccaaa gctagttgta agtgacacaa aaaattatgc gtactcattg     120
aacatatctg ttacactcac taactagaca tgtttagtgc atctacgtta gctagttgca     180
gaccccaatc ctatattgtt cataaatttt tatcataagg ttccctgctg caatttagat     240
atccagcatg ctcttcaatt ttggtgctca cccttacggg tatgccctca ctgccttta     300 taattgtata agggaaatat tattcaatat aatgtcctaa aaattggcaa tatcaatcta     360
aaaatcgtta tgaataggat gtaaacaaag ctactatctg tccatatata acgtcacagg     420
aaggacaaaa aattcagtca gcgatcgaga acggcaaaga aaaccatat tattgttgct     480 tgccgacata aatttaagta taggacaaaa aaaaagcca catcatatta catactatgg     540
gcttaccaga caaaatgaaa taaacgtgtg catgcatgca tgcatggtac gaacgtctgg     600
atagagtctc cgagctgagt gtggtccgac gtggaagtgt acgtctcaac acacgacgca     660
tgtgaccgac aagggcaagt tgaagtctat gcatggatgg gcctgagcgc cgcgctgaat     720
gaatctggac gggtggtagg gcatctcggt gggcaaaaca ataactccg tgtgctgcat     780 ggctgccttt ggaatctttg catgcagctg tgtgctgaac tgaaacccctt cgctctatct     840 atataaacag atgcccttcg ctctcgtctc agcaggcagc atcgtctcaa gttttgttct     900
```

```
cctctcctag ctagccagca cctgcagatc tgctcgttgc cttggtaatt catcatgtag    960
tacgtagcat cagctagtat ttatctcaag tatatatata cgcatatgtg tcgtcgcagt   1020
actttccctt atctctctat acacactaca cgcatacata ccaataccat ccgtcttaac   1080
tcttaatctt tgcctgcata cgtacactgc acgtacgtac tgcagggcta ctgattttgt   1140
ggaacgaagc g                                                        1151
```

<210> SEQ ID NO 32
<211> LENGTH: 911
<212> TYPE: DNA
<213> ORGANISM: Zea mays
<220> FEATURE:
<221> NAME/KEY: misc_feature
<223> OTHER INFORMATION: ZM-PCO118362A PRO (TR 2)

<400> SEQUENCE: 32

```
atccagcatg ctcttcaatt ttggtgctca cccttacggg tatgccctca ctgcctttta    60
taattgtata agggaaatat tattcaatat aatgtcctaa aaattggcaa tatcaatcta   120
aaaatcgtta tgaataggat gtaaacaaag ctactatctg tccatatata acgtcacagg   180
aaggacaaaa aattcagtca gcgatcgaga acggcaaaga aaaaccatat tattgttgct   240
tgccgacata aatttaagta taggacaaaa aaaaagcca catcatatta catactatgg   300
gcttaccaga caaaatgaaa taaacgtgtg catgcatgca tgcatggtac gaacgtctgg   360
atagagtctc cgagctgagt gtggtccgac gtggaagtgt acgtctcaac acacgacgca   420
tgtgaccgac aagggcaagt tgaagtctat gcatggatgg gcctgagcgc cgcgctgaat   480
gaatctggac gggtggtagg gcatctcggt gggcaaaaca aataactccg tgtgctgcat   540
ggctgccttt ggaatctttg catgcagctg tgtgctgaac tgaaacccct cgctctatct   600
atataaacag atgcccttcg ctctcgtctc agcaggcagc atcgtctcaa gttttgttct   660
cctctcctag ctagccagca cctgcagatc tgctcgttgc cttggtaatt catcatgtag   720
tacgtagcat cagctagtat ttatctcaag tatatatata cgcatatgtg tcgtcgcagt   780
actttccctt atctctctat acacactaca cgcatacata ccaataccat ccgtcttaac   840
tcttaatctt tgcctgcata cgtacactgc acgtacgtac tgcagggcta ctgattttgt   900
ggaacgaagc g                                                        911
```

<210> SEQ ID NO 33
<211> LENGTH: 1710
<212> TYPE: DNA
<213> ORGANISM: Sorghum bicolor
<220> FEATURE:
<221> NAME/KEY: misc_feature
<223> OTHER INFORMATION: SB-RCC3 PRO [No RCST fix]

<400> SEQUENCE: 33

```
ttttaagtat gaccaatttt taagtataaa cccctcacga ttggttattt ttttaagtat    60
aaccaatttt taagtataaa cccctcacca atttttaagt ataaacctag cgactaataa   120
acacaacttc ttgccaaagt gtgagcatca ccattggatc tgcgcccctc acgaacagtc   180
ttcgccgggg taaaattctc caaattaaag tcatcttgat gtccttgatc acctgtccat   240
aaggcccaat cccagctcca cgtatacttc tgataagatt gacatagtca cttgcatgcc   300
agtgtggaac tctggatgcc taggtcagag gctagtgact ggccttcccg gcatgctagc   360
atgtagcatg ccaaggatct ggctgctcca ggtttgttat gcctgacatc accataggga   420
```

```
tgagagcaag tataataata ggctgtaagc tttaaatgct caggtggaga aaaaaaggag    480
aggagaggag agagaaaagt gggctataag cttatagctg tgttagacat aagaatcaga    540
aacttcgtat gagagacagg tgagctatat attaataaca aagagctaac tattatatga    600
gtgaaccgag agaaggctgt aaaaaaactt acacaatcaa cgatcgacat tattattaac    660
cttgctctgt cttgcgagac ctctttgaca aagctacatc aatgccggcc aagtgccttg    720
ggatttggga atggcttctt tcctcccttc ctcggttgtc ccccaaggcc taggcttgcc    780
acgctgtatt cagtcgcagc cgcctttact tttgcccttt gtggaagttt tgtaataaat    840
ggtctgattc tatcttcgga tagatgaagc cggatgtttc atccattatc taaaaaaaag    900
ttggttgctt tgctgagcta agaaagtgta atccagagtg ctcgtaacgt attcatgtac    960
ataactatta tctaatataa atcttctttt gtcgcaaaaa aaggtcggcc catcagaaca   1020
aatgatcaat gtaaggccca aaatttgtgt ctcaaatgtc atttacgttt ccaagctaaa   1080
caaaaacaca ggattcatat aattttgctg gtggcttagg cttcgtccaa tagtgcttag   1140
tttaatttgt atatacctgc accatggtat tcgtctggcc ttggatcttg cgcatcaatt   1200
gcctatggac gatgatcgca gccacgccac attcattttt aatcgccatt tgcttgacac   1260
ccaatgcctc tgcaccactt gcgcacgcta cgcaccgtct gatacgccaa gatcccgagc   1320
taaaataaca cccaatcatc agatgaaaac aagcgcgagt gcgagccagc ccatggcagc   1380
gatcttggcc atttgcggag ccaactgaaa gccgtgcaca aaatattcga caccgtataa   1440
gggaaaacac tagttatacg aggtgggcaa taatccagat ctcggactct tcctaacccg   1500
gttcacatgc atagcatata tgatggccgg ccggggttca catgaacgcc atcccgtgcc   1560
ctagtgcact gatttcttaa tcccgggtct caactataaa tacccccttg gtgacaccgc   1620
gatcaaagca tcgcaaacaa gcctagctaa gagctctcta actacattag atagagtgat   1680
ctcgagaggt aactggcttg tgatcgagca                                    1710
```

<210> SEQ ID NO 34
<211> LENGTH: 1066
<212> TYPE: DNA
<213> ORGANISM: Sorghum bicolor
<220> FEATURE:
<221> NAME/KEY: misc_feature
<223> OTHER INFORMATION: SB-TIP2-3 PRO (TR 3)

<400> SEQUENCE: 34

```
cctttttggt gtcatcatct tcgtttgtgc aataatactg caactcaatg aagtcactgc     60
gactcataag agccctgtca tcaccttgca actggcagtt ttcaattggt gtaccagcgc    120
aagatccata gattaatctt gtttgcctca cctaccccaa atggaggatg ttcactgcat    180
tgatgtcaca atccgacctt cttaaccgct ctatgtcaca actttaacat gaatgatata    240
tcgtttcctc aaaaacatga atgatatatc actacagaac tcagtatgca gtagattcct    300
gaacgcaaga gctgttgcaa tgttaatcta ctaggtgata tcttactcgg taagatactc    360
aggccgaggt ccgaggaatt acccttttgt tgcaggagaa ccaagtcata tgaatgaagc    420
agcagctcag taatgatcca ccgactacgc tacttctagc atagaattag taatcttttc    480
taatactgtt gtaaatttgt aacaacaaaa caagaaccac gccacggaag aacggtgaga    540
aaaagaaacc tttgctaacg tactattcat gaatttgaag attttgtatg gatgcatcag    600
tagacgatgc agggtagaaa taaaggatcg attcagataa tcaatccgca ccgccattga    660
tttgtttagg gatgagatga gaattgagaa ttgggataac atatatctgc tccaaggtct    720
```

```
tgttctcctc gctgtcttat ggtgtatcct aacgtggctc ggcctaaaca accacaattc      780
cacagcagtt tagcgagtta gggcggttgg tcggccaata tcagccacaa aacacgaagc      840
aaaatttaaa ttatcaatca tgtggtgatc attgcacacc gcccatagta ttgtattgca      900
catctgaggc agggctccag cctccaggtc cattagcgcc ttatgatgtg tatttaagga      960
gactgagctg aaggaactct cgcatcagcc tgataagcta tagccagcca tcttctctga     1020
attccaactc agtccaaggg ctggaagcta aagtaccgt cagaga                     1066
```

<210> SEQ ID NO 35
<211> LENGTH: 2583
<212> TYPE: DNA
<213> ORGANISM: Artificial Sequence
<220> FEATURE:
<223> OTHER INFORMATION: Synthetic

<400> SEQUENCE: 35

```
cgtgtgcatg catgcatgca tggtacgaac gtctggatag agtctccgag ctgagtgtgg       60
tccgacgtgg aagtgtacgt ctcaacacac gacgcatgtg accgacaagg gcaagttgaa      120
gtctatgcat ggatgggcct gagcgccgcg ctgaatgaat ctggacgggt ggtagggcat      180
ctcggtgggc aaaacaaata actccgtgtg ctgcatggct gcctttggaa tctttgcatg      240
cagctgtgtg ctgaactact cgccttgtgg ctcctcctga accacctgct cttctcctgt      300
gggggggtgt gagacagcaa gggtgagctc acacatgatc atagctcaac aagttgtggg      360
gaaccagtgg acatgaactc acaaggtgg gagttcatgt gatggttcct ctagatgctc       420
aacttgttgc attatattac gcaattgctc cgacgcttca tcaattaatc ctccttagtg      480
atattaaata acggaataat attagagaaa taaacaataa tctaagacat tagcgcataa      540
agatgtgaca aaatgattga gtctggtcat attccctcc ttcatccttt attgcataaa       600
agattgtagt ttacaccttc ggctttacaa aggagagctc gaaggtaata ttacagcttc      660
gaaggcggag tgatttgatt ctcccttgtt caaaaagcga gatctcttca tatcattgtg      720
cctctattta tagtaaccaa gtacaatttc atatgaaatt acaaacatgc tcatggacat      780
gataattcca gtgcacatcc aaccctgctt gatacaaaac atgctcataa tcatgatgat      840
tcaagtgcac atccaccctg ctcgatacaa cagttggcga cctggtgtga gagtcagacc      900
agacgggctt tcacaatcgc catgcatgtc attctctcgt ggtccacgtg tttattaata      960
ttgccattaa ttggagggaa ataaaatcaa caagaatagc ttattgatga gtcatatatt     1020
atgaatacat cttatcatct taccaaacaa aaacatatga ccgtcgatga cctgaaacta     1080
gactattcgg gatctgcaat gatctgcttg taaatattaa tttgcacatc acgccattgc     1140
atgcacatcg gcgtgggcat tattaatttg gattggacga aaaatcaacc agagggcgtc     1200
acccttttgc tagttggcct tgtaatacct agcatgtagc atgccaagga tctggctgct     1260
ccaggtttgt tatgcctgac atcaccatag ggatgagagc aagtataata ataggctgta     1320
agctttaaat gctcaggtgg agaaaaaaag gagaggagag gagagagaaa agtgggctat     1380
aagcttatag ctgtgttaga cataagaatc agaaacttcg tatgagagac aggtgagcta     1440
tatattaata acaaagagct aactattata tgagtgaacc gagagaaggc tgtaaaaaaa     1500
cttacacaat caacgatcga cattattatt aaccttgctc tgtcttgcga gacctctttg     1560
acaaagctac atcaatgccg gccaagtgcc ttgggatttg gaatggctt ctttcctccc      1620 ttcctcggtt gtccccaag gcctaggctt gccacgctgt attcagtcgc agccgccttt      1680
acttttgccc tttgtggaag ttttgtaata aatggtctga ttctatcttc ggatagatga     1740
```

-continued

| | |
|---|---|
| agccggatgt tcatccatt atctaaaaaa aagttggttg ctttgctgag ctaagaaagt | 1800 |
| gtaatccaga gtgctcgtaa cgtattaatg tacataacta ttatctaata taaatcttct | 1860 |
| tttgtcgcaa aaaaggtcg gcccatcaga acaaatgatc aatgtaaggc ccaaatttg | 1920 |
| tgtctcaaat gtcatttacg tttccaagct aaacaaaaac acaggattca tataattttg | 1980 |
| ctggtggctt aggcttcgtc caatagtgct tagtttaatt tgtatatacc tgcaccatgg | 2040 |
| tattcgtctg gccttggatc ttgcgcatca attgcctatg gacgatgatc gcagccacgc | 2100 |
| cacattcatt tttaatcgcc atttgcttga cacccaatgc ctctgcacca cttgcgcacg | 2160 |
| ctacgcaccg tctgatacgc caagatcccg agctaaaata cacccaatc atcagatgaa | 2220 |
| aacaagcgcg agtgcgagcc agcccatggc agcgatcttg gccatttgcg gagccaactg | 2280 |
| aaagccgtgc acaaaatatt cgacaccgta taagggaaaa cactagttat acgaggtggg | 2340 |
| caataatcca gatctcggac tcttcctaac ccggttcaca tgcatagcat atatgatggc | 2400 |
| cggccggggt tcacatgaac gccatcccgt gccctagtgc actgatttct taatcccggg | 2460 |
| tctcaactat aaatacccc ttggtgacac cgcgatcaaa gcatcgcaaa caagcctagc | 2520 |
| taagagctct ctaactacat tagatagagt gatctcgaga ggtaactggc ttgtgatcga | 2580 |
| gca | 2583 |

<210> SEQ ID NO 36
<211> LENGTH: 2625
<212> TYPE: DNA
<213> ORGANISM: Artificial Sequence
<220> FEATURE:
<223> OTHER INFORMATION: Synthetic

<400> SEQUENCE: 36

| | |
|---|---|
| ctagcatgta gcatgccaag gatctggctg ctccaggttt gttatgcctg acatcaccat | 60 |
| agggatgaga gcaagtataa taataggctg taagctttaa atgctcaggt ggagaaaaaa | 120 |
| aggagaggag aggagagaga aagtgggct ataagcttat agctgtgtta gacataagaa | 180 |
| tcagaaactt cgtatgagag acaggtgagc tatatattaa taacaaagag ctaactatta | 240 |
| tatgagtgaa ccgagagaag gctgtaaaaa aacttacaca atcaacgatc gacattatta | 300 |
| ttaaccttgc tctgtcttgc gagacctctt tgacaaagct acatcaatgc cggccaagtg | 360 |
| ccttgggatt tgggaatggc ttctttcctc ccttcctcgg ttgtcccca aggcctaggc | 420 |
| ttgccacgct gtattcagtc gcagccgcct ttacttttgc cctttgtgga agttttgtaa | 480 |
| taaatggtct gattctatct tcggatagat gaagccggat gtttcatcca ttatctaaaa | 540 |
| aaaagttggt tgctttgctg agctaagaaa gtgtaatcca gagtgctcgt aacgtattaa | 600 |
| tgtacataac tattatctaa tataaatctt cttttgtcgc aaaaaaaggt cggcccatca | 660 |
| gaacaaatga tcaatgtaag gcccaaaatt tgtgtctcaa atgtcattta cgtttccaag | 720 |
| ctaaacaaaa acacaggatt catataattt tgctggtggc ttaggcttcg tccaatagtg | 780 |
| cttagtttaa tttgtatata cctgcaccat ggtattcgtc tggccttgga tcttgcgcat | 840 |
| caattgccta tggacgatga tcgcagccac gccacattca ttttaatcg ccatttgctt | 900 |
| gacacccaat gcctctgcac cacttgcgca cgctacgcac cgtctgatac gccaagatcc | 960 |
| cgagctaaaa taacacccaa tcatcagatg aaaacaagcg cgagtgcgag ccagcccatg | 1020 |
| gcagcgatct tggccatttg cggagccaac tgaaagccgt gcacaaaata ttcgacaccg | 1080 |
| tataagggaa aacactagtt atacgaggtg ggcaataatc cagatctcgg actcttccta | 1140 |

```
acccggttca catgcatagc atatatgatg gccggccggg gttcacatga acgccatccc    1200
gtgccctagt gcactgattt cttaatcccc gtgtgcatgc atgcatgcat ggtacgaacg    1260
tctggataga gtctccgagc tgagtgtggt ccgacgtgga agtgtacgtc tcaacacacg    1320
acgcatgtga ccgacaaggg caagttgaag tctatgcatg gatgggcctg agcgccgcgc    1380
tgaatgaatc tggacgggtg gtagggcatc tcggtgggca aaacaaataa ctccgtgtgc    1440
tgcatggctg cctttggaat ctttgcatgc agctgtgtgc tgaactactc gccttgtggc    1500
tcctcctgaa ccacctgctc ttctcctgtg gggggtgtg agacagcaag ggtgagctca     1560
cacatgatca tagctcaaca agttgtgggg aaccagtgga catgaactca caaaggtggg    1620
agttcatgtg atggttcctc tagatgctca acttgttgca ttatattacg caattgctcc    1680
gacgcttcat caattaatcc tccttagtga tattaaataa cggaataata ttagagaaat    1740
aaacaataat ctaagacatt agcgcataaa gatgtgacaa aatgattgag tctggtcata    1800
ttaccctcct tcatccttta ttgcataaaa gattgtagtt tacaccttcg gctttacaaa    1860
ggagagctcg aagtaatat tacagcttcg aaggcggagt gatttgattc tcccttgttc     1920
aaaaagcgag atctcttcat atcattgtgc ctctatttat agtaaccaag tacaatttca    1980
tatgaaatta caaacatgct catggacatg ataattccag tgcacatcca accctgcttg    2040
atacaaaaca tgctcataat catgatgatt caagtgcaca tccaccctgc tcgatacaac    2100
agttggcgac ctggtgtgag agtcagacca gacgggcttt cacaatcgcc atgcatgtca    2160
ttctctcgtg gtccacgtgt ttattaatat tgccattaat tggagggaaa taaaatcaac    2220
aagaatagct tattgatgag tcatatatta tgaatacatc ttatcatctt accaaacaaa    2280
aacatatgac cgtcgatgac ctgaaactag actattcggg atctgcaatg atctgcttgt    2340
aaatattaat ttgcacatca cgccattgca tgcacatcgg cgtgggcatt attaatttgg    2400
attggacgaa aaatcaacca gagggcgtca ccctttttgct agttggcctt gtaatactta    2460
taataattat ccgtatagtc tagtacgtac gggacatcac gccattgcct gttgtgtata    2520
aaaagcgagc atgagctagg ttgggagcag agcaaagcgt agtcatcacc tgtgtctagg    2580
ttgggagcaa agcaaagaga gagaggaaag ctagctagct agcgg                    2625
```

<210> SEQ ID NO 37
<211> LENGTH: 2625
<212> TYPE: DNA
<213> ORGANISM: Artificial Sequence
<220> FEATURE:
<223> OTHER INFORMATION: Synthetic

<400> SEQUENCE: 37

```
cgtgtgcatg catgcatgca tggtacgaac gtctggatag agtctccgag ctgagtgtgg      60
tccgacgtgg aagtgtacgt ctcaacacac gacgcatgtg accgacaagg gcaagttgaa     120
gtctatgcat ggatgggcct gagcgccgcg ctgaatgaat ctggacgggt ggtagggcat     180
ctcggtgggc aaaacaaata actccgtgtg ctgcatggct gcctttggaa tctttgcatg     240
cagctgtgtg ctgaactagc atgtagcatg ccaaggatct ggctgctcca ggtttgttat     300
gcctgacatc accataggga tgagagcaag tataataata ggctgtaagc tttaaatgct     360
caggtggaga aaaaaggag aggagaggag agagaaaagt gggctataag cttatagctg      420
tgttagacat aagaatcaga aacttcgtat gagagacagg tgagctatat attaataaca     480
aagagctaac tattatatga gtgaaccgag agaaggctgt aaaaaaactt acacaatcaa     540
cgatcgacat tattattaac cttgctctgt cttgcgagac ctctttgaca aagctacatc     600
```

```
aatgccggcc aagtgccttg ggatttggga atggcttctt tcctcccttc ctcggttgtc    660 cccccaaggcc taggcttgcc acgctgtatt cagtcgcagc cgcctttact tttgcccttt    720
gtggaagttt tgtaataaat ggtctgattc tatcttcgga tagatgaagc cggatgtttc    780
atccattatc taaaaaaaag ttggttgctt tgctgagcta agaaagtgta atccagagtg    840
ctcgtaacgt attaatgtac ataactatta tctaatataa atcttctttt gtcgcaaaaa    900
aaggtcggcc catcagaaca aatgatcaat gtaaggccca aaatttgtgt ctcaaatgtc    960
atttacgttt ccaagctaaa caaaaacaca ggattcatat aattttgctg gtggcttagg   1020
cttcgtccaa tagtgcttag tttaatttgt atatacctgc accatggtat tcgtctggcc   1080
ttggatcttg cgcatcaatt gcctatggac gatgatcgca gccacgccac attcattttt   1140
aatcgccatt tgcttgacac ccaatgcctc tgcaccactt gcgcacgcta cgcaccgtct   1200
gatacgccaa gatcccgagc taaaataaca cccaatcatc agatgaaaac aagcgcgagt   1260
gcgagccagc ccatggcagc gatcttggcc atttgcggag ccaactgaaa gccgtgcaca   1320
aaatattcga caccgtataa gggaaaacac tagttatacg aggtgggcaa taatccagat   1380
ctcggactct tcctaacccg gttcacatgc atagcatata tgatggccgg ccggggttca   1440
catgaacgcc atcccgtgcc ctagtgcact gatttcttaa tcccctactc gccttgtggc   1500
tcctcctgaa ccacctgctc ttctcctgtg gggggtgtg agacagcaag ggtgagctca   1560
cacatgatca tagctcaaca agttgtgggg aaccagtgga catgaactca caaaggtggg   1620
agttcatgtg atggttcctc tagatgctca acttgttgca ttatattacg caattgctcc   1680
gacgcttcat caattaatcc tccttagtga tattaaataa cggaataata ttagagaaat   1740
aaacaataat ctaagacatt agcgcataaa gatgtgacaa aatgattgag tctggtcata   1800
ttaccctcct tcatccttta ttgcataaaa gattgtagtt tacaccttcg gctttacaaa   1860
ggagagctcg aaggtaatat tacagcttcg aaggcggagt gatttgattc tcccttgttc   1920
aaaaagcgag atctcttcat atcattgtgc ctctatttat agtaaccaag tacaatttca   1980
tatgaaatta caaacatgct catggacatg ataattccag tgcacatcca accctgcttg   2040
atacaaaaca tgctcataat catgatgatt caagtgcaca tccaccctgc tcgatacaac   2100
agttggcgac ctggtgtgag agtcagacca gacgggcttt cacaatcgcc atgcatgtca   2160
ttctctcgtg gtccacgtgt ttattaatat tgccattaat tggagggaaa taaatcaac   2220 aagaatagct tattgatgag tcatatatta tgaatacatc ttatcatctt accaaacaaa   2280
aacatatgac cgtcgatgac ctgaaactag actattcggg atctgcaatg atctgcttgt   2340
aaatattaat ttgcacatca cgccattgca tgcacatcgg cgtgggcatt attaatttgg   2400
attggacgaa aaatcaacca gagggcgtca ccctttgct agttggcctt gtaatactta   2460
taataattat ccgtatagtc tagtacgtac gggacatcac gccattgcct gttgtgtata   2520
aaaagcgagc atgagctagg ttgggagcag agcaaagcgt agtcatcacc tgtgtctagg   2580
ttgggagcaa agcaaagaga gagaggaaag ctagctagct agcgg         2625
```

<210> SEQ ID NO 38
<211> LENGTH: 3979
<212> TYPE: DNA
<213> ORGANISM: Artificial Sequence
<220> FEATURE:
<223> OTHER INFORMATION: Synthetic

<400> SEQUENCE: 38

-continued

```
agtcgtagag gccaattgat gatgtgccta atagatacat atggtaagga taataatcat    60
ttcttactac attattcata caaaaaataa ttaagaatca aaaattatga gaaacacctc   120
ttggtgtggt gtagttgtgg gtgcatcact ccacccatta gggtccaaat cttggtgctc   180
acattatgcc ggggtctccc ttacattctt cctatcaatt ttttttgtaa atctacagta   240
gatgtctata atgaaaattt tcaaatatct aaaatagcaa cgaaatctc atatgttacc    300
tgtagaagct caacactttt gtattgcaca caatgttaat aaaataaaac tcttgctaaa   360
acttgtaatg actacctaat aacaacatat tgtgttgtat atgaatttaa gcccatctaa   420
atattcggaa tattcgctta tcattcaaaa gatttagatc aacaaaaaga agtgaagaac   480
tttatatttt ggtaggtaaa atgtataaca aaacaaatct ttcagaaaat cacttgatat   540
ttccaaacac aatacatcta aattgcaata aaaagaatt ttagaaaaca aaaacataaa    600
aatatgggtg ttgctgtttg aatttcaata ctacaaaagg acatatatgt gacgtcatat   660
tagtgtcggg cccagcagga ccgccaatga tgtatagcat cagtgttggt cggtgcaaaa   720
cccgccactg atatacagct gcgcgtttcc cactttcgac ctgatgaaca tcagtggcgg   780
gcgttgcacc cgcccgccac taattttaa gtagaggacc ttaaatctaa gttgacgtat    840
gagaaccatt ggattaagat ataatggcac tctcttctct tctacttgct atcgttggat   900
taatatccga cggtcaagca catcggctca tgtctaacaa aaaaaaggca acttcttaat   960
agcaaaaccg taaaaatata tattttatta tacaagtcta gcccgcgagc tgcttggttc  1020
accctgctag ttaagatagt aacttgtagc tcttcttgtt gcgtataagt tgttaaacat  1080
tgtaaaagcc tcctcaagta tcatgtatac ctgtgatacc tcacgacgat ttaaacgcac  1140
aattgctgta taatggatat agattggttc taggctccag cgatcgatta tccatgtaac  1200
tacgtacaaa cgagtaaacc tccaaaatca caccgctgtc acacatcgtc tgcacgcagt  1260
tgcctgaaac caatccactg cacctagccc acgggttgaa taaaaccgcc cgcgccggcc  1320
tcttcaacgt gcatccacgc agtgtgtcat tcccgtcacg gactctcgtc tcatccggcc  1380
ccttctctcg agcaacaccc accaatctcc tacgcagttg tccttttggta cattcacaag  1440
tttgatctta tcatcaccat cagaagttca gaaagtctcg tagaaaacaa atggaaatga  1500
atactgctta cttagctcaa attcatattc cgttgttaca ggatacttaa aaaaggtacc  1560
aaaggctgtt cctaatcata cgctgaagtc gttgccacca atggcagctg tactgtcata  1620
ttgtcgtggt ttttcaattg ctgtacctga tgcaaacgta atgggtttac taatcttgca  1680
cccgccgact tcaaaatgaa gagtgctaat ttggttcacg tcaccatcac cggctcgaac  1740
tgtctagaat ggcaggcaaa gatgattgga caggcatgca gggaaaaaga gcaccgatga  1800
cgatctatgc gagttccac cattgcgagc aatgattatc agccacacga cttactcttc    1860
agagctaacc actgccatgc agagaaaaag tgaagcatat tgtcaggatc tacaacgaag  1920
tgaaacaatc aggcatgcta aagtgctgaa actttactga tctctcatgt tggacaacaa  1980
agaatacggg aatacatcag caacgcaact cttgagcttt gcttgctgaa tgaccagcta  2040
gaatttccaa gcatttacag gaacatgact ttaagtttca gaaaacaaa tacaaggcca   2100
ctaagggcat gttcacttca gcttataagc cggctgaaaa gctgaacgg ctgatttgtt    2160
gtgagaggaa aacactgttt ggtggctgat aagccggctg aataagctga agcgaacagg  2220
ctgtaaataa gcgtggggat aacatatcct ccagatgaca ggcaatctgc aacttgcagc  2280
gattcaaatg tacgattaac aaaatattta agcgctacac gagataatat atcctccaat  2340
tagggccttt agtattgtca ttagctcata agcatggtgc atcctcacat ggacgctgca  2400
```

-continued

```
taagaagttc ataatagcaa cagacatatg aacaaagcat ggtgcgcctg cccggccgga      2460
ctagctagta ctaccaatca tggaataagc tagtaccca aatgaaatta aaatggtttt       2520
tagcgattat ccacgccgtc cagaatactc taatccacaa gttgaggccg cccatgaagc      2580
cgcaaactca gttatcacc aaagaccaaa catgtgaaa tcagtctcta ttttgtccaa        2640
gagcatgtgg cccttggagc tttgcggctt cttcatgttg ctacatctct tcaatatgcc     2700
gatatattta ctaaggggttg tcaattgtta tcttcatcaa cttctgatct aatctcaatg    2760
tttgctcctc ttccggttga gactactggg ggatattaga atatgaatag ccaaaaagtc    2820
ttgtatagtc taaaataaag agtctcaaat agttcacttg agcttaggaa ccgaatttgt     2880
cgtcagcagt gttttttgct catagtaaat tagccaacaa tactttctat cacaccttaa     2940
cagagtactt tctttctgcc atggcttatc aaccaacagt attttttgtc aaaagcagtg     3000
attatctgtc aatcactagc gcccctctg ccggtatatc tagcgctccc atcggatctg      3060
actagagcag atcttgagcg tgggttggtg gctcagggct tgcaggaggc gttggccgtc     3120
gccggcgtag agcagtagtc gtaggcggat ctgcatcttc aagctctcct ccggtcgatt    3180
cgtgtgagtc ttcgacctct gctcaggtcg attcatgccg gcgaggggct cagtgctcgg    3240
ctcacgacgc gaaattacga gcggcagcag caaaccgggc tttcaagccc ggctctcctc    3300
gtgagctgcc ttagggctcg ttcgtttaac tattgttccc gatggattca ttcctgatga    3360
taaaaatagt ataaatttac acaatgttcc tggctggaat catttcagac ctgcattcca    3420
tgagaaacga acgggctttt agcgggccac gtgacagtga cgaagggtcg cagtcgctgc    3480
tggacggact acagacagag aggcgaagca tgcaattgaa ttttcgctag cggaaagtta    3540
tcatctaatc tccaacccctc cttcctacgg ctggatctga aaattgacga cctgaacccc   3600
tgaacggtgc cggtagcaat tgcaggtctc actcacatgc taaatccagc aaccaaacac   3660
gaaggaatat atgtgatctg gacagaacat gcaagcgaat aatacataga gtcgtaccaa   3720
ccctacacag ttcaacgaat taatcactgg gttcacgggc atgctcacgt ccaaaatccc   3780
agcgacattt tataagcgct aagcggaatg atccagacgg ggccagctcg agcaccacat   3840
ggcgtcgctc catctcgcat ctataaatac cattggccat gcacaccccgc actcccacac  3900 agcaatacag cacactagca gcagcagcag cagctcgagc tagcttagct actacgtgtg   3960
tgcaatcagc tcgatcgcc                                                 3979
```

<210> SEQ ID NO 39
<211> LENGTH: 3975
<212> TYPE: DNA
<213> ORGANISM: Artificial Sequence
<220> FEATURE:
<223> OTHER INFORMATION: Synthetic

<400> SEQUENCE: 39

```
caaactcagt ttatcaccaa agaccaaaca tgtggaaatc agtctctatt ttgtccaaga      60
gcatgtggcc cttggagctt tgcggcttct tcatgttgct acatctcttc aatatgccga    120
tatatttact aaggggttgtc aattgttatc ttcatcaact tctgatctaa tctcaatgtt   180
tgctcctctt ccggttgaga ctactggggg atattagaat atgaatagcc aaaaagtctt    240
gtatagtcta aaataaagag tctcaaatag ttcacttgag cttaggaacc gaatttgtcg    300
tcagcagtgt tttttgctca tagtaaatta gccaacaata ctttctatca cccttaaca    360 gagtactttc tttctgccat ggcttatcaa ccaacagtat tttttgtcaa aagcagtgat    420
```

```
tatctgtcaa tcactagcgc cccctctgcc ggtatatcta gcgctcccat cggatctgac    480
tagagcagat cttgagcgtg ggttggtggc tcagggcttg caggaggcgt tggccgtcgc    540
cggcgtagag cagtagtcgt aggcggatct gcatcttcaa gctctcctcc ggtcgattcg    600
tgtgagtctt cgacctctgc tcaggtcgat tcatgccggc gaggggctca gtgctcggct    660
cacgacgcga aattacgagc ggcagcagca aaccgggctt tcaagcccgg ctctcctcgt    720
gagctgcctt agggctcgtt cgtttaacta ttgttcccga tggattcatt cctgatgata    780
aaaatagtat aaatttacac aatgttcctg gctggaatca tttcagacct gcattccatg    840
agaaacgaac ggggctttag cgggccacgt gacagtgacg aagggtcgca gtcgctgctg    900
gacggactac agacagagag gcgaagcatg caattgaatt ttcgctagcg gaaagttatc    960
atctaatctc caaccctcct tcctacggct ggatctgaaa attgacgacc tgaacccctg   1020
aacggtgccg gtagcaattg caggtctcac tcacatgcta aatccagcaa ccaaacacga   1080
aggaatatat gtgatctgga cagaacatgc aagcgaataa tacatagagt cgtaccaacc   1140
ctacacagtt caacgaatta atcactgggt tcacgggcat gctcacgtcc aaaatcccag   1200
cgacatttta taagcgctaa gcggaatgat ccagacgggg ccagctcgag caccacatga   1260
gtcgtagagg ccaattgatg atgtgcctaa tagatacata tggtaaggat aataatcatt   1320
tcttactaca ttattcatac aaaaaataat taagaatcaa aaattatgag aaacacctct   1380
tggtgtggtg tagttgtggg tgcatcactc cacccattag ggtccaaatc ttggtgctca   1440
cattatgccg gggtctccct tacattcttc ctatcaattt tttttgtaaa tctacagtag   1500
atgtctataa tgaaaatttt caaatatcta aaatagcaac gaaaatctca tatgttacct   1560
gtagaagctc aacactttg tattgcacac aatgttaata aaataaaact cttgctaaaa   1620
cttgtaatga ctacctaata acaacatatt gtgttgtata tgaatttaag cccatctaaa   1680
tattcggaat attcgcttat cattcaaaag atttagatca acaaaagaa gtgaagaact   1740
ttatattttg gtaggtaaaa tgtataacaa aacaaatctt tcagaaaatc acttgatatt   1800
tccaaacaca atacatctaa attgcaataa aaagaatttt tagaaaacaa aaacataaaa   1860
atatgggtgt tgctgtttga atttcaatac tacaaaagga catatatgtg acgtcatatt   1920
agtgtcgggc ccagcaggac cgccaatgat gtatagcatc agtgttggtc ggtgcaaaac   1980
ccgccactga tatacagctg cgcgtttccc actttcgacc tgatgaacat cagtggcggg   2040
cgttgcaccc gcccgccact aattttttaag tagaggacct taaatctaag ttgacgtatg   2100
agaaccattg gattaagata taatggcact ctcttctctt ctacttgcta tcgttggatt   2160
aatatccgac ggtcaagcac atcggctcat gtctaacaaa aaaaggcaa cttcttaata   2220
gcaaaaccgt aaaatatat attttattat acaagtctag cccgcgagct gcttggttca   2280
ccctgctagt taagatagta acttgtagct cttcttgttg cgtataagtt gttaaacatt   2340
gtaaaagcct cctcaagtat catgtatacc tgtgatacct cacgacgatt taaacgcaca   2400
attgctgtat aatggatata gattggttct aggctccagc gatcgattat ccatgtaact   2460
acgtacaaac gagtaaacct ccaaaatcac accgctgtca cacatcgtct gcacgcagtt   2520
gcctgaaacc aatccactgc acctagccca cgggttgaat aaaaccgccc gcgcggcct   2580
cttcaacgtg catccacgca gtgtgtcatt cccgtcacgg actctcgtct catccggccc   2640
cttctctcga gcaacaccca ccaatctcct acgcagttgt cctttggtac attcacaagt   2700
ttgatcttat catcaccatc agaagttcag aaagtctcgt agaaaacaaa tggaaatgaa   2760
tactgcttac ttagctcaaa ttcatattcc gttgttacag gatacttaaa aaaggtacca   2820
```

```
aaggctgttc ctaatcatac gctgaagtcg ttgccaccaa tggcagctgt actgtcatat    2880
tgtcgtggtt tttcaattgc tgtacctgat gcaaacgtaa tgggtttact aatcttgcac    2940
ccgccgactt caaaatgaag agtgctaatt tggttcacgt caccatcacc ggctcgaact    3000
gtctagaatg gcaggcaaag atgattggac aggcatgcag ggaaaaagag caccgatgac    3060
gatctatgcg agttcccacc attgcgagca atgattatca gccacacgac ttactcttca    3120
gagctaacca ctgccatgca gagaaaaagt gaagcatatt gtcaggatct acaacgaagt    3180
gaaacaatca ggcatgctaa agtgctgaaa ctttactgat ctctcatgtt ggacaacaaa    3240
gaatacggga atacatcagc aacgcaactc ttgagctttg cttgctgaat gaccagctag    3300
aatttccaag catttacagg aacatgactt taagtttcag aaaaacaaat acaaggccac    3360
taagggcatg ttcacttcag cttataagcc ggctgaaaag ctgaacggc tgatttgttg     3420 tgagaggaaa acactgtttg gtggctgata agccggctga ataagctgaa gcgaacaggc    3480
tgtaaataag cgtggggata acatatcctc cagatgacag gcaatctgca acttgcagcg    3540
attcaaatgt acgattaaca aaatatttaa gcgctacatg agataatata tcctccaatt    3600
agggccttta gtattgtcat tagctctcaa agcatggtgca tcctcacatg gacgctgcat    3660
aagaagttca taatagcaac agacatatga acaaagcatg gtgcgcctgc ccggccggac    3720
tagctagtac taccaatcat ggaataagct agtaccctaa atgaaattaa atggttttt    3780 agcgattatc cacgccgtcc agaatactct aatccacaag ttgaggccgc ccatgaagcc    3840
gcgagagggc gacgccatgt gtataaaagg ggcctaagct gagtggactt gctgcatcag    3900
attagtaagc aatctcaagc gcagagagcc aaagctttcg gtgtagctcg aagagcaaag    3960
cgaaggcaag gtcgt                                                     3975
```

<210> SEQ ID NO 40
<211> LENGTH: 3975
<212> TYPE: DNA
<213> ORGANISM: Artificial Sequence
<220> FEATURE:
<223> OTHER INFORMATION: Synthetic

<400> SEQUENCE: 40

```
agtcgtagag gccaattgat gatgtgccta atagatacat atggtaagga taataatcat     60
ttcttactac attattcata caaaaaataa ttaagaatca aaaattatga gaaacacctc    120
ttggtgtggt gtagttgtgg gtgcatcact ccacccatta gggtccaaat cttggtgctc    180
acattatgcc ggggtctccc ttacattctt cctatcaatt ttttttgtaa atctacagta    240
gatgtctata atgaaaattt tcaaatatct aaaatagcaa cgaaaatctc atatgttacc    300
tgtagaagct caaacttttt gtattgcaca caatgttaat aaaataaaac tcttgctaaa    360
acttgtaatg actacctaat aacaacatat tgtgttgtat atgaatttaa gcccatctaa    420
atattcggaa tattcgctta tcattcaaaa gatttagatc aacaaaaaga agtgaagaac    480
tttatatttt ggtaggtaaa atgtataaca aaacaaatct ttcagaaaat cacttgatat    540
ttccaaacac aatacatcta aattgcaata aaaagaatt ttagaaaaca aaaacataaa    600
aatatgggtg ttgctgtttg aatttcaata ctacaaaagg acatatatgt gacgtcatat    660
tagtgtcggg cccagcagga ccgccaatga tgtatagcat cagtgttggt cggtgcaaaa    720
cccgccactg atatacagct gcgcgttccc cactttcgac ctgatgaaca tcagtggcgg    780
gcgttgcacc cgcccgccac taattttaa gtagaggacc ttaaatctaa gttgacgtat    840
```

```
gagaaccatt ggattaagat ataatggcac tctcttctct tctacttgct atcgttggat    900
taatatccga cggtcaagca catcggctca tgtctaacaa aaaaaaggca acttcttaat    960
agcaaaaccg taaaaatata tattttatta tacaagtcta gcccgcgagc tgcttggttc   1020
accctgctag ttaagatagt aacttgtagc tcttcttgtt gcgtataagt tgttaaacat   1080
tgtaaaagcc tcctcaagta tcatgtatac ctgtgatacc tcacgacgat ttaaacgcac   1140
aattgctgta taatggatat agattggttc taggctccag cgatcgatta tccatgtaac   1200
tacgtacaaa cgagtaaacc tccaaaatca caccgctgtc acacatcgtc tgcacgcagt   1260
tgcctgaaac caatccactg cacctagccc acgggttgaa taaaccgcc cgcgccggcc    1320 tcttcaacgt gcatccacgc agtgtgtcat tcccgtcacg gactctcgtc tcatccggcc   1380
ccttctctcg agcaacaccc accaatctcc caaactcagt ttatcaccaa agaccaaaca   1440
tgtggaaatc agtctctatt tgtccaaga gcatgtggcc cttggagctt tgcggcttct    1500
tcatgttgct acatctcttc aatatgccga tatatttact aagggttgtc aattgttatc   1560
ttcatcaact tctgatctaa tctcaatgtt tgctcctctt ccggttgaga ctactggggg   1620
atattagaat atgaatagcc aaaaagtctt gtatagtcta aaataaagag tctcaaatag   1680
ttcacttgag cttaggaacc gaatttgtcg tcagcagtgt tttttgctca tagtaaatta   1740
gccaacaata ctttctatca caccttaaca gagtactttc tttctgccat ggcttatcaa   1800
ccaacagtat tttttgtcaa aagcagtgat tatctgtcaa tcactagcgc ccctctgcc    1860 ggtatatcta gcgctcccat cggatctgac tagagcagat cttgagcgtg gttggtggc    1920 tcagggcttg caggaggcgt tggccgtcgc cggcgtagag cagtagtcgt aggcggatct   1980
gcatcttcaa gctctcctcc ggtcgattcg tgtgagtctt cgacctctgc tcaggtcgat   2040
tcatgccggc gaggggctca gtgctcggct cacgacgcga aattacgagc ggcagcagca   2100
aaccgggctt tcaagcccgg ctctcctcgt gagctgcctt agggctcgtt cgtttaacta   2160
ttgttcccga tggattcatt cctgatgata aaaatagtat aaatttacac aatgttcctg   2220
gctggaatca tttcagacct gcattccatg agaaacgaac ggggctttag cgggccacgt   2280
gacagtgacg aagggtcgca gtcgctgctg gacggactac agacagagag gcgaagcatg   2340
caattgaatt ttcgctagcg gaaagttatc atctaatctc caaccctcct tcctacggct   2400
ggatctgaaa attgacgacc tgaacccctg aacggtgccg gtagcaattg caggtctcac   2460
tcacatgcta aatccagcaa ccaaacacga aggaatatat gtgatctgga cagaacatgc   2520
aagcgaataa tacatagagt cgtaccaacc ctacacagtt caacgaatta atcactgggt   2580
tcacgggcat gctcacgtcc aaaatcccag cgacatttta taagcgctaa gcggaatgat   2640
ccagacgggg ccagctcgag caccacatgt acgcagttgt cctttggtac attcacaagt   2700
ttgatcttat catcaccatc agaagttcag aaagtctcgt agaaaacaaa tggaaatgaa   2760
tactgcttac ttagctcaaa ttcatattcc gttgttacag gatacttaaa aaaggtacca   2820
aaggctgttc ctaatcatac gctgaagtcg ttgccaccaa tggcagctgt actgtcatat   2880
tgtcgtggtt tttcaattgc tgtacctgat gcaaacgtaa tgggtttact aatcttgcac   2940
ccgccgactt caaaatgaag agtgctaatt tggttcacgt caccatcacc ggctcgaact   3000
gtctagaatg gcaggcaaag atgattggac aggcatgcag ggaaaaagag caccgatgac   3060
gatctatgcg agttcccacc attgcgagca atgattatca gccacacgac ttactcttca   3120
gagctaacca ctgccatgca gagaaaaagt gaagcatatt gtcaggatct acaacgaagt   3180
gaaacaatca ggcatgctaa agtgctgaaa ctttactgat ctctcatgtt ggacaacaaa   3240
```

```
gaatacggga atacatcagc aacgcaactc ttgagctttg cttgctgaat gaccagctag    3300
aatttccaag catttacagg aacatgactt taagtttcag aaaaacaaat acaaggccac    3360
taagggcatg ttcacttcag cttataagcc ggctgaaaag ctgaacggc tgatttgttg     3420 tgagaggaaa acactgtttg gtggctgata agccggctga ataagctgaa gcgaacaggc    3480
tgtaaataag cgtggggata acatatcctc cagatgacag gcaatctgca acttgcagcg    3540
attcaaatgt acgattaaca aaatatttaa gcgctacatg agataatata tcctccaatt    3600
agggccttta gtattgtcat tagctcataa gcatggtgca tcctcacatg gacgctgcat    3660
aagaagttca taatagcaac agacatatga acaaagcatg gtgcgcctgc ccggccggac    3720
tagctagtac taccaatcat ggaataagct agtaccctaa atgaaattaa aatggttttt    3780
agcgattatc cacgccgtcc agaatactct aatccacaag ttgaggccgc ccatgaagcc    3840
gcgagagggc gacgccatgt gtataaaagg ggcctaagct gagtggactt gctgcatcag    3900
attagtaagc aatctcaagc gcagagagcc aaagctttcg gtgtagctcg aagagcaaag    3960
cgaaggcaag gtcgt                                                     3975
```

```
<210> SEQ ID NO 41
<211> LENGTH: 1816
<212> TYPE: DNA
<213> ORGANISM: Artificial Sequence
<220> FEATURE:
<223> OTHER INFORMATION: Synthetic

<400> SEQUENCE: 41
ctagcatgta gcatgccaag gatctggctg ctccaggttt gttatgcctg acatcaccat      60
agggatgaga gcaagtataa taataggctg taagctttaa atgctcaggt ggagaaaaaa     120
aggagaggag aggagagaga aaagtgggct ataagcttat agctgtgtta gacataagaa     180
tcagaaactt cgtatgagag acaggtgagc tatatattaa taacaaagag ctaactatta     240
tatgagtgaa ccgagagaag gctgtaaaaa aacttacaca atcaacgatc gacattatta     300
ttaaccttgc tctgtcttgc gagacctctt tgacaaagct acatcaatgc cggccaagtg     360
ccttgggatt tgggaatggc ttctttcctc ccttcctcgg ttgtccccca aggcctaggc     420
ttgccacgct gtattcagtc gcagccgcct ttactttttgc cctttgtgga agttttgtaa     480
taaatggtct gattctatct tcggatagat gaagccggat gtttcatcca ttatctaaaa     540
aaaagttggt tgctttgctg agctaagaaa gtgtaatcca gagtgctcgt aacgtattaa     600
tgtacataac tattatctaa tataaatctt cttttgtcgc aaaaaaaggt cggcccatca     660
gaacaaatga tcaatgtaag gcccaaaatt tgtgtctcaa atgtcattta cgtttccaag     720
ctaaacaaaa acacaggatt catataattt tgctggtggc ttaggcttcg tccaatagtg     780
cttagtttaa tttgtatata cctgcaccat ggtattcgtc tggccttgga tcttgcgcat     840
caattgccta tggacgatga tcgcagccac gccacattca tttttaatcg ccatttgctt     900
gacacccaat gcctctgcac cacttgcgca cgctacgcac cgtctgatac gccaagatcc     960
cgagctaaaa taacacccaa tcatcagatg aaaacaagcg cgagtgcgag ccagcccatg    1020
gcagcgatct tggccatttg cggagccaac tgaaagccgt gcacaaaata ttcgacaccg    1080
tataagggaa acactagtt atacgaggtg ggcaataatc cagatctcgg actcttccta    1140
acccggttca catgcatagc atatatgatg gccggccggg gttcacatga acgccatccc    1200
gtgccctagt gcactgattt cttaatcccc gtgtgcatgc atgcatgcat ggtacgaacg    1260
```

| | |
|---|---|
| tctggataga gtctccgagc tgagtgtggt ccgacgtgga agtgtacgtc tcaacacacg | 1320 |
| acgcatgtga ccgacaaggg caagttgaag tctatgcatg gatgggcctg agcgccgcgc | 1380 |
| tgaatgaatc tggacgggtg gtagggcatc tcggtgggca aaacaaataa ctccgtgtgc | 1440 |
| tgcatggctg cctttggaat cttttgcatg agctgtgtgc tgaactgaaa cccttcgctc | 1500 |
| tatctatata aacagatgcc cttcgctctc gtctcagcag gcagcatcgt ctcaagtttt | 1560 |
| gttctcctct cctagctagc cagcacctgc agatctgctc gttgccttgg taattcatca | 1620 |
| tgtagtacgt agcatcagct agtatttatc tcaagtatat atacgcat atgtgtcgtc | 1680 |
| gcagtacttt cccttatctc tctatacaca ctacacgcat acataccaat accatccgtc | 1740 |
| ttaactctta atctttgcct gcatacgtac actgcacgta cgtactgcag ggctactgat | 1800 |
| tttgtggaac gaagcg | 1816 |

<210> SEQ ID NO 42
<211> LENGTH: 2328
<212> TYPE: DNA
<213> ORGANISM: Artificial Sequence
<220> FEATURE:
<223> OTHER INFORMATION: Synthetic

<400> SEQUENCE: 42

| | |
|---|---|
| ctactcgcct tgtggctcct cctgaaccac ctgctcttct cctgtggggg ggtgtgagac | 60 |
| agcaagggtg agctcacaca tgatcatagc tcaacaagtt gtggggaacc agtggacatg | 120 |
| aactcacaaa ggtgggagtt catgtgatgg ttcctctaga tgctcaactt gttgcattat | 180 |
| attacgcaat tgctccgacg cttcatcaat taatcctcct tagtgatatt aaataacgga | 240 |
| ataatattag agaaataaac aataatctaa gacattagcg cataaagatg tgacaaaatg | 300 |
| attgagtctg gtcatattac cctccttcat ccttttattgc ataaaagatt gtagtttaca | 360 |
| ccttcggctt tacaaaggag agctcgaagg taatattaca gcttcgaagg cggagtgatt | 420 |
| tgattctccc ttgttcaaaa agcgagatct cttcatatca ttgtgcctct atttatagta | 480 |
| accaagtaca atttcatatg aaattacaaa catgctcatg gacatgataa ttccagtgca | 540 |
| catccaaccc tgcttgatac aaaacatgct cataatcatg atgattcaag tgcacatcca | 600 |
| ccctgctcga tacaacagtt ggcgacctgg tgtgagagtc agaccagacg ggctttcaca | 660 |
| atcgccatgc atgtcattct ctcgtggtcc acgtgtttat taatattgcc attaattgga | 720 |
| gggaaataaa atcaacaaga atagcttatt gatgagtcat atattatgaa tacatcttat | 780 |
| catcttacca aacaaaaaca tatgaccgtc gatgacctga aactagacta ttcgggatct | 840 |
| gcaatgatct gcttgtaaat attaattttgc acatcacgcc attgcatgca catcggcgtg | 900 |
| ggcattatta atttggattg gacgaaaaat caaccagagg gcgtcaccct tttgctagtt | 960 |
| ggccttgtaa tacctagcat gtagcatgcc aaggatctgg ctgctccagg tttgttatgc | 1020 |
| ctgacatcac catagggatg agagcaagta taataatagg ctgtaagctt taaatgctca | 1080 |
| ggtggagaaa aaaggagag gagaggagag agaaaagtgg gctataagct tatagctgtg | 1140 |
| ttagacataa gaatcagaaa cttcgtatga gagacaggtg agctatatat taataacaaa | 1200 |
| gagctaaacta ttatatgagt gaaccgagag aaggctgtaa aaaaacttac acaatcaacg | 1260 |
| atcgacatta ttattaacct tgctctgtct tgcgagacct ctttgacaaa gctacatcaa | 1320 |
| tgccggccaa gtgccttggg atttgggaat ggcttctttc ctcccttcct cggttgtccc | 1380 |
| ccaaggccta ggcttgccac gctgtattca gtcgcagccg cctttacttt tgcccttgt | 1440 |
| ggaagttttg taataaatgg tctgattcta tcttcggata gatgaagccg gatgtttcat | 1500 |

```
ccattatcta aaaaaaagtt ggttgctttg ctgagctaag aaagtgtaat ccagagtgct   1560
cgtaacgtat taatgtacat aactattatc taatataaat cttcttttgt cgcaaaaaaa   1620
ggtcggccca tcagaacaaa tgatcaatgt aaggcccaaa atttgtgtct caaatgtcat   1680
ttacgtttcc aagctaaaca aaaacacagg attcatataa ttttgctggt ggcttaggct   1740
tcgtccaata gtgcttagtt taatttgtat atacctgcac catggtattc gtctggcctt   1800
ggatcttgcg catcaattgc ctatggacga tgatcgcagc cacgccacat tcatttttaa   1860
tcgccatttg cttgacaccc aatgcctctg caccacttgc gcacgctacg caccgtctga   1920
tacgccaaga tcccgagcta aaataacacc caatcatcag atgaaaacaa gcgcgagtgc   1980
gagccagccc atggcagcga tcttggccat tgcggagcc aactgaaagc cgtgcacaaa    2040
atattcgaca ccgtataagg gaaaacacta gttatacgag gtgggcaata atccagatct   2100
cggactcttc ctaacccggt tcacatgcat agcatatatg atggccggcc ggggttcaca   2160
tgaacgccat cccgtgccct agtgcactga tttcttaatc ccgggtctca actataaata   2220
cccccttggt gacaccgcga tcaaagcatc gcaaacaagc ctagctaaga gctctctaac   2280
tacattagat agagtgatct cgagaggtaa ctggcttgtg atcgagca                2328
```

<210> SEQ ID NO 43
<211> LENGTH: 2370
<212> TYPE: DNA
<213> ORGANISM: Artificial Sequence
<220> FEATURE:
<223> OTHER INFORMATION: Synthetic

<400> SEQUENCE: 43

```
ctagcatgta gcatgccaag gatctggctg ctccaggttt gttatgcctg acatcaccat     60
agggatgaga gcaagtataa taataggctg taagctttaa atgctcaggt ggagaaaaaa    120
aggagaggag aggagagaga aaagtgggct ataagcttat agctgtgtta gacataagaa    180
tcagaaactt cgtatgagag acaggtgagc tatatattaa taacaaagag ctaactatta    240
tatgagtgaa ccgagagaag gctgtaaaaa aacttacaca atcaacgatc gacattatta    300
ttaaccttgc tctgtcttgc gagacctctt tgacaaagct acatcaatgc cggccaagtg    360
ccttgggatt tgggaatggc ttcttttcctc ccttcctcgg ttgtccccca aggcctaggc    420
ttgccacgct gtattcagtc gcagccgcct ttacttttgc cctttgtgga agttttgtaa    480
taaatggtct gattctatct tcggatagat gaagccggat gtttcatcca ttatctaaaa    540
aaaagttggt tgctttgctg agctaagaaa gtgtaatcca gagtgctcgt aacgtattaa    600
tgtacataac tattatctaa tataaatctt cttttgtcgc aaaaaaaggt cggcccatca    660
gaacaaatga tcaatgtaag gcccaaaatt tgtgtctcaa atgtcattta cgtttccaag    720
ctaaacaaaa acacaggatt catataattt tgctggtggc ttaggcttcg tccaatagtg    780
cttagtttaa tttgtatata cctgcaccat ggtattcgtc tggccttgga tcttgcgcat    840
caattgccta tggacgatga tcgcagccac gccacattca tttttaatcg ccatttgctt    900
gacacccaat gcctctgcac cacttgcgca cgctacgcac cgtctgatac gccaagatcc    960
cgagctaaaa taacacccaa tcatcagatg aaaacaagcg cgagtgcgag ccagcccatg   1020
gcagcgatct tggccatttg cggagccaac tgaaagccgt gcacaaaata ttcgacaccg   1080
tataagggaa aacactagtt atacgaggtg ggcaataatc cagatctcgg actcttccta   1140
acccggttca catgcatagc atatatgatg gccggcgggg ttcacatga acgccatccc    1200
```

| | |
|---|---|
| gtgccctagt gcactgattt cttaatcccc tactcgcctt gtggctcctc ctgaaccacc | 1260 |
| tgctcttctc ctgtgggggg gtgtgagaca gcaagggtga gctcacacat gatcatagct | 1320 |
| caacaagttg tggggaacca gtggacatga actcacaaag gtgggagttc atgtgatggt | 1380 |
| tcctctagat gctcaacttg ttgcattata ttacgcaatt gctccgacgc ttcatcaatt | 1440 |
| aatcctcctt agtgatatta aataacggaa taatattaga gaaataaaca ataatctaag | 1500 |
| acattagcgc ataaagatgt gacaaaatga ttgagtctgg tcatattacc ctccttcatc | 1560 |
| ctttattgca taaaagattg tagtttacac cttcggcttt acaaaggaga gctcgaaggt | 1620 |
| aatattacag cttcgaaggc ggagtgattt gattctccct tgttcaaaaa gcgagatctc | 1680 |
| ttcatatcat tgtgcctcta tttatagtaa ccaagtacaa tttcatatga aattacaaac | 1740 |
| atgctcatgg acatgataat tccagtgcac atccaaccct gcttgataca aaacatgctc | 1800 |
| ataatcatga tgattcaagt gcacatccac cctgctcgat acaacagttg gcgacctggt | 1860 |
| gtgagagtca gaccagacgg gctttcacaa tcgccatgca tgtcattctc tcgtggtcca | 1920 |
| cgtgtttatt aatattgcca ttaattggag ggaaataaaa tcaacaagaa tagcttattg | 1980 |
| atgagtcata tattatgaat acatcttatc atcttaccaa acaaaaacat atgaccgtcg | 2040 |
| atgacctgaa actagactat tcgggatctg caatgatctg cttgtaaata ttaatttgca | 2100 |
| catcacgcca ttgcatgcac atcggcgtgg gcattattaa tttggattgg acgaaaaatc | 2160 |
| aaccagaggg cgtcacccct ttgctagttg gcctttgtaat acttataata attatccgta | 2220 |
| tagtctagta cgtacgggac atcacgccat tgcctgttgt gtataaaaag cgagcatgag | 2280 |
| ctaggttggg agcagagcaa agcgtagtca tcacctgtgt ctaggttggg agcaaagcaa | 2340 |
| agagagagag gaaagctagc tagctagcgg | 2370 |

<210> SEQ ID NO 44
<211> LENGTH: 1560
<212> TYPE: DNA
<213> ORGANISM: Artificial Sequence
<220> FEATURE:
<223> OTHER INFORMATION: Synthetic

<400> SEQUENCE: 44

| | |
|---|---|
| ctactcgcct tgtggctcct cctgaaccac ctgctcttct cctgtggggg ggtgtgagac | 60 |
| agcaagggtg agctcacaca tgatcatagc tcaacaagtt gtggggaacc agtggacatg | 120 |
| aactcacaaa ggtgggagtt catgtgatgg ttcctctaga tgctcaactt gttgcattat | 180 |
| attacgcaat tgctccgacg cttcatcaat taatcctcct tagtgatatt aaataacgga | 240 |
| ataatattag agaaataaac aataatctaa gacattagcg cataaagatg tgacaaaatg | 300 |
| attgagtctg gtcatattac cctccttcat ccttattgc ataaaagatt gtagtttaca | 360 |
| ccttcggctt tacaaaggag agctcgaagg taatattaca gcttcgaagg cggagtgatt | 420 |
| tgattctccc ttgttcaaaa agcgagatct cttcatatca ttgtgcctct atttatagta | 480 |
| accaagtaca atttcatatg aaattacaaa catgctcatg gacatgataa ttccagtgca | 540 |
| catccaaccc tgcttgatac aaaacatgct cataatcatg atgattcaag tgcacatcca | 600 |
| ccctgctcga tacaacagtt ggcgacctgg tgtgagagtc agaccagacg ggctttcaca | 660 |
| atcgccatgc atgtcattct ctcgtggtcc acgtgtttat taatattgcc attaattgga | 720 |
| gggaaataaa atcaacaaga atagcttatt gatgagtcat atattatgaa tacatcttat | 780 |
| catcttacca aacaaaaaca tatgaccgtc gatgacctga actagactat tcgggatct | 840 |
| gcaatgatct gcttgtaaat attaatttgc acatcacgcc attgcatgca catcggcgtg | 900 |

| | |
|---|---|
| ggcattatta atttggattg gacgaaaaat caaccagagg gcgtcaccct tttgctagtt | 960 |
| ggccttgtaa taccgtgtgc atgcatgcat gcatggtacg aacgtctgga tagagtctcc | 1020 |
| gagctgagtg tggtccgacg tggaagtgta cgtctcaaca cacgacgcat gtgaccgaca | 1080 |
| agggcaagtt gaagtctatg catggatggg cctgagcgcc gcgctgaatg aatctggacg | 1140 |
| ggtggtaggg catctcggtg ggcaaaacaa ataactccgt gtgctgcatg gctgcctttg | 1200 |
| gaatctttgc atgcagctgt gtgctgaact gaaacccttc gctctatcta tataaacaga | 1260 |
| tgcccttcgc tctcgtctca gcaggcagca tcgtctcaag ttttgttctc ctctcctagc | 1320 |
| tagccagcac ctgcagatct gctcgttgcc ttggtaattc atcatgtagt acgtagcatc | 1380 |
| agctagtatt tatctcaagt atatatatac gcatatgtgt cgtcgcagta ctttccctta | 1440 |
| tctctctata cacactacac gcatacatac caataccatc cgtcttaact cttaatcttt | 1500 |
| gcctgcatac gtacactgca cgtacgtact gcagggctac tgattttgtg gaacgaagcg | 1560 |

<210> SEQ ID NO 45
<211> LENGTH: 1396
<212> TYPE: DNA
<213> ORGANISM: Artificial Sequence
<220> FEATURE:
<223> OTHER INFORMATION: Synthetic

<400> SEQUENCE: 45

| | |
|---|---|
| cgtgtgcatg catgcatgca tggtacgaac gtctggatag agtctccgag ctgagtgtgg | 60 |
| tccgacgtgg aagtgtacgt ctcaacacac gacgcatgtg accgacaagg caagttgaa | 120 |
| gtctatgcat ggatgggcct gagcgccgcg ctgaatgaat ctggacgggt ggtagggcat | 180 |
| ctcggtgggc aaaacaaata actccgtgtg ctgcatggct gcctttggaa tctttgcatg | 240 |
| cagctgtgtg ctgaactact cgccttgtgg ctcctcctga accacctgct cttctcctgt | 300 |
| gggggggtgt gagacagcaa gggtgagctc acacatgatc atagctcaac aagttgtggg | 360 |
| gaaccagtgg acatgaactc acaaaggtgg gagttcatgt gatggttcct ctagatgctc | 420 |
| aacttgttgc attatattac gcaattgctc cgacgcttca tcaattaatc ctccttagtg | 480 |
| atattaaata acggaataat attagagaaa taaacaataa tctaagacat tagcgcataa | 540 |
| agatgtgaca aaatgattga gtctggtcat attaccctcc ttcatccttt attgcataaa | 600 |
| agattgtagt ttacaccttc ggctttacaa aggagagctc gaaggtaata ttacagcttc | 660 |
| gaaggcggag tgatttgatt ctcccttgtt caaaaagcga gatctcttca tatcattgtg | 720 |
| cctctattta tagtaaccaa gtacaatttc atatgaaatt acaaacatgc tcatggacat | 780 |
| gataattcca gtgcacatcc aaccctgctt gatacaaaac atgctcataa tcatgatgat | 840 |
| tcaagtgcac atccaccctg ctcgatacaa cagttggcga cctggtgtga gagtcagacc | 900 |
| agacgggctt tcacaatcgc catgcatgtc attctctcgt ggtccacgtg tttattaata | 960 |
| ttgccattaa ttggagggaa ataaaatcaa caagaatagc ttattgatga gtcatatatt | 1020 |
| atgaatacat cttatcatct taccaaacaa aaacatatga ccgtcgatga cctgaaacta | 1080 |
| gactattcgg gatctgcaat gatctgcttg taaatattaa tttgcacatc acgccattgc | 1140 |
| atgcacatcg gcgtgggcat tattaatttg gattggacga aaaatcaacc agagggcgtc | 1200 |
| acccttttgc tagttggcct tgtaatactt ataataatta tccgtatagt ctagtacgta | 1260 |
| cgggacatca cgccattgcc tgttgtgtat aaaaagcgag catgagctag gttgggagca | 1320 |
| gagcaaagcg tagtcatcac ctgtgtctag gttgggagca aagcaaagag agagaggaaa | 1380 |

```
gctagctagc tagcgg                                                      1396

<210> SEQ ID NO 46
<211> LENGTH: 1610
<212> TYPE: DNA
<213> ORGANISM: Artificial Sequence
<220> FEATURE:
<223> OTHER INFORMATION: Synthetic

<400> SEQUENCE: 46
cgtgtgcatg catgcatgca tggtacgaac gtctggatag agtctccgag ctgagtgtgg        60
tccgacgtgg aagtgtacgt ctcaacacac gacgcatgtg accgacaagg gcaagttgaa       120
gtctatgcat ggatgggcct gagcgccgcg ctgaatgaat ctggacgggt ggtagggcat       180
ctcggtgggc aaaacaaata actccgtgtg ctgcatggct gcctttggaa tctttgcatg       240
cagctgtgtg ctgaactagc atgtagcatg ccaaggatct ggctgctcca ggtttgttat       300
gcctgacatc accataggga tgagagcaag tataataata ggctgtaagc tttaaatgct       360
caggtggaga aaaaaggag aggagaggag agagaaaagt gggctataag cttatagctg        420
tgttagacat aagaatcaga aacttcgtat gagagacagg tgagctatat attaataaca       480
aagagctaac tattatatga gtgaaccgag agaaggctgt aaaaaaactt acacaatcaa       540
cgatcgacat tattattaac cttgctctgt cttgcgagac ctctttgaca aagctacatc       600
aatgccggcc aagtgccttg ggatttggga atggcttctt cctcccttc ctcggttgtc        660 ccccaaggcc taggcttgcc acgctgtatt cagtcgcagc cgcctttact tttgcccttt       720
gtggaagttt tgtaataaat ggtctgattc tatcttcgga tagatgaagc cggatgtttc       780
atccattatc taaaaaaaag ttggttgctt tgctgagcta agaaagtgta atccagagtg       840
ctcgtaacgt attaatgtac ataactatta tctaatataa atcttctttt gtcgcaaaaa       900
aaggtcggcc catcagaaca aatgatcaat gtaaggccca aaatttgtgt ctcaaatgtc       960
atttacgttt ccaagctaaa caaaaacaca ggattcatat aattttgctg gtggcttagg      1020
cttcgtccaa tagtgcttag tttaatttgt atatacctgc accatggtat tcgtctggcc      1080
ttggatcttg cgcatcaatt gcctatggac gatgatcgca gccacgccac attcattttt      1140
aatcgccatt tgcttgacac ccaatgcctc tgcaccactt gcgcacgcta cgcaccgtct      1200
gatacgccaa gatcccgagc taaaataaca cccaatcatc agatgaaaac aagcgcgagt      1260
gcgagccagc ccatggcagc gatcttggcc atttgcggag ccaactgaaa gccgtgcaca      1320
aaatattcga caccgtataa gggaaaacac tagttatacg aggtgggcaa taatccagat      1380
ctcggactct tcctaacccg gttcacatgc atagcatata tgatggccgg ccggggttca      1440
catgaacgcc atcccgtgcc ctagtgcact gatttcttaa tcccgggtct caactataaa      1500 taccccttg gtgacaccgc gatcaaagca tcgcaaacaa gcctagctaa gagctctcta       1560
actacattag atagagtgat ctcgagaggt aactggcttg tgatcgagca                 1610

<210> SEQ ID NO 47
<211> LENGTH: 1517
<212> TYPE: DNA
<213> ORGANISM: Artificial Sequence
<220> FEATURE:
<223> OTHER INFORMATION: Synthetic

<400> SEQUENCE: 47
tacttaactt tactagaggt ggacgtagaa agttagtagg gcctgctaac ttcctagatg        60
aggtcgtagg aagttagtga ctctttgacc gcgctcgttt gtcaatagtt gaaagctaaa       120
```

```
tttctagagg aggctgtagg aagttagtgg ctcgtttgat cgcgctcgtt tgtcaacagc      180
tgaaagctaa ctttctagag gagaccgccc ctgctaactt cctacgacct tgtggttgg      240
ggctataaat acccgacctt tgtggccttc tcaacggaga gtaggttatt tggaaccaaa     300
cctcggaaaa caaatcaccg tgttcatttg tgttgatctt catcacttga tttgtttctt     360
ccctctcctc tctctaaagt tctcttgctc acattgtttt gagtttgctt ctaaagttat     420
ctgtattgat tgagtaactc atagcaaaaa gaactatctt ttgcactccg aaatattact     480
aacactaacc ccgagtataa tgcgtgttca aactttataa atttcagatt tcgtctattt     540
atcctctttta gacgactttc aaagtttata tttttggtgt aatggctacc acatcaacat    600
gcttgatttc ctggcacatg catttatttt tgtcaatact tttgcgtggc ccttttcacg     660
tatagaagag tgaagctaac attacattac ataaatattt ttccctctaa ttgcggcaat     720
caagcacgaa cgcactagct agtaagcttt ttgtgaggat ttggcatgtt gctgtgactg     780
tgagtggatt accgcgacga cagggacgac atgcgtgccc ttatctcttg gagatttcct    840
cgggcccgac catcagacga acaacacatg catgtgctag cccgtgtcag caatctagat    900
gacctctcaa ttttccacac gaggtggggc cctcgccacc tcatctcttg tcttttccca    960
gttaggtgac atggagcaca tgagcctccg agctcaccgg ggggtgacgc cacccccgt    1020
cgacctcgag agagcctagc ccacctaagc cgagcgtgat gaactgatga acccactacc   1080
actagtcaag gcaaaccaca accacaaatg gatcaattga tctagaacaa tccgaaggag   1140
gggaggccac gtcacactca caccaaccga aatatctgcc agtatcagat caaccggcca   1200
ataggacgcc agcgagccca cacctagcg acgccgcaaa attcaccgcg aggggcaccg    1260
ggcacggcaa aaacaaaagc ccggcgcggt gagaatatct ggcgactggc ggagacctgg   1320
tggccagcgc gcggccacat cagccacccc atccgcccac ctcacctccg gcgagccaat   1380
ggcaactcgt cttaagattc cacgagataa ggacccgatc gccggcgacg ctatttagcc   1440
aggtgcgccc cccacggtac actccaccag cggcatctat agcaaccggt ccaacacttt   1500
cacgctcagc ttcagca                                                  1517

<210> SEQ ID NO 48
<211> LENGTH: 486
<212> TYPE: DNA
<213> ORGANISM: Zea mays

<400> SEQUENCE: 48
gagcctagcc cacctaagcc gagcgtgatg aactgatgaa cccactacca ctagtcaagg     60
caaaccacaa ccacaaatgg atcaattgat ctagaacaat ccgaaggagg ggaggccacg    120
tcacactcac accaaccgaa atatctgcca gtatcagatc aaccggccaa taggacgcca    180
gcgagcccaa cacctagcga cgccgcaaaa ttcaccgcga ggggcaccgg gcacggcaaa    240
aacaaaagcc cggcgcggtg agaatatctg cgactggcg gagacctggt ggccagcgcg     300
cggccacatc agccacccca tccgcccacc tcacctccgg cgagccaatg gcaactcgtc    360
ttaagattcc acgagataag gacccgatcg ccggcgacgc tatttagcca ggtgcgcccc    420
ccacggtaca ctccaccagc ggcatctata gcaaccggtc aaacactttc acgctcagct    480
tcagca                                                              486

<210> SEQ ID NO 49
<211> LENGTH: 995
<212> TYPE: DNA
```

<213> ORGANISM: Brachypodium distachyon

<400> SEQUENCE: 49

```
accaacttgc tctgtgatgt taatgttttt ggtgattagt gacaagggtg cctaatttct      60
tttctgatgt taatattttg aaagattctc actctgaaaa aaaaatgcat gttcatatcc     120
atgtttctct aaaaataatc catagccagt gtgtgatact ttctactagt tcccactaaa     180
tgcattgtga aattaaattc tataaaattt tgtaatttct aatatttagt aagggtagaa     240
acagagattt ttttcttaat tttaaatcat catgtatcag gagtcgcaaa ggtccaggaa     300
tgatatgcaa gattgctaca tggttggtat cctcttaatg tcatccttgg cagggagttg     360
tggtggatat gccttctgct gccaggcact ggggcacaag aagaatggtg tctgccacac     420
aagccaccct gcaccctaca acaactcac agctggaatg gttatcacca aaccaatgac      480
agaaaaaact gtgtattcca cgtaattgat ggttactggc aaaattcatg gatgtaatac     540
atcagggcat ctcaaccgtc gaaagatgct catgggcact actcctcggc gaaatgcgcc     600
cacagaaacc cagaattgtt catcagccaa gaccatcctt aaggtcaaga atgtccagat     660
aatatttatg gacggtgcag cgcaaacgat aaaattccag tattgcagat tttacatggt     720
acacagagaa gctaaggaaa tcatagagac aagctagtgg cagagccagg acaaaaacag     780
aaggtggcaa gagagttgga gcaaccaaat cacagccatt catatccaga aggccagcct     840
ccacctcaca actcatatcc tttgtactca ggtactcacc cttaaatctg agcaggcgct     900
tcacttctca ccccccctaa ggaaaggctg caattgcaag cttgtgtcaa agaagagggt     960
agcacctgat cctcttgcct ttggagccag aaaca                                995
```

<210> SEQ ID NO 50
<211> LENGTH: 4259
<212> TYPE: DNA
<213> ORGANISM: Artificial Sequence
<220> FEATURE:
<223> OTHER INFORMATION: Synthetic

<400> SEQUENCE: 50

```
agcccactat aaaagggcta aaatagcaaa ttttccctg cgtccgtgca cccacgccga      60
gcttgccgct gcgaccgtgg ccgagcagat cacgcacacg acatgcattg ctttgttcgt     120
cttcaaaaca aacccaaaaa aaatggtttt gcggttttgc ccgaccagcc tggagcacgg     180
tggtgctcag ccagacagcc aataggacat tcttgattct tgatgttgta ttgtatttgt     240
tgagtttgtg atctaaattt tgtttatagg acatattagc aagtaaagcg gaggcttgtt     300
ataggtttgg gccggagtat attgctgact ctaattaggg tttctgttgc gtcataattt     360
ttactcctct tataagccgt cgtacaaaga cggcgttatg taaacatttc tacatatagt     420
gaaggttttc gtaattttc tctttgcatt aaggacctgt ttggttagag gtctctcagg     480
cacttgcctg ccaagtaagg aatcctagcc catgtattca aaatctaacg cctggaatct     540
gtgcaacttt ggccggctcc aaactaaata agccttaaaa gaatttctat gtaaatctat     600
gtatggtgct ctgtggtttg ttgtttgatc ttccctgttt tgtctgctaa cggtatccat     660
ccgtccattg gtgctccggc cctttccaa tgtcctgtgc tggatcttga tagcttgggc      720
agttgagttt ggcgtgtgaa gtggacgtgg acttggcgag cgtcagtcag cacttcctga     780
atgaggctat agcttctgca agctttcgtg gatagatttt ccgagattct cagcttgcat     840
ccgatccagc aagctctcag ttccgtttag cccccacta atgactaaaa gtagactgaa      900
aagttgagac gcgcgcacat gcagctacgc cgctacgcta tggctggttc acccaccgga     960
```

-continued

```
gcctgcaacg cgctccctgt ggagagagaa aagaagctct gccacccgtc cacacattcc    1020
tgtgatagat cgcattcatc cagctggcta ctgaatgcgc gttgtgctgc gtaggacacg    1080
tatggcgagc tagcctacag ataaggtcga gtagcccact ataaaagggc taaaatagca    1140
aatttttccc tgcgtccgtg cacccacgcc gagcttgccg ctgcgaccgt ggccgagcag    1200
atcacgcaca cgacatgcat tgctttgttc gtcttcaaaa caaacccaaa aaaaatggtt    1260
ttgcggtttt gcccgaccag cctggagcac ggtggtgctc agccagacag ccaataggac    1320
attcttgatt cttgatgttg tattgtattt gttgagtttg tgatctaaat tttgtttata    1380
ggacatatta gcaagtaaag cggaggcttg ttataggttt gggccggagt atattgctga    1440
ctctaattag ggtttctgtt gcgtcataat ttttactcct cttataagcc gtcgtacaaa    1500
gacggcgtta tgtaaacatt tctacatata gtgaaggttc tcgtaatttt tctctttgca    1560
ttaaggacct gtttggttag aggtctctca ggcacttgcc tgccaagtaa ggaatcctag    1620
cccatgtatt caaaatctaa cgcctggaat ctgtgcaact ttggccggct ccaaactaaa    1680
taagccttaa aagaatttct atgtaaatct atgtatggtg ctctgtggtt tgttgtttga    1740
tcttccctgt tttgtctgct aacggtatcc atccgtccat tggtgctccg gccctttccc    1800
aatgtcctgt gctggatctt gatagcttgg gcagttgagt ttggcgtgtg aagtggacgt    1860
ggacttggcg agcgtcagtc agcacttcct gaatgaggct atagcttctg caagctttcg    1920
tggatagatt ttccgagatt ctcagcttgc atccgatcca gcaagctctc agttccgttt    1980 agcccccac taatgactaa aagtagactg aaaagttgag acgcgcgcac atgcagctac    2040
gccgctacgc tatggctggt tcacccaccg gagcctgcaa cgcgctccct gtggagagag    2100
aaaagaagct ctgccacccg tccacacatt cctgtgatag atcgcattca tccagctggc    2160
tactgaatgc gcgttgtgct gcgtaggaca cgtatggcga gctagcctac agataaggtc    2220
gagtagccca ctataaaagg gctaaaatag caaatttttc cctgcgtccg tgcacccacg    2280
ccgagcttgc cgctgcgacc gtggccgagc agatcacgca cacgacatgc attgctttgt    2340
tcgtcttcaa aacaaaccca aaaaaaatgg ttttgcggtt ttgcccgacc agcctggagc    2400
acggtggtgc tcagccagac agccaatagg acattcttga ttcttgatgt tgtattgtat    2460
ttgttgagtt tgtgatctaa attttgttta taggacatat tagcaagtaa agcggaggct    2520
tgttataggt ttgggccgga gtatattgct gactctaatt agggtttctg ttgcgtcata    2580
atttttactc ctcttataag ccgtcgtaca aagacggcgt tatgtaaaca tttctacata    2640
tagtgaaggt tttcgtaatt tttctctttg cattaaggac ctgtttggtt agaggtctct    2700
caggcacttg cctgccaagt aaggaatcct agcccatgta ttcaaaatct aacgcctgga    2760
atctgtgcaa ctttggccgg ctccaaacta aataagcctt aaaagaattt ctatgtaaat    2820
ctatgtatgg tgctctgtgg tttgttgttt gatcttccct gttttgtctg ctaacggtat    2880
ccatccgtcc attggtgctc cggccctttc caatgtcct gtgctggatc ttgatagctt    2940
gggcagttga gtttggcgtg tgaagtggac gtggacttgg cgagcgtcag tcagcacttc    3000
ctgaatgagg ctatagcttc tgcaagcttt cgtggataga ttttccgaga ttctcagctt    3060
gcatccgatc cagcaagctc tcagttccgt ttagcccccc actaatgact aaaagtagac    3120
tgaaaagttg agacgcgcgc acatgcagct acgccgctac gctatggctg gttcacccac    3180
cggagcctgc aacgcgctcc ctgtggagag agaaaagaag ctctgccacc cgtccacaca    3240
ttcctgtgat agatcgcatt catccagctg gctactgaat gcgcgttgtg ctgcgtagga    3300
```

| | |
|---|---|
| cacgtatggc gagctagcct acagataagg tcgagcacca acttgctctg tgatgttaat | 3360 |
| gttttggtg attagtgaca agggtgccta atttcttttc tgatgttaat attttgaaag | 3420 |
| attctcactc tgaaaaaaaa atgcatgttc atatccatgt ttctctaaaa ataatccata | 3480 |
| gccagtgtgt gatactttct actagttccc actaaatgca ttgtgaaatt aaattctata | 3540 |
| aaattttgta atttctaata tttagtaagg gtagaaacag attttttt cttaattta | 3600 |
| aatcatcatg tatcaggagt cgcaaaggtc caggaatgat atgcaagatt gctacatggt | 3660 |
| tggtatcctc ttaatgtcat ccttggcagg gagttgtggt ggatatgcct tctgctgcca | 3720 |
| ggcactgggg cacaagaaga atggtgtctg ccacacaagc caccctgcac cctacaaaca | 3780 |
| actcacagct ggaatggtta tcaccaaacc aatgacagaa aaaactgtgt attccacgta | 3840 |
| attgatggtt actggcaaaa ttcatggatg taatacatca gggcatctca accgtcgaaa | 3900 |
| gatgctcatg ggcactactc ctcggcgaaa tgcgcccaca gaaacccaga attgttcatc | 3960 |
| agccaagacc atccttaagg tcaagaatgt ccagataata tttatggacg gtgcagcgca | 4020 |
| aacgataaaa ttccagtatt gcagatttta catggtacac agagaagcta aggaaatcat | 4080 |
| agagacaagc tagtggcaga gccaggacaa aaacagaagg tggcaagaga gttggagcaa | 4140 |
| ccaaatcaca gccattcata tccagaaggc cagcctccac ctcacaactc atatcctctc | 4200 |
| catgcctcca cgccggttat aagatagagt ttgaggcaac ccctcggagt cacaacaac | 4259 |

<210> SEQ ID NO 51
<211> LENGTH: 4289
<212> TYPE: DNA
<213> ORGANISM: Artificial Sequence
<220> FEATURE:
<223> OTHER INFORMATION: Synthetic

<400> SEQUENCE: 51

| | |
|---|---|
| agcccactat aaaagggcta aaatagcaaa ttttccctg cgtccgtgca cccacgccga | 60 |
| gcttgccgct gcgaccgtgg ccgagcagat cacgcacacg acatgcattg ctttgttcgt | 120 |
| cttcaaaaca aacccaaaaa aaatggtttt gcggttttgc ccgaccagcc tggagcacgg | 180 |
| tggtgctcag ccagacagcc aataggacat tcttgattct tgatgttgta ttgtatttgt | 240 |
| tgagtttgtg atctaaattt tgtttatagg acatattagc aagtaaagcg gaggcttgtt | 300 |
| ataggtttgg gccggagtat attgctgact ctaattaggg tttctgttgc gtcataattt | 360 |
| ttactcctct tataagccgt cgtacaaaga cggcgttatg taaacatttc tacatatagt | 420 |
| gaaggttttc gtaattttc tctttgcatt aaggacctgt ttggttagag gtctctcagg | 480 |
| cacttgcctg ccaagtaagg aatcctagcc catgtattca aaatctaacg cctggaatct | 540 |
| gtgcaacttt ggccggctcc aaactaaata agccttaaaa gaatttctat gtaaatctat | 600 |
| gtatggtgct ctgtggtttg ttgtttgatc ttccctgttt tgtctgctaa cggtatccat | 660 |
| ccgtccattg gtgctccggc cctttcccaa tgtcctgtgc tggatcttga tagcttgggc | 720 |
| agttgagttt ggcgtgtgaa gtggacgtgg acttggcgag cgtcagtcag cacttcctga | 780 |
| atgaggctat agcttctgca agctttcgtg gatagatttt ccgagattct cagcttgcat | 840 |
| ccgatccagc aagctctcag ttccgtttag cccccacta atgactaaaa gtagactgaa | 900 |
| aagttgagac gcgcgcacat gcagctacgc cgctacgcta tggctggttc acccaccgga | 960 |
| gcctgcaacg cgctccctgt ggagagagaa aagaagctct gccacccgtc cacacattcc | 1020 |
| tgtgatagat cgcattcatc cagctggcta ctgaatgcgc gttgtgctgc gtaggacacg | 1080 |
| tatggcgagc tagcctacag ataaggtcga gtagcccact ataaaagggc taaaatagca | 1140 |

```
aatttttccc tgcgtccgtg cacccacgcc gagcttgccg ctgcgaccgt ggccgagcag    1200
atcacgcaca cgacatgcat tgctttgttc gtcttcaaaa caaacccaaa aaaaatggtt    1260
ttgcggtttt gcccgaccag cctggagcac ggtggtgctc agccagacag ccaataggac    1320
attcttgatt cttgatgttg tattgtattt gttgagtttg tgatctaaat tttgttata    1380 ggacatatta gcaagtaaag cggaggcttg ttataggttt gggccggagt atattgctga    1440
ctctaattag ggtttctgtt gcgtcataat ttttactcct cttataagcc gtcgtacaaa    1500
gacggcgtta tgtaaacatt tctacatata gtgaaggttt tcgtaatttt tctctttgca    1560
ttaaggacct gtttggttag aggtctctca ggcacttgcc tgccaagtaa ggaatcctag    1620
cccatgtatt caaaatctaa cgcctggaat ctgtgcaact ttggccggct ccaaactaaa    1680
taagccttaa aagaatttct atgtaaatct atgtatggtg ctctgtggtt tgttgtttga    1740
tcttccctgt tttgtctgct aacggtatcc atccgtccat tggtgctccg gccctttccc    1800
aatgtcctgt gctggatctt gatagcttgg gcagttgagt ttggcgtgtg aagtggacgt    1860
ggacttggcg agcgtcagtc agcacttcct gaatgaggct atagcttctg caagctttcg    1920
tggatagatt ttccgagatt ctcagcttgc atccgatcca gcaagctctc agttccgttt    1980 agcccccac taatgactaa agtagactg aaaagttgag acgcgcgcac atgcagctac    2040
gccgctacgc tatggctggt tcacccaccg gagcctgcaa cgcgctccct gtggagagag    2100
aaaagaagct ctgccacccg tccacacatt cctgtgatag atcgcattca tccagctggc    2160
tactgaatgc gcgttgtgct gcgtaggaca cgtatggcga gctagcctac agataaggtc    2220
gagtagccca ctataaaagg gctaaaatag caaattttc cctgcgtccg tgcacccacg    2280
ccgagcttgc cgctgcgacc gtggccgagc agatcacgca cacgacatgc attgctttgt    2340
tcgtcttcaa aacaaaccca aaaaaatgg ttttgcggtt tgcccgacc agcctggagc    2400 acggtggtgc tcagccagac agccaatagg acattcttga ttcttgatgt tgtattgtat    2460
ttgttgagtt tgtgatctaa attttgttta taggacatat tagcaagtaa agcggaggct    2520
tgttataggt ttgggccgga gtatattgct gactctaatt agggtttctg ttgcgtcata    2580
atttttactc ctcttataag ccgtcgtaca aagacggcgt tatgtaaaca tttctacata    2640
tagtgaaggt tttcgtaatt tttctctttg cattaaggac ctgtttggtt agaggtctct    2700
caggcacttg cctgccaagt aaggaatcct agcccatgta ttcaaaatct aacgcctgga    2760
atctgtgcaa ctttggccgg ctccaaacta ataagcctt aaaagaattt ctatgtaaat    2820
ctatgtatgg tgctctgtgg tttgttgttt gatcttccct gttttgtctg ctaacggtat    2880
ccatccgtcc attggtgctc cggcccttc ccaatgtcct gtgctggatc ttgatagctt    2940
gggcagttga gtttggcgtg tgaagtggac gtggacttgg cgagcgtcag tcagcacttc    3000
ctgaatgagg ctatagcttc tgcaagcttt cgtggataga ttttccgaga ttctcagctt    3060
gcatccgatc cagcaagctc tcagttccgt ttagccccc actaatgact aaaagtagac    3120
tgaaaagttg agacgcgcgc acatgcagct acgccgctac gctatggctg gttcacccac    3180
cggagcctgc aacgcgctcc ctgtggagag agaaaagaag ctctgccacc cgtccacaca    3240
ttcctgtgat agatcgcatt catccagctg gctactgaat gcgcgttgtg ctgcgtagga    3300
cacgtatggc gagctagcct acagataagg tcgagcacca acttgctctg tgatgttaat    3360 gttttggtg attagtgaca agggtgccta atttctttc tgatgttaat attttgaaag    3420
attctcactc tgaaaaaaaa atgcatgttc atatccatgt ttctctaaaa ataatccata    3480
```

```
gccagtgtgt gatactttct actagttccc actaaatgca ttgtgaaatt aaattctata    3540
aaattttgta atttctaata tttagtaagg gtagaaacag agatttttt cttaatttta     3600 aatcatcatg tatcaggagt cgcaaaggtc caggaatgat atgcaagatt gctacatggt    3660
tggtatcctc ttaatgtcat ccttggcagg gagttgtggt ggatatgcct tctgctgcca    3720
ggcactgggg cacaagaaga atggtgtctg ccacacaagc caccctgcac cctacaaaca    3780
actcacagct ggaatggtta tcaccaaacc aatgacagaa aaaactgtgt attccacgta    3840
attgatggtt actggcaaaa ttcatggatg taatacatca gggcatctca accgtcgaaa    3900
gatgctcatg ggcactactc ctcggcgaaa tgcgcccaca gaaacccaga attgttcatc    3960
agccaagacc atccttaagg tcaagaatgt ccagataata tttatggacg gtgcagcgca    4020
aacgataaaa ttccagtatt gcagatttta catggtacac agagaagcta aggaaatcat    4080
agagacaagc tagtggcaga gccaggacaa aaacagaagg tggcaagaga gttggagcaa    4140
ccaaatcaca gccattcata tccagaaggc cagcctccac ctcacaactc atatcctaat    4200
gccatttggt gtacaactat atattgtacc ccattcacc gattgcaggc accaaatgaa      4260
atccaagtca atcggtgtac attgaccaa                                        4289
```

<210> SEQ ID NO 52
<211> LENGTH: 4330
<212> TYPE: DNA
<213> ORGANISM: Artificial Sequence
<220> FEATURE:
<223> OTHER INFORMATION: Synthetic

<400> SEQUENCE: 52

```
agcccactat aaaagggcta aaatagcaaa ttttttcctg cgtccgtgca cccacgccga      60
gcttgccgct cgaccgtgg ccgagcagat cacgcacacg acatgcattg ctttgttcgt      120
cttcaaaaca aacccaaaaa aaatggtttt gcggttttgc ccgaccagcc tggagcacgg     180
tggtgctcag ccagacagcc aataggacat tcttgattct tgatgttgta ttgtatttgt     240
tgagtttgtg atctaaattt tgtttatagg acatattagc aagtaaagcg gaggcttgtt     300
ataggtttgg gccggagtat attgctgact ctaattaggg tttctgttgc gtcataattt     360
ttactcctct tataagccgt cgtacaaaga cggcgttatg taaacatttc tacatatagt     420
gaaggttttc gtaattttc tctttgcatt aaggacctgt ttggttagag gtctctcagg      480
cacttgcctg ccaagtaagg aatcctagcc catgtattca aaatctaacg cctggaatct     540
gtgcaacttt ggccggctcc aaactaaata agccttaaaa gaatttctat gtaaatctat     600
gtatggtgct ctgtggtttg ttgtttgatc ttccctgttt tgtctgctaa cggtatccat     660
ccgtccattg gtgctccggc cctttcccaa tgtcctgtgc tggatcttga tagcttgggc     720
agttgagttt ggcgtgtgaa gtggacgtgg acttggcgag cgtcagtcag cacttcctga    780
atgaggctat agcttctgca agctttcgtg gatagatttt ccgagattct cagcttgcat    840
ccgatccagc aagctctcag ttccgtttag ccccccacta atgactaaaa gtagactgaa    900
aagttgagac gcgcgcacat gcagctacgc cgctacgcta tggctggttc acccaccgga    960
gcctgcaacg cgctccctgt ggagagagaa aagaagctct gccacccgtc cacacattcc    1020
tgtgatagat cgcattcatc cagctggcta ctgaatgcgc gttgtgctgc gtaggacacg    1080
tatggcgagc tagcctacag ataaggtcga gtagcccact ataaaagggc taaaatagca    1140 aattttccc tgcgtccgtg cacccacgcc gagcttgccg ctgcgaccgt ggccgagcag     1200
atcacgcaca cgacatgcat tgctttgttc gtcttcaaaa caaacccaaa aaaatggtt     1260
```

-continued

```
ttgcggtttt gcccgaccag cctggagcac ggtggtgctc agccagacag ccaataggac    1320
attcttgatt cttgatgttg tattgtattt gttgagtttg tgatctaaat tttgtttata    1380
ggacatatta gcaagtaaag cggaggcttg ttataggttt gggccggagt atattgctga    1440
ctctaattag ggtttctgtt gcgtcataat ttttactcct cttataagcc gtcgtacaaa    1500
gacggcgtta tgtaaacatt tctacatata gtgaaggttt tcgtaatttt tctctttgca    1560
ttaaggacct gtttggttag aggtctctca ggcacttgcc tgccaagtaa ggaatcctag    1620
cccatgtatt caaaatctaa cgcctggaat ctgtgcaact ttggccggct ccaaactaaa    1680
taagccttaa aagaatttct atgtaaatct atgtatggtg ctctgtggtt tgttgtttga    1740
tcttccctgt tttgtctgct aacggtatcc atccgtccat tggtgctccg gccctttccc    1800
aatgtcctgt gctggatctt gatagcttgg gcagttgagt ttggcgtgtg aagtggacgt    1860
ggacttggcg agcgtcagtc agcacttcct gaatgaggct atagcttctg caagctttcg    1920
tggatagatt ttccgagatt ctcagcttgc atccgatcca gcaagctctc agttccgttt    1980 agcccccac taatgactaa agtagactg aaaagttgag acgcgcgcac atgcagctac       2040
gccgctacgc tatggctggt tcacccaccg gagcctgcaa cgcgctccct gtggagagag    2100 aaagaagct ctgccacccg tccacacatt cctgtgatag atcgcattca tccagctggc     2160
tactgaatgc gcgttgtgct gcgtaggaca cgtatggcga gctagcctac agataaggtc    2220
gagtagccca ctataaaagg gctaaaatag caaattttc cctgcgtccg tgcacccacg     2280
ccgagcttgc cgctgcgacc gtggccgagc agatcacgca cacgcatgc attgctttgt     2340 tcgtcttcaa aacaaaccca aaaaaaatgg ttttgcggtt ttgcccgacc agcctggagc    2400
acggtggtgc tcagccagac agccaatagg acattcttga ttcttgatgt tgtattgtat    2460
ttgttgagtt tgtgatctaa attttgttta taggacatat tagcaagtaa agcggaggct    2520
tgttataggt ttgggccgga gtatattgct gactctaatt agggtttctg ttgcgtcata    2580 attttttactc ctcttataag ccgtcgtaca agacggcgt tatgtaaaca tttctacata    2640
tagtgaaggt tttcgtaatt tttctctttg cattaaggac ctgtttggtt agaggtctct    2700
caggcacttg cctgccaagt aaggaatcct agcccatgta ttcaaaatct aacgcctgga    2760
atctgtgcaa ctttggccgg ctccaaacta aataagcctt aaaagaattt ctatgtaaat    2820
ctatgtatgg tgctctgtgg tttgttgttt gatcttccct gttttgtctg ctaacggtat    2880
ccatccgtcc attggtgctc cggccctttc ccaatgtcct gtgctggatc ttgatagctt    2940
gggcagttga gtttggcgtg tgaagtggac gtggacttgg cgagcgtcag tcagcacttc    3000
ctgaatgagg ctatagcttc tgcaagcttt cgtggataga ttttccgaga ttctcagctt    3060
gcatccgatc cagcaagctc tcagttccgt ttagcccccc actaatgact aaaagtagac    3120
tgaaaagttg agacgcgcgc acatgcagct acgccgctac gctatggctg gttcacccac    3180
cggagcctgc aacgcgctcc ctgtggagag agaaaagaag ctctgccacc cgtccacaca    3240
ttcctgtgat agatcgcatt catccagctg gctactgaat gcgcgttgtg ctgcgtagga    3300
cacgtatggc gagctagcct acagataagg tcgagcacca acttgctctg tgatgttaat    3360 gttttggtg attagtgaca agggtgccta atttcttttc tgatgttaat attttgaaag     3420
attctcactc tgaaaaaaaa atgcatgttc atatccatgt ttctctaaaa ataatccata    3480
gccagtgtgt gatactttct actagttccc actaaatgca ttgtgaaatt aaattctata    3540
aaattttgta atttctaata tttagtaagg gtagaaacag agattttttt cttaattta     3600
```

| | |
|---|---|
| aatcatcatg tatcaggagt cgcaaaggtc caggaatgat atgcaagatt gctacatggt | 3660 |
| tggtatcctc ttaatgtcat ccttggcagg gagttgtggt ggatatgcct tctgctgcca | 3720 |
| ggcactgggg cacaagaaga atggtgtctg ccacacaagc caccctgcac cctacaaaca | 3780 |
| actcacagct ggaatggtta tcaccaaacc aatgacagaa aaaactgtgt attccacgta | 3840 |
| attgatggtt actggcaaaa ttcatggatg taatacatca gggcatctca accgtcgaaa | 3900 |
| gatgctcatg ggcactactc ctcggcgaaa tgcgcccaca gaaacccaga attgttcatc | 3960 |
| agccaagacc atccttaagg tcaagaatgt ccagataata tttatggacg gtgcagcgca | 4020 |
| aacgataaaa ttccagtatt gcagatttta catggtacac agagaagcta aggaaatcat | 4080 |
| agagacaagc tagtggcaga gccaggacaa aaacagaagg tggcaagaga gttggagcaa | 4140 |
| ccaaatcaca gccattcata tccagaaggc cagcctccac ctcacaactc atatcctcaa | 4200 |
| tccccggctc tcatctctat aagaggagcc tttgtattca gttgcaagca tgcaagtcac | 4260 |
| acactgcaag cttacttctg agcaaaaaga gttttgagtg aaataaattt gaagttcccc | 4320 |
| cttacatctt | 4330 |

<210> SEQ ID NO 53
<211> LENGTH: 4087
<212> TYPE: DNA
<213> ORGANISM: Artificial Sequence
<220> FEATURE:
<223> OTHER INFORMATION: Synthetic

<400> SEQUENCE: 53

| | |
|---|---|
| agcccactat aaagggcta aaatagcaaa ttttccctg cgtccgtgca cccacgccga | 60 |
| gcttgccgct gcgaccgtgg ccgagcagat cacgcacacg acatgcattg ctttgttcgt | 120 |
| cttcaaaaca aacccaaaaa aaatggtttt gcggttttgc ccgaccagcc tggagcacgg | 180 |
| tggtgctcag ccagacagcc aataggacat tcttgattct tgatgttgta ttgtatttgt | 240 |
| tgagtttgtg atctaaattt tgtttatagg acatattagc aagtaaagcg gaggcttgtt | 300 |
| ataggtttgg gccggagtat attgctgact ctaattaggg tttctgttgc gtcataattt | 360 |
| ttactcctct tataagccgt cgtacaaaga cggcgttatg taaacatttc tacatatagt | 420 |
| gaaggttttc gtaattttc tctttgcatt aaggacctgt ttggttagag gtctctcagg | 480 |
| cacttgcctg ccaagtaagg aatcctagcc catgtattca aaatctaacg cctggaatct | 540 |
| gtgcaacttt ggccggctcc aaactaaata agccttaaaa gaatttctat gtaaatctat | 600 |
| gtatggtgct ctgtggtttg ttgtttgatc ttccctgttt tgtctgctaa cggtatccat | 660 |
| ccgtccattg gtgctccggc cctttcccaa tgtcctgtgc tggatcttga tagcttgggc | 720 |
| agttgagttt ggcgtgtgaa gtggacgtgg acttggcgag cgtcagtcag cacttcctga | 780 |
| atgaggctat agcttctgca agctttcgtg gatagatttt ccgagattct cagcttgcat | 840 |
| ccgatccagc aagctctcag ttccgtttag cccccccacta atgactaaaa gtagactgaa | 900 |
| aagttgagac gcgcgcacat gcagctacgc cgctacgcta tggctggttc acccaccgga | 960 |
| gcctgcaacg cgctccctgt ggagagagaa aagaagctct gccacccgtc cacacattcc | 1020 |
| tgtgatagat cgcattcatc cagctggcta ctgaatgcgc gttgtgctgc gtaggacacg | 1080 |
| tatggcgagc tagcctacag ataaggtcga gtagcccact ataaaagggc taaaatagca | 1140 |
| aattttccc tgcgtccgtg cacccacgcc gagcttgccg ctgcgaccgt ggccgagcag | 1200 |
| atcacgcaca cgacatgcat tgctttgttc gtcttcaaaa caaacccaaa aaaatggttt | 1260 |
| tgcggttttt gcccgaccag cctggagcac ggtggtgctc agccagacag ccaataggac | 1320 |

```
attcttgatt cttgatgttg tattgtattt gttgagtttg tgatctaaat tttgtttata    1380
ggacatatta gcaagtaaag cggaggcttg ttataggttt gggccggagt atattgctga    1440
ctctaattag ggtttctgtt gcgtcataat ttttactcct cttataagcc gtcgtacaaa    1500
gacggcgtta tgtaaacatt tctacatata gtgaaggttt tcgtaatttt tctctttgca    1560
ttaaggacct gtttggttag aggtctctca ggcacttgcc tgccaagtaa ggaatcctag    1620
cccatgtatt caaaatctaa cgcctggaat ctgtgcaact ttggccggct ccaaactaaa    1680
taagccttaa aagaatttct atgtaaatct atgtatggtg ctctgtggtt tgttgtttga    1740
tcttccctgt tttgtctgct aacggtatcc atccgtccat tggtgctccg gcccttcccc    1800
aatgtcctgt gctggatctt gatagcttgg gcagttgagt ttggcgtgtg aagtggacgt    1860
ggacttggcg agcgtcagtc agcacttcct gaatgaggct atagcttctg caagctttcg    1920
tggatagatt ttccgagatt ctcagcttgc atccgatcca gcaagctctc agttccgttt    1980 agcccccac taatgactaa aagtagactg aaaagttgag acgcgcgcac atgcagctac    2040
gccgctacgc tatggctggt tcacccaccg gagcctgcaa cgcgctccct gtggagagag    2100
aaaagaagct ctgccacccg tccacacatt cctgtgatag atcgcattca tccagctggc    2160
tactgaatgc gcgttgtgct gcgtaggaca cgtatggcga gctagcctac agataaggtc    2220
gagcaccaac ttgctctgtg atgttaatgt ttttggtgat tagtgacaag ggtgcctaat    2280 ttctttctg atgttaatat tttgaaagat tctcactctg aaaaaaaaat gcatgttcat    2340
atccatgttt ctctaaaaat aatccatagc cagtgtgtga tactttctac tagttcccac    2400
taaatgcatt gtgaaattaa attctataaa attttgtaat ttctaatatt tagtaagggt    2460
agaaacagag attttttct taattttaaa tcatcatgta tcaggagtcg caaaggtcca    2520
ggaatgatat gcaagattgc tacatggttg gtatcctctt aatgtcatcc ttggcaggga    2580
gttgtggtgg atatgccttc tgctgccagg cactggggca caagaagaat ggtgtctgcc    2640
acacaagcca ccctgcaccc tacaaacaac tcacagctgg aatggttatc accaaaccaa    2700
tgacagaaaa aactgtgtat tccacgtaat tgatggttac tggcaaaatt catggatgta    2760
atacatcagg gcatctcaac cgtcgaaaga tgctcatggg cactactcct cggcgaaatg    2820
cgcccacaga aacccagaat tgttcatcag ccaagaccat ccttaaggtc aagaatgtcc    2880
agataatatt tatggacggt gcagcgcaaa cgataaaatt ccagtattgc agattttaca    2940
tggtacacag agaagctaag gaaatcatag agacaagcta gtggcagagc caggacaaaa    3000
acagaaggtg gcaagagagt tggagcaacc aaatcacagc cattcatatc cagaaggcca    3060
gcctccacct cacaactcat atcctgtcga gcaccaactt gctctgtgat gttaatgttt    3120
ttggtgatta gtgacaaggg tgcctaattt cttttctgat gttaatattt tgaaagattc    3180
tcactctgaa aaaaaatgc atgttcatat ccatgtttct ctaaaaataa tccatagcca    3240
gtgtgtgata ctttctacta gttcccacta aatgcattgt gaaattaaat tctataaaat    3300
tttgtaattt ctaatattta gtaagggtag aaacagagat ttttttctta attttaaatc    3360
atcatgtatc aggagtcgca aaggtccagg aatgatatgc aagattgcta catggttggt    3420
atcctcttaa tgtcatcctt ggcagggagt gtggtggat atgccttctg ctgccaggca    3480
ctggggcaca agaagaatgg tgtctgccac acaagccacc ctgcacccta caaacaactc    3540
acagctggaa tggttatcac caaaccaatg acagaaaaaa ctgtgtattc cacgtaattg    3600
atggttactg gcaaaattca tggatgtaat acatcagggc atctcaaccg tcgaaagatg    3660
```

```
ctcatgggca ctactcctcg gcgaaatgcg cccacagaaa cccagaattg ttcatcagcc    3720
aagaccatcc ttaaggtcaa gaatgtccag ataatattta tggacggtgc agcgcaaacg    3780
ataaaattcc agtattgcag attttacatg gtacacagag aagctaagga aatcatagag    3840
acaagctagt ggcagagcca ggacaaaaac agaaggtggc aagagagttg gagcaaccaa    3900
atcacagcca ttcatatcca gaaggccagc ctccacctca caactcatat cctttgtact    3960
caggtactca cccttaaatc tgagcaggcg cttcacttct cacccccct aaggaaaggc    4020 tgcaattgca agcttgtgtc aaagaagagg gtagcacctg atcctcttgc ctttggagcc    4080
agaaaca                                                              4087

<210> SEQ ID NO 54
<211> LENGTH: 3766
<212> TYPE: DNA
<213> ORGANISM: Artificial Sequence
<220> FEATURE:
<223> OTHER INFORMATION: Synthetic

<400> SEQUENCE: 54
acgtggttag ctactaatat aaatgtaagg tcattcgatg gttttttctat tttcaattac      60 ctagcattat ctcatttcta attgtgataa caaatgcatt agaccataat tctgtaaata     120
tgtacattta agcacacagt ctatatttta aaattcttct ttttgtgtgg atatcccaac     180
ccaaatccac ctctctcttc aatccgtgca tgttcaccgc tgccaagtgc caacaacaca     240
tcgcatcgtg catatctttg ttggcttgtg cacggtcggc gccaatggag gagacacctg     300
tacggtgccc ttggtagaac aacatcctta tccctatatg tatggtgccc ttcgtagaat     360 gacaccccctt atccctacaa tagccatgta tgcataccaa gaattaaata tactttttct     420
tgaaccacaa taatttatta tagcggcact tcttgttcag gttgaacact tatttggaac     480
aataaaatgc cgagttccta accacaggtt cacttttttt tttccttatc ctcctaggaa     540
actaaatttt aaaatcataa atttaattta aatgttaatg gaaacaaaaa attatctaca     600
aagacgactc ttagccacag ccgcctcact gcaccctcaa ccacatcctg caaacagaca     660
ccctcgccac atccctccag attcttcact ccgatgcagc ctacttgcta acagacgccc     720
tctccacatc ctgcaaagca ttcctccaaa ttcttgcgat cccccgaatc cagcattaac     780
tgctaaggga cgccctctcc acatcctgct acccaattag ccaacggaat aacacaagaa     840
ggcaggtgag cagtgacaaa gcacgtcaac agcaccgagc caagccaaaa aggagcaagg     900
aggagcaagc ccaagccgca gccgcagctc tccaggtccc cttgcgattg ccgccagcag     960
tagcagacac ccctctccac atcccctccg gccgctaaca gcagcaagcc aagccaaaaa    1020
ggagcctcag ccgcagccgg ttccgttgcg gttaccgccg atcacatgcc caaggccgcg    1080
cctttccgaa cgccgagggc cgcccgttcc cgtgcacagc cacacacaca gtcgagtagc    1140
ccactataaa agggctaaaa tagcaaattt ttccctgcgt ccgtgcaccc acgccgagct    1200
tgccgctgcg accgtggccg agcagatcac gcacacgaca tgcattgctt tgttcgtctt    1260
caaaacaaac ccaaaaaaaa tggttttgcg gttttgcccg accagcctgg agcacggtgg    1320
tgctcagcca gacagccaat aggacattct tgattcttga tgttgtattg tatttgttga    1380
gtttgtgatc taaattttgt ttataggaca tattagcaag taaagcggag cttgttata    1440 ggtttgggcc ggagtatatt gctgactcta attagggttt ctgttgcgtc ataattttta    1500
ctcctcttat aagccgtcgt acaaagacgg cgttatgtaa acatttctac atatagtgaa    1560
ggttttcgta atttttctct ttgcattaag gacctgtttg gttagaggtc tctcaggcac    1620
```

```
ttgcctgcca agtaaggaat cctagcccat gtattcaaaa tctaacgcct ggaatctgtg    1680
caactttggc cggctccaaa ctaaataagc cttaaaagaa tttctatgta aatctatgta    1740
tggtgctctg tggtttgttg tttgatcttc cctgttttgt ctgctaacgg tatccatccg    1800
tccattggtg ctccggccct ttcccaatgt cctgtgctgg atcttgatag cttgggcagt    1860
tgagtttggc gtgtgaagtg gacgtggact tggcgagcgt cagtcagcac ttcctgaatg    1920
aggctatagc ttctgcaagc tttcgtggat agattttccg agattctcag cttgcatccg    1980
atccagcaag ctctcagttc cgtttagccc cccactaatg actaaaagta gactgaaaag    2040
ttgagacgcg cgcacatgca gctacgccgc tacgctatgg ctggttcacc caccggagcc    2100
tgcaacgcgc tccctgtgga gagagaaaag aagctctgcc acccgtccac acattcctgt    2160
gatagatcgc attcatccag ctggctactg aatgcgcgtt gtgctgcgta ggacacgtat    2220
ggcgagctag cctacagata aggtcgagtt acttaacttt actagaggtg gacgtagaaa    2280
gttagtaggg cctgctaact tcctagatga ggtcgtagga agttagtgac tctttgaccg    2340
cgctcgtttg tcaatagttg aaagctaaat ttctagagga ggctgtagga agttagtggc    2400
tcgtttgatc gcgctcgttt gtcaacagct gaaagctaac tttctagagg agaccgcccc    2460
tgctaacttc ctacgacctt tgtggttggg gctataaata cccgaccttt gtggccttct    2520
caacggagag taggttattt ggaaccaaac ctcggaaaac aaatcaccgt gttcatttgt    2580
gttgatcttc atcacttgat tgtttcttc cctctcctct ctctaaagtt ctcttgctca    2640
cattgttttg agtttgcttc taaagttatc tgtattgatt gagtaactca tagcaaaaag    2700
aactatcttt tgcactccga aatattacta acactaaccc cgagtataat gcgtgttcaa    2760
actttataaa tttcagattt cgtctattta tcctctttag acgactttca aagtttatat    2820
ttttggtgta atggctacca catcaacatg cttgatttcc tggcacatgc atttattttt    2880
gtcaatactt ttgcgtggcc cttttcacgt atagaagagt gaagctaaca ttacattaca    2940
taaatatttt tccctctaat tgcggcaatc aagcacgaac gcactagcta gtaagctttt    3000
tgtgaggatt tggcatgttg ctgtgactgt gagtggatta ccgcgacgac agggacgaca    3060
tgcgtgccct tatctcttgg agatttcctc gggcccgacc atcagacgaa caacacatgc    3120
atgtgctagc ccgtgtcagc aatctagatg acctctcaat tttccacacg aggtggggcc    3180
ctcgccacct catctcttgt ctttttcccag ttaggtgaca tggagcacat gagcctccga    3240
gctcaccggg gggtgacgcc accccccgtc gacctcgaga gagcctagcc cacctaagcc    3300
gagcgtgatg aactgatgaa cccactacca ctagtcaagg caaaccacaa ccacaaatgg    3360
atcaattgat ctagaacaat ccgaaggagg ggaggccacg tcacactcac accaaccgaa    3420
atatctgcca gtatcagatc aaccggccaa taggacgcca gcgagcccaa cacctagcga    3480
cgccgcaaaa ttcaccgcga ggggcaccgg gcacggcaaa aacaaaagcc cggcgcggtg    3540
agaatatctg gcgactggcg gagacctggt ggccagcgcg cggccacatc agccaccca    3600 tccgcccacc tcacctccgg cgagccaatg gcaactcgtc ttaagattcc acgagataag    3660
gacccgatcg ccggcgacgc tatttagcca ggtgcgcccc ccacggtaca ctccaccagc    3720
ggcatctata gcaaccggtc caacactttc acgctcagct tcagca              3766
```

<210> SEQ ID NO 55
<211> LENGTH: 3760
<212> TYPE: DNA
<213> ORGANISM: Artificial Sequence
<220> FEATURE:

<223> OTHER INFORMATION: Synthetic

<400> SEQUENCE: 55

```
tacttaactt tactagaggt ggacgtagaa agttagtagg gcctgctaac ttcctagatg      60
aggtcgtagg aagttagtga ctctttgacc gcgctcgttt gtcaatagtt gaaagctaaa     120
tttctagagg aggctgtagg aagttagtgg ctcgtttgat cgcgctcgtt tgtcaacagc     180
tgaaagctaa ctttctagag gagaccgccc ctgctaactt cctacgacct tgtggttgg      240
ggctataaat acccgacctt tgtggccttc tcaacggaga gtaggttatt tggaaccaaa     300
cctcggaaaa caaatcaccg tgttcatttg tgttgatctt catcacttga tttgtttctt     360
ccctctcctc tctctaaagt tctcttgctc acattgtttt gagtttgctt ctaaagttat     420
ctgtattgat tgagtaactc atagcaaaaa gaactatctt ttgcactccg aaatattact     480
aacactaacc ccgagtataa tgcgtgttca aactttataa atttcagatt tcgtctattt     540
atcctcttta gacgactttc aaagtttata tttttggtgt aatggctacc acatcaacat     600
gcttgatttc ctggcacatg catttatttt tgtcaatact tttgcgtggc ccttttcacg     660
tatagaagag tgaagctaac attacattac ataaatattt ttccctctaa ttgcggcaat     720
caagcacgaa cgcactagct agtaagcttt ttgtgaggat ttggcatgtt gctgtgactg     780
tgagtggatt accgcgacga cagggacgac atgcgtgccc ttatctcttg gagatttcct     840
cgggcccgac catcagacga acaacacatg catgtgctag cccgtgtcag caatctagat     900
gacctctcaa ttttccacac gaggtggggc cctcgccacc tcatctcttg tctttttccca    960
gttaggtgac atggagcaca tgagcctccg agctcaccgg ggggtgacgc caccccccgt    1020
cgagtagccc actataaaag ggctaaaata gcaaattttt ccctgcgtcc gtgcacccac    1080
gccgagcttg ccgctgcgac cgtggccgag cagatcacgc acacgacatg cattgctttg    1140
ttcgtcttca aaacaaaccc aaaaaaaatg gttttgcggt tttgcccgac cagcctggag    1200
cacggtggtg ctcagccaga cagccaatag gacattcttg attcttgatg ttgtattgta    1260
tttgttgagt ttgtgatcta aattttgttt ataggacata ttagcaagta aagcggaggc    1320
ttgttatagg tttgggccgg agtatattgc tgactctaat tagggtttct gttgcgtcat    1380
aatttttact cctcttataa gccgtcgtac aaagacggcg ttatgtaaac atttctacat    1440
atagtgaagg ttttcgtaat ttttctcttt gcattaagga cctgtttggt tagaggtctc    1500
tcaggcactt gcctgccaag taaggaatcc tagcccatgt attcaaaatc taacgcctgg    1560
aatctgtgca actttggccg gctccaaact aaataagcct taaaagaatt tctatgtaaa    1620
tctatgtatg gtgctctgtg gtttgttgtt tgatcttccc tgttttgtct gctaacggta    1680
tccatccgtc cattggtgct ccggcccttt cccaatgtcc tgtgctggat cttgatagct    1740
tgggcagttg agtttggcgt gtgaagtgga cgtggacttg gcgagcgtca gtcagcactt    1800
cctgaatgag gctatagctt ctgcaagctt tcgtggatag attttccgag attctcagct    1860
tgcatccgat ccagcaagct ctcagttccg tttagccccc cactaatgac taaaagtaga    1920
ctgaaaagtt gagacgcgcg cacatgcagc tacgccgcta cgctatggct ggttcaccca    1980
ccggagcctg caacgcgctc cctgtggaga gagaaaagaa gctctgccac ccgtccacac    2040
attcctgtga tagatcgcat tcatccagct ggctactgaa tgcgcgttgt gctgcgtagg    2100
acacgtatgg cgagctagcc tacagataag gtcgagcacg tggttagcta ctaatataaa    2160
tgtaaggtca ttcgatggtt tttctatttt caattaccta gcattatctc atttctaatt    2220
gtgataacaa atgcattaga ccataattct gtaaatatgt acatttaagc acacagtcta    2280
```

```
tatttttaaaa ttcttcttttt tgtgtggata tcccaaccca aatccacctc tctcttcaat    2340
ccgtgcatgt tcaccgctgc caagtgccaa caacacatcg catcgtgcat atctttgttg    2400
gcttgtgcac ggtcggcgcc aatggaggag acacctgtac ggtgcccttg gtagaacaac    2460
atccttatcc ctatatgtat ggtgcccttc gtagaatgac accccttatc cctacaatag    2520
ccatgtatgc ataccaagaa ttaaatatac ttttcttga accacaataa tttattatag     2580
cggcacttct tgttcaggtt gaacacttat ttggaacaat aaaatgccga gttcctaacc    2640
acaggttcac ttttttttt ccttatcctc ctaggaaact aaattttaaa atcataaatt     2700
taatttaaat gttaatggaa acaaaaaatt atctacaaag acgactctta gccacagccg    2760
cctcactgca ccctcaacca catcctgcaa acagacaccc tcgccacatc cctccagatt    2820
cttcactccg atgcagccta cttgctaaca gacgccctct ccacatcctg caaagcattc    2880
ctccaaattc ttgcgatccc ccgaatccag cattaactgc taagggacgc cctctccaca    2940
tcctgctacc caattagcca acggaataac acaagaaggc aggtgagcag tgacaaagca    3000
cgtcaacagc accgagccaa gccaaaaagg agcaaggagg agcaagccca gccgcagcc     3060 gcagctctcc aggtcccctt gcgattgccg ccagcagtag cagacacccc tctccacatc    3120
ccctccggcc gctaacagca gcaagccaag ccaaaaagga gcctcagccg cagccggttc    3180
cgttgcggtt accgccgatc acatgcccaa ggccgcgcct ttccgaacgc cgagggccgc    3240
ccgttcccgt gcacagccac acacacagtc gagagagcct agcccaccta gccgagcgt    3300 gatgaactga tgaacccact accactagtc aaggcaaacc acaaccacaa atggatcaat    3360
tgatctagaa caatccgaag gaggggaggc cacgtcacac tcacaccaac cgaaatatct    3420
gccagtatca gatcaaccgg ccaataggac gccagcgagc ccaacaccta gcgacgccgc    3480
aaaattcacc gcgaggggca ccgggcacgg caaaaacaaa agcccggcgc ggtgagaata    3540
tctggcgact ggcggagacc tggtggccag cgcgcggcca catcagccac cccatccgcc    3600
cacctcacct ccggcgagcc aatggcaact cgtcttaaga ttccacgaga taaggacccg    3660
atcgccggcg acgctattta gccaggtgcg ccccccacgg tacactccac cagcggcatc    3720
tatagcaacc ggtccaacac tttcacgctc agcttcagca                          3760
```

<210> SEQ ID NO 56
<211> LENGTH: 2629
<212> TYPE: DNA
<213> ORGANISM: Artificial Sequence
<220> FEATURE:
<223> OTHER INFORMATION: Synthetic

<400> SEQUENCE: 56

```
agcccactat aaagggcta aaatagcaaa ttttcccctg cgtccgtgca cccacgccga       60
gcttgccgct gcgaccgtgg ccgagcagat cacgcacacg acatgcattg ctttgttcgt    120
cttcaaaaca aacccaaaaa aaatggtttt gcggttttgc ccgaccagcc tggagcacgg    180
tggtgctcag ccagacagcc aataggacat tcttgattct tgatgttgta ttgtatttgt    240
tgagtttgtg atctaaattt tgtttatagg acatattagc aagtaaagcg gaggcttgtt    300
ataggtttgg gccggagtat attgctgact ctaattaggg tttctgttgc gtcataattt    360
ttactcctct tataagccgt cgtacaaaga cggcgttatg taaacatttc tacatatagt    420
gaaggttttc gtaatttttc tctttgcatt aaggacctgt ttggttagag gtctctcagg    480
cacttgcctg ccaagtaagg aatcctagcc catgtattca aaatctaacg cctggaatct    540
```

| | |
|---|---|
| gtgcaactt tggccggctcc aaactaaata agccttaaaa gaatttctat gtaaatctat | 600 |
| gtatggtgct ctgtggtttg ttgtttgatc ttccctgttt tgtctgctaa cggtatccat | 660 |
| ccgtccattg gtgctccggc cctttcccaa tgtcctgtgc tggatcttga tagcttgggc | 720 |
| agttgagttt ggcgtgtgaa gtggacgtgg acttggcgag cgtcagtcag cacttcctga | 780 |
| atgaggctat agcttctgca agctttcgtg gatagatttt ccgagattct cagcttgcat | 840 |
| ccgatccagc aagctctcag ttccgtttag ccccccacta atgactaaaa gtagactgaa | 900 |
| aagttgagac gcgcgcacat gcagctacgc cgctacgcta tggctggttc acccaccgga | 960 |
| gcctgcaacg cgctccctgt ggagagagaa aagaagctct gccacccgtc cacacattcc | 1020 |
| tgtgatagat cgcattcatc cagctggcta ctgaatgcgc gttgtgctgc gtaggacacg | 1080 |
| tatggcgagc tagcctacag ataaggtcga gttacttaac tttactagag gtggacgtag | 1140 |
| aaagttagta gggcctgcta acttcctaga tgaggtcgta ggaagttagt gactctttga | 1200 |
| ccgcgctcgt ttgtcaatag ttgaaagcta aatttctaga ggaggctgta ggaagttagt | 1260 |
| ggctcgtttg atcgcgctcg tttgtcaaca gctgaaagct aactttctag aggagaccgc | 1320 |
| ccctgctaac ttcctacgac ctttgtggtt ggggctataa ataccccgacc tttgtggcct | 1380 |
| tctcaacgga gagtaggtta tttggaacca aacctcggaa aacaaatcac cgtgttcatt | 1440 |
| tgtgttgatc ttcatcactt gatttgtttc ttccctctcc tctctctaaa gttctcttgc | 1500 |
| tcacattgtt ttgagtttgc ttctaaagtt atctgtattg attgagtaac tcatagcaaa | 1560 |
| aagaactatc ttttgcactc cgaaatatta ctaacactaa ccccgagtat aatgcgtgtt | 1620 |
| caaactttat aaatttcaga tttcgtctat ttatcctctt tagacgactt tcaaagttta | 1680 |
| tatttttggt gtaatggcta ccacatcaac atgcttgatt tcctggcaca tgcatttatt | 1740 |
| tttgtcaata cttttgcgtg gccctttca cgtatagaag agtgaagcta acattacatt | 1800 |
| acataaatat ttttccctct aattgcggca atcaagcacg aacgcactag ctagtaagct | 1860 |
| ttttgtgagg atttggcatg ttgctgtgac tgtgagtgga ttaccgcgac gacagggacg | 1920 |
| acatgcgtgc ccttatctct tggagatttc ctcgggcccg accatcagac gaacaacaca | 1980 |
| tgcatgtgct agcccgtgtc agcaatctag atgacctctc aattttccac acgaggtggg | 2040 |
| gccctcgcca cctcatctct tgtctttttcc cagttaggtg acatggagca catgagcctc | 2100 |
| cgagctcacc gggggtgac gccaccccc gtcgacctcg agagagccta gcccacctaa | 2160 |
| gccgagcgtg atgaactgat gaacccacta ccactagtca aggcaaacca caaccacaaa | 2220 |
| tggatcaatt gatctagaac aatccgaagg aggggaggcc acgtcacact cacaccaacc | 2280 |
| gaaatatctg ccagtatcag atcaaccggc caataggacg ccagcgagcc caacacctag | 2340 |
| cgacgccgca aaattcaccg cgaggggcac cgggcacggc aaaaacaaaa gcccggcgcg | 2400 |
| gtgagaatat ctggcgactg gcggagacct ggtggccagc gcgcggccac atcagccacc | 2460 |
| ccatccgccc acctcacctc cggcgagcca atggcaactc gtcttaagat tccacgagat | 2520 |
| aaggacccga tcgccggcga cgctatttag ccaggtgcgc cccccacggt acactccacc | 2580 |
| agcggcatct atagcaaccg gtccaacact ttcacgctca gcttcagca | 2629 |

<210> SEQ ID NO 57
<211> LENGTH: 2385
<212> TYPE: DNA
<213> ORGANISM: Artificial Sequence
<220> FEATURE:
<223> OTHER INFORMATION: Synthetic

<400> SEQUENCE: 57

```
accaacttgc tctgtgatgt taatgttttt ggtgattagt gacaagggtg cctaatttct      60
tttctgatgt taatattttg aaagattctc actctgaaaa aaaaatgcat gttcatatcc     120
atgtttctct aaaataatc catagccagt gtgtgatact ttctactagt tcccactaaa      180
tgcattgtga aattaaattc tataaaattt tgtaatttct aatatttagt aagggtagaa     240
acagagattt ttttcttaat tttaaatcat catgtatcag gagtcgcaaa ggtccaggaa     300
tgatatgcaa gattgctaca tggttggtat cctcttaatg tcatccttgg cagggagttg     360
tggtggatat gccttctgct gccaggcact ggggcacaag aagaatggtg tctgccacac     420
aagccaccct gcaccctaca aacaactcac agctggaatg gttatcacca aaccaatgac     480
agaaaaaact gtgtattcca cgtaattgat ggttactggc aaaattcatg gatgtaatac     540
atcagggcat ctcaaccgtc gaaagatgct catgggcact actcctcggc gaaatgcgcc     600
cacagaaacc cagaattgtt catcagccaa gaccatcctt aaggtcaaga atgtccagat     660
aatatttatg gacggtgcag cgcaaacgat aaaattccag tattgcagat tttacatggt     720
acacagagaa gctaaggaaa tcatagagac aagctagtgg cagagccagg acaaaaacag     780
aaggtggcaa gagagttgga gcaaccaaat cacagccatt catatccaga aggccagcct     840
ccacctcaca actcatatcc tgtcgagtta cttaaccttta ctagaggtgg acgtagaaag     900
ttagtagggc ctgctaactt cctagatgag gtcgtaggaa gttagtgact ctttgaccgc     960
gctcgtttgt caatagttga aagctaaatt tctagaggag gctgtaggaa gttagtggct    1020 cgttgatcg cgctcgtttg tcaacagctg aaagctaact ttctagagga accgccccct    1080
gctaacttcc tacgaccttt gtggttgggg ctataaatac ccgaccttg tggccttctc     1140 aacggagagt aggttatttg gaaccaaacc tcggaaaaca aatcaccgtg ttcatttgtg    1200
ttgatcttca tcacttgatt tgtttcttcc ctctcctctc tctaaagttc tcttgctcac    1260
attgttttga gtttgcttct aaagttatct gtattgattg agtaactcat agcaaaaaga    1320
actatctttt gcactccgaa atattactaa cactaacccc gagtataatg cgtgttcaaa    1380
ctttataaat ttcagatttc gtctatttat cctctttaga cgactttcaa agtttatatt    1440
tttggtgtaa tggctaccac atcaacatgc ttgatttcct ggcacatgca tttatttttg    1500
tcaatacttt tgcgtggccc ttttcacgta tagaagagtg aagctaacat tacattacat    1560 aaatatttt ccctctaatt gcggcaatca agcacgaacg cactagctag taagcttttt    1620
gtgaggattt ggcatgttgc tgtgactgtg agtggattac cgcgacgaca gggacgacat    1680
gcgtgccctt atctcttgga gatttcctcg ggcccgacca tcagacgaac aacacatgca    1740
tgtgctagcc cgtgtcagca atctagatga cctctcaatt ttccacacga ggtggggccc    1800
tcgccacctc atctcttgtc ttttcccagt taggtgacat ggagcacatg agcctccgag    1860
ctcaccgggg ggtgacgcca cccccgtcg acctcgagag agcctagccc acctaagccg    1920
agcgtgatga actgatgaac ccactaccac tagtcaaggc aaaccacaac cacaaatgga    1980
tcaattgatc tagaacaatc cgaaggaggg gaggccacgt cacactcaca ccaaccgaaa    2040
tatctgccag tatcagatca accggccaat aggacgccag cgagcccaac acctagcgac    2100
gccgcaaaat tcaccgcgag gggcaccggg cacggcaaaa acaaaagccc ggcgcggtga    2160
gaatatctgg cgactggcgg agacctggtg gccagcgcgc ggccacatca gccaccccat    2220
ccgcccacct cacctccggc gagccaatgg caactcgtct taagattcca cgagataagg    2280
acccgatcgc cggcgacgct atttagccag gtgcgccccc cacggtacac tccaccagcg    2340
```

```
gcatctatag caaccggtcc aacactttca cgctcagctt cagca              2385

<210> SEQ ID NO 58
<211> LENGTH: 4331
<212> TYPE: DNA
<213> ORGANISM: Artificial Sequence
<220> FEATURE:
<223> OTHER INFORMATION: Synthetic

<400> SEQUENCE: 58
agcccactat aaaagggcta aaatagcaaa tttttccctg cgtccgtgca cccacgccga    60
gcttgccgct cgcaccgtgg ccgagcagat cacgcacacg acatgcattg ctttgttcgt   120
cttcaaaaca aacccaaaaa aaatggtttt gcggttttgc ccgaccagcc tggagcacgg   180
tggtgctcag ccagacagcc aataggacat tcttgattct tgatgttgta ttgtatttgt   240
tgagtttgtg atctaaattt tgtttatagg acatattagc aagtaaagcg gaggcttgtt   300
ataggtttgg gccggagtat attgctgact ctaattaggg tttctgttgc gtcataattt   360
ttactcctct tataagccgt cgtacaaaga cggcgttatg taaacatttc tacatatagt   420
gaaggttttc gtaatttttc tctttgcatt aaggacctgt ttggttagag gtctctcagg   480
cacttgcctg ccaagtaagg aatcctagcc catgtattca aaatctaacg cctggaatct   540
gtgcaacttt ggccggctcc aaactaaata agccttaaaa gaatttctat gtaaatctat   600
gtatggtgct ctgtggtttg ttgtttgatc ttccctgttt tgtctgctaa cggtatccat   660
ccgtccattg gtgctccggc cctttcccaa tgtcctgtgc tggatcttga tagcttgggc   720
agttgagttt ggcgtgtgaa gtggacgtgg acttggcgag cgtcagtcag cacttcctga   780
atgaggctat agcttctgca agctttcgtg gatagatttt ccgagattct cagcttgcat   840
ccgatccagc aagctctcag ttccgtttag cccccactaa tgactaaaa gtagactgaa    900 aagttgagac gcgcgcacat gcagctacgc cgctacgcta tggctggttc acccaccgga   960
gcctgcaacg cgctccctgt ggagagagaa aagaagctct gccacccgtc cacacattcc  1020
tgtgatagat cgcattcatc cagctggcta ctgaatgcgc gttgtgctgc gtaggacacg  1080
tatggcgagc tagcctacag ataaggtcga gtagcccact ataaaagggc taaaatagca  1140
aattttcccc tgcgtccgtg cacccacgcc gagcttgccg ctgcgaccgt ggccgagcag  1200
atcacgcaca cgacatgcat tgctttgttc gtcttcaaaa caaacccaaa aaaatggtt   1260 tgcggttttt gcccgaccag cctggagcac ggtggtgctc agccagacag ccaataggac  1320
attcttgatt cttgatgttg tattgtattt gttgagtttg tgatctaaat tttgttttata 1380 ggacatatta gcaagtaaag cggaggcttg ttataggttt gggccggagt atattgctga  1440
ctctaattag ggtttctgtt gcgtcataat ttttactcct cttataagcc gtcgtacaaa  1500
gacggcgtta tgtaaacatt tctacatata gtgaaggttt tcgtaatttt tctctttgca  1560
ttaaggacct gtttggttag aggtctctca ggcacttgcc tgccaagtaa ggaatcctag  1620
cccatgtatt caaaatctaa cgcctggaat ctgtgcaact ttggccggct ccaaactaaa  1680
taagccttaa agaatttct atgtaaatct atgtatggtg ctctgtggtt tgttgtttga   1740
tcttccctgt tttgtctgct aacggtatcc atccgtccat tggtgctccg gccctttccc  1800
aatgtcctgt gctggatctt gatagcttgg gcagttgagt ttggcgtgtg aagtggacgt  1860
ggacttggcg agcgtcagtc agcacttcct gaatgaggct atagcttctg caagctttcg  1920
tggatagatt ttccgagatt ctcagcttgc atccgatcca gcaagctctc agttccgttt  1980 agcccccac taatgactaa aagtagactg aaaagttgag acgcgcgcac atgcagctac   2040
```

```
gccgctacgc tatggctggt tcacccaccg gagcctgcaa cgcgctccct gtggagagag    2100
aaaagaagct ctgccacccg tccacacatt cctgtgatag atcgcattca tccagctggc    2160
tactgaatgc gcgttgtgct gcgtaggaca cgtatggcga gctagcctac agataaggtc    2220
gagtagccca ctataaaagg gctaaaatag caaattttc cctgcgtccg tgcacccacg     2280
ccgagcttgc cgctgcgacc gtggccgagc agatcacgca cacgacatgc attgctttgt    2340
tcgtcttcaa aacaaaccca aaaaaatgg ttttgcggtt ttgcccgacc agcctggagc     2400
acggtggtgc tcagccagac agccaatagg acattcttga ttcttgatgt tgtattgtat    2460
ttgttgagtt tgtgatctaa attttgttta taggacatat tagcaagtaa agcggaggct    2520
tgttataggt ttgggccgga gtatattgct gactctaatt agggtttctg ttgcgtcata    2580 attttactc ctcttataag ccgtcgtaca aagacggcgt tatgtaaaca tttctacata     2640
tagtgaaggt tttcgtaatt tttctctttg cattaaggac ctgtttggtt agaggtctct    2700
caggcacttg cctgccaagt aaggaatcct agcccatgta ttcaaaatct aacgcctgga    2760
atctgtgcaa ctttggccgg ctccaaacta aataagcctt aaaagaattt ctatgtaaat    2820
ctatgtatgt tgctctgtgg tttgttgttt gatcttccct gttttgtctg ctaacggtat    2880
ccatccgtcc attggtgctc cggcccttc ccaatgtcct gtgctggatc ttgatagctt     2940
gggcagttga gttggcgtg tgaagtggac gtggacttgg cgagcgtcag tcagcacttc      3000
ctgaatgagg ctatagcttc tgcaagcttt cgtggataga ttttccgaga ttctcagctt    3060
gcatccgatc cagcaagctc tcagttccgt ttagccccccc actaatgact aaaagtagac    3120
tgaaaagttg agacgcgcgc acatgcagct acgccgctac gctatggctg gttcacccac    3180
cggagcctgc aacgcgctcc ctgtggagag agaaaagaag ctctgccacc cgtccacaca    3240
ttcctgtgat agatcgcatt catccagctg gctactgaat gcgcgttgtg ctgcgtagga    3300
cacgtatggc gagctagcct acagataagg tcgagcacca acttgctctg tgatgttaat    3360 gttttttggtg attagtgaca agggtgccta attctttttc tgatgttaat attttgaaag    3420
attctcactc tgaaaaaaaa atgcatgttc atatccatgt ttctctaaaa ataatccata    3480
gccagtgtgt gatactttct actagttccc actaaatgca ttgtgaaatt aaattctata    3540
aaattttgta atttctaata tttagtaagg gtagaaacag agatttttt cttaattta      3600 aatcatcatg tatcaggagt cgcaaaggtc caggaatgat atgcaagatt gctacatggt    3660
tggtatcctc ttaatgtcat ccttggcagg gagttgtggt ggatatgcct tctgctgcca    3720
ggcactgggg cacaagaaga atggtgtctg ccacacaagc caccctgcac cctacaaaca    3780
actcacagct ggaatggtta tcaccaaacc aatgacagaa aaactgtgt attccacgta     3840 attgatggtt actggcaaaa ttcatggatg taatacatca gggcatctca accgtcgaaa    3900
gatgctcatg ggcactactc ctcggcgaaa tgcgcccaca gaaacccaga attgttcatc    3960
agccaagacc atccttaagg tcaagaatgt ccagataata tttatggacg gtgcagcgca    4020
aacgataaaa ttccagtatt gcagatttta catggtacac agagaagcta aggaaatcat    4080
agagacaagc tagtggcaga gccaggacaa aaacagaagg tggcaagaga gttggagcaa    4140
ccaaatcaca gccattcata tccagaaggc cagcctccac ctcacaactc atatcctttg    4200
tactcaggta ctcacccta aatctgagca ggcgcttcac ttctcacccc ccctaaggaa      4260
aggctgcaat gcaagcttg tgtcaaagaa gagggtagca cctgatcctc ttgcctttgg     4320
agccagaaac a                                                         4331
```

<210> SEQ ID NO 59
<211> LENGTH: 4051
<212> TYPE: DNA
<213> ORGANISM: Artificial Sequence
<220> FEATURE:
<223> OTHER INFORMATION: Synthetic

<400> SEQUENCE: 59

| | | | | | |
|---|---|---|---|---|---|
| accaacttgc | tctgtgatgt | taatgttttt | ggtgattagt | gacaagggtg | cctaatttct | 60 |
| tttctgatgt | taatatttg | aaagattctc | actctgaaaa | aaaatgcat | gttcatatcc | 120 |
| atgtttctct | aaaaataatc | catagccagt | gtgtgatact | ttctactagt | tcccactaaa | 180 |
| tgcattgtga | aattaaattc | tataaaattt | tgtaatttct | aatatttagt | aagggtagaa | 240 |
| acagagattt | ttttcttaat | tttaaatcat | catgtatcag | gagtcgcaaa | ggtccaggaa | 300 |
| tgatatgcaa | gattgctaca | tggttggtat | cctcttaatg | tcatccttgg | cagggagttg | 360 |
| tggtggatat | gccttctgct | gccaggcact | ggggcacaag | aagaatggtg | tctgccacac | 420 |
| aagccaccct | gcaccctaca | aacaactcac | agctggaatg | gttatcacca | aaccaatgac | 480 |
| agaaaaaact | gtgtattcca | cgtaattgat | ggttactggc | aaaattcatg | gatgtaatac | 540 |
| atcagggcat | ctcaaccgtc | gaaagatgct | catgggcact | actcctcggc | gaaatgcgcc | 600 |
| cacagaaacc | cagaattgtt | catcagccaa | gaccatcctt | aaggtcaaga | atgtccagat | 660 |
| aatatttatg | gacggtgcag | cgcaaacgat | aaaattccag | tattgcagat | tttacatggt | 720 |
| acacagagaa | gctaaggaaa | tcatagagac | aagctagtgg | cagagccagg | acaaaaacag | 780 |
| aaggtggcaa | gagagttgga | gcaaccaaat | cacagccatt | catatccaga | aggccagcct | 840 |
| ccacctcaca | actcatatcc | tgtcgagcac | caacttgctc | tgtgatgtta | atgttttgg | 900 |
| tgattagtga | caagggtgcc | taatttcttt | tctgatgtta | atattttgaa | agattctcac | 960 |
| tctgaaaaaa | aaatgcatgt | tcatatccat | gtttctctaa | aaataatcca | tagccagtgt | 1020 |
| gtgatacttt | ctactagttc | ccactaaatg | cattgtgaaa | ttaaattcta | taaaattttg | 1080 |
| taatttctaa | tatttagtaa | gggtagaaac | agagattttt | tcttaatttt | aaatcatca | 1140 |
| tgtatcagga | gtcgcaaagg | tccaggaatg | atatgcaaga | ttgctacatg | gttggtatcc | 1200 |
| tcttaatgtc | atccttggca | gggagttgtg | gtggatatgc | cttctgctgc | caggcactgg | 1260 |
| ggcacaagaa | gaatggtgtc | tgccacacaa | gccaccctgc | accctacaaa | caactcacag | 1320 |
| ctggaatggt | tatcaccaaa | ccaatgacag | aaaaaactgt | gtattccacg | taattgatgg | 1380 |
| ttactggcaa | aattcatgga | tgtaatacat | cagggcatct | caaccgtcga | agatgctca | 1440 |
| tgggcactac | tcctcggcga | aatgcgccca | cagaaaccca | gaattgttca | tcagccaaga | 1500 |
| ccatccttaa | ggtcaagaat | gtccagataa | tatttatgga | cggtgcagcg | caaacgataa | 1560 |
| aattccagta | ttgcagattt | tacatggtac | acagagaagc | taaggaaatc | atagagacaa | 1620 |
| gctagtggca | gagccaggac | aaaaacagaa | ggtggcaaga | gagttggagc | aaccaaatca | 1680 |
| cagccattca | tatccagaag | gccagcctcc | acctcacaac | tcatatcctg | tcgagtagcc | 1740 |
| cactataaaa | gggctaaaat | agcaaatttt | tccctgcgtc | cgtgcaccca | cgccgagctt | 1800 |
| gccgctgcga | ccgtggccga | gcagatcacg | cacacgacat | gcattgcttt | gttcgtcttc | 1860 |
| aaaacaaacc | caaaaaaat | ggttttgcgg | ttttgcccga | ccagcctgga | gcacggtggt | 1920 |
| gctcagccag | acagccaata | ggacattctt | gattcttgat | gttgtattgt | atttgttgag | 1980 |
| tttgtgatct | aaatttgtt | tataggacat | attagcaagt | aaagcggagg | cttgttatag | 2040 |
| gtttgggccg | gagtatattg | ctgactctaa | ttagggtttc | tgttgcgtca | taattttac | 2100 |

| | |
|---|---|
| tcctcttata agccgtcgta caaagacggc gttatgtaaa catttctaca tatagtgaag | 2160 |
| gttttcgtaa tttttctctt tgcattaagg acctgtttgg ttagaggtct ctcaggcact | 2220 |
| tgcctgccaa gtaaggaatc ctagcccatg tattcaaaat ctaacgcctg gaatctgtgc | 2280 |
| aactttggcc ggctccaaac taaataagcc ttaaaagaat ttctatgtaa atctatgtat | 2340 |
| ggtgctctgt ggtttgttgt ttgatcttcc ctgttttgtc tgctaacggt atccatccgt | 2400 |
| ccattggtgc tccggccctt tcccaatgtc ctgtgctgga tcttgatagc ttgggcagtt | 2460 |
| gagtttggcg tgtgaagtgg acgtggactt ggcgagcgtc agtcagcact tcctgaatga | 2520 |
| ggctatagct tctgcaagct ttcgtggata gattttccga gattctcagc ttgcatccga | 2580 |
| tccagcaagc tctcagttcc gtttagcccc ccactaatga ctaaaagtag actgaaaagt | 2640 |
| tgagacgcgc gcacatgcag ctacgccgct acgctatggc tggttcaccc accggagcct | 2700 |
| gcaacgcgct ccctgtggag agagaaaaga agctctgcca cccgtccaca cattcctgtg | 2760 |
| atagatcgca ttcatccagc tggctactga atgcgcgttg tgctgcgtag gacacgtatg | 2820 |
| gcgagctagc ctacagataa ggtcgagtag cccactataa aagggctaaa atagcaaatt | 2880 |
| tttccctgcg tccgtgcacc cacgccgagc ttgccgctgc gaccgtggcc gagcagatca | 2940 |
| cgcacacgac atgcattgct ttgttcgtct tcaaaacaaa cccaaaaaaa atggttttgc | 3000 |
| ggttttgccc gaccagcctg gagcacggtg gtgctcagcc agacagccaa taggacattc | 3060 |
| ttgattcttg atgttgtatt gtatttgttg agtttgtgat ctaaattttg tttataggac | 3120 |
| atattagcaa gtaaagcgga ggcttgttat aggtttgggc cggagtatat tgctgactct | 3180 |
| aattagggtt tctgttgcgt cataattttt actcctctta taagccgtcg tacaaagacg | 3240 |
| gcgttatgta aacatttcta catatagtga aggttttcgt aattttttctc tttgcattaa | 3300 |
| ggacctgttt ggttagaggt ctctcaggca cttgcctgcc aagtaaggaa tcctagccca | 3360 |
| tgtattcaaa atctaacgcc tggaatctgt gcaactttgg ccggctccaa actaaataag | 3420 |
| ccttaaaaga atttctatgt aaatctatgt atggtgctct gtggtttgtt gtttgatctt | 3480 |
| ccctgttttg tctgctaacg gtatccatcc gtccattggt gctccggccc tttcccaatg | 3540 |
| tcctgtgctg atcttgata gcttgggcag ttgagtttgg cgtgtgaagt ggacgtggac | 3600 |
| ttggcgagcg tcagtcagca cttcctgaat gaggctatag cttctgcaag ctttcgtgga | 3660 |
| tagattttcc gagattctca gcttgcatcc gatccagcaa gctctcagtt ccgtttagcc | 3720 |
| ccccactaat gactaaaagt agactgaaaa gttgagacgc gcgcacatgc agctacgccg | 3780 |
| ctacgctatg gctggttcac ccaccggagc ctgcaacgcg ctccctgtgg agagagaaaa | 3840 |
| gaagctctgc cacccgtcca cacattcctg tgatagatcg cattcatcca gctggctact | 3900 |
| gaatgcgcgt tgtgctgcgt aggacacgta tggcgagcta gcctacagat aagcctgggg | 3960 |
| aatggtttca tatgcatccg gctcgcgcag gtttctggca ttgagcagtc tgcggaatct | 4020 |
| cgattagtct ggaagacatc gctactaccc c | 4051 |

<210> SEQ ID NO 60
<211> LENGTH: 1203
<212> TYPE: DNA
<213> ORGANISM: Zea mays

<400> SEQUENCE: 60

| | |
|---|---|
| agcccactat aaaagggcta aaatagcaaa ttttccctg cgtccgtgca cccacgccga | 60 |
| gcttgccgct gcgaccgtgg ccgagcagat cacgcacacg atgcattg ctttgttcgt | 120 |

```
cttcaaaaca aacccaaaaa aaatggtttt gcggttttgc ccgaccagcc tggagcacgg    180
tggtgctcag ccagacagcc aataggacat tcttgattct tgatgttgta ttgtatttgt    240
tgagtttgtg atctaaattt tgtttatagg acatattagc aagtaaagcg gaggcttgtt    300
ataggtttgg gccggagtat attgctgact ctaattaggg tttctgttgc gtcataattt    360
ttactcctct tataagccgt cgtacaaaga cggcgttatg taaacatttc tacatatagt    420
gaaggttttc gtaattttt ctttgcatt aaggacctgt ttggttagag gtctctcagg     480
cacttgcctg ccaagtaagg aatcctagcc catgtattca aaatctaacg cctggaatct    540
gtgcaacttt ggccggctcc aaactaaata agccttaaaa gaatttctat gtaaatctat    600
gtatggtgct ctgtggtttg ttgtttgatc ttccctgttt tgtctgctaa cggtatccat    660
ccgtccattg gtgctccggc ccttttccaa tgtcctgtgc tggatcttga tagcttgggc    720
agttgagttt ggcgtgtgaa gtggacgtgg acttggcgag cgtcagtcag cacttcctga    780
atgaggctat agcttctgca agctttcgtg gatagatttt ccgagattct cagcttgcat    840
ccgatccagc aagctctcag ttccgtttag cccccccacta atgactaaaa gtagactgaa    900
aagttgagac gcgcgcacat gcagctacgc cgctacgcta tggctggttc acccaccgga    960
gcctgcaacg cgctccctgt ggagagagaa aagaagctct gccacccgtc cacacattcc   1020
tgtgatagat cgcattcatc cagctggcta ctgaatgcgc gttgtgctgc gtaggacacg   1080 tatgcgagc tagcctacag ataagcctgg ggaatggttt catatgcatc cggctcgcgc    1140
aggtttctgg cattgagcag tctgcggaat ctcgattagt ctggaagaca tcgctactac   1200
ccc                                                                 1203

<210> SEQ ID NO 61
<211> LENGTH: 1018
<212> TYPE: DNA
<213> ORGANISM: Zea mays

<400> SEQUENCE: 61
tacttaactt tactagaggt ggacgtagaa agttagtagg gcctgctaac ttcctagatg     60
aggtcgtagg aagttagtga ctcttgacc gcgctcgttt gtcaatagtt gaaagctaaa    120
tttctagagg aggctgtagg aagttagtgg ctcgtttgat cgcgctcgtt tgtcaacagc    180
tgaaagctaa cttctagag gagaccgccc ctgctaactt cctacgacct tgtggttgg     240 ggctataaat acccgacctt tgtggccttc tcaacggaga gtaggttatt tggaaccaaa    300
cctcggaaaa caaatcaccg tgttcatttg tgttgatctt catcacttga tttgtttctt    360
ccctctcctc tctctaaagt tctcttgctc acattgtttt gagtttgctt ctaaagttat    420
ctgtattgat tgagtaactc atagcaaaaa gaactatctt ttgcactccg aaatattact    480
aacactaacc ccgagtataa tgcgtgttca aactttataa atttcagatt tcgtctattt    540
atcctcttta gacgactttc aaagtttata ttttggtgt aatggctacc acatcaacat    600
gcttgatttc ctggcacatg catttatttt tgtcaatact tttgcgtggc cttttcacg    660 tatagaagag tgaagctaac attacattac ataaatattt tcccctctaa ttgcggcaat    720
caagcacgaa cgcactagct agtaagcttt ttgtgaggat ttggcatgtt gctgtgactg    780
tgagtggatt accgcgacga cagggacgac atgcgtgccc ttatctcttg agatttcct    840 cgggcccgac catcagacga acaacacatg catgtgctag cccgtgtcag caatctagat    900
gacctctcaa ttttccacac gaggtggggc cctgccacc tcatctcttg tcttttccca    960
gttaggtgac atggagcaca tgagcctccg agctcaccgg ggggtgacgc cacccccc    1018
```

<210> SEQ ID NO 62
<211> LENGTH: 1105
<212> TYPE: DNA
<213> ORGANISM: Zea mays

<400> SEQUENCE: 62

| | | | | | |
|---|---|---|---|---|---|
| agcccactat | aaaagggcta | aaatagcaaa | tttttccctg | cgtccgtgca | cccacgccga | 60 |
| gcttgccgct | gcgaccgtgg | ccgagcagat | cacgcacacg | acatgcattg | ctttgttcgt | 120 |
| cttcaaaaca | aacccaaaaa | aaatggtttt | gcggttttgc | ccgaccagcc | tggagcacgg | 180 |
| tggtgctcag | ccagacagcc | aataggacat | tcttgattct | tgatgttgta | ttgtatttgt | 240 |
| tgagtttgtg | atctaaattt | tgtttatagg | acatattagc | aagtaaagcg | gaggcttgtt | 300 |
| ataggtttgg | gccggagtat | attgctgact | ctaattaggg | tttctgttgc | gtcataattt | 360 |
| ttactcctct | tataagccgt | cgtacaaaga | cggcgttatg | taaacatttc | tacatatagt | 420 |
| gaaggttttc | gtaattttc | tctttgcatt | aaggacctgt | ttggttagag | gtctctcagg | 480 |
| cacttgcctg | ccaagtaagg | aatcctagcc | catgtattca | aaatctaacg | cctggaatct | 540 |
| gtgcaacttt | ggccggctcc | aaactaaata | agccttaaaa | gaatttctat | gtaaatctat | 600 |
| gtatggtgct | ctgtggtttg | ttgtttgatc | ttccctgttt | tgtctgctaa | cggtatccat | 660 |
| ccgtccattg | gtgctccggc | cctttcccaa | tgtcctgtgc | tggatcttga | tagcttgggc | 720 |
| agttgagttt | ggcgtgtgaa | gtggacgtgg | acttggcgag | cgtcagtcag | cacttcctga | 780 |
| atgaggctat | agcttctgca | agctttcgtg | gatagatttt | ccgagattct | cagcttgcat | 840 |
| ccgatccagc | aagctctcag | ttccgtttag | ccccccacta | atgactaaaa | gtagactgaa | 900 |
| aagttgagac | gcgcgcacat | gcagctacgc | cgctacgcta | tggctggttc | acccaccgga | 960 |
| gcctgcaacg | cgctccctgt | ggagagagaa | aagaagctct | gccacccgtc | cacacattcc | 1020 |
| tgtgatagat | cgcattcatc | cagctggcta | ctgaatgcgc | gttgtgctgc | gtaggacacg | 1080 |
| tatggcgagc | tagcctacag | ataag | | | | 1105 |

<210> SEQ ID NO 63
<211> LENGTH: 1130
<212> TYPE: DNA
<213> ORGANISM: Zea mays

<400> SEQUENCE: 63

| | | | | | |
|---|---|---|---|---|---|
| acgtggttag | ctactaatat | aaatgtaagg | tcattcgatg | gttttctat | tttcaattac | 60 |
| ctagcattat | ctcatttcta | attgtgataa | caaatgcatt | agaccataat | tctgtaaata | 120 |
| tgtacattta | agcacacagt | ctatatttta | aaattcttct | ttttgtgtgg | atatcccaac | 180 |
| ccaaatccac | ctctctcttc | aatccgtgca | tgttcaccgc | tgccaagtgc | caacaacaca | 240 |
| tcgcatcgtg | catatctttg | ttggcttgtg | cacggtcggc | gccaatggag | gagacacctg | 300 |
| tacggtgccc | ttggtagaac | aacatcctta | tccctatatg | tatggtgccc | ttcgtagaat | 360 |
| gacacccctt | atccctacaa | tagccatgta | tgcataccaa | gaattaaata | tacttttttct | 420 |
| tgaaccacaa | taatttatta | tagcggcact | tcttgttcag | gttgaacact | tatttggaac | 480 |
| aataaaatgc | cgagttccta | accacaggtt | cactttttt | tttccttatc | ctcctaggaa | 540 |
| actaaatttt | aaaatcataa | atttaattta | aatgttaatg | gaaacaaaaa | attatctaca | 600 |
| aagacgactc | ttagccacag | ccgcctcact | gcacccctcaa | ccacatcctg | caaacagaca | 660 |
| ccctcgccac | atccctccag | attcttcact | ccgatgcagc | ctacttgcta | acagacgccc | 720 |

```
tctccacatc ctgcaaagca ttcctccaaa ttcttgcgat cccccgaatc cagcattaac    780
tgctaaggga cgccctctcc acatcctgct acccaattag ccaacggaat aacacaagaa    840
ggcaggtgag cagtgacaaa gcacgtcaac agcaccgagc caagccaaaa aggagcaagg    900
aggagcaagc ccaagccgca gccgcagctc tccaggtccc cttgcgattg ccgccagcag    960
tagcagacac ccctctccac atcccctccg ccgctaaca gcagcaagcc aagccaaaaa   1020
ggagcctcag ccgcagccgg ttccgttgcg gttaccgccg atcacatgcc caaggccgcg   1080
cctttccgaa cgccgagggc cgcccgttcc cgtgcacagc cacacacaca              1130

<210> SEQ ID NO 64
<211> LENGTH: 861
<212> TYPE: DNA
<213> ORGANISM: Brachypodium distachyon

<400> SEQUENCE: 64
accaacttgc tctgtgatgt taatgttttt ggtgattagt gacaagggtg cctaatttct     60
tttctgatgt taatattttg aaagattctc actctgaaaa aaaatgcat gttcatatcc    120 atgtttctct aaaaataatc catagccagt gtgtgatact ttctactagt tcccactaaa    180
tgcattgtga aattaaattc tataaaattt tgtaatttct aatatttagt aagggtagaa    240
acagagattt ttttcttaat tttaaatcat catgtatcag gagtcgcaaa ggtccaggaa    300
tgatatgcaa gattgctaca tggttggtat cctcttaatg tcatccttgg cagggagttg    360
tggtggatat gccttctgct gccaggcact ggggcacaag aagaatggtg tctgccacac    420
aagccaccct gcaccctaca acaactcac agctggaatg ttatcacca aaccaatgac      480 agaaaaaact gtgtattcca cgtaattgat ggttactggc aaaattcatg gatgtaatac    540
atcagggcat ctcaaccgtc gaaagatgct catgggcact actcctcggc gaaatgcgcc    600
cacagaaacc cagaattgtt catcagccaa gaccatcctt aaggtcaaga atgtccagat    660
aatatttatg gacggtgcag cgcaaacgat aaaattccag tattgcagat ttacatggt     720 acacagagaa gctaaggaaa tcatagagac aagctagtgg cagagccagg acaaaaacag    780
aaggtggcaa gagagttgga gcaaccaaat cacagccatt catatccaga aggccagcct    840
ccacctcaca actcatatcc t                                              861

<210> SEQ ID NO 65
<211> LENGTH: 133
<212> TYPE: DNA
<213> ORGANISM: Banana Streak Virus (AY)

<400> SEQUENCE: 65
caatccccgg ctctcatctc tataagagga gcctttgtat tcagttgcaa gcatgcaagt     60
cacacactgc aagcttactt ctgagcaaaa agagtttga gtgaaataaa tttgaagttc     120 cccctttacat ctt                                                      133

<210> SEQ ID NO 66
<211> LENGTH: 92
<212> TYPE: DNA
<213> ORGANISM: Hollyhock Leaf Crumple Virus

<400> SEQUENCE: 66
aatgccattt ggtgtacaac tatatattgt accccattac accgattgca ggcaccaaat     60
gaaatccaag tcaatcggtg tacattgacc aa                                   92
```

```
<210> SEQ ID NO 67
<211> LENGTH: 62
<212> TYPE: DNA
<213> ORGANISM: Bean Yellow Dwarf Virus

<400> SEQUENCE: 67
ctccatgcct ccacgccggt tataagatag agtttgaggc aacccctcgg agtcacaaca      60
ac                                                                    62

<210> SEQ ID NO 68
<211> LENGTH: 2165
<212> TYPE: DNA
<213> ORGANISM: Zea mays

<400> SEQUENCE: 68
ttcgttacca actgggttgc ataggatttc atgattaaga gtgtgtttgg tttagctgtg      60
agttttctcc tatgaaaaaa ctgttgtgag aaaaaatagt tggaagtcgt ttagttcaaa     120
ctgttgtgag ttatccactg taaacaaatt gtatattgtt tatatacact ctgtttaaat     180
atatctctta atcagtatat ataattaaaa actaatttc acatttgtgt tcctaatatt      240
ttttacaaat aaatcattgt ttaattccat ttgtaataag ttttattaa aattgctttt      300 atttcattta ttataaacat ttaattgttt taatcctatt ttagttttaa tttattgtat     360
ctatttatta atataacgaa cttcgataag aaacaaaagc aaggtcaagg tgttttttca     420
aagtagttgt ggaaaagctg aacccctttt attcaacttt tagaagcagg aaaacagaac     480
caaacagacc ctaaaaatgt gtgaatttt agcaggttaa ttattcgcat ctcttttggtc     540 atgtttaaga ggctggaata gatcaactgc aagaacacat agcagagtgg ataggggggg     600
ggggggggag ggtcgtcgtc tccctatctg acctctcttc tgcattggat tgccttttc     660 ggtactctat ttaaaactta aaagtacaaa tgaggtgccg gattgatgga gtgatatata     720
agtttgatgt gttttttcaca taagtgacaa gtattattga agagaacat ttgcattgct     780 actgtttgca tatgggaaaa ttgagaattg tatcatgcct tggccgatca gttctttact     840
tagctcgatg taatgcacaa tgttgatagt atgtcgagga tctagcgatg taatggtgtt     900
aggacacgtg gttagctact aatataaatg taaggtcatt cgatggtttt tctattttca     960
attacctagc attatctcat ttctaattgt gataacaaat gcattagacc ataattctgt    1020
aaatatgtac atttaagcac acagtctata ttttaaaatt cttcttttttg tgtggatatc    1080 ccaacccaaa tccacctctc tcttcaatcc gtgcatgttc accgctgcca agtgccaaca    1140
acacatcgca tcgtgcatat ctttgttggc ttgtgcacgg tcggcgccaa tggaggagac    1200
acctgtacgg tgcccttggt agaacaacat ccttatccct atatgtatgg tgcccttcgt    1260
agaatgacac cccttatccc tacaatagcc atgtatgcat accaagaatt aaatatactt    1320
tttcttgaac cacaataatt tattatagcg gcacttcttg ttcaggttga acacttattt    1380
ggaacaataa aatgccgagt tcctaaccac aggttcactt tttttttcc ttatcctcct    1440 aggaaactaa atttaaaat cataaattta atttaaatgt taatgaaac aaaaaattat     1500 ctacaaagac gactcttagc cacagccgcc tcactgcacc ctcaaccaca tcctgcaaac    1560
agacaccctc gccacatccc tccagattct tcactccgat gcagcctact tgctaacaga    1620
cgccctctcc acatcctgca aagcattcct ccaaattctt gcgatccccc gaatccagca    1680
ttaactgcta agggacgccc tctccacatc ctgctaccca attagccaac ggaataacac    1740
aagaaggcag gtgagcagtg acaaagcacg tcaacagcac cgagccaagc caaaaaggag    1800
```

-continued

| | |
|---|---|
| caaggaggag caagcccaag ccgcagccgc agctctccag gtcccctttgc gattgccgcc | 1860 |
| agcagtagca gacacccctc tccacatccc ctccggccgc taacagcagc aagccaagcc | 1920 |
| aaaaaggagc ctcagccgca gccggttccg ttgcggttac cgccgatcac atgcccaagg | 1980 |
| ccgcgccttt ccgaacgccg agggccgccc gttcccgtgc acagccacac acacacccgc | 2040 |
| ccgccaacga ctccccatcc ctatttgaac ccacccgcgc actgcattga tcaccaatcg | 2100 |
| catcgcagca gcacgagcag cacgccgtgc cgctccaacc atctcgcttc cgtgcttagc | 2160 |
| ttccc | 2165 |

<210> SEQ ID NO 69
<211> LENGTH: 587
<212> TYPE: DNA
<213> ORGANISM: Zea mays

<400> SEQUENCE: 69

| | |
|---|---|
| cgtgtgcatg catgcatgca tggtacgaac gtctggatag agtctccgag ctgagtgtgg | 60 |
| tccgacgtgg aagtgtacgt ctcaacacac gacgcatgtg accgacaagg gcaagttgaa | 120 |
| gtctatgcat ggatgggcct gagcgccgcg ctgaatgaat ctggacgggt ggtagggcat | 180 |
| ctcggtgggc aaaacaaata actccgtgtg ctgcatggct gcctttggaa tctttgcatg | 240 |
| cagctgtgtg ctgaactgaa acccttcgct ctatctatat aaacagatgc ccttcgctct | 300 |
| cgtctcagca ggcagcatcg tctcaagttt tgttctcctc tcctagctag ccagcacctg | 360 |
| cagatctgct cgttgccttg gtaattcatc atgtagtacg tagcatcagc tagtatttat | 420 |
| ctcaagtata tatatacgca tatgtgtcgt cgcagtactt tcccttatct ctctatacac | 480 |
| actacacgca tacataccaa taccatccgt cttaactctt aatctttgcc tgcatacgta | 540 |
| cactgcacgt acgtactgca gggctactga ttttgtggaa cgaagcg | 587 |

<210> SEQ ID NO 70
<211> LENGTH: 1229
<212> TYPE: DNA
<213> ORGANISM: Sorghum bicolor

<400> SEQUENCE: 70

| | |
|---|---|
| ctagcatgta gcatgccaag gatctggctg ctccaggttt gttatgcctg acatcaccat | 60 |
| agggatgaga gcaagtataa aataggctg taagctttaa atgctcaggt ggagaaaaaa | 120 |
| aggagaggag aggagagaga aaagtgggct ataagcttat agctgtgtta gacataagaa | 180 |
| tcagaaactt cgtatgagag acaggtgagc tatatattaa taacaaagag ctaactatta | 240 |
| tatgagtgaa ccgagagaag gctgtaaaaa aacttacaca atcaacgatc gacattatta | 300 |
| ttaaccttgc tctgtcttgc gagacctctt tgacaaagct acatcaatgc cggccaagtg | 360 |
| ccttgggatt tgggaatggc ttctttcctc ccttcctcgg ttgtccccca aggcctaggc | 420 |
| ttgccacgct gtattcagtc gcagccgcct ttacttttgc cctttgtgga agttttgtaa | 480 |
| taaatggtct gattctatct tcggatagat gaagccggat gtttcatcca ttatctaaaa | 540 |
| aaaagttggt tgctttgctg agctaagaaa gtgtaatcca gagtgctcgt aacgtattaa | 600 |
| tgtacataac tattatctaa tataaatctt cttttgtcgc aaaaaaaggt cggcccatca | 660 |
| gaacaaatga tcaatgtaag gcccaaaatt tgtgtctcaa atgtcattta cgtttccaag | 720 |
| ctaaacaaaa acacaggatt catataaattt tgctggtggc ttaggcttcg tccaatagtg | 780 |
| cttagtttaa tttgtatata cctgcaccat ggtattcgtc tggccttgga tcttgcgcat | 840 |
| caattgccta tggacgatga tcgcagccac gccacattca tttttaatcg ccatttgctt | 900 |

```
gacacccaat gcctctgcac cacttgcgca cgctacgcac cgtctgatac gccaagatcc    960
cgagctaaaa taacacccaa tcatcagatg aaaacaagcg cgagtgcgag ccagcccatg   1020
gcagcgatct tggccatttg cggagccaac tgaaagccgt gcacaaaata ttcgacaccg   1080
tataagggaa aacactagtt atacgaggtg ggcaataatc cagatctcgg actcttccta   1140
acccggttca catgcatagc atatatgatg gccggccggg gttcacatga acgccatccc   1200
gtgccctagt gcactgattt cttaatccc                                     1229

<210> SEQ ID NO 71
<211> LENGTH: 973
<212> TYPE: DNA
<213> ORGANISM: Zea mays

<400> SEQUENCE: 71
ctactcgcct tgtggctcct cctgaaccac ctgctcttct cctgtggggg ggtgtgagac     60
agcaagggtg agctcacaca tgatcatagc tcaacaagtt gtggggaacc agtggacatg    120
aactcacaaa ggtgggagtt catgtgatgg ttcctctaga tgctcaactt gttgcattat    180
attacgcaat tgctccgacg cttcatcaat taatcctcct tagtgatatt aaataacgga    240
ataatattag agaaataaac aataatctaa gacattagcg cataaagatg tgacaaaatg    300
attgagtctg gtcatattac cctccttcat cctttattgc ataaaagatt gtagtttaca    360
ccttcggctt tacaaaggag agctcgaagg taatattaca gcttcgaagg cggagtgatt    420
tgattctccc ttgttcaaaa agcgagatct cttcatatca ttgtgcctct atttatagta    480
accaagtaca atttcatatg aaattacaaa catgctcatg gacatgataa ttccagtgca    540
catccaaccc tgcttgatac aaaacatgct cataatcatg atgattcaag tgcacatcca    600
ccctgctcga tacaacagtt ggcgacctgg tgtgagagtc agaccagacg ggctttcaca    660
atcgccatgc atgtcattct ctcgtggtcc acgtgtttat taatattgcc attaattgga    720
gggaaataaa atcaacaaga atagcttatt gatgagtcat atattatgaa tacatcttat    780
catcttacca aacaaaaaca tatgaccgtc gatgacctga aactagacta ttcgggatct    840
gcaatgatct gcttgtaaat attaatttgc acatcacgcc attgcatgca catcggcgtg    900
ggcattatta atttggattg gacgaaaaat caaccagagg gcgtcaccct tttgctagtt    960
ggccttgtaa tac                                                      973

<210> SEQ ID NO 72
<211> LENGTH: 1397
<212> TYPE: DNA
<213> ORGANISM: Sorghum bicolor

<400> SEQUENCE: 72
caaactcagt ttatcaccaa agaccaaaca tgtggaaatc agtctctatt ttgtccaaga     60
gcatgtggcc cttggagctt tgcggcttct tcatgttgct acatctcttc aatatgccga    120
tatatttact aagggttgtc aattgttatc ttcatcaact tctgatctaa tctcaatgtt    180
tgctcctctt ccggttgaga ctactggggg atattagaat atgaatagcc aaaaagtctt    240
gtatagtcta aataaagag tctcaaatag ttcacttgag cttaggaacc gaatttgtcg    300
tcagcagtgt ttttgctca tagtaaatta gccaacaata ctttctatca caccttaaca    360
gagtactttc tttctgccat ggcttatcaa ccaacagtat tttttgtcaa agcagtgat    420 tatctgtcaa tcactagcgc ccctctgcc ggtatatcta gcgctcccat cggatctgac    480
```

```
tagagcagat cttgagcgtg ggttggtggc tcagggcttg caggaggcgt tggccgtcgc    540
cggcgtagag cagtagtcgt aggcggatct gcatcttcaa gctctcctcc ggtcgattcg    600
tgtgagtctt cgacctctgc tcaggtcgat tcatgccggc gaggggctca gtgctcggct    660
cacgacgcga aattacgagc ggcagcagca aaccgggctt tcaagcccgg ctctcctcgt    720
gagctgcctt agggctcgtt cgtttaacta ttgttcccga tggattcatt cctgatgata    780
aaaatagtat aaatttacac aatgttcctg gctggaatca tttcagacct gcattccatg    840
agaaacgaac ggggctttag cgggccacgt gacagtgacg aagggtcgca gtcgctgctg    900
gacggactac agacagagag gcgaagcatg caattgaatt ttcgctagcg aaagttatc    960 atctaatctc caaccctcct tcctacggct ggatctgaaa attgacgacc tgaaccectg   1020 aacggtgccg gtagcaattg caggtctcac tcacatgcta aatccagcaa ccaaacacga   1080
aggaatatat gtgatctgga cagaacatgc aagcgaataa tacatagagt cgtaccaacc   1140
ctacacagtt caacgaatta atcactgggt tcacgggcat gctcacgtcc aaaatcccag   1200
cgacatttta taagcgctaa gcggaatgat ccagacgggg ccagctcgag caccacatgg   1260
cgtcgctcca tctcgcatct ataaatacca ttggccatgc acaccogcac tcccacacag   1320 caatacagca cactagcagc agcagcagca gctcgagcta gcttagctac tacgtgtgtg   1380
caatcagctc gatcgcc                                                   1397

<210> SEQ ID NO 73
<211> LENGTH: 1172
<212> TYPE: DNA
<213> ORGANISM: Setaria italica

<400> SEQUENCE: 73
tacgcagttg tcctttggta cattcacaag tttgatctta tcatcaccat cagaagttca    60
gaaagtctcg tagaaaacaa atggaaatga atactgctta cttagctcaa attcatattc   120
cgttgttaca ggatacttaa aaaaggtacc aaaggctgtt cctaatcata cgctgaagtc   180
gttgccacca atggcagctg tactgtcata ttgtcgtggt ttttcaattg ctgtacctga   240
tgcaaacgta atgggtttac taatcttgca cccgccgact tcaaaatgaa gagtgctaat   300
ttggttcacg tcaccatcac cggttcgaac tgtctagaat ggcaggcaaa gatgattgga   360
caggcatgca gggaaaaaga gcaccgatga cgatctatgc gagttcccac cattgcgagc   420
aatgattatc agccacacga cttactcttc agagctaacc actgccatgc agagaaaaag   480
tgaagcatat tgtcaggatc tacaacgaag tgaaacaatc aggcatgcta aagtgctgaa   540
actttactga tctctcatgt tggacaacaa agaatacggg aatacatcag caacgcaact   600
cttgagcttt gcttgctgaa tgaccagcta gaatttccaa gcatttacag gaacatgact   660
ttaagtttca gaaaaacaaa tacaaggcca ctaagggcat gttcacttca gcttataagc   720
cggctgaaaa gctgaaacgg ctgatttgtt gtgagaggaa acactgtttt ggtggctgat   780
aagccggctg aataagctga agcgaacagg ctgtaaataa gcgtggggat aacatatcct   840
ccagatgaca ggcaatctgc aacttgcagc gattcaaatg tacgattaac aaaatattta   900
agcgctacat gagataatat atcctccaat tagggccttt agtattgtca ttagctcata   960
agcatggtgc atcctcacat ggacgctgca taagaagttc ataatagcaa cagacatatg  1020
aacaaagcat ggtgcgcctg cccggccgga ctagctagta ctaccaatca tggaataagc  1080
tagtacccta aatgaaatta aaatggtttt tagcgattat ccacgccgtc cagatactc   1140 taatccacaa gttgaggccg cccatgaagc cg                                 1172
```

```
<210> SEQ ID NO 74
<211> LENGTH: 1410
<212> TYPE: DNA
<213> ORGANISM: Brachypodium distachyon

<400> SEQUENCE: 74
agtcgtagag gccaattgat gatgtgccta atagatacat atggtaagga taataatcat      60
ttcttactac attattcata caaaaaataa ttaagaatca aaaattatga gaaacacctc     120
ttggtgtggt gtagttgtgg gtgcatcact ccacccatta gggtccaaat cttggtgctc     180
acattatgcc ggggtctccc ttacattctt cctatcaatt tttttgtaa atctacagta      240 gatgtctata atgaaaattt tcaaatatct aaaatagcaa cgaaaatctc atatgttacc     300
tgtagaagct caacactttt gtattgcaca caatgttaat aaaataaaac tcttgctaaa     360
acttgtaatg actacctaat aacaacatat tgtgttgtat atgaatttaa gcccatctaa     420
atattcggaa tattcgctta tcattcaaaa gatttagatc aacaaaaaga agtgaagaac     480
tttatatttt ggtaggtaaa atgtataaca aaacaaatct ttcagaaaat cacttgatat     540
ttccaaacac aatacatcta aattgcaata aaaaagaatt ttagaaaaca aaaacataaa     600
aatatgggtg ttgctgtttg aatttcaata ctacaaaagg acatatatgt gacgtcatat     660
tagtgtcggg cccagcagga ccgccaatga tgtatagcat cagtgttggt cggtgcaaaa     720
cccgccactg atatacagct gcgcgtttcc cactttcgac ctgatgaaca tcagtggcgg     780
gcgttgcacc cgcccgccac taatttttaa gtagaggacc ttaaatctaa gttgacgtat     840
gagaaccatt ggattaagat ataatggcac tctcttctct tctacttgct atcgttggat     900
taatatccga cggtcaagca catcggctca tgtctaacaa aaaaaaggca acttcttaat     960
agcaaaaccg taaaaatata tattttatta tacaagtcta gcccgcgagc tgcttggttc    1020
accctgctag ttaagatagt aacttgtagc tcttcttgtt gcgtataagt tgttaaacat    1080
tgtaaaagcc tcctcaagta tcatgtatac ctgtgatacc tcacgacgat ttaaacgcac    1140
aattgctgta taatggatat agattggttc taggctccag cgatcgatta tccatgtaac    1200
tacgtacaaa cgagtaaacc tccaaaatca caccgctgtc acacatcgtc tgcacgcagt    1260
tgcctgaaac caatccactg cacctagccc acgggttgaa taaaaccgcc cgcgccggcc    1320
tcttcaacgt gcatccacgc agtgtgtcat tcccgtcacg gactctcgtc tcatccggcc    1380
ccttctctcg agcaacaccc accaatctcc                                     1410
```

PLANT REGULATORY ELEMENTS AND METHODS OF USE THEREOF

CROSS-REFERENCE TO RELATED APPLICATIONS

This application claims priority to International Patent Application PCT/US2017/036503 filed on Jun. 8, 2017, which claims priority to U.S. Provisional Application No. 62/354,374, filed Jun. 24, 2016, the contents of which are herein incorporated by reference in their entirety.

REFERENCE TO SEQUENCE LISTING SUBMITTED ELECTRONICALLY

A sequence listing having the file name "5243WOPCT Seq List.txt" created on May 12, 2017, and having a size of 231 kilobytes is filed in computer readable form concurrently with the specification. The sequence listing is part of the specification and is herein incorporated by reference in its entirety.

FIELD

The present disclosure relates to the field of plant molecular biology, more particularly to the regulation of gene expression in plants.

BACKGROUND

Expression of heterologous DNA sequences in a plant host is dependent upon the presence of operably linked regulatory elements that are functional within the plant host. Choice of promoter sequence may determine when and where within the organism a heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Genetically altering plants through the use of genetic engineering techniques and thus producing a plant with useful traits may require the availability of a variety of regulatory elements. An accumulation of promoters and other regulatory elements would enable the investigator to express at desired levels and cellular locales recombinant DNA molecules. Therefore, a collection of promoters would allow for a new trait to be expressed at the desired level in the desired tissue. Thus, isolation, characterization, and creation of hybrid regulatory elements that may produce an expression pattern that is unique and serve as regulatory regions for expression of heterologous nucleotide sequences of interest are useful for the genetic manipulation of plants.

BRIEF SUMMARY

Compositions and methods for regulating expression of a heterologous polynucleotide sequence of interest in a plant or plant cell are provided. Synthetic DNA molecules comprising novel polynucleotide sequences for regulatory elements having gene regulatory activity are provided. In some embodiments the regulatory element has promoter activity initiating transcription in the plant cell. Certain embodiments comprise the nucleotide sequences set forth in SEQ ID NOs: 1-74. Also included are functional fragments, segments, or variants of the sequences set forth in SEQ ID NOs: 1-74 wherein said sequences initiate transcription in a plant cell, or a polynucleotide sequence comprising a sequence having at least 85% sequence identity to the sequences set forth in SEQ ID NOs: 1-74, wherein said sequences initiate transcription in the plant cell. Embodiments also include DNA constructs comprising a regulatory element operably linked to a heterologous nucleotide sequence of interest, wherein said regulatory element is capable of driving expression of said heterologous nucleotide sequence in a plant cell and said regulatory element comprises a nucleotide sequence disclosed herein. Embodiments further provide expression vectors, and plants or plant cells having stably incorporated into their genomes a DNA construct as is described above. Additionally, compositions include transgenic seed of such plants.

In one embodiment, hybrid regulatory elements are provided that produce an expression pattern in plants that is unique for each of the hybrid regulatory elements relative to any source or parent regulatory material from which the hybrid regulatory element is produced, wherein the hybrid regulatory element contains a segment of each parent regulatory element. In one embodiment, the hybrid regulatory element produces a tissue specific expression pattern that is different relative to the parent regulatory elements. In another embodiment, the hybrid regulatory elements provide a broadened expression pattern in plant tissues relative to narrower expression patterns expressed from a given set of parent regulatory elements. In another embodiment, hybrid regulatory elements may produce a constitutive expression pattern that differs from a non-constitutive expression pattern of the parent regulatory elements.

Methods and compositions are provided that relate to the construction of hybrid regulatory elements. In one embodiment, a hybrid regulatory element may be created using one or more previously characterized regulatory elements and assembling segments of the previously characterized one or more regulatory elements. In a further embodiment, the characterized regulatory elements may be evaluated for potential motifs to aid in defining segments that may be useful in a hybrid regulatory element. In one embodiment, the 3' end of the hybrid promoter contains a TATA box from a parental regulatory element. In another embodiment, a method provided relates to expressing a nucleotide sequence in a plant or plant cell comprising introducing into the plant or the plant cell an expression cassette comprising a hybrid regulatory element operably linked to a nucleotide sequence of interest, wherein said hybrid regulatory element produces a tissue expression pattern of the nucleotide sequence of interest that is unique relative to each of the individual parental regulatory element tissue expression patterns.

In one embodiment, parent regulatory elements that may be used to make a hybrid regulatory element comprise SEQ ID NOs: 1-10, 31-34, and 61-74 or variants thereof. Also included are functional fragments, segments, or variants of the polynucleotide sequences set forth in SEQ ID NOs: 1-10, 31-34, and 61-74 wherein said polynucleotide sequences initiate transcription in a plant cell, or a polynucleotide sequence comprising a sequence having at least 85% sequence identity to the polynucleotide sequences set forth in SEQ ID NOs: 1-10, 31-34, and 61-74, and wherein said polynucleotide sequences initiate transcription in a plant cell. In another embodiment, parent regulatory elements that may be used to make a hybrid regulatory element comprise one or more of SEQ ID NOs: 1-74 or variants thereof.

Embodiments also include DNA constructs comprising a hybrid regulatory element operably linked to a heterologous nucleotide sequence of interest, wherein said hybrid regulatory element is capable of driving expression of said heterologous nucleotide sequence in a plant cell and said promoter comprises one of SEQ ID NOs: 1-74, or a functional fragment thereof, as disclosed herein. Embodiments further provide expression vectors, and plants or plant cells having stably incorporated into their genomes a DNA construct as is described above. Additionally, compositions include transgenic seed of such plants.

Downstream from the transcriptional initiation region of the regulatory element will be a sequence of interest that will provide for modification of the phenotype of the plant. Such modification includes modulating the production of an endogenous product as to amount, relative distribution, or the like, or production of an exogenous expression product, to provide for a novel or modulated function or product in the plant. For example, a heterologous polynucleotide sequence that encodes a gene product that confers resistance or tolerance to herbicide, salt, cold, drought, pathogen, nematodes or insects is encompassed.

In a further embodiment, a method for modulating expression of a gene in a stably transformed plant is provided, comprising the steps of (a) transforming a plant cell with a DNA construct comprising a regulatory element disclosed herein, or a functional fragment thereof, operably linked to at least one heterologous polynucleotide sequence; (b) growing the plant cell under plant growing conditions and (c) regenerating a stably transformed plant from the plant cell wherein expression of the linked nucleotide sequence alters the phenotype of the plant. In another embodiment, the DNA construct further comprises a heterologous enhancer element.

Expression cassettes comprising the regulatory element sequences of SEQ ID NOs: 1-74 operably linked to a heterologous nucleotide sequence of interest are provided. Additionally, provided are transformed plant cells, plant tissues, seeds, and plants.

DESCRIPTION OF THE DRAWINGS

FIG. 2 Shows the segments used to make several root hybrid regulatory elements.

FIG. 3 Shows the segments used to make each aerial hybrid regulatory element.

DETAILED DESCRIPTION

Figure 1:
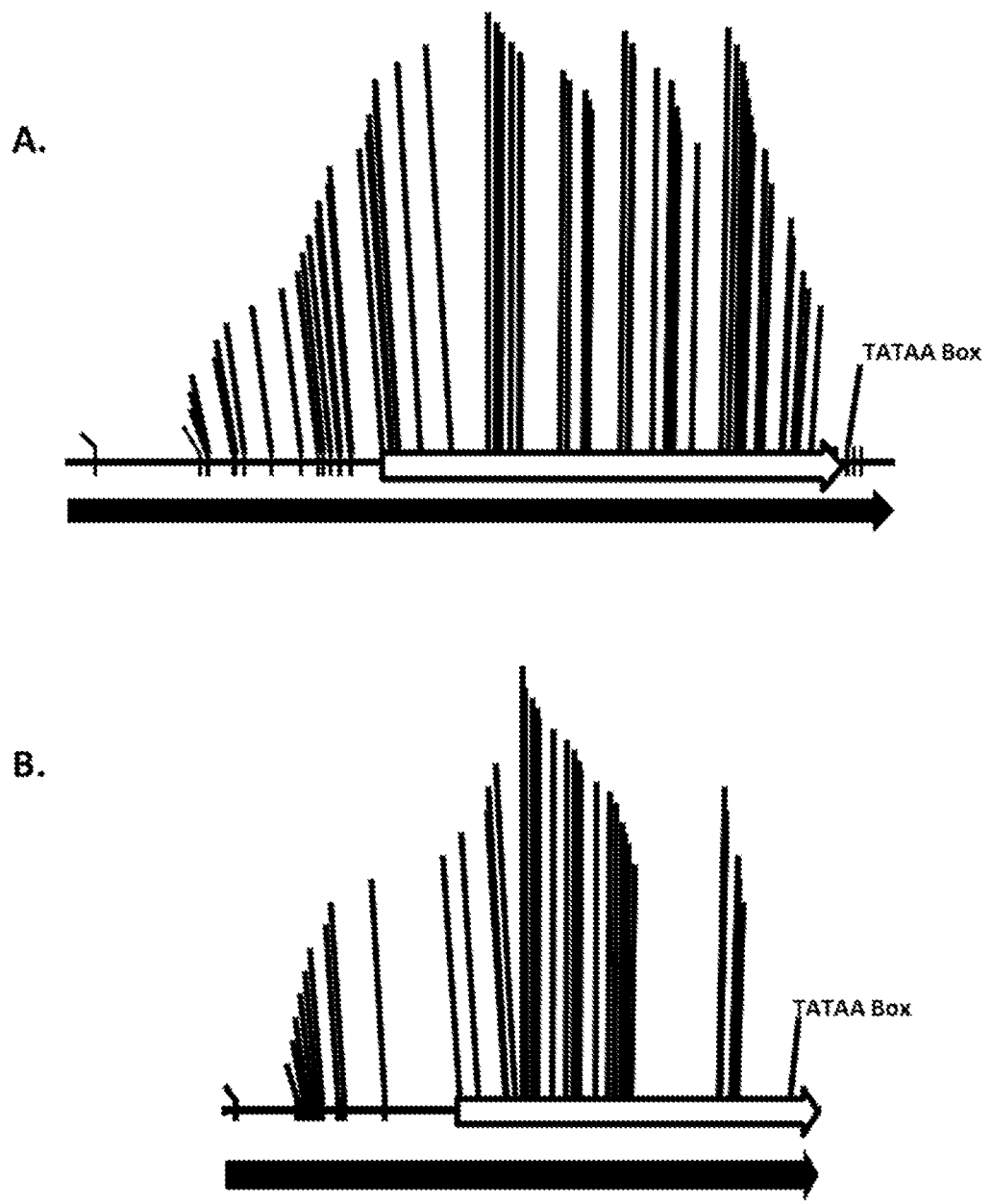
FIG. 1 Shows a distribution of motifs used to assist defining the region of the regulatory element segment that would be incorporated into a hybrid regulatory element. The vertical lines indicate motif positions, the white arrow indicates the segment used in a hybrid regulatory element, and the black arrow indicates the full-length parent regulatory element. A. A representation of SI-TIP2-3B (MOD 1) regulatory element (SEQ ID NO: 10) and the 5' region upstream of the TATAA box selected for use as a segment in a hybrid regulatory element based on clustering of motifs, and B. A representation of BD-GRP3 PRO (MOD 1) regulatory element (SEQ ID NO: 2) and the 3' downstream region including the TATAA box selected for use as a segment in a hybrid regulatory element based on clustering of motifs.

The article "a" and "an" are used herein to refer to one or more than one (i.e., to at least one) of the grammatical object of the article. By way of example, "an element" means one or more element.

The disclosure relates to compositions and methods drawn to plant regulatory elements and methods of their use. The compositions and methods further relate to hybrid regulatory elements and methods of making and using hybrid regulatory elements.

Plant tissues are complex organs that can be divided into different regions; for example, in root tissue the tissue regions include the cap, meristem, elongation region and mature region. These regions reflect different stages of cell identity and maturity. Genes in these cells are consequently activated and inactivated during development, and therefore may not be expressed simultaneously in all regions of the root or other tissue. However, combining pieces of regulatory elements from these genes as taught herein, a synthetic regulatory element can be created that drives expression in the different regions of a particular tissue. The regulatory elements provided may retain tissue specificity, although unique expression patterns may be created.

The disclosure relates to compositions and methods drawn to plant hybrid regulatory elements and methods of their use. The compositions comprise polynucleotide sequences for the regulatory elements set forth in SEQ ID NOs: 1-74, and fragments, variants and complements thereof. In one embodiment, the compositions comprise polynucleotide sequences for hybrid regulatory elements set forth in SEQ ID NOs: 11-30, 35-47, and 50-59, and fragments, variants and complements thereof.

Compositions may include the nucleotide sequences for the regulatory elements, fragments and variants thereof. In specific embodiments, the hybrid regulatory element sequences disclosed herein are useful for changing the expression pattern relative to a native regulatory element. The nucleotide sequences also find use in the construction of expression vectors for subsequent expression of a heterologous nucleotide sequence in a plant of interest or as probes for the isolation of other regulatory elements. One embodiment is provided for DNA constructs comprising a regulatory element polynucleotide sequence set forth in SEQ ID NOs: 1-10, 31-34, and 61-74, or a hybrid regulatory elements set forth in SEQ ID NOs: 11-30 and 35-60, or a functional fragment or variants thereof, operably linked to a heterologous polynucleotide sequence of interest, and any combinations thereof.

The term "regulatory element" refers to a nucleic acid molecule having gene regulatory activity, i.e. one that has the ability to affect the transcriptional and/or translational expression pattern of an operably linked transcribable polynucleotide. The term "gene regulatory activity" thus refers to the ability to affect the expression of an operably linked transcribable polynucleotide molecule by affecting the transcription and/or translation of that operably linked transcribable polynucleotide molecule. Gene regulatory activity may be positive and/or negative and the effect may be characterized by its temporal, spatial, developmental, tissue, environmental, physiological, pathological, cell cycle, and/or chemically responsive qualities as well as by quantitative or qualitative indications.

Regulatory elements such as promoters, enhancers, leaders, and intron regions are nucleic acid molecules that have gene regulatory activity and play an integral part in the overall expression of genes in living cells. Isolated regulatory elements, such as promoters and leaders that function in plants are therefore useful for modifying plant phenotypes through the methods of genetic engineering. A promoter is useful as a regulatory element for modulating the expression of an operably linked transcribable polynucleotide molecule.

As used herein, a "gene expression pattern" is any pattern of transcription of an operably linked nucleic acid molecule into a transcribed RNA molecule. Expression may be characterized by its temporal, spatial, developmental, tissue, environmental, physiological, pathological, cell cycle, and/or chemically responsive qualities as well as by quantitative or qualitative indications. The transcribed RNA molecule may be translated to produce a protein molecule or may provide an antisense or other regulatory RNA molecule, such as a dsRNA, a tRNA, an rRNA, a miRNA, and the like. As used herein, a "unique gene expression pattern" is any pattern of transcription of an operably linked nucleic acid molecule into a transcribed RNA molecule that differs from another regulatory element by its specific tissue or sub-tissue regional transcriptional expression pattern, or cell type or cell state expression pattern and not merely a difference in the quantitative amount of transcription. A "unique gene expression pattern," as used herein, does not include a constitutive expression pattern. In one embodiment, a unique gene expression pattern includes a reduction or elimination of transcription of a heterologous nucleic acid in a particular tissue. In another embodiment, a unique gene expression pattern includes an increase or production of transcription of a heterologous nucleic acid in a particular tissue. As used herein, a "regional transcriptional expression pattern" or "sub-regional transcriptional expression pattern" is intended to mean any expression pattern that is not ubiquitous, only has detectable expression in certain regions of a certain tissue(s), and any other expression outside of the region or regions should be at nominal baseline levels ("ectopic expression"). The term "aerial expression" refers to a gene expression pattern of a polynucleotide in one or more above ground tissues of a plant. In one embodiment, heterologous polynucleotide sequence of interest is expressed in a ubiquitous root expression pattern or a ubiquitous aerial expression pattern. In one embodiment, aerial expression does not include expression in the pollen of a plant.

The regulatory element sequences or variants or fragments thereof, when operably linked to a heterologous nucleotide sequence of interest may drive constitutive expression of the heterologous polynucleotide sequence in the tissue of the plant expressing this construct. The term "constitutive expression," means that expression of the heterologous nucleotide sequence is found throughout the plant or in a majority of tissues of the plant.

As used herein, the term "protein expression" is any pattern of translation of a transcribed RNA molecule into a protein molecule. Protein expression may be characterized by its temporal, spatial, developmental, or morphological qualities as well as by quantitative or qualitative indications.

As used herein, the term "promoter" refers generally to a nucleic acid molecule that is involved in recognition and binding of RNA polymerase II and other proteins (trans-acting transcription factors) to initiate transcription. A promoter may be initially isolated from the 5' flanking region of a genomic copy of a gene. Alternately, promoters may be synthetically produced or manipulated DNA molecules. Regulatory elements may comprise promoters and promoter activity.

In one embodiment, fragments are provided of a regulatory element disclosed herein. Regulatory element fragments may exhibit promoter activity, and may be useful alone or in combination with other regulatory elements and regulatory element fragments, such as in constructing hybrid regulatory elements. In specific embodiments, fragments of a regulatory element are provided comprising, or alternatively consisting of or consisting essentially of, at least about 50, 95, 150, 250, 500, or about 750 or more contiguous nucleotides of a polynucleotide molecule having promoter activity disclosed herein. Such fragments may exhibit at least about 85 percent, about 90 percent, about 95 percent, about 98 percent, or about 99 percent, or greater, identity with a reference sequence when optimally aligned to the reference sequence. As used herein, the term "regulatory element segment" is a fragment of a regulatory element characterized by an abundance of recognizable regulatory element motifs using at least those described by Higo, K et al. (1998) Nucleic Acids Research (incorporated by reference in its entirety), wherein the regulatory element segment produces a desired or unique expression pattern when combined with at least one other regulatory element segment. As used herein, a "regulatory element segment" is used interchangeably with a "segment," a "defined segment," and "parent segment." In one embodiment, an abundance of recognizable regulatory element motifs includes at least 25 motifs, at least 30 motifs, at least 40 motifs, or at least 50 motifs. In specific embodiments, segments of a regulatory element are provided comprising at least about 50, 95, 150, 250, 500, 750, 1000, 1250, 1500, or about 1750 contiguous nucleotides of a polynucleotide molecule disclosed herein. In another embodiment, a segment comprises at least about 50, 95, 150, 250, 500, 750, 1000, 1250, 1500, or about 1750 contiguous nucleotides of a polynucleotide molecule, but less than the full length of the parent polynucleotide molecule. In one embodiment, a regulatory element segment comprises a fragment of a parent regulatory element, wherein the fragment comprises not more than about 2000, 1900, 1800, 1700, 1600, 1500, 1400, 1300, 1200, 1100, 1000, or 500 contiguous nucleotides of a parent regulatory element. In a further embodiment, a hybrid regulatory element comprises contiguous polynucleotide segments, wherein the continuous polynucleotide segments initiate transcription in a plant cell and produces a unique tissue expression pattern. As used herein, an "assembly" means two or more operably linked regulatory element segments. In one embodiment, an assembly of segments includes segments that are contiguous. In another embodiment, an assembly of segments includes one or more of the segments are not contiguous, but still produce an expression pattern.

A regulatory element or a regulatory element segment may also be analyzed for the presence of known promoter motifs, i.e. DNA sequence characteristics, such as a TATAA-box and other known transcription factor binding site motifs. Identification of such known motifs may be used by one of skill in the art to design hybrid regulatory elements having a desired or unique expression pattern when compared to the source or parent regulatory element. Nucleotide sequence motifs found in regulatory elements have been previously characterized and are available in the PLACE database (Higo, K et al. (1998) Nucleic Acids Research; dna.af-frc.go.jp/htdocs/PLACE/, which can be accessed on the world-wide web using the "www" prefix; See also, PCT Application Number WO 2014/164399). In one embodiment, a motif comprises a sequence of at least six nucleotides. In some embodiments, a regulatory element segment comprises about 15, 20, 25, 30, 35, 40, 45, 50, 75, 100, 125, or 150 motifs per 1000 nucleotides. In some embodiments, a regulatory element comprises at least one motif for about every 5, 10, 15, 20, 25, 30, 35, 40, 45, or 50 nucleotides.

As used herein, the term "enhancer" or "enhancer element" refers to a cis-acting transcriptional regulatory element, a.k.a. cis-element, which confers an aspect of the overall expression pattern, but is usually insufficient alone to drive transcription, of an operably linked polynucleotide sequence. Unlike promoters, enhancer elements do not usually include a transcription start site (TSS) or TATA box. A regulatory element may naturally comprise one or more enhancer elements that affect the transcription of an operably linked polynucleotide sequence. An isolated enhancer element may also be fused to a heterologous promoter to produce a heterologous promoter cis-element, which confers an aspect of the overall modulation of gene expression. A regulatory element or regulatory element fragment disclosed herein may comprise one or more enhancer elements that effect the transcription of operably linked genes. Many enhancer elements are believed to bind DNA-binding proteins and/or affect DNA topology, producing local conformations that selectively allow or restrict access of RNA polymerase to the DNA template or that facilitate selective opening of the double helix at the site of transcriptional initiation. An enhancer element may function to bind transcription factors that regulate transcription. Some enhancer elements bind more than one transcription factor, and transcription factors may interact with different affinities with more than one enhancer domain Enhancer elements may be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis using known cis-element motifs or enhancer elements as a target sequence or target motif with conventional DNA sequence comparison methods, such as BLAST. The fine structure of an enhancer domain may be further studied by mutagenesis (or substitution) of one or more nucleotides or by other conventional methods. Enhancer elements may be obtained by chemical synthesis or by isolation from regulatory elements that include such elements, and they may be synthesized with additional flanking nucleotides that contain useful restriction enzyme sites to facilitate subsequence manipulation. Thus, the design, construction, and use of enhancer elements according to the methods disclosed herein for modulating the expression of operably linked transcribable polynucleotide molecules are encompassed.

As used herein, the term "5' flanking region" refers to a DNA molecule isolated from a genomic copy of a gene and is defined generally as a polynucleotide segment beginning at the protein coding sequence start site and extending 5' through the 5' untranslated region and into the promoter region. These sequences, or leaders, may be synthetically produced or manipulated DNA elements. A leader may be used as a 5' regulatory element for modulating expression of an operably linked transcribable polynucleotide molecule. Leader molecules may be used with heterologous elements or with their native elements.

As used herein, the term "hybrid" refers to a single synthetic DNA molecule produced by fusing a first DNA molecule to a second DNA molecule, where neither first nor second DNA molecule would normally be found in that configuration, i.e. fused to the other. The hybrid DNA molecule is thus a new DNA molecule not normally found in nature. As used herein, the term "hybrid regulatory element" refers to a regulatory element produced through such manipulation of DNA molecules. A hybrid regulatory element may combine two or more DNA segments. Thus, the design, construction, and use of hybrid regulatory element according to the methods disclosed herein for modulating the expression of operably linked transcribable polynucleotide molecules are encompassed. In one embodiment, a hybrid regulatory element comprises two or more DNA segments. In another embodiment, a hybrid regulatory element comprises three or more DNA segments. In another embodiment, a hybrid regulatory element comprises four or more DNA segments. In one embodiment, a DNA fragment segment may be a parent segment. As used herein, a "segment," and "parent segment" are interchangeable and intended to refer to fragments of native "parent regulatory elements" that have been analyzed for motifs that are predicted to produce a regional tissue expression pattern. A combination of parent segments or variants thereof, may result in a hybrid regulatory element expressing a gene of interest in a ubiquitous tissue expression pattern that is unique from each individual expression pattern of the parent regulatory elements. In one embodiment, a parent segment may be a variant of a parent regulatory element. In one embodiment, parent regulatory elements set forth in SEQ ID NOs: 1-10, 31-34, and 61-74 may be used as parent regulatory elements to generate parent segments and variants thereof. Also, included as parent regulatory elements are functional fragments, segments, or variants of the polynucleotide sequences set forth in SEQ ID NOs: 1-10, 31-34, and 61-74 wherein said polynucleotide sequences initiate transcription in a plant cell, and a polynucleotide sequence comprising a sequence having at least 85% sequence identity to the polynucleotide sequences set forth in SEQ ID NOs: 1-10, 31-34, and 61-74, wherein said polynucleotide sequences initiate transcription in a plant cell. In certain embodiments, a parent regulatory element may include a parent regulatory element originating from a plant. In another embodiment, a parent regulatory element may include a parent regulatory element originating from a bacteria or a virus.

Hybrid regulatory elements are provided that produce an expression pattern in plants that is unique relative to parent regulatory elements, wherein the hybrid regulatory element contains segments or fragments of more than one parent regulatory element. In one embodiment, the hybrid regulatory element produces a tissue specific expression pattern that is different relative to the parent regulatory elements. In another embodiment, the hybrid regulatory elements broaden the expression pattern to a ubiquitous expression pattern in a plant tissue relative to regional tissue expression patterns expressed from a given set of parent regulatory elements. In another embodiment, the hybrid regulatory elements express a narrower range of expression relative to a broader range of expression patterns expressed from a given set of parent regulatory elements. In another embodiment, the hybrid root regulatory elements may produce a constitutive expression pattern that differs from a non-constitutive expression pattern of the parent regulatory elements.

In one embodiment, the polynucleotide sequences disclosed herein, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. A post-transcriptional regulatory element may include elements that are active following transcription initiation, for example translational and transcriptional enhancers, translational and transcriptional repressors, and mRNA stability determinants.

The regulatory elements, or variants or fragments thereof, may be operatively associated with one or more heterologous regulatory elements in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element and modulating post-transcriptional events. For example, one or more regulatory elements, or fragments thereof, may be operatively associated with constitutive, inducible, or tissue specific promoters or fragment thereof, to modulate the activity of such promoters within desired tissues in plant cells.

The compositions may encompass isolated or recombinant nucleic acid. An "isolated" or "recombinant" nucleic acid molecule is used herein to refer to a nucleic acid sequence that is no longer in its natural environment, for example in an in vitro or in a heterologous recombinant bacterial or plant host cell. An isolated or recombinant nucleic acid molecule, or biologically active portion thereof, is substantially free of other cellular material or culture medium when produced by recombinant techniques, or substantially free of chemical precursors or other chemicals when chemically synthesized. An isolated or recombinant nucleic acid is free of sequences (optimally protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule may contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. The hybrid regulatory element sequences disclosed herein may be isolated from the 5' untranslated region flanking their respective transcription initiation sites. As used herein, the terms "polynucleotide" and "nucleotide" are both intended to mean one or more nucleotide and may be used interchangeably in the singular or plural.

Fragments and variants of the disclosed regulatory element polynucleotide sequences are also encompassed by the present disclosure. As used herein, the term "fragment" refers to a portion of the nucleic acid sequence. Fragments of regulatory sequences may retain the biological activity of initiating transcription, more particularly driving transcription in a tissue specific or sub-tissue specific manner. Alternatively, fragments of a polynucleotide sequence that are useful as hybridization probes may not necessarily retain biological activity. Fragments of a polynucleotide sequence for the regulatory region may range from at least about 20 nucleotides, about 50 nucleotides, about 100 nucleotides, and up to one nucleotide less than the full length of any one of SEQ ID NOs: 1-74.

A biologically active portion of a regulatory element may be prepared by isolating a portion of the regulatory sequence, and assessing the promoter activity of the portion. Nucleic acid molecules that are fragments of a regulatory polynucleotide sequence comprise at least about 16, 50, 75, 100, 150, 200, 250, 300, 350, 400, 450, 500, 550, 600, 650, 700 or 800 nucleotides or up to the number of nucleotides present in a full-length regulatory sequence disclosed herein.

For polynucleotide sequences, a variant comprises a deletion and/or addition of one or more nucleotides at one or more internal sites within the native polynucleotide sequence and/or a substitution of one or more nucleotides at one or more sites in the native polynucleotide. For polynucleotide sequences, variants may be identified with the use of well-known molecular biology techniques, as, for example, with polymerase chain reaction (PCR) and hybridization techniques as outlined below. Variant polynucleotide sequences may include synthetically derived polynucleotide sequences, such as those generated, for example, by using site-directed mutagenesis. Generally, variants of a particular nucleotide sequence, including SEQ ID NOs: 1-74, of the disclosure will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular nucleotide sequence as determined by sequence alignment programs and parameters described elsewhere herein. A biologically active variant of a polynucleotide sequence of the disclosure may differ from that sequence by as few as 1-15 nucleic acid residues, as few as 1-10, as few as 6-10, as few as 5, as few as 4, 3, 2, or even 1 nucleic acid residue.

Variant polynucleotide sequences also encompass sequences derived from a mutagenic and recombinogenic procedure such as DNA shuffling. With such a procedure, regulatory element polynucleotide sequences may be manipulated to create new regulatory elements. In this manner, libraries of recombinant polynucleotides are generated from a population of related sequence polynucleotides comprising sequence regions that have substantial sequence identity and may be homologously recombined in vitro or in vivo. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

The polynucleotide sequences of the disclosure may be used to isolate corresponding sequences from other organisms, particularly other plants, more particularly other monocots. In this manner, methods such as PCR, hybridization and the like may be used to identify such sequences based on their sequence homology to the sequences set forth herein. Sequences isolated based on their sequence identity to the entire sequences set forth herein or to fragments thereof are encompassed by the present disclosure.

In a PCR approach, oligonucleotide primers may be designed for use in PCR reactions to amplify corresponding DNA sequences from cDNA or genomic DNA extracted from any plant of interest. Methods for designing PCR primers and PCR cloning are generally known in the art and are disclosed in, Sambrook, supra. See also, Innis, et al., eds.

(1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide sequence is used as a probe that selectively hybridizes to other corresponding polynucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides and may be labeled with a detectable group such as $^{32}$P or any other detectable marker. Thus, for example, probes for hybridization may be made by labeling synthetic oligonucleotides based on the regulatory element sequences of the disclosure. Methods for preparation of probes for hybridization and for construction of genomic libraries are generally known in the art and are disclosed in Sambrook, supra.

For example, an entire regulatory element sequence disclosed herein, or one or more portions thereof, may be used as a probe capable of specifically hybridizing to corresponding regulatory element sequences and messenger RNAs. To achieve specific hybridization under a variety of conditions, such probes include sequences that are unique among regulatory element sequences and are generally at least about 10 nucleotides in length or at least about 20 nucleotides in length. Such probes may be used to amplify corresponding regulatory element sequences from a chosen plant by PCR. This technique may be used to isolate additional coding sequences from a desired organism or as a diagnostic assay to determine the presence of coding sequences in an organism. Hybridization techniques include hybridization screening of plated DNA libraries (either plaques or colonies, see, for example, Sambrook, supra).

In general, sequences that have promoter activity and hybridize to the polynucleotide sequences, and fragments thereof, disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 81%, 82%, 83%, 84%, 85%, 86%, 87%, 88%, 89%, 90%, 91%, 92%, 93%, 94%, 95%, 96%, 97%, 98%, 99% sequence identity.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

Modifications of the isolated regulatory element sequences of the present disclosure may provide for a range of expression of the heterologous polynucleotide sequence. Thus, they may be modified to be weak promoters or strong promoters. Generally, a "weak promoter" means a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

The regulatory elements disclosed herein may be used to increase or decrease expression, thereby resulting in a change in phenotype of the transformed plant. The polynucleotide sequences disclosed herein, as well as variants and fragments thereof, are useful in the genetic manipulation of any plant. The regulatory element sequences are useful in this aspect when operably linked with a heterologous nucleotide sequence whose expression is to be controlled to achieve a desired phenotypic response. The term "operably linked" means that the transcription or translation of the heterologous nucleotide sequence is under the influence of the regulatory element sequence. In this manner, the regulatory element sequences disclosed herein may be provided in expression cassettes along with heterologous polynucleotide sequences of interest for expression in the plant of interest, more particularly for expression in the reproductive tissue of the transformed plant.

The regulatory elements of the embodiments may be provided in DNA constructs for expression in the organism of interest. An "expression cassette" as used herein means a DNA construct comprising a regulatory element of the embodiments operably linked to a heterologous polynucleotide expressing a transcript or gene of interest. Such expression cassettes will comprise a transcriptional initiation region comprising one of the regulatory element polynucleotide sequences of the present disclosure, or variants or fragments thereof, operably linked to the heterologous nucleotide sequence. Such an expression cassette may be provided with a plurality of restriction sites for insertion of the polynucleotide sequence to be under the transcriptional regulation of the regulatory regions. The expression cassette may additionally contain selectable marker genes as well as 3' termination regions.

The expression cassette may include, in the 5'-3' direction of transcription, a transcriptional initiation region (i.e., a hybrid promoter, or variant or fragment thereof, of the disclosure), a translational initiation region, a heterologous polynucleotide sequence of interest, a translational termination region and optionally, a transcriptional termination region functional in the host organism. The regulatory regions (i.e., promoters, enhancers, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other.

As used herein, "heterologous" in reference to a sequence is a sequence that originates from a foreign species or, if from the same species, is substantially modified from its native form in composition and/or genomic locus by deliberate human intervention. For example, a regulatory element operably linked to a heterologous polynucleotide is from a species different from the species from which the polynucleotide was derived or, if from the same/analogous species, one or both are substantially modified from their original form and/or genomic locus or the regulatory element is not the native regulatory element for the operably linked polynucleotide.

The termination region may be native with the transcriptional initiation region, may be native with the operably linked DNA sequence of interest, may be native with the plant host, or may be derived from another source (i.e., foreign or heterologous to the regulatory element, the DNA sequence being expressed, the plant host, or any combination thereof).

The regulatory elements disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part or plant the genotype of which has been altered by the presence of heterologous nucleic acid, including those transgenics initially so altered as well as those created by sexual crosses or asexual propagation from the initial transgenic.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant and selection of a particular plant characterized by insertion into a particular genome location. An event is characterized phenotypically by the expression of the transgene. At the genetic level, an event is part of the genetic makeup of a plant. The term "event" also refers to progeny produced by a sexual cross between the transformant and another plant wherein the progeny include the heterologous DNA.

As used herein, the term plant includes whole plants, plant organs (e.g., leaves, stems, roots, etc.), plant cells, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers and the like. Grain is intended to mean the mature seed produced by commercial growers for purposes other than growing or reproducing the species. Progeny, variants and mutants of the regenerated plants are also included within the scope of the disclosure, provided that these parts comprise the introduced polynucleotides. As used herein, the term tis includes The compositions and methods disclosed herein may be used for transformation of any plant species, including, but not limited to, monocots and dicots. Examples of plant species include corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed include, for example, pines such as loblolly pine (*Pinus taeda*), slash pine (*Pinus elliotii*), ponderosa pine (*Pinusponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true first such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of may be crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Heterologous coding sequences expressed by a regulatory element sequence disclosed herein may be used for varying the phenotype of a plant. Various changes in phenotype are of interest including modifying expression of a gene in a plant, altering a plant's pathogen or insect defense mechanism, increasing a plant's tolerance to herbicides, altering plant development to respond to environmental stress, modulating the plant's response to salt, temperature (hot and cold), drought and the like. These results may be achieved by the expression of a heterologous polynucleotide sequence of interest comprising an appropriate gene product. In specific embodiments, the heterologous polynucleotide sequence of interest is an endogenous plant sequence whose expression level is increased in the plant or plant part. Results may be achieved by providing for altered expression of one or more endogenous gene products, particularly hormones, receptors, signaling molecules, enzymes, transporters or cofactors or by affecting nutrient uptake in the plant. These changes result in a change in phenotype of the transformed plant. In certain embodiments the expression patterns of the regulatory elements disclosed herein are useful for many types of screening.

General categories of polynucleotide sequences of interest that may be utilized with the regulatory sequences disclosed herein include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, environmental stress resistance (altered tolerance to cold, salt, drought, etc) and grain characteristics. Still other categories of transgenes include genes for inducing expression of exogenous products such as enzymes, cofactors, and hormones from plants and other eukaryotes as well as prokaryotic organisms. It is recognized that any gene of interest can be operably linked to the regulatory element of the disclosure and expressed in the plant.

By way of illustration, without intending to be limiting, the following is a list of other examples of the types of genes which may be used in connection with the regulatory elements disclosed herein.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*); McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens* strain CHA0 and Pf-5 (previously *fluorescens*) (Pechy-Tarr, (2008) *Environmental Microbiology* 10:2368-2386: GenBank Accession No. EU400157); from *Pseudomonas Taiwanensis* (Liu, et al., (2010) *J. Agric. Food Chem.* 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of U.S. Ser. No. 13/792,861; an AfIP-1A and/or AfIP-1B polypeptide of U.S. Ser. No. 13/800,233; a PHI-4 polypeptide of U.S. Ser. No. 13/839,702; a PIP-47 polypeptide of PCT Serial Number PCT/US14/51063; a PIP-72 polypeptide of PCT Serial Number PCT/US14/55128; a PtIP-50 polypeptide and a PtIP-65 polypeptide of PCT Publication Number WO2015/120270; a PtIP-83 polypeptide of PCT Publication Number WO2015/120276; a PtIP-96 polypeptide of PCT Serial Number PCT/US15/55502; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of δ-endotoxin genes and the *B. thuringiensis* cytolytic Cyt1 and Cyt2 genes. Members of these classes of *B. thuringiensis* insecticidal proteins include, but are not limited to Cry1Aa1 (Accession #AAA22353); Cry1Aa2 (Accession #Accession #AAA22552); Cry1Aa3 (Accession #BAA00257); Cry1Aa4 (Accession #CAA31886); Cry1Aa5 (Accession #BAA04468); Cry1Aa6 (Accession #AAA86265); Cry1Aa7 (Accession #AAD46139); Cry1Aa8 (Accession #126149); Cry1Aa9 (Accession #BAA77213); Cry1Aa10 (Accession #AAD55382); Cry1Aa11 (Accession #CAA70856); Cry1Aa12 (Accession #AAP80146); Cry1Aa13 (Accession #AAM44305); Cry1Aa14 (Accession #AAP40639); Cry1Aa15 (Accession #AAY66993); Cry1Aa16 (Accession #HQ439776); Cry1Aa17 (Accession #HQ439788); Cry1Aa18 (Accession #HQ439790); Cry1Aa19 (Accession #HQ685121); Cry1Aa20 (Accession #JF340156); Cry1Aa21 (Accession #JN651496); Cry1Aa22 (Accession #KC158223); Cry1Ab1 (Accession #AAA22330); Cry1Ab2 (Accession #AAA22613); Cry1Ab3 (Accession #AAA22561); Cry1Ab4 (Accession #BAA00071); Cry1Ab5 (Accession #CAA28405); Cry1Ab6 (Accession #AAA22420); Cry1Ab7 (Accession #CAA31620); Cry1Ab8 (Accession #AAA22551); Cry1Ab9 (Accession #CAA38701); Cry1Ab10 (Accession #A29125); Cry1Ab11 (Accession #I12419); Cry1Ab12 (Accession #AAC64003); Cry1Ab13 (Accession #AAN76494); Cry1Ab14 (Accession #AAG16877); Cry1Ab15 (Accession #AA013302); Cry1Ab16 (Accession #AAK55546); Cry1Ab17 (Accession #AAT46415); Cry1Ab18 (Accession #AAQ88259); Cry1Ab19 (Accession #AAW31761); Cry1Ab20 (Accession #ABB72460); Cry1Ab21 (Accession #ABS18384); Cry1Ab22 (Accession

ABW87320); Cry1Ab23 (Accession #HQ439777); Cry1Ab24 (Accession #HQ439778); Cry1Ab25 (Accession #HQ685122); Cry1Ab26 (Accession #HQ847729); Cry1Ab27 (Accession #JN135249); Cry1Ab28 (Accession #JN135250); Cry1Ab29 (Accession #JN135251); Cry1Ab30 (Accession #JN135252); Cry1Ab31 (Accession #JN135253); Cry1Ab32 (Accession #JN135254); Cry1Ab33 (Accession #AAS93798); Cry1Ab34 (Accession #KC156668); Cry1Ab-like (Accession #AAK14336); Cry1Ab-like (Accession #AAK14337); Cry1Ab-like (Accession #AAK14338); Cry1Ab-like (Accession #ABG88858); Cry1Ac1 (Accession #AAA22331); Cry1Ac2 (Accession #AAA22338); Cry1Ac3 (Accession #CAA38098); Cry1Ac4 (Accession #AAA73077); Cry1Ac5 (Accession #AAA22339); Cry1Ac6 (Accession #AAA86266); Cry1Ac7 (Accession #AAB46989); Cry1Ac8 (Accession #AAC44841); Cry1Ac9 (Accession #AAB49768); Cry1Ac10 (Accession #CAA05505); Cry1Ac11 (Accession #CAA10270); Cry1Ac12 (Accession #I12418); Cry1Ac13 (Accession #AAD38701); Cry1Ac14 (Accession #AAQ06607); Cry1Ac15 (Accession #AAN07788); Cry1Ac16 (Accession #AAU87037); Cry1Ac17 (Accession #AAX18704); Cry1Ac18 (Accession #AAY88347); Cry1Ac19 (Accession #ABD37053); Cry1Ac20 (Accession #ABB89046); Cry1Ac21 (Accession #AAY66992); Cry1Ac22 (Accession #ABZ01836); Cry1Ac23 (Accession #CAQ30431); Cry1Ac24 (Accession #ABL01535); Cry1Ac25 (Accession #FJ513324); Cry1Ac26 (Accession #FJ617446); Cry1Ac27 (Accession #FJ617447); Cry1Ac28 (Accession #ACM90319); Cry1Ac29 (Accession #DQ438941); Cry1Ac30 (Accession #GQ227507); Cry1Ac31 (Accession #GU446674); Cry1Ac32 (Accession #HM061081); Cry1Ac33 (Accession #GQ866913); Cry1Ac34 (Accession #HQ230364); Cry1Ac35 (Accession #JF340157); Cry1Ac36 (Accession #JN387137); Cry1Ac37 (Accession #JQ317685); Cry1Ad1 (Accession #AAA22340); Cry1Ad2 (Accession #CAA01880); Cry1Ae1 (Accession #AAA22410); Cry1Af1 (Accession #AAB82749); Cry1Ag1 (Accession #AAD46137); Cry1Ah1 (Accession #AAQ14326); Cry1Ah2 (Accession #ABB76664); Cry1Ah3 (Accession #HQ439779); Cry1Ai1 (Accession #AAO39719); Cry1Ai2 (Accession #HQ439780); Cry1A-like (Accession #AAK14339); Cry1Ba1 (Accession #CAA29898); Cry1Ba2 (Accession #CAA65003); Cry1Ba3 (Accession #AAK63251); Cry1Ba4 (Accession #AAK51084); Cry1Ba5 (Accession #AB020894); Cry1Ba6 (Accession #ABL60921); Cry1Ba7 (Accession #HQ439781); Cry1Bb1 (Accession #AAA22344); Cry1Bb2 (Accession #HQ439782); Cry1Bc1 (Accession #CAA86568); Cry1Bd1 (Accession #AAD10292); Cry1Bd2 (Accession #AAM93496); Cry1Be1 (Accession #AAC32850); Cry1Be2 (Accession #AAQ52387); Cry1Be3 (Accession #ACV96720); Cry1Be4 (Accession #HM070026); Cry1Bf1 (Accession #CAC50778); Cry1Bf2 (Accession #AAQ52380); Cry1Bg1 (Accession #AAO39720); Cry1Bh1 (Accession #HQ589331); Cry1Bi1 (Accession #KC156700); Cry1Ca1 (Accession #CAA30396); Cry1Ca2 (Accession #CAA31951); Cry1Ca3 (Accession #AAA22343); Cry1Ca4 (Accession #CAA01886); Cry1Ca5 (Accession #CAA65457); Cry1Ca6 [1] (Accession #AAF37224); Cry1Ca7 (Accession #AAG50438); Cry1Ca8 (Accession #AAM00264); Cry1Ca9 (Accession #AAL79362); Cry1Ca10 (Accession #AAN16462); Cry1Ca11 (Accession #AAX53094); Cry1Ca12 (Accession #HM070027); Cry1Ca13 (Accession #HQ412621); Cry1Ca14 (Accession #JN651493); Cry1Cb1 (Accession #M97880); Cry1Cb2 (Accession #AAG35409); Cry1Cb3 (Accession #ACD50894); Cry1Cb-like (Accession #AAX63901); Cry1Da1 (Accession #CAA38099); Cry1Da2 (Accession #I76415); Cry1Da3 (Accession #HQ439784); Cry1db1 (Accession #CAA80234); Cry1db2 (Accession #AAK48937); Cry1Dc1 (Accession #ABK35074); Cry1Ea1 (Accession #CAA37933); Cry1Ea2 (Accession #CAA39609); Cry1Ea3 (Accession #AAA22345); Cry1Ea4 (Accession #AAD04732); Cry1Ea5 (Accession #A15535); Cry1Ea6 (Accession #AAL50330); Cry1Ea7 (Accession #AAW72936); Cry1Ea8 (Accession #ABX11258); Cry1Ea9 (Accession #HQ439785); Cry1Ea10 (Accession #ADR00398); Cry1Ea11 (Accession #JQ652456); Cry1Eb1 (Accession #AAA22346); Cry1Fa1 (Accession #AAA22348); Cry1Fa2 (Accession #AAA22347); Cry1Fa3 (Accession #HM070028); Cry1Fa4 (Accession #HM439638); Cry1Fb1 (Accession #CAA80235); Cry1Fb2 (Accession #BAA25298); Cry1Fb3 (Accession #AAF21767); Cry1Fb4 (Accession #AAC10641); Cry1Fb5 (Accession #AAO13295); Cry1Fb6 (Accession #ACD50892); Cry1Fb7 (Accession #ACD50893); Cry1Ga1 (Accession #CAA80233); Cry1Ga2 (Accession #CAA70506); Cry1Gb1 (Accession #AAD10291); Cry1Gb2 (Accession #AAO13756); Cry1Gc1 (Accession #AAQ52381); Cry1Ha1 (Accession #CAA80236); Cry1Hb1 (Accession #AAA79694); Cry1Hb2 (Accession #HQ439786); Cry1H-like (Accession #AAF01213); Cry1Ia1 (Accession #CAA44633); Cry1Ia2 (Accession #AAA22354); Cry1Ia3 (Accession #AAC36999); Cry1Ia4 (Accession #AAB00958); Cry1Ia5 (Accession #CAA70124); Cry1Ia6 (Accession #AAC26910); Cry1Ia7 (Accession #AAM73516); Cry1Ia8 (Accession #AAK66742); Cry1Ia9 (Accession #AAQ08616); Cry1Ia10 (Accession #AAP86782); Cry1Ia11 (Accession #CAC85964); Cry1Ia12 (Accession #AAV53390); Cry1Ia13 (Accession #ABF83202); Cry1Ia14 (Accession #ACG63871); Cry1Ia15 (Accession #FJ617445); Cry1Ia16 (Accession #FJ617448); Cry1Ia17 (Accession #GU989199); Cry1Ia18 (Accession #ADK23801); Cry1Ia19 (Accession #HQ439787); Cry1Ia20 (Accession #JQ228426); Cry1Ia21 (Accession #JQ228424); Cry1Ia22 (Accession #JQ228427); Cry1Ia23 (Accession #JQ228428); Cry1Ia24 (Accession #JQ228429); Cry1Ia25 (Accession #JQ228430); Cry1Ia26 (Accession #JQ228431); Cry1Ia27 (Accession #JQ228432); Cry1Ia28 (Accession #JQ228433); Cry1Ia29 (Accession #JQ228434); Cry1Ia30 (Accession #JQ317686); Cry1Ia31 (Accession #JX944038); Cry1Ia32 (Accession #JX944039); Cry1Ia33 (Accession #JX944040); Cry1Ib1 (Accession #AAA82114); Cry1Ib2 (Accession #ABW88019); Cry1Ib3 (Accession #ACD75515); Cry1Ib4 (Accession #HM051227); Cry1Ib5 (Accession #HM070028); Cry1Ib6 (Accession #ADK38579); Cry1Ib7 (Accession #JN571740); Cry1Ib8 (Accession #JN675714); Cry1Ib9 (Accession #JN675715); Cry1Ib10 (Accession #JN675716); Cry1Ib11 (Accession #JQ228423); Cry1Ic1 (Accession #AAC62933); Cry1Ic2 (Accession #AAE71691); Cry1Id1 (Accession #AAD44366); Cry1Id2 (Accession #JQ228422); Cry1Ie1 (Accession #AAG43526); Cry1Ie2 (Accession #HM439636); Cry1Ie3 (Accession #KC156647); Cry1Ie4 (Accession #KC156681); Cry1If1 (Accession #AAQ52382); Cry1Ig1 (Accession #KC156701); Cry1I-like (Accession #AAC31094); Cry1I-like (Accession #ABG88859); Cry1Ja1 (Accession #AAA22341); Cry1Ja2 (Accession #HM070030); Cry1Ja3 (Accession #JQ228425); Cry1Jb1 (Accession #AAA98959); Cry1Jc1 (Accession #AAC31092); Cry1Jc2 (Accession #AAQ52372); Cry1Jd1

(Accession #CAC50779); Cry1Ka1 (Accession #AAB00376); Cry1Ka2 (Accession #HQ439783); Cry1La1 (Accession #AAS60191); Cry1La2 (Accession #HM070031); Cry1Ma1 (Accession #FJ884067); Cry1Ma2 (Accession #KC156659); Cry1Na1 (Accession #KC156648); Cry1Nb1 (Accession #KC156678); Cry1-like (Accession #AAC31091); Cry2Aa1 (Accession #AAA22335); Cry2Aa2 (Accession #AAA83516); Cry2Aa3 (Accession #D86064); Cry2Aa4 (Accession #AAC04867); Cry2Aa5 (Accession #CAA10671); Cry2Aa6 (Accession #CAA10672); Cry2Aa7 (Accession #CAA10670); Cry2Aa8 (Accession #AAO13734); Cry2Aa9 (Accession #AAO13750); Cry2Aa10 (Accession #AAQ04263); Cry2Aa11 (Accession #AAQ52384); Cry2Aa12 (Accession #ABI83671); Cry2Aa13 (Accession #ABL01536); Cry2Aa14 (Accession #ACF04939); Cry2Aa15 (Accession #JN426947); Cry2Ab1 (Accession #AAA22342); Cry2Ab2 (Accession #CAA39075); Cry2Ab3 (Accession #AAG36762); Cry2Ab4 (Accession #AAO13296); Cry2Ab5 (Accession #AAQ04609); Cry2Ab6 (Accession #AAP59457); Cry2Ab7 (Accession #AAZ66347); Cry2Ab8 (Accession #ABC95996); Cry2Ab9 (Accession #ABC74968); Cry2Ab10 (Accession #EF157306); Cry2Ab11 (Accession #CAM84575); Cry2Ab12 (Accession #ABM21764); Cry2Ab13 (Accession #ACG76120); Cry2Ab14 (Accession #ACG76121); Cry2Ab15 (Accession #HM037126); Cry2Ab16 (Accession #GQ866914); Cry2Ab17 (Accession #HQ439789); Cry2Ab18 (Accession #JN135255); Cry2Ab19 (Accession #JN135256); Cry2Ab20 (Accession #JN135257); Cry2Ab21 (Accession #JN135258); Cry2Ab22 (Accession #JN135259); Cry2Ab23 (Accession #JN135260); Cry2Ab24 (Accession #JN135261); Cry2Ab25 (Accession #JN415485); Cry2Ab26 (Accession #JN426946); Cry2Ab27 (Accession #JN415764); Cry2Ab28 (Accession #JN651494); Cry2Ac1 (Accession #CAA40536); Cry2Ac2 (Accession #AAG35410); Cry2Ac3 (Accession #AAQ52385); Cry2Ac4 (Accession #ABC95997); Cry2Ac5 (Accession #ABC74969); Cry2Ac6 (Accession #ABC74793); Cry2Ac7 (Accession #CAL18690); Cry2Ac8 (Accession #CAM09325); Cry2Ac9 (Accession #CAM09326); Cry2Ac10 (Accession #ABN15104); Cry2Ac11 (Accession #CAM83895); Cry2Ac12 (Accession #CAM83896); Cry2Ad1 (Accession #AAF09583); Cry2Ad2 (Accession #ABC86927); Cry2Ad3 (Accession #CAK29504); Cry2Ad4 (Accession #CAM32331); Cry2Ad5 (Accession #CAO78739); Cry2Ae1 (Accession #AAQ52362); Cry2Af1 (Accession #AB030519); Cry2Af2 (Accession #GQ866915); Cry2Ag1 (Accession #ACH91610); Cry2Ah1 (Accession #EU939453); Cry2Ah2 (Accession #ACL80665); Cry2Ah3 (Accession #GU073380); Cry2Ah4 (Accession #KC156702); Cry2Ai1 (Accession #FJ788388); Cry2Aj (Accession #); Cry2Ak1 (Accession #KC156660); Cry2Ba1 (Accession #KC156658); Cry3Aa1 (Accession #AAA22336); Cry3Aa2 (Accession #AAA22541); Cry3Aa3 (Accession #CAA68482); Cry3Aa4 (Accession #AAA22542); Cry3Aa5 (Accession #AAA50255); Cry3Aa6 (Accession #AAC43266); Cry3Aa7 (Accession #CAB41411); Cry3Aa8 (Accession #AAS79487); Cry3Aa9 (Accession #AAW05659); Cry3Aa10 (Accession #AAU29411); Cry3Aa11 (Accession #AAW82872); Cry3Aa12 (Accession #ABY49136); Cry3Ba1 (Accession #CAA34983); Cry3Ba2 (Accession #CAA00645); Cry3Ba3 (Accession #JQ397327); Cry3Bb1 (Accession #AAA22334); Cry3Bb2 (Accession #AAA74198); Cry3Bb3 (Accession #115475); Cry3Ca1 (Accession #CAA42469); Cry4Aa1 (Accession #CAA68485); Cry4Aa2 (Accession #BAA00179); Cry4Aa3 (Accession #CAD30148); Cry4Aa4 (Accession #AFB18317); Cry4A-like (Accession #AAY96321); Cry4Ba1 (Accession #CAA30312); Cry4Ba2 (Accession #CAA30114); Cry4Ba3 (Accession #AAA22337); Cry4Ba4 (Accession #BAA00178); Cry4Ba5 (Accession #CAD30095); Cry4Ba-like (Accession #ABC47686); Cry4Ca1 (Accession #EU646202); Cry4Cb1 (Accession #FJ403208); Cry4Cb2 (Accession #FJ597622); Cry4Cc1 (Accession #FJ403207); Cry5Aa1 (Accession #AAA67694); Cry5Ab1 (Accession #AAA67693); Cry5Ac1 (Accession #134543); Cry5Ad1 (Accession #ABQ82087); Cry5Ba1 (Accession #AAA68598); Cry5Ba2 (Accession #ABW88931); Cry5Ba3 (Accession #AFJ04417); Cry5Ca1 (Accession #HM461869); Cry5Ca2 (Accession #ZP_04123426); Cry5Da1 (Accession #HM461870); Cry5Da2 (Accession #ZP_04123980); Cry5Ea1 (Accession #HM485580); Cry5Ea2 (Accession #ZP_04124038); Cry6Aa1 (Accession #AAA22357); Cry6Aa2 (Accession #AAM46849); Cry6Aa3 (Accession #ABH03377); Cry6Ba1 (Accession #AAA22358); Cry7Aa1 (Accession #AAA22351); Cry7Ab1 (Accession #AAA21120); Cry7Ab2 (Accession #AAA21121); Cry7Ab3 (Accession #ABX24522); Cry7Ab4 (Accession #EU380678); Cry7Ab5 (Accession #ABX79555); Cry7Ab6 (Accession #ACI44005); Cry7Ab7 (Accession #ADB89216); Cry7Ab8 (Accession #GU145299); Cry7Ab9 (Accession #ADD92572); Cry7Ba1 (Accession #ABB70817); Cry7Bb1 (Accession #KC156653); Cry7Ca1 (Accession #ABR67863); Cry7Cb1 (Accession #KC156698); Cry7Da1 (Accession #ACQ99547); Cry7Da2 (Accession #HM572236); Cry7Da3 (Accession #KC156679); Cry7Ea1 (Accession #HM035086); Cry7Ea2 (Accession #HM132124); Cry7Ea3 (Accession #EEM19403); Cry7Fa1 (Accession #HM035088); Cry7Fa2 (Accession #EEM19090); Cry7Fb1 (Accession #HM572235); Cry7Fb2 (Accession #KC156682); Cry7Ga1 (Accession #HM572237); Cry7Ga2 (Accession #KC156669); Cry7Gb1 (Accession #KC156650); Cry7Gc1 (Accession #KC156654); Cry7Gd1 (Accession #KC156697); Cry7Ha1 (Accession #KC156651); Cry7Ia1 (Accession #KC156665); Cry7Ja1 (Accession #KC156671); Cry7Ka1 (Accession #KC156680); Cry7Kb1 (Accession #BAM99306); Cry7La1 (Accession #BAM99307); Cry8Aa1 (Accession #AAA21117); Cry8Ab1 (Accession #EU044830); Cry8Ac1 (Accession #KC156662); Cry8Ad1 (Accession #KC156684); Cry8Ba1 (Accession #AAA21118); Cry8Bb1 (Accession #CAD57542); Cry8Bc1 (Accession #CAD57543); Cry8Ca1 (Accession #AAA21119); Cry8Ca2 (Accession #AAR98783); Cry8Ca3 (Accession #EU625349); Cry8Ca4 (Accession #ADB54826); Cry8Da1 (Accession #BAC07226); Cry8Da2 (Accession #BD133574); Cry8Da3 (Accession #BD133575); Cry8db1 (Accession #BAF93483); Cry8Ea1 (Accession #AAQ73470); Cry8Ea2 (Accession #EU047597); Cry8Ea3 (Accession #KC855216); Cry8Fa1 (Accession #AAT48690); Cry8Fa2 (Accession #HQ174208); Cry8Fa3 (Accession #AFH78109); Cry8Ga1 (Accession #AAT46073); Cry8Ga2 (Accession #ABC42043); Cry8Ga3 (Accession #FJ198072); Cry8Ha1 (Accession #AAW81032); Cry8Ia1 (Accession #EU381044); Cry8Ia2 (Accession #GU073381); Cry8Ia3 (Accession #HM044664); Cry8Ia4 (Accession #KC156674); Cry8Ib1 (Accession #GU325772); Cry8Ib2 (Accession #KC156677); Cry8Ja1 (Accession #EU625348); Cry8Ka1 (Accession #FJ422558); Cry8Ka2 (Accession #ACN87262); Cry8Kb1 (Accession #HM123758);

Cry8Kb2 (Accession #KC156675); Cry8La1 (Accession #GU325771); Cry8Ma1 (Accession #HM044665); Cry8Ma2 (Accession #EEM86551); Cry8Ma3 (Accession #HM210574); Cry8Na1 (Accession #HM640939); Cry8Pa1 (Accession #HQ388415); Cry8Qa1 (Accession #HQ441166); Cry8Qa2 (Accession #KC152468); Cry8Ra1 (Accession #AFP87548); Cry8Sa1 (Accession #JQ740599); Cry8Ta1 (Accession #KC156673); Cry8-like (Accession #FJ770571); Cry8-like (Accession #ABS53003); Cry9Aa1 (Accession #CAA41122); Cry9Aa2 (Accession #CAA41425); Cry9Aa3 (Accession #GQ249293); Cry9Aa4 (Accession #GQ249294); Cry9Aa5 (Accession #JX174110); Cry9Aa like (Accession #AAQ52376); Cry9Ba1 (Accession #CAA52927); Cry9Ba2 (Accession #GU299522); Cry9Bb1 (Accession #AAV28716); Cry9Ca1 (Accession #CAA85764); Cry9Ca2 (Accession #AAQ52375); Cry9Da1 (Accession #BAA19948); Cry9Da2 (Accession #AAB97923); Cry9Da3 (Accession #GQ249293); Cry9Da4 (Accession #GQ249297); Cry9db1 (Accession #AAX78439); Cry9Dc1 (Accession #KC156683); Cry9Ea1 (Accession #BAA34908); Cry9Ea2 (Accession #AAO12908); Cry9Ea3 (Accession #ABM21765); Cry9Ea4 (Accession #ACE88267); Cry9Ea5 (Accession #ACF04743); Cry9Ea6 (Accession #ACG63872); Cry9Ea7 (Accession #FJ380927); Cry9Ea8 (Accession #GQ249292); Cry9Ea9 (Accession #JN651495); Cry9Eb1 (Accession #CAC50780); Cry9Eb2 (Accession #GQ249298); Cry9Eb3 (Accession #KC156646); Cry9Ec1 (Accession #AAC63366); Cry9Ed1 (Accession #AAX78440); Cry9Ee1 (Accession #GQ249296); Cry9Ee2 (Accession #KC156664); Cry9Fa1 (Accession #KC156692); Cry9Ga1 (Accession #KC156699); Cry9-like (Accession #AAC63366); Cry10Aa1 (Accession #AAA22614); Cry10Aa2 (Accession #E00614); Cry10Aa3 (Accession #CAD30098); Cry10Aa4 (Accession #AFB18318); Cry10A-like (Accession #DQ167578); Cry11Aa1 (Accession #AAA22352); Cry11Aa2 (Accession #AAA22611); Cry11Aa3 (Accession #CAD30081); Cry11Aa4 (Accession #AFB18319); Cry11Aa-like (Accession #DQ166531); Cry11Ba1 (Accession #CAA60504); Cry11Bb1 (Accession #AAC97162); Cry11Bb2 (Accession #HM068615); Cry12Aa1 (Accession #AAA22355); Cry13Aa1 (Accession #AAA22356); Cry14Aa1 (Accession #AAA21516); Cry14Ab1 (Accession #KC156652); Cry15Aa1 (Accession #AAA22333); Cry16Aa1 (Accession #CAA63860); Cry11Aa1 (Accession #CAA67841); Cry18Aa1 (Accession #CAA67506); Cry18Ba1 (Accession #AAF89667); Cry18Ca1 (Accession #AAF89668); Cry19Aa1 (Accession #CAA68875); Cry19Ba1 (Accession #BAA32397); Cry19Ca1 (Accession #AFM37572); Cry20Aa1 (Accession #AAB93476); Cry20Ba1 (Accession #ACS93601); Cry20Ba2 (Accession #KC156694); Cry20-like (Accession #GQ144333); Cry21Aa1 (Accession #132932); Cry21Aa2 (Accession #166477); Cry21Ba1 (Accession #BAC06484); Cry21Ca1 (Accession #JF521577); Cry21Ca2 (Accession #KC156687); Cry21Da1 (Accession #JF521578); Cry22Aa1 (Accession #134547); Cry22Aa2 (Accession #CAD43579); Cry22Aa3 (Accession #ACD93211); Cry22Ab1 (Accession #AAK50456); Cry22Ab2 (Accession #CAD43577); Cry22Ba1 (Accession #CAD43578); Cry22Bb1 (Accession #KC156672); Cry23Aa1 (Accession #AAF76375); Cry24Aa1 (Accession #AAC61891); Cry24Ba1 (Accession #BAD32657); Cry24Ca1 (Accession #CAJ43600); Cry25Aa1 (Accession #AAC61892); Cry26Aa1 (Accession #AAD25075); Cry27Aa1 (Accession #BAA82796); Cry28Aa1 (Accession #AAD24189); Cry28Aa2 (Accession #AAG00235); Cry29Aa1 (Accession #CAC80985); Cry30Aa1 (Accession #CAC80986); Cry30Ba1 (Accession #BAD00052); Cry30Ca1 (Accession #BAD67157); Cry30Ca2 (Accession #ACU24781); Cry30Da1 (Accession #EF095955); Cry30db1 (Accession #BAE80088); Cry30Ea1 (Accession #ACC95445); Cry30Ea2 (Accession #FJ499389); Cry30Fa1 (Accession #ACI22625); Cry30Ga1 (Accession #ACG60020); Cry30Ga2 (Accession #HQ638217); Cry31Aa1 (Accession #BAB11757); Cry31Aa2 (Accession #AAL87458); Cry31Aa3 (Accession #BAE79808); Cry31Aa4 (Accession #BAF32571); Cry31Aa5 (Accession #BAF32572); Cry31Aa6 (Accession #BAI44026); Cry31Ab1 (Accession #BAE79809); Cry31Ab2 (Accession #BAF32570); Cry31Ac1 (Accession #BAF34368); Cry31Ac2 (Accession #AB731600); Cry31Ad1 (Accession #BAI44022); Cry32Aa1 (Accession #AAG36711); Cry32Aa2 (Accession #GU063849); Cry32Ab1 (Accession #GU063850); Cry32Ba1 (Accession #BAB78601); Cry32Ca1 (Accession #BAB78602); Cry32Cb1 (Accession #KC156708); Cry32Da1 (Accession #BAB78603); Cry32Ea1 (Accession #GU324274); Cry32Ea2 (Accession #KC156686); Cry32Eb1 (Accession #KC156663); Cry32Fa1 (Accession #KC156656); Cry32Ga1 (Accession #KC156657); Cry32Ha1 (Accession #KC156661); Cry32Hb1 (Accession #KC156666); Cry32Ia1 (Accession #KC156667); Cry32Ja1 (Accession #KC156685); Cry32Ka1 (Accession #KC156688); Cry32La1 (Accession #KC156689); Cry32Ma1 (Accession #KC156690); Cry32Mb1 (Accession #KC156704); Cry32Na1 (Accession #KC156691); Cry32Oa1 (Accession #KC156703); Cry32Pa1 (Accession #KC156705); Cry32Qa1 (Accession #KC156706); Cry32Ra1 (Accession #KC156707); Cry32Sa1 (Accession #KC156709); Cry32Ta1 (Accession #KC156710); Cry32Ua1 (Accession #KC156655); Cry33Aa1 (Accession #AAL26871); Cry34Aa1 (Accession #AAG50341); Cry34Aa2 (Accession #AAK64560); Cry34Aa3 (Accession #AAT29032); Cry34Aa4 (Accession #AAT29030); Cry34Ab1 (Accession #AAG41671); Cry34Ac1 (Accession #AAG50118); Cry34Ac2 (Accession #AAK64562); Cry34Ac3 (Accession #AAT29029); Cry34Ba1 (Accession #AAK64565); Cry34Ba2 (Accession #AAT29033); Cry34Ba3 (Accession #AAT29031); Cry35Aa1 (Accession #AAG50342); Cry35Aa2 (Accession #AAK64561); Cry35Aa3 (Accession #AAT29028); Cry35Aa4 (Accession #AAT29025); Cry35Ab1 (Accession #AAG41672); Cry35Ab2 (Accession #AAK64563); Cry35Ab3 (Accession #AY536891); Cry35Ac1 (Accession #AAG50117); Cry35Ba1 (Accession #AAK64566); Cry35Ba2 (Accession #AAT29027); Cry35Ba3 (Accession #AAT29026); Cry36Aa1 (Accession #AAK64558); Cry37Aa1 (Accession #AAF76376); Cry38Aa1 (Accession #AAK64559); Cry39Aa1 (Accession #BAB72016); Cry40Aa1 (Accession #BAB72018); Cry40Ba1 (Accession #BAC77648); Cry40Ca1 (Accession #EU381045); Cry40Da1 (Accession #ACF15199); Cry41Aa1 (Accession #BAD35157); Cry41Ab1 (Accession #BAD35163); Cry41Ba1 (Accession #HM461871); Cry41Ba2 (Accession #ZP_04099652); Cry42Aa1 (Accession #BAD35166); Cry43Aa1 (Accession #BAD15301); Cry43Aa2 (Accession #BAD95474); Cry43Ba1 (Accession #BAD15303); Cry43Ca1 (Accession #KC156676); Cry43Cb1 (Accession #KC156695); Cry43Cc1 (Accession #KC156696); Cry43-like (Accession #BAD15305); Cry44Aa (Accession #BAD08532); Cry45Aa (Accession #BAD22577); Cry46Aa (Accession #BAC79010); Cry46Aa2 (Accession #BAG68906); Cry46Ab (Accession #BAD35170); Cry47Aa (Accession

AAY24695); Cry48Aa (Accession #CAJ18351); Cry48Aa2 (Accession #CAJ86545); Cry48Aa3 (Accession #CAJ86546); Cry48Ab (Accession #CAJ86548); Cry48Ab2 (Accession #CAJ86549); Cry49Aa (Accession #CAH56541); Cry49Aa2 (Accession #CAJ86541); Cry49Aa3 (Accession #CAJ86543); Cry49Aa4 (Accession #CAJ86544); Cry49Ab1 (Accession #CAJ86542); Cry50Aa1 (Accession #BAE86999); Cry50Ba1 (Accession #GU446675); Cry50Ba2 (Accession #GU446676); Cry51Aa1 (Accession #ABI14444); Cry51Aa2 (Accession #GU570697); Cry52Aa1 (Accession #EF613489); Cry52Ba1 (Accession #FJ361760); Cry53Aa1 (Accession #EF633476); Cry53Ab1 (Accession #FJ361759); Cry54Aa1 (Accession #ACA52194); Cry54Aa2 (Accession #GQ140349); Cry54Ba1 (Accession #GU446677); Cry55Aa1 (Accession #ABW88932); Cry54Ab1 (Accession #JQ916908); Cry55Aa2 (Accession #AAE33526); Cry56Aa1 (Accession #ACU57499); Cry56Aa2 (Accession #GQ483512); Cry56Aa3 (Accession #JX025567); Cry57Aa1 (Accession #ANC87261); Cry58Aa1 (Accession #ANC87260); Cry59Ba1 (Accession #JN790647); Cry59Aa1 (Accession #ACR43758); Cry60Aa1 (Accession #ACU24782); Cry60Aa2 (Accession #EA057254); Cry60Aa3 (Accession #EEM99278); Cry60Ba1 (Accession #GU810818); Cry60Ba2 (Accession #EA057253); Cry60Ba3 (Accession #EEM99279); Cry61Aa1 (Accession #HM035087); Cry61Aa2 (Accession #HM132125); Cry61Aa3 (Accession #EEM19308); Cry62Aa1 (Accession #HM054509); Cry63Aa1 (Accession #BAI44028); Cry64Aa1 (Accession #BAJ05397); Cry65Aa1 (Accession #HM461868); Cry65Aa2 (Accession #ZP_04123838); Cry66Aa1 (Accession #HM485581); Cry66Aa2 (Accession #ZP_04099945); Cry67Aa1 (Accession #HM485582); Cry67Aa2 (Accession #ZP_04148882); Cry68Aa1 (Accession #HQ113114); Cry69Aa1 (Accession #HQ401006); Cry69Aa2 (Accession #JQ821388); Cry69Ab1 (Accession #JN209957); Cry70Aa1 (Accession #JN646781); Cry70Ba1 (Accession #AD051070); Cry70Bb1 (Accession #EEL67276); Cry71Aa1 (Accession #JX025568); Cry72Aa1 (Accession #JX025569).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; TIC3131, TIC 3400, and TIC3407 of US Patent Application Publication Number 2015/0047076; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US20090144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011)

*Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605)); Cry34Ab/35Ab and Cry6Aa (US20130167269); Cry34Ab/VCry35Ab & Cry3Aa (US20130167268); Cry3A and Cry1Ab or Vip3Aa (US20130116170); and Cry1F, Cry34Ab1, and Cry35Ab1 (PCT/US2010/060818). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) An insect-specific hormone or pheromone such as an ecdysteroid and juvenile hormone, a variant thereof, a mimetic based thereon, or an antagonist or agonist thereof. See, for example, the disclosure by Hammock, et al., (1990) *Nature* 344:458, of baculovirus expression of cloned juvenile hormone esterase, an inactivator of juvenile hormone.

(D) An insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4): 385-403. See also, U.S. Pat. No. 5,266,317 to Tomalski, et al., who disclose genes encoding insect-specific toxins.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 93/02197 in the name of Scott, et al., which discloses the nucleotide sequence of a callase gene. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase, and Kawalleck, et al., (1993) *Plant Molec. Biol.* 21:673, who provide the nucleotide sequence of the parsley ubi4-2 polyubiquitin gene, U.S. patent application Ser. Nos. 10/389,432, 10/692,367 and U.S. Pat. No. 6,563,020.

(G) A molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A hydrophobic moment peptide. See, PCT Application Number WO 95/16776 and U.S. Pat. No. 5,580,852 (disclosure of peptide derivatives of Tachyplesin which inhibit fungal plant pathogens) and PCT Application Number WO 95/18855 and U.S. Pat. No. 5,607,914 (teaches synthetic antimicrobial peptides that confer disease resistance).

(I) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki, et al., (1993) *Nature* 366:469, who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2):128-131, Pieterse and Van Loon, (2004) *Curr. Opin. Plant Bio.* 7(4):456-64 and Somssich, (2003) *Cell* 113(7): 815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. No. 09/950,933.

(Q) Detoxification genes, such as for fumonisin, beauvericin, moniliformin and zearalenone and their structurally related derivatives. For example, see, U.S. Pat. No. 5,792, 931.

(R) Cystatin and cysteine proteinase inhibitors. See, U.S. application Ser. No. 10/947,979.

(S) Defensin genes. See, WO03/000863 and U.S. application Ser. No. 10/178,213.

(T) Genes conferring resistance to nematodes. See, WO 03/033651 and Urwin, et. al., (1998) *Planta* 204:472-479, Williamson (1999) *Curr Opin Plant Bio.* 2(4):327-31.

(U) Genes such as rcg1conferring resistance to Anthracnose stalk rot, which is caused by the fungus *Colletotrichum graminiola*. See, Jung, et al., Generation-means analysis and quantitative trait locus mapping of Anthracnose Stalk Rot genes in Maize, *Theor. Appl. Genet.* (1994) 89:413-418, as well as, U.S. Provisional Patent Application No. 60/675, 664.

(V) Nucleic Acids that relate to down-regulation of expression of target genes in insect pest species by interfering ribonucleic acid (RNA) molecules, which control the insect pest species. PCT Publication WO 2011/025860 and WO 2014/153254 describe methods of inhibiting expression of target genes in invertebrate plant pests including *Diabrotica* plant pests. Furthermore, PCT Publication WO 2009/091864 describes compositions and methods for the suppression of target genes from insect pest species including pests from the *Lygus* genus.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Mild, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824 and international publication WO 96/33270.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes) and pyridinoxy or phenoxy proprionic acids and cycloshexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338, 961; 6,248,876 B1; 6,040,497; 5,804,425; 5,633,435; 5,145, 783; 4,971,908; 5,312,910; 5,188,642; 4,940,835; 5,866, 775; 6,225,114 B1; 6,130,366; 5,310,667; 4,535,060; 4,769, 061; 5,633,448; 5,510,471; Re. 36,449; RE 37,287 E and 5,491,288 and international publications EP1173580; WO 01/66704; EP1173581 and EP1173582. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. patent application Ser. Nos. 11/405,845 and 10/427,692 and PCT Application Number US01/46227. A DNA molecule encoding a mutant aroA gene can be obtained under ATCC Accession Number 39256 and the nucleotide sequence of the mutant gene is disclosed in U.S. Pat. No. 4,769,061 to Comai. EP Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Patent Numbers 0 242 246 and 0 242 236 to Leemans, et al., De Greef, et al., (1989) *Bio/Technology* 7:61 which describe the production of transgenic plants that express chimeric bar genes coding for phosphinothricin acetyl transferase activity. See also, U.S. Pat. Nos. 5,969, 213; 5,489,520; 5,550,318; 5,874,265; 5,919,675; 5,561, 236; 5,648,477; 5,646,024; 6,177,616 B1 and 5,879,903. Exemplary genes conferring resistance to phenoxy proprionic acids and cycloshexones, such as sethoxydim and haloxyfop, are the Acc1-S1, Acc1-S2 and Acc1-S3 genes described by Marshall, et al., (1992) *Theor. Appl. Genet.* 83:435.

(C) A herbicide that inhibits photosynthesis, such as a triazine (psbA and gs+ genes) and a benzonitrile (nitrilase gene). Przibilla, et al., (1991) *Plant Cell* 3:169, describe the transformation of *Chlamydomonas* with plasmids encoding mutant psbA genes. Nucleotide sequences for nitrilase genes are disclosed in U.S. Pat. No. 4,810,648 to Stalker, herein incorporated by reference in its entirety, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173.

(D) Acetohydroxy acid synthase, which has been found to make plants that express this enzyme resistant to multiple types of herbicides, has been introduced into a variety of plants (see, e.g., Hattori, et al., (1995) *Mol Gen Genet* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106(1): 17-23), genes for glutathione reductase and superoxide dismutase (Aono, et al., (1995) *Plant Cell Physiol* 36:1687, and genes for various phosphotransferases (Datta, et al., (1992) *Plant Mol Biol* 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. No. 6,288,306 B1; 6,282,837 B1 and 5,767,373; and international publication number WO 01/12825.

3. Transgenes that Confer or Contribute to an Altered Grain Characteristic, Such as:

(A) Altered fatty acids, for example, by
  (1) Down-regulation of stearoyl-ACP desaturase to increase stearic acid content of the plant. See, Knultzon, et al., (1992) *Proc. Natl. Acad. Sci. USA* 89:2624 and WO99/64579 (Genes for Desaturases to Alter Lipid Profiles in Corn),
  (2) Elevating oleic acid via FAD-2 gene modification and/or decreasing linolenic acid via FAD-3 gene modification (see, U.S. Pat. Nos. 6,063,947; 6,323,392; 6,372,965 and WO 93/11245),
  (3) Altering conjugated linolenic or linoleic acid content, such as in WO 01/12800,
  (4) Altering LEC1, AGP, Dek1, Superal1, milps, various 1pa genes such as 1pa1, lpa3, hpt or hggt. For example, see, WO 02/42424, WO 98/22604, WO 03/011015, U.S. Pat. Nos. 6,423,886, 6,197,561, 6,825,397, US Patent Application Publication Numbers 2003/0079247, 2003/0204870, WO02/057439, WO03/011015 and Rivera-Madrid, et. al., (1995) *Proc. Natl. Acad. Sci.* 92:5620-5624.

(B) Altered phosphorus content, for example, by the
  (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.
  (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 02/059324, US Patent Application Publication Number 2003/0009011, WO 03/027243, US Patent Application Publication Number 2003/0079247, WO 99/05298, U.S. Pat. Nos. 6,197,561, 6,291,224, 6,391,348, WO2002/059324, US Patent Application Publication Number 2003/0079247, WO98/45448, WO99/55882, WO01/04147.

(C) Altered carbohydrates effected, for example, by altering a gene for an enzyme that affects the branching pattern of starch or a gene altering thioredoxin such as NTR and/or TRX (see, U.S. Pat. No. 6,531,648) and/or a gamma zein knock out or mutant such as cs27 or TUSC27 or en27 (see, U.S. Pat. No. 6,858,778 and US Patent Application Publication Numbers 2005/0160488 and 2005/0204418). See, Shiroza, et al., (1988) *J. Bacteriol.* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 99/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned above may also be used to affect starch content and/or composition through the inter-relationship of the starch and oil pathways.

(D) Altered antioxidant content or composition, such as alteration of tocopherol or tocotrienols. For example, see U.S. Pat. No. 6,787,683, US Patent Application Publication Number 2004/0034886 and WO 00/68393 involving the manipulation of antioxidant levels through alteration of a phytl prenyl transferase (ppt), WO 03/082899 through alteration of a homogentisate geranyl geranyl transferase (hggt).

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO99/40209 (alteration of amino acid compositions in seeds), WO99/29882 (methods for altering amino acid content of proteins), U.S. Pat. No. 5,850,016 (alteration of amino acid compositions in seeds), WO98/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO98/56935 (plant amino acid biosynthetic enzymes), WO98/45458 (engineered seed protein having higher percentage of essential amino acids), WO98/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO96/01905 (increased threonine), WO95/15392 (increased lysine), US Patent Application Publication Number 2003/0163838, US Patent Application Publication Number 2003/0150014, US Patent Application Publication Number 2004/0068767, U.S. Pat. No. 6,803,498, WO01/79516, and WO00/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP).

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant and thus creating a plant that is male sterile because the inducible promoter is not "on" resulting in the male fertility gene not being transcribed. Fertility is restored by inducing, or turning "on", the promoter, which in turn allows the gene conferring male fertility to be transcribed.

(A) Introduction of a deacetylase gene under the control of a tapetum-specific promoter and with the application of the chemical N—Ac-PPT (WO 01/29237).

(B) Introduction of various stamen-specific promoters (WO 92/13956, WO 92/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859, 341; 6,297,426; 5,478,369; 5,824,524; 5,850,014 and 6,265, 640.

5. Genes that Create a Site for Site Specific DNA Integration

This includes the introduction of FRT sites that may be used in the FLP/FRT system and/or Lox sites that may be used in the Cre/Loxp system. For example, see Lyznik, et al., (2003) *Plant Cell Rep* 21:925-932 and WO 99/25821. Other systems that may be used include the Gin recombinase of phage Mu (Maeser, et al., 1991; Vicki Chandler, *The Maize Handbook* ch. 118 (Springer-Verlag 1994), the Pin recombinase of *E. coli* (Enomoto, et al., 1983), and the R/RS system of the pSR1 plasmid (Araki, et al., 1992).

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see, WO 00/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, WO2000060089, WO2001026459, WO2001035725, WO2001034726, WO2001035727, WO2001036444, WO2001036597, WO2001036598, WO2002015675, WO2002017430, WO2002077185, WO2002079403, WO2003013227, WO2003013228, WO2003014327, WO2004031349, WO2004076638, WO9809521, and WO9938977 describing genes, including CBF genes and transcription factors effective in mitigating the negative effects of freezing, high salinity, and drought on plants, as well as conferring other positive effects on plant phenotype; US Patent Application Publication Number 2004/0148654 and WO01/36596 where abscisic acid is altered in plants resulting in improved plant phenotype such as increased yield and/or increased tolerance to abiotic stress; WO2000/006341, WO04/090143, U.S. patent application Ser. No. 10/817,483 and U.S. Pat. No. 6,992,237, where cytokinin expression is modified resulting in plants with increased stress tolerance, such as drought tolerance, and/or increased yield, herein incorporated by reference in their entirety. Also see WO0202776, WO2003052063, JP2002281975, U.S. Pat. No. 6,084,153, WO0164898, U.S. Pat. Nos. 6,177,275 and 6,107,547 (enhancement of nitrogen utilization and altered nitrogen responsiveness). For ethylene alteration, see US Patent Application Publication Number 2004/0128719, US Patent Application Publication Number 2003/0166197 and WO200032761. For plant transcription factors or transcriptional regulators of abiotic stress, see, e.g., US Patent Application Publication Number 2004/0098764 or US Patent Application Publication Number 2004/0078852.

Other genes and transcription factors that affect plant growth and agronomic traits such as yield, flowering, plant growth and/or plant structure, can be introduced or introgressed into plants, see, e.g., WO97/49811 (LHY), WO98/56918 (ESD4), WO97/10339 and U.S. Pat. No. 6,573,430 (TFL), U.S. Pat. No. 6,713,663 (FT), WO96/14414 (CON), WO96/38560, WO01/21822 (VRN1), WO00/44918 (VRN2), WO99/49064 (GI), WO00/46358 (FRI), WO97/29123, U.S. Pat. Nos. 6,794,560, 6,307,126 (GAI), WO99/09174 (D8 and Rht) and WO2004076638 and WO2004031349 (transcription factors).

"RNAi" refers to a series of related techniques to reduce the expression of genes (see, for example, U.S. Pat. No. 6,506,559). These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020). Such techniques rely on the use of constructs resulting in the accumulation of double stranded RNA with one strand complementary to the target gene to be silenced. The regulatory sequences disclosed herein may be used to drive expression of constructs that will result in RNA interference including microRNAs and siRNAs.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus.

Nucleic acid molecules including silencing elements for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR, HP2, and PAT3. US Patent Application publication 2011/0054007 describes polynucleotide silencing elements targeting RPS10. PCT publication WO 2016/205445 describes polynucleotide silencing elements that reduce fecundity, including NCLB, MAEL, BOULE, and VgR. PCT publications WO/2016/138106, WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

The isolated regulatory element sequences disclosed herein may be modified to provide for a range of expression levels of the heterologous nucleotide sequence. Thus, less than the entire regulatory element region may be utilized and the ability to drive expression of the nucleotide sequence of interest retained. It is recognized that expression levels of the mRNA may be altered in different ways with deletions of portions of the promoter sequences. The mRNA expression levels may be decreased, or alternatively, expression may be increased as a result of regulatory element deletions if, for example, there is a negative regulatory element (for a repressor) that is removed during the truncation process. Generally, at least about 20 nucleotides of an isolated regulatory element sequence will be used to drive expression of a polynucleotide sequence.

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acid Res.* 15:9627-9639.

Expression cassettes comprising sequences disclosed herein may also contain at least one additional nucleotide sequence for a gene to be cotransformed into the organism. Alternatively, the additional sequence(s) can be provided on another expression cassette.

Where appropriate, the polynucleotide sequences whose expression is to be under the control of a hybrid regulatory element sequence of the present disclosure and any additional nucleotide sequence(s) may be optimized for increased expression in the transformed plant. That is, these nucleotide sequences can be synthesized using plant preferred codons for improved expression. See, for example, Campbell and Gowri, (1990) *Plant Physiol.* 92:1-11, for a discussion of host-preferred codon usage. Methods are available in the art for synthesizing plant-preferred genes. See, for example, Murray, et al., (1989) *Nucleic Acids Res.* 17:477-498.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the heterologous polynucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences may act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci. USA* 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA*, pages 237-256) and maize chlorotic mottle virus leader (MCMV) (Lommel, et al., (1991) *Virology* 81:382-385). See, also, Della-Cioppa, et al., (1987) *Plant Physiology* 84:965-968. Methods known to enhance mRNA stability may also be utilized, for example, introns, such as the maize Ubiquitin intron (Christensen and Quail, (1996) *Transgenic Res.* 5:213-218; Christensen, et al., (1992) *Plant Molecular Biology* 18:675-689) or the maize Adhl intron (Kyozuka, et al., (1991) *Mol. Gen. Genet.* 228:40-48; Kyozuka, et al., (1990) *Maydica* 35:353-357) and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

Reporter genes or selectable marker genes may also be included in expression cassettes. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *Bio Techniques* 19:650-655 and Chiu, et al., (1996) *Current Biology* 6:325-330.

Selectable marker genes for selection of transformed cells or tissues may include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213; Meijer, et al., (1991) *Plant Mol. Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518).

Other genes that could serve utility in the recovery of transgenic events would include, but are not limited to, examples such as GUS (beta-glucuronidase; Jefferson, (1987) *Plant Mol. Biol. Rep.* 5:387), GFP (green fluorescence protein; Chalfie, et al., (1994) *Science* 263:802), luciferase (Riggs, et al., (1987) *Nucleic Acids Res.* 15(19): 8115 and Luehrsen, et al., (1992) *Methods Enzymol.* 216: 397-414) and the maize genes encoding for anthocyanin production (Ludwig, et al., (1990) *Science* 247:449).

Expression cassette comprising a hybrid regulatory element operably linked to a polynucleotide sequence of interest may be used to transform any plant. In another embodiment, an expression cassette comprising the sequences of SEQ ID NOs: 1-74 operably linked to a polynucleotide sequence of interest may be used to transform any plant. In this manner, genetically modified plants, plant cells, plant tissue, seed, root and the like may be obtained.

Certain disclosed methods involve introducing a polynucleotide into a plant. As used herein, "introducing" is intended to mean presenting to the plant the polynucleotide in such a manner that the sequence gains access to the interior of a cell of the plant. The methods of the disclosure do not depend on a particular method for introducing a sequence into a plant, only that the polynucleotide gains access to the interior of at least one cell of the plant. Methods for introducing polynucleotide into plants are known in the art including, but not limited to, stable transformation methods, transient transformation methods and virus-mediated methods.

A "stable transformation" is a transformation in which the polynucleotide construct introduced into a plant integrates into the genome of the plant and is capable of being inherited by the progeny thereof. "Transient transformation" means that a polynucleotide is introduced into the plant and does not integrate into the genome of the plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (Townsend, et al., U.S. Pat. No. 5,563,055 and Zhao, et al., U.S. Pat. No. 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244; 5,932,782; Tomes, et al., (1995) in Plant Cell, Tissue, and Organ Culture: Fundamental Methods, ed. Gamborg and Phillips (Springer-Verlag, Berlin); McCabe, et al., (1988) *Biotechnology* 6:923-926) and Lec1 transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., and (1996) *Nature Biotechnology* 14:745-750 (maize via *Agrobacterium tumefaciens*).

In one embodiment, DNA constructs comprising a hybrid regulatory element may be provided to a plant using a variety of transient transformation methods. In another embodiment, DNA constructs comprising the disclosed sequences SEQ ID NOs: 1-74 may be provided to a plant using a variety of transient transformation methods. Such transient transformation methods include, but are not limited to, viral vector systems and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

In other embodiments, a polynucleotide may be introduced into plants by contacting plants with a virus or viral nucleic acids. Generally, such methods involve incorporating a polynucleotide construct of the disclosure within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931 and Porta, et al., (1996) *Molecular Biotechnology* 5:209-221.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855 and WO99/25853. Briefly, the polynucleotide of the disclosure can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a polynucleotide construct, for example, an expression cassette comprising one of SEQ ID NOs: 1-74, stably incorporated into its genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polynucleotide is cultivated using methods well known to one skilled in the art.

The embodiments provide compositions for screening compounds that modulate expression within plants. The vectors, cells and plants can be used for screening candidate molecules for agonists and antagonists of the regulatory element sequences of SEQ ID NOs: 1-74. For example, a reporter gene can be operably linked to a regulatory element sequence and expressed as a transgene in a plant.

Compounds to be tested are added and reporter gene expression is measured to determine the effect on promoter activity.

In one embodiment, a regulatory element, for example sequences SEQ ID NOs: 1-74 may be edited or inserted into a plant by genome editing using a CRISPR/Cas9 system.

In an aspect, the disclosed regulatory elements may be introduced into the genome of a plant using genome editing technologies, or previously introduced regulatory elements in the genome of a plant may be edited using genome editing technologies. For example, the disclosed regulatory elements may be introduced into a desired location in the genome of a plant through the use of double-stranded break technologies such as TALENs, meganucleases, zinc finger nucleases, CRISPR-Cas, and the like. For example, the disclosed regulatory elements may be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing regulatory elements of interest could be either an endogenous regulatory elements or a previously introduced regulatory elements.

In another aspect, where the disclosed regulatory element has previously been introduced into a genome, genome editing technologies may be used to alter or modify the introduced regulatory element sequence. Site specific modifications that can be introduced into the disclosed regulatory elements compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide.

An "altered target site," "altered target sequence," "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

All publications, patents and patent applications mentioned in the specification are indicative of the level of those skilled in the art to which this disclosure pertains. All publications, patents and patent applications are herein incorporated by reference to the same extent as if each individual publication, patent or patent application was specifically and individually indicated to be incorporated by reference.

The above description of various illustrated embodiments of the disclosure is not intended to be exhaustive or to limit the scope to the precise form disclosed. While specific embodiments of examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

Efforts have been made to ensure accuracy with respect to the numbers used (e.g. amounts, temperature, concentrations, etc.), but some experimental errors and deviations should be allowed for. Unless otherwise indicated, parts are parts by weight; molecular weight is average molecular weight; temperature is in degrees centigrade; and pressure is at or near atmospheric.

EXPERIMENTAL

Example 1: Root Hybrid Regulatory Elements

Roots are complex organs that can be divided into different regions; for example, the cap, meristem, elongation region and mature region. These regions reflect different stages of root cell identity and maturity. Genes in these cells are activated and inactivated and therefore may not express simultaneously in all regions of the root. Regulatory elements control the expression of these genes. Identifying naturally occurring regulatory elements with needed expression characteristics presents challenges at many different levels and can result in unanticipated expression levels and patterns in transgenic plants. An alternative to naturally occurring regulatory elements is a hybrid regulatory element that is created by combining segments of different regulatory elements. Segments of regulatory elements that function in different regions of the maize root can be combined, such that a hybrid regulatory element is created that functions in all or most regions of the root. Preferably, root specificity is maintained, although ectopic expression could occur.

Example 2: Construction of Hybrid Root Regulatory Element Sequences

The hybrid regulatory sequences (SEQ ID NOs: 11-30 and 35-60) were each constructed using segments of regulatory elements that had been previously characterized for expression (Step 1; Table 1). The native regulatory elements were broadly categorized into two groups by expression pattern, root tip and mature region. The root tip included the cap, meristem, and the area of the elongation region adjacent to the meristem. The mature region included the mature region of the root and the portion of the elongation region adjacent to the mature region. The regulatory elements, belonging to either class, were evaluated for potential motifs using public and proprietary databases to aid in defining segments that may be used in the hybrid regulatory element (Step 2). Motifs algorithms useful for screening in the process are known in the art, such as Higo, K et al. (1998) Nucleic Acids Research. The process was initiated by assessing the position of motifs, the size and type of motifs as well as the clustering of motifs. Motif clustering between the TATA box and about 1 kb upstream of the TATA box was favored as a segment to use in a hybrid promoter over segments that were more distal. The third step (Step 3) comprised assembly of chosen segments that contributed the 3' end of the hybrid regulatory element, including the TATA box, and then the segments comprising the 5' end of the hybrid regulatory element (Table 2). The assembly process generally placed the root tip segments at the 3' end of the regulatory element. SEQ ID NOs: 11-18 were each cloned into a respective expression vector for introduction into maize plants. The β-glucuronidase (GUS) gene was used as a reporter gene to characterize expression directed by each of the hybrid regulatory elements. Approximately 10 maize transgenic events were regenerated for each vector.

TABLE 1

Expression Pattern of Root Promoters in Transgenic Maize Plants

| Parent Regulatory Element | Fragment category | Species of origin | Cap | Meristem | Elongation region | Mature region |
|---|---|---|---|---|---|---|
| SEQ ID NO: 1 | root tip | Bd | +++ | + | − | − |
| SEQ ID NO: 2 | root tip | Bd | − | ++++ | + | − |
| SEQ ID NO: 3 | root tip | Bd | − | ++ | + | − |
| SEQ ID NO: 4 | root tip | Zm | − | +++ | ++ | − |
| SEQ ID NO: 5 | mature region | Sb | − | − | ++ | ++ |
| SEQ ID NO: 6 | mature region | Sb | − | − | +++ | +++ |
| SEQ ID NO: 7 | mature region | Sb | − | + | − | ++ |
| SEQ ID NO: 8 | mature region | Zm | − | − | + | +++ |
| SEQ ID NO: 9 | mature region | Zm | − | − | + | +++ |
| SEQ ID NO: 10 | mature region | Si | − | − | + | ++ |

Based on histochemical staining

Zm = maize;

Sb = *sorghum*;

Bd = *Brachypodium distachyon*;

Si = *Setaria italica*

TABLE 2

Parent Regulatory Elements that Contribute Segments to the Root Hybrid Promoters

| Hybrid Regulatory Element | Element 4 | size of element 4 (bp) | Element 3 | size of element 3 (bp) | Element 2 | size of element 2 (bp) | Element 1 (TATA box) | size of element 1 (bp) |
|---|---|---|---|---|---|---|---|---|
| SEQ ID NO: 11 | SEQ ID NO: 8 (Zm) | 973 | SEQ ID NO: 8 (Zm) | 973 | SEQ ID NO: 8 (Zm) | 1008 | SEQ ID NO: 4 (Zm) | 1152 |
| SEQ ID NO: 12 | SEQ ID NO: 6 (Sb) | 1581 | SEQ ID NO: 6 (Sb) | 1581 | SEQ ID NO: 6 (Sb) | 1581 | SEQ ID NO: 4 (Zm) | 1152 |
| SEQ ID NO: 13 | | | SEQ ID NO: 8 (Zm) | 973 | SEQ ID NO: 6 (Sb) | 1229 | SEQ ID NO: 4 (Zm) | 587 |
| SEQ ID NO: 14 | | | SEQ ID NO: 6 (Sb) | 1581 | SEQ ID NO: 5 (Sb) | 441 | SEQ ID NO: 2 (Bd) | 1115 |
| SEQ ID NO: 15 | | | SEQ ID NO: 9 (Zm) | 781 | SEQ ID NO: 5 (Sb) | 441 | SEQ ID NO: 2 (Bd) | 1115 |
| SEQ ID NO: 16 | | | SEQ ID NO: 6 (Sb) | 1581 | SEQ ID NO: 5 (Sb) | 441 | SEQ ID NO: 1 (Bd) | 962 |
| SEQ ID NO: 17 | | | SEQ ID NO: 10 (Si) | 1172 | SEQ ID NO: 5 (Sb) | 1259 | SEQ ID NO: 3 (Bd) | 1551 |
| SEQ ID NO: 18 | | | SEQ ID NO: 10 (Si) | 1172 | SEQ ID NO: 7 (Sb) | 816 | SEQ ID NO: 3 (Bd) | 1551 |

Zm = maize;
Sb = *sorghum*;
Bd = *Brachypodium distachyon*;
Si = *Setaria italica*

Example 3: Expression Analysis of Regulatory Elements in Transgenic Maize

Table 3 shows the expression result for each hybrid regulatory element in roots. Overall, each hybrid regulatory element drove expression and provided an expression pattern that was generally ubiquitous in the root. Expression was most consistent in the meristem, elongation region, and mature region between events. Expression in the cap was more variable as only one naturally occurring promoter (SEQ ID NO: 1; Table 1) explicitly drove expression in the cap. Therefore, expression in the cap was ectopic in the absence of SEQ ID NO: 1 in these experiments. Expression levels of the hybrid regulatory elements were generally higher than the individual parents by 2-fold or more; however, not all expressed at higher levels and were either equivalent to the highest expressing parent or slightly below.

SEQ ID NO: 11 was constructed using segments from parents with spatial expression characteristics that minimally overlapped (SEQ ID NO: 8 and SEQ ID NO: 4). Three copies of a segment from SEQ ID NO: 8 were fused to one copy of a segment from SEQ ID NO: 4. The results from histochemically stained transgenic maize roots showed expression was mostly in the meristem and mature region of transgenic roots, reflective of both parent regulatory segments. In higher expressing events, the expression pattern blended together for more uniform expression across the meristem, elongation and mature regions. Neither parent segment of SEQ ID NO: 11 drove expression in the cap; however, some events did display ectopic expression in the cap. An additional observation was expression in the stalk, which was exhibited by the parent regulatory element set forth in SEQ ID NO: 4.

SEQ ID NO: 12 demonstrates that segments from different species may act together in a hybrid format. SEQ ID NO: 6 is sourced from *sorghum* and drives expression at higher levels in the elongation region than SEQ ID NO: 8. Three copies of a parental regulatory element segment from SEQ ID NO: 6 were placed upstream of a parental regulatory element segment from SEQ ID NO: 4 in a configuration similar to SEQ ID NO: 11. The result of the construction was a more uniform expression pattern relative to SEQ ID NO: 11 in histochemically stained transgenic roots. Quantitative data showed the expression level directed by SEQ ID NO: 12 exceeded the level of the individual parent regulatory elements of SEQ ID NO: 6 and SEQ ID NO: 4, respectively. The increase was approximately 3-fold. Ectopic expression in the root cap was observed, and expression in stalk was observed as well.

SEQ ID NO: 13 eliminated repeated segments by combining one copy of each segment from SEQ ID NOs: 8, 6 and 4, respectively. Histochemical staining results showed uniform expression in the cap, meristem, elongation region and mature region. Histochemical staining is the result of immersing sampled tissue in a solution containing a substrate, X-Gluc (sodium salt), that results in the appearance of a blue precipitate at the site in the tissue where the B-glucuronidase enzyme is being expressed.

SEQ ID NOs: 14 and 15 were hybrid regulatory elements built with segments other than those from SEQ ID NO: 8, 6 and 4. In SEQ ID NO: 14, a segment from SEQ ID NO: 4 was replaced with a segment from SEQ ID NO: 2. SEQ ID NO: 2 has an expression pattern similar to SEQ ID NO: 4, but is from *Brachypodium distachyon* whereas SEQ ID NO: 4 is from maize. A segment from SEQ ID NO: 5 was added between segments from SEQ ID NO: 2 and SEQ ID NO: 6. SEQ ID NO: 15 consisted of segments from three species. SEQ ID NO: 9 originated from maize, SEQ ID NO: 5 was from *sorghum*, and SEQ ID NO: 2 was obtained from *Brachypodium* (Table 2). SEQ ID NO: 15 is very similar to SEQ ID NO: 14, with a difference of a SEQ ID NO: 6 segment substituted for a segment from SEQ ID NO: 9. Both SEQ ID NO: 14 and SEQ ID NO: 15 drove expression in maize roots (Table 3). Ectopic expression was observed in the cap. Other sites of expression included some SEQ ID NO: 14 and SEQ ID NO: 15 events with low levels of stalk and husk expression which differed from SEQ ID NO: 13 which had stalk and low levels of leaf expression.

SEQ ID NO: 16 demonstrates additional flexibility by replacing segments with similar expression patterns, such as SEQ ID NO: 2 and SEQ ID NO: 4, that were used for expression mostly in the meristem, with a segment from a parent regulatory element driving expression in a different part of the root tip. SEQ ID NO: 1 was selected for its root cap preference in transgenic maize plants and was used in place of SEQ ID NO: 2 in a SEQ ID NO: 14 configuration. SEQ ID NO: 16 drove expression in the cap and the other regions of the root (Table 3). Expression outside of roots was not detected.

SEQ ID NO: 17 explored using another regulatory element segment from *Brachypodium*, SEQ ID NO: 3, in place of SEQ ID NO: 2 and a segment from *Setaria italica*, SEQ ID NO: 10, to replace the maize segment, SEQ ID NO: 9.

SEQ ID NO: 18 was similar to SEQ ID NO: 17, with the exception that SEQ ID NO: 5 from *sorghum* was replaced with another segment from *sorghum*, SEQ ID NO: 7 (Table 2). Both SEQ ID NO: 17 and SEQ ID NO: 18 functioned in transgenic maize roots with SEQ ID NO: 17 producing more ectopic expression in the cap than SEQ ID NO: 18 (Table 3). A few events for SEQ ID NOs: 17 and 18 had some stalk expression.

The combined results from SEQ ID NOs: 11-18 demonstrate that segments from maize, *sorghum*, *Brachypodium* and *Setaria italica* that function in different regions of the maize root may be assembled to produce a hybrid regulatory element that functions in all regions of a maize root (Table 3).

TABLE 3

Expression Results for Each Hybrid Regulatory Element in Transgenic Maize Roots

| Hybrid Regulatory Element | Cap | Meristem | Elongation region | Mature region |
|---|---|---|---|---|
| Seq ID 11 | + | ++++ | ++ | +++ |
| Seq ID 12 | ++ | ++++ | ++++ | ++++ |
| Seq ID 13 | ++++ | ++++ | ++++ | ++++ |
| Seq ID 14 | ++++ | ++++ | ++++ | ++ |
| Seq ID 15 | ++ | ++++ | ++++ | ++ |
| Seq ID 16 | ++++ | +++ | ++++ | +++ |

TABLE 3-continued

Expression Results for Each Hybrid Regulatory Element in Transgenic Maize Roots

| Hybrid Regulatory Element | Cap | Meristem | Elongation region | Mature region |
|---|---|---|---|---|
| Seq ID 17 | ++++ | ++++ | ++++ | ++++ |
| Seq ID 18 | + | ++++ | ++ | +++ |

Based on histochemical staining

Additional segment combinations comprising the segment components of hybrid promoters, SEQ ID NOs: 13 and 17, were tested in maize plants. The three segments for each parental regulatory element were assigned a position with "A" indicating the 5' segment, "B" the middle segment and "C" the 3' segment (See FIG. 2). The segments were then put in re-ordered combinations as indicated in FIG. 2 and Tables 4 and 5 to test relative location of segments in a hybrid promoter. Altering the order of the three segments for SEQ ID NO: 13 resulted in parental-type expression for two of the three combinations (Table 4). The combination not showing parental-type expression had reduced expression in the root cap. These results indicate flexibility in the position of segments within the regulatory element, but that not all combinations will produce the same outcome. These results are supported by the reordering of SEQ ID NO: 17 which is comprised of different segments than SEQ ID NO: 13. Two of the three combinations resulted in parental type expression and like SEQ ID NO: 13, one did not (Table 5). The combination not showing the parental phenotype also had a different segment arrangement compared to SEQ ID NO: 13 (CBA versus CAB).

TABLE 4

Expression of Relative Orientation of Segments of a Hybrid Regulatory Element in Transgenic Maize Roots

| Hybrid Regulatory Element | Order | fragments assembled (5'-3') | Cap | Meristem | Elongation region | Mature region |
|---|---|---|---|---|---|---|
| SEQ ID NO: 13 | ROOT HYBRID 2 (ABC) | Mature, mature-elongation, elongation-mature | ++++ | ++++ | ++++ | +++ |
| SEQ ID NO: 35 | CAB | Elongation-meristem, mature, mature-elongation | ++++ | ++++ | ++++ | +++ |
| SEQ ID NO: 36 | BCA | Mature-elongation, elongation-meristem, mature | ++++ | ++++ | ++++ | +++ |
| SEQ ID NO: 37 | CBA | Elongation-meristem, mature-elongation, mature | + | ++++ | ++++ | +++ |

Based on histochemical staining

TABLE 5

Expression of Relative Orientation of Segments of a Hybrid Regulatory Element in Transgenic Maize Roots

| Hybrid Regulatory Element | Order | fragments assembled (5'-3') | Cap | Meristem | Elongation region | Mature region |
|---|---|---|---|---|---|---|
| SEQ ID NO: 17 | ROOT HYBRID 4 | Mature, mature-elongation, meristem-elongation | ++++ | ++++ | ++++ | +++ |
| SEQ ID NO: 38 | CAB (4) | Meristem-elongation, mature, mature-elongation | + | ++++ | +++ | +++ |
| SEQ ID NO: 39 | BCA (4) | Elongation-mature, meristem-elongation, mature | ++++ | ++++ | ++++ | +++ |
| SEQ ID NO: 40 | CBA (4) | Meristem-elongation, elongation-mature, mature | ++++ | ++++ | ++++ | ++++ |

In order to test the use of only two segments of parental regulatory elements to produce a unique expression pattern in a hybrid promoter, pairwise combinations using two segments of SEQ ID NO: 13 were made and compared back to the expression of SEQ ID NO: 13 (Table 6). Results showed combinations could be made that reflected SEQ ID NO: 13 expression, but others did not. Of those that did not, one combination (CA) did not entirely reflect the contribution of each segment. The results indicate that two segments are sufficient to produce a promoter that functions across different regions of the root, but the segments put together and how they are put together may impact the expression result.

TABLE 6

Expression of Relative Orientation of Segments of a Hybrid Regulatory Element in Transgenic Maize Roots

| Hybrid Regulatory Element | Order | fragments assembled (5'-3') | Cap | Meristem | Elongation region | Mature region |
|---|---|---|---|---|---|---|
| SEQ ID NO: 13 | ROOT HYBRID 2 (ABC) | Mature, mature-elongation, elongation-mature | ++++ | ++++ | ++++ | +++ |
| SEQ ID NO: 41 | BC | Mature-elongation, elongation-meristem | ++++ | ++++ | ++++ | +++ |
| SEQ ID NO: 42 | AB | Mature, mature-elongation | + | ++++ | ++++ | +++ |
| SEQ ID NO: 43 | BA | Mature-elongation, mature | − | ++++ | ++++ | +++ |
| SEQ ID NO: 44 | AC | Mature, elongation-meristem | + | ++++ | +++ | ++ |
| SEQ ID NO: 45 | CA | Elongation-meristem, mature | ++ | ++ | + | + |
| SEQ ID NO: 46 | CB | Elongation-meristem, mature-elongation | +++ | ++++ | ++++ | +++ |

Example 4: Hybrid Aerial Regulatory Elements

The methods used to create the hybrid root regulatory elements may also be applied to other hybrid regulatory element types, including above ground tissue expressing hybrid regulatory elements ("aerial regulatory elements"). Segments from a maize silk-preferred parent regulatory element (SEQ ID NO: 48) and a *Brachypodium* green tissue parent regulatory element (SEQ ID NO: 49) are combined, as described in Example 3 for SEQ ID NO: 11, where repeated segments from a silk-preferred regulatory element are placed upstream of a green tissue segment that supply a TATA box for SEQ ID NO: 48. The reverse was also performed where a silk-expressed segment from the maize silk-preferred parent regulatory element (SEQ ID NO: 48) provides the TATA box and multiple segments of the *Brachypodium* green tissue parent regulatory element (SEQ ID NO: 49) are upstream for an aerial hybrid regulatory element. The outcome of combing these elements, shown in Table 7 and FIG. 3, were that the resulting hybrid regulatory element drove transgene expression in both the leaves and silks of maize plants. Expression in other tissues such as root and stalk were not significantly different compared to the parents. Taken together, vegetative green tissue promoter segments can be combined with reproductive non-green tissue segments to produce a desired expression pattern in maize. The segments from parent regulatory elements may originate from different species.

Combining the segments was not necessarily expected to increase expression in the tissues of interest much beyond the level provided by the parents. So, to help modulate expression in the direction of increased levels, the −20 regions of three different plant viral promoters were used in replace of the −20 region of the segment providing the TATA box for aerial hybrid regulatory elements. Viral promoters are generally strong promoters in plants, so the −20 regions of these promoters, which consist of the TATA box region and other sequences that interact with the basal transcription machinery, may be viewed as "optimized" for expression. Therefore, linking upstream regulatory segments to these "optimized" sequence elements may result in increased expression levels of the hybrid regulatory element. The three viral promoters selected to provide the −20 regions were BYDV (Bean Yellow Dwarf Virus, SEQ ID NO: 67, HLCV (Hollyhock Leaf Crumple Virus, SEQ ID NO: 66 and Banana Streak Virus (AY), SEQ ID NO: 65. These represent the Geminiviridae and Caulimoviridae virus families, although other virus promoters and promoters from other families than the Geminiviridae and Caulimoviridae families may be used. Table 7 shows each of the −20 regions positively affected expression in leaves and silk. Expression in roots and stalk was not impacted the same way. The BSV(AY) −20 region provided the most significant increase in expression which included an increase in husk expression.

TABLE 7

Geminiviridae and Caulimoviridae Family −20 Regions
Positively Affected Expression in Leaves and Silk

| Upstream Activation Element | Base | Leaf | Root (tip) | Root (mature region) | Stalk | Silk | Husk |
|---|---|---|---|---|---|---|---|
| SEQ ID NO: 49 | BD-FBPA PRO | 10 | <0.1 | <0.1 | 1 | 1 | 3 |
| SEQ ID NO: 60 | ZM-OEBF PRO | <0.1 | <0.1 | <0.1 | <0.1 | 5 | <0.1 |

TABLE 7-continued

Geminiviridae and Caulimoviridae Family −20 Regions
Positively Affected Expression in Leaves and Silk

| Upstream Activation Element | Base | Leaf | Root (tip) | Root (mature region) | Stalk | Silk | Husk |
|---|---|---|---|---|---|---|---|
| SEQ ID NO: 58 | BD-FBPA | 8 | <0.1 | <0.1 | 2 | 9 | 3 |
| SEQ ID NO: 50 | BD-FBPA-BYDV CORE PRO | 15 | <0.1 | <0.1 | 2 | 17 | 2 |
| SEQ ID NO: 51 | BD-FBPA-HLCV CORE PRO | 12 | <0.1 | <0.1 | <0.1 | 18 | 1 |
| SEQ ID NO: 52 | BD-FBPA-BSV(AY) CORE PRO | 38 | <0.1 | <0.1 | 4 | 65 | 10 |

A set of hybrid regulatory elements was made consisting of non-redundant parental segments. The segment providing the TATA box (SEQ ID NO: 48) generates expression in leaf and silk tissues, but where silk expression is lower than the leaf (Table 8). In an effort to increase the silk expression, segments from two different from silk-preferred promoters (SEQ ID NO: 61 and 62) were tested in combination with SEQ ID NO: 48. In the first hybrid regulatory element, one segment from SEQ ID NO: 61 was added (SEQ ID NO: 47). An increase in silk expression was observed. Leaf and root expression remained about the same, and stalk expression increased slightly. Adding SEQ ID NO: 62 (SEQ ID NO: 56) resulted in a more significant increase in silk expression. Leaf and stalk expression decreased slightly, and root expression had no change. In a third hybrid regulatory element, the 5' most silk segment from the hybrid regulatory element of SEQ ID NO: 56 was replaced with a green tissue segment (SEQ ID NO: 64) to produce the aerial hybrid regulatory element of SEQ ID NO: 57. The result was an increase in leaf expression and a return of silk expression to previous levels. Stalk expression increased slightly and root expression remained unchanged. These results demonstrate the capability to use non-redundant parent regulatory element segments, where the non-redundant segments may be from a different species (in this case *Brachypodium distachyon*), to produce a hybrid regulatory element that functions in targeted tissues of maize

TABLE 8

Expression Results for Each Hybrid Regulatory Element in Transgenic Maize

| Upstream Activation Element | Base | Leaf | Root (tip) | Root (mature region) | Stalk | Silk | Husk |
|---|---|---|---|---|---|---|---|
| SEQ ID NO: 48 | ZM-SILK12 PRO | 31 | <0.1 | <0.1 | 3 | 10 | 16 |
| SEQ ID NO: 47 | ZM-SILK12 PRO | 30 | <0.1 | <0.1 | 8 | 18 | 18 |
| SEQ ID NO: 56 | ZM-SILK12 PRO | 23 | <0.1 | <0.1 | 4 | 36 | 20 |
| SEQ ID NO: 57 | ZM-SILK12 PRO | 43 | <0.1 | <0.1 | 7 | 10 | 20 |

Similar to root hybrid regulatory elements, the segments relative orientation to each other may impact the expression result in hybrid regulatory elements designed for expression in other tissues (see FIG. 2 for segment orientation). Table 9 shows expression results a green tissue segment is placed at the 5' end of a hybrid regulatory element (SEQ ID NO: 54)

versus a 3' position where it is providing the TATA box (SEQ ID NO: 55). When the green tissue segment is placed in the 5' position, there is no increase in leaf expression (SEQ ID NO: 54; Table 9). However, when the green tissue segment is placed in the 3' position, leaf expression increases. Position also affected husk expression with somewhat of a reverse effect.

TABLE 9

Expression of Relative Orientation of Segments of a Hybrid Regulatory Element in Transgenic Maize

| Upstream Activation Element | Base | Leaf | Root (tip) | Root (mature region) | Stalk | Silk | Husk |
|---|---|---|---|---|---|---|---|
| SEQ ID NO: 48 | ZM-SILK12 PRO | 31 | <0.1 | <0.1 | 3 | 10 | 16 |
| SEQ ID NO: 47 | ZM-SILK12 PRO | 30 | <0.1 | <0.1 | 8 | 18 | 18 |
| SEQ ID NO: 54 | ZM-SILK12 PRO | 30 | <0.1 | <0.1 | 5 | 40 | 23 |
| SEQ ID NO: 55 | ZM-SILK12 PRO | 40 | <0.1 | <0.1 | 4 | 33 | 12 |

In another example, two copies of the silk segment used in Table 7 (from the parental regulatory element of SEQ ID NO: 60) were placed upstream of two copies of the green tissue segment also in Table 7 (from the parental regulatory element of SEQ ID NO: 49). Leaf and silk expression increased about two-fold relative to the parents in this configuration (SEQ ID NO: 53; Table 10). However, reversing the arrangement so that two copies of the green tissue segment are upstream of the two copies of the silk segment resulted in no leaf expression (SEQ ID NO: 59; Table 10). The combined results suggest the segment providing the TATA box or 3' segments may impact or influence expression provided by the hybrid regulatory element.

TABLE 10

Expression of Relative Orientation of Segments of a Hybrid Regulatory Element in Transgenic Maize

| Upstream Activation Element | Base | Leaf | Root (tip) | Root (mature region) | Stalk | Silk | Husk |
|---|---|---|---|---|---|---|---|
| SEQ ID NO: 49 | BD-FBPA PRO | 10 | <0.1 | <0.1 | 1 | 1 | 3 |
| SEQ ID NO: 60 | ZM-OEBF PRO | <0.1 | <0.1 | <0.1 | <0.1 | 5 | <0.1 |
| SEQ ID NO: 53 | BD-FBPA PRO | 20 | <0.1 | <0.1 | 2 | 10 | 6 |
| SEQ ID NO: 59 | ZM-OEBF PRO | <0.1 | <0.1 | <0.1 | <0.1 | 6 | <0.1 |

Example 10: *Agrobacterium*-Mediated Transformation of Maize and Regeneration of Transgenic Plants For *Agrobacterium*-mediated transformation of maize polynucleotides of the disclosure, the method of Zhao was employed (U.S. Pat. No. 5,981,840, and PCT patent publication WO98/32326). Briefly, immature embryos were isolated from maize and the embryos contacted with a suspension of *Agrobacterium* under conditions whereby the bacteria were capable of transferring the regulatory element sequence of the disclosure to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following the co-cultivation period an optional "resting" step was performed. In this resting step, the embryos were incubated in the presence of at least one antibiotic known to inhibit the growth of *Agrobacterium* without the addition of a selective agent for plant transformants (step 3: resting step). Next, inoculated embryos were cultured on medium containing a selective agent and growing transformed calli were recovered (step 4: the selection step). Plantlets were regenerated from the calli (step 5: the regeneration step) prior to transfer to the greenhouse.

What is claimed is:

1. A hybrid regulatory element comprising a nucleic acid molecule comprising the sequence of SEQ ID NO: 12, wherein the hybrid regulatory element produces a root region tissue expression pattern.

2. The hybrid regulatory element of claim 1, wherein the hybrid regulatory element comprises more than one copy of the same plant-derived regulatory element.

3. A DNA construct comprising the hybrid regulatory element of claim 1.

4. The DNA construct of claim 3, wherein the hybrid regulatory element is operably linked to a polynucleotide of interest.

5. An expression cassette comprising the DNA construct of claim 4.

6. A host cell comprising the expression cassette of claim 5.

7. The host cell of claim 5, wherein the host cell comprises a plant cell, a bacterial cell, or an animal cell.

8. A transgenic plant comprising the expression cassette of claim 5.

* * * * *